US007855294B2

(12) United States Patent
Takahashi et al.

(10) Patent No.: US 7,855,294 B2
(45) Date of Patent: Dec. 21, 2010

(54) CYCLOALKANOPYRIDINE DERIVATIVE

(75) Inventors: Hirobumi Takahashi, Ushiku (JP);
Yuichi Sugimoto, Tsukuba (JP);
Takashi Yoshizumi, Ushiku (JP);
Tetsuya Kato, Tsukuba (JP); Masanori Asai, Tsukuba (JP); Hiroshi Miyazoe, Tsukuba (JP)

(73) Assignee: Banyu Pharmaceutical Co., Ltd., Kudankita, Chiyoda-Ku, Tokyo (JP)

( * ) Notice: Subject to any disclaimer, the term of this patent is extended or adjusted under 35 U.S.C. 154(b) by 1140 days.

(21) Appl. No.: 10/590,585

(22) PCT Filed: Mar. 4, 2005

(86) PCT No.: PCT/JP2005/004264

§ 371 (c)(1),
(2), (4) Date: Aug. 24, 2006

(87) PCT Pub. No.: WO2005/085228

PCT Pub. Date: Sep. 15, 2005

(65) Prior Publication Data
US 2007/0191419 A1 Aug. 16, 2007

(30) Foreign Application Priority Data
Mar. 5, 2004 (JP) .............................. 2004-062405

(51) Int. Cl.
*C07D 215/26* (2006.01)
*C07D 491/20* (2006.01)
*C07D 491/107* (2006.01)
*C07D 401/06* (2006.01)
*A61K 31/438* (2006.01)
*A61K 31/4709* (2006.01)
*A61K 31/46* (2006.01)

(52) U.S. Cl. ........................ 546/17; 546/126; 546/153; 514/278; 514/304; 514/312

(58) Field of Classification Search .................. 546/148, 546/177, 178, 179, 196, 200, 17, 126, 153; 544/363; 514/278, 304, 312
See application file for complete search history.

(56) References Cited

U.S. PATENT DOCUMENTS

| 4,016,281 | A | 4/1977 | Jonas et al. |
| 4,130,646 | A | 12/1978 | Vogt et al. |
| 6,166,209 | A | 12/2000 | Adam et al. |
| 6,869,960 | B2 | 3/2005 | Ito et al. |
| 7,115,633 | B2 | 10/2006 | Barlocco et al. |
| 7,125,877 | B2 | 10/2006 | Kobayashi et al. |
| 7,223,867 | B2 | 5/2007 | Palombi et al. |

OTHER PUBLICATIONS

Churakov et. al. "Progress in 1,2,3,4-Tetrazine" Chemistry Chemical Reviews 2004, 104, 2601-2616.*
Martin, Yvonne C. et. al. "Do Structurally Similar Molecules Have Similar Biological Activity?" Journal of Medicinal Chemistry 2002, 45, 4350-4358.*
Sugimoto et. al. "Design, synthesis, and biological evaluation of indole derivatives as novel nociceptin/orphanin FQ (N/OFQ) receptor antagonists" Bioorganic & Medicinal Chemistry Letters 16 (2006) 3569-3573.*
Chen et. al. "Design and Parallel Synthesis of Piperidine Libraries Targeting the Nociceptin (N/OFQ) Receptor." Bioorganic & Medicinal Chemistry Letters 2003, 13, 3247-3252.*
In the Pipeline, online, accessed Jun. 16, 2008, "http://pipeline.corante.com/archives/2006/01/24/the_examiner_finally_snaps.php".*
Bigan et al., "Recent Advances Towards the Discovery of ORL-1 Receptor Agonists and Antagonists", Expert Opin. Ther. Patents, vol. 15, pp. 357-388, 2005.
Chiou et al., "Nociceptin/Orphanin FQ Peptide Receptors: Pharmacology and Clinical Implications", Current Drug Targets, vol. 8, pp. 117-135, 2007.
Niiyama et al., "6-Carboxy-5,7-Diarylcyclopentenol[1,2-b]Pyridine Derivatives: A Novel Class of Endothelin Receptor Antagonists", Biorg. Med. Chem., vol. 10, pp. 2461-2470, 2002.
Pita et al., "A Simple, Efficient Method for Regioselective Synthesis of 7-Aminomehtyl-7,8-Dihydro-6H-Quinolin-5-ones, New Potential CNS Agents", Tetrahedron Letters, vol. 41, pp. 9829-9833, 2000.

(Continued)

*Primary Examiner*—Rita J Desai
*Assistant Examiner*—David K O'Dell
(74) *Attorney, Agent, or Firm*—J. Eric Thies; Gerard M. Devlin

(57) ABSTRACT

Provided are cycloalkanopyridine derivatives of formula [I]:

[wherein the symbols are the same as those stated in the description]. The compounds act as a nociceptin receptor antagonist, and are useful as medicines for diseases associated with a nociceptin receptor, for example, as a reliever against tolerance to a narcotic analgesic; a reliever against dependence on or addiction to a narcotic analgesic; an analgesic enhancer; an antiobesitic or appetite suppressor; a treating or prophylactic agent for cognitive impairment and dementia/amnesia; an agent for treating developmental cognitive abnormality; a remedy for schizophrenia; an agent for treating neurodegenerative diseases; an anti-depressant or treating agent for affective disorder; a treating or prophylactic agent for diabetes insipidus; a treating or prophylactic agent for polyuria; or a remedy for hypotension.

20 Claims, No Drawings

OTHER PUBLICATIONS

Ronzoni et al., "Lead Generation and Lead Optimisation Approaches in the Discovery of Selective, Non-Peptide ORL-1 Receptor Agonists and Antagonists", Expert. Opin. Ther. Patents, vol. 11, pp. 525-546, 2001.

Zaratin et al., "Modification of Nociception and Morphine Tolerance by the Selective Opiate Receptor-Like Orphan Receptor Antagonist (−) Cis-1-Methyl-7[[4-2,6-Dicholorphenyl) Piperidin-1-yl]Methyl]-6,7,8,9-Tetrahydro-5H-Benzocyclophepten-5-ol (SB-612111)", J. of Pharmacology and Experimental Therapeutics, vol. 308, pp. 454-461, 2004.

Yoshizumi et al., "A Novel Class of Cycloalkano[b] Pyridines as Potent and Orally Active Opioid Receptor-Like 1 Antagonists with Minimal Binding Affinity to the hERG K+ Channel", J. Med. Chem, vol. 51, pp. 4021-4029, 2008.

Zaveri et al., "Peptide and NonPeptide Ligands for the Nociceptin/ Orphanin FQ Receptor ORL1: Research Tools and Potential Therapeutic Agents", Life Sciences, vol. 73, pp. 663-678, 2003.

* cited by examiner

CYCLOALKANOPYRIDINE DERIVATIVE

CROSS REFERENCE TO RELATED APPLICATIONS

This application is a U.S. National Phase application under 35 U.S.C. §371 of PCT Application No. PCT/JP2005/004264, filed Mar. 4, 2005, which claims priority under 35 U.S.C. §119 from JP Application No. JP2004-062405, filed Mar. 5, 2004.

TECHNICAL FIELD

The present invention relates to novel compounds, cycloalkanopyridine derivatives. The compounds exhibit an antagonism to binding of nociceptin to a nociceptin receptor ORL1 (opioid receptor-like-1 receptor) and are useful as medicines relating to the effect associated with the nociceptin receptor, for example, relating to pain and appetite control or memory and learning.

BACKGROUND ART

Nociceptin (the same substance as orphanin FQ) is a peptide comprising 17 amino acid units having a similar structure to that of opioid peptide. Nociceptin has an augmenting activity on reaction against nociceptive stimulation, an appetite stimulating activity, an activity for reducing a space learning ability, an antagonism against an analgesic action of classic opiate agonists, a dopamine release inhibitory action, a water diuresis action, a vasodilative action and a systemic blood pressure-lowering action, and it is considered to take part in intracerebral controlling of pain, appetite and memory learning through the nociceptin receptor ORL1 [cf. *Nature*, Vol. 377, 532 (1995); *Society for Neuroscience*, Vol. 22, 455 (1996); *NeuroReport*, Vol. 8, 423 (1997); *Eur. J. Neuroscience*, Vol. 9, 194 (1997); *Neuroscience*, Vol. 75, 1 (1996); ibid., 333 (1996); *Life Science*, Vol. 60, PL15 (1997); ibid., PL141 (1997); *Proceedings for National Academy of Sciences*, Vol. 94, 14858 (1997)].

Further, it is known that morphine tolerance is reduced or memory and learning ability is improved in knockout mice in which expression of the nociceptin receptor ORL1 is inhibited [cf. *Neuroscience Letters*, Vol. 237, 136 (1997); *Nature*, Vol. 394, 577 (1998)].

It has also been reported that nociceptin itself induces symptoms resembling withdrawal symptoms observed with morphine addicts, and that a non-peptide nociceptin receptor antagonist improves morphine tolerance, dependence and symptoms resembling withdrawal symptoms [cf. *Psychopharmacology*, Vol. 151, 344-350 (2000); *Journal of Neuroscience*, Vol. 20, 7640 (2000)].

On the other hand, nociceptin protein precursor-defective mice are reported to show behaviors resembling anxiety and changes in stress response [cf. *Proceedings for National Academy of Sciences*, Vol. 96, 10444 (1999)].

Hence the substances which specifically inhibit binding of nociceptin to the nociceptin receptor ORL1 are useful as an analgesic against diseases accompanied with pains such as cancerous pain, postoperative pain, migraine, gout, chronic rheumatism, chronic pain and neuralgia; a reliever against tolerance to a narcotic analgesic such as morphine; a reliever against dependence on or addiction to a narcotic analgesic such as morphine; an analgesic enhancer; an antiobesitic or appetite suppressor; a treating or prophylactic agent for cognitive impairment and dementia/amnesia in aging, cerebrovascular diseases and Alzheimer's disease; an agent for treating developmental cognitive abnormality such as attention deficit hyperactivity disorder and learning disability; a remedy for schizophrenia; an agent for treating neurodegenerative diseases such as Parkinsonism and chorea; an antidepressant or treating agent for affective disorder; a treating or prophylactic agent for diabetes insipidus; a treating or prophylactic agent for polyuria; a remedy for hypotension, and the like.

Substances which specifically inhibit binding of nociceptin to the nociceptin receptor ORL1 are disclosed, for example, in WO99/029696, WO00/27815, WO01/83454, WO03/40099, WO03/64425. These compounds all have a skeleton having a cycloalkane condensed with a benzene nucleus, which, however, differ from the compounds of the present invention in point of the skeleton thereof. Precisely, the compounds of the present invention has a skeleton having a cycloalkane condensed with a pyridine nucleus.

On the other hand, *Tetrahedron Letters*, Vol. 41, pp. 9829-9833 (2000) discloses a compound having the following structure:

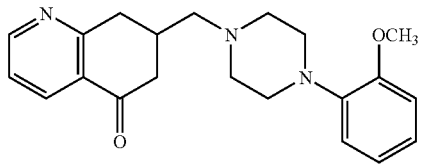

The compound was developed as a derivative of haloperidol, and its effect and mechanism differ from those of the compounds of the present invention.

Patent Reference 1: WO99/029696

Patent Reference 2: WO00/27815

Patent Reference 3: WO01/83454

Patent Reference 4: WO03/40099

Patent Reference 5: WO03/64425

Non-Patent Reference 1: *Tetrahedron Letters*, Vol. 41, pp. 9829-9833 (2000)

DISCLOSURE OF THE INVENTION

We, the present inventors have assiduously studied compounds capable of inhibiting the binding of nociceptin to the nociceptin receptor ORL1, and, as a result, have found that compounds having a specific amine bonding to a cycloalkanopyridine skeleton formed through condensation of a pyridine skeleton and a cycloalkane are antagonistic to the bonding of nociceptin to the nociceptin receptor ORL1, and have extremely excellent properties as medicines in that they have a high selectivity to the nociceptin receptor have no side effects, and that the compounds are effective as remedies for various diseases associated with the nociceptin receptor. On the basis of these findings, we have completed the present invention.

Specifically, an object of the invention is to provide the following:

(1) A cycloalkanopyridine derivative of the following general formula [I], and pharmaceutically-acceptable salt thereof:

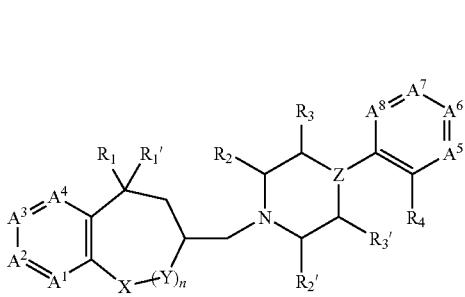

wherein;

$A^1, A^2, A^3$ and $A^4$ each independently represent —C($R_5$)— or —N—, provided that at least one of $A^1, A^2, A^3$ and $A^4$ is —N—;

$A^5, A^6, A^7$ and $A^8$ each independently represent —C($R_6$)— or —N—;

$R_1$ and $R_1'$ each independently represent a hydrogen atom, a halogen atom, a hydroxyl group, a cyano group, a $C_{1-6}$ alkyloxy group, a $C_{1-6}$ alkyloxyalkyloxy group, a $C_{1-6}$ alkyloxycarbonyl group, a $C_{1-6}$ alkyloxycarbonylamino group, a $C_{1-6}$ alkylcarbonyl group, a $C_{1-6}$ alkylcarbonyloxy group, a $C_{1-6}$ alkylcarbonylamino group, a $C_{1-6}$ alkylsulfonyl group, a $C_{1-6}$ alkylsulfonylamino group, a $C_{1-6}$ alkylsulfonyl-$C_{1-6}$ alkylamino group, a carbamoylamino group, a ($C_{1-6}$ alkyl)carbamoylamino group, a di($C_{1-6}$ alkyl)carbamoylamino group, a pyrazolyl group, a triazolyl group, an oxazolyl group, or a $C_{1-6}$ alkyl group optionally having a substituent selected from the following group [α]; or $R_1$ and $R_1'$ together form an oxo group or a $C_{1-3}$ alkyleneketal group;

$R_2$ represents a hydrogen atom or a $C_{1-6}$ alkyl group optionally having a hydroxyl group, or $R_2$ and $R_2'$ or $R_3'$ together form a $C_{1-3}$ alkylene group or an oxy-$C_{1-3}$ alkylene group;

$R_2'$ represents a hydrogen atom or a $C_{1-6}$ alkyl group optionally having a hydroxyl group, or $R_2'$ and $R_2$ or $R_3$ together form a $C_{1-3}$ alkylene group or an oxy-$C_{1-3}$ alkylene group;

$R_3$ represents a hydrogen atom, a hydroxyl group, a halogen atom, a $C_{1-6}$ alkyloxy group, a $C_{1-6}$ alkylcarbonyl group, a $C_{1-6}$ alkyloxycarbonyl group, a $C_{1-6}$ alkylsulfonyl group, a $C_{1-6}$ alkylsulfonylamino group, a $C_{1-6}$ alkylsulfonylalkylamino group, a cyano group, or a $C_{1-6}$ alkyl group optionally having a substituent selected from the group [α]; or $R_3$ and $R_3'$ or $R_2'$ together form a $C_{1-3}$ alkylene group or an oxy-$C_{1-3}$ alkylene group;

$R_3'$ represents a hydrogen atom, a hydroxyl group, a halogen atom, a $C_{1-6}$ alkyloxy group, a $C_{1-6}$ alkylcarbonyl group, a $C_{1-6}$ alkyloxycarbonyl group, a $C_{1-6}$ alkylsulfonyl group, a $C_{1-6}$ alkylsulfonylamino group, a $C_{1-6}$ alkylsulfonylaminoalkyl group, a cyano group, or a $C_{1-6}$ alkyl group optionally having a substituent selected from the group [α]; or $R_3'$ and $R_3$ or $R_2$ together form a $C_{1-3}$ alkylene group or an oxy-$C_{1-3}$ alkylene group;

$R_4$ represents a hydrogen atom, a halogen atom, a $C_{1-6}$ alkyl group optionally having a hydroxyl group, a halogeno-$C_{1-6}$ alkyl group, a $C_{1-6}$ alkyloxy-$C_{1-6}$ alkyl group, a $C_{1-6}$ alkylcarbonyl group, a cyano group, a formyl group, a $C_{1-6}$ alkyloxycarbonyl group, a $C_{1-6}$ alkylcarbonylamino group, a $C_{1-6}$ alkylcarbonyl-$C_{1-6}$ alkylamino group or a $C_{1-6}$ alkylsulfonyl group; or when Z is —C($R_7$)—, then $R_4$ and $R_7$ together form —C($R_8$)($R_8'$)—O—, —C($R_8$)($R_8'$)—CO—, —C($R_8$)($R_8'$)—C($R$)($R_8'$)—, —O—CO—, —CO—O—, —CO—C($R_8$)($R_8'$)—, —O—C($R_8$)($R_8'$)—, —CH($R_8$)—N($R_9$)— or —N($R_9$)—CH($R_8$)—;

$R_5$ represents a hydrogen atom, a hydroxyl group, a fluorine atom, a chlorine atom, a $C_{1-6}$ alkyl group, a $C_{1-6}$ alkylamino group, a $C_{1-6}$ alkylcarbonyl group, a $C_{1-6}$ alkylcarbonylamino group, a $C_{1-6}$ alkylcarbonyl-($C_{1-6}$)alkylamino group, or a cyano group;

$R_6$ represents a hydrogen atom, a halogen atom, a $C_{1-6}$ alkyl group optionally having a hydroxyl group, a halogeno-$C_{1-6}$ alkyl group, a $C_{1-6}$ alkyloxy-$C_{1-6}$ alkyl group, a $C_{1-6}$ alkylcarbonyl group, a cyano group, a formyl group, a $C_{1-6}$ alkyloxycarbonyl group, a $C_{1-6}$ alkylcarbonylamino group, a $C_{1-6}$ alkylcarbonyl-$C_{1-6}$ alkylamino group, or a $C_{1-6}$ alkylsulfonyl group;

$R_7$ represents a hydrogen atom, a halogen atom, a cyano group, a $C_{1-6}$ alkyl group, a $C_{1-6}$ alkyloxy group; or $R_7$ and $R_4$ together form —C($R_8$)($R_8'$)—O—, —C($R_8$)($R_8'$)—CO—, —C($R_8$)($R_8'$)—C($R_8$)($R_8'$)—, —O—CO—, —CO—O—, —CO—C($R_8$)($R_8'$)—, —O—C($R_8$)($R_8'$)—, —CH($R_8$)—N($R_9$)— or —CH($R_8$)—N($R_9$)—;

$R_8$ and $R_8'$ each independently represent a hydrogen atom, a hydroxyl group, a $C_{1-6}$ alkyl group optionally having a hydroxyl group, or a $C_{1-6}$ alkylsulfonyl group;

$R_9$ represents a hydrogen atom, a $C_{1-6}$ alkyl group, a $C_{1-6}$ alkylsulfonyl group, a $C_{1-6}$ alkyloxycarbonyl group, or a formyl group;

Ra represents a hydrogen atom, a $C_{1-6}$ alkyl group, a $C_{1-6}$ alkyloxycarbonyl group, a carbamoyl group, a ($C_{1-6}$ alkyl)carbamoyl group, a di($C_{1-6}$ alkyl)carbamoyl group, a $C_{1-6}$ alkylsulfonyl group, a pyrazolyl group, a triazolyl group, or an oxazolyl group;

X represents —$CH_2$—, —CH(OH)—, —N(Ra)—, —O—, —S— or —$SO_2$—;

Y represents —$CH_2$— or —N(Ra)—;

Z represents —C($R_7$)— or —N—;

n indicates an integer of 0 or 1;

Group α: a halogen atom, a hydroxyl group, a $C_{1-6}$ alkylcarbonyl group, a $C_{1-6}$ alkylcarbonyloxy group, a $C_{1-6}$ alkylcarbonylamino group, a $C_{1-6}$ alkylcarbonyl-$C_{1-6}$ alkylamino group, a $C_{1-6}$ alkyloxy group, a $C_{1-6}$ alkyloxycarbonyl group, a $C_{1-6}$ alkyloxycarbonylamino group, a $C_{1-6}$ alkyloxycarbonyl-$C_{1-6}$ alkylamino group, a $C_{1-6}$ alkylamino group, a di-$C_{1-6}$ alkylamino group, a sulfamoyl group, a $C_{1-6}$ alkylsulfamoyl group, a di-$C_{1-6}$ alkylsulfamoyl group, a sulfamoylamino group, a $C_{1-6}$ alkylsulfamoylamino group, a di-$C_{1-6}$ alkylsulfamoylamino group, a $C_{1-6}$ alkylsulfamoyl-$C_{1-6}$ alkylamino group, a di-$C_{1-6}$ alkylsulfamoyl-$C_{1-6}$ alkylamino group, a sulfamoyloxy group, a $C_{1-6}$ alkylsulfamoyloxy group, a di-$C_{1-6}$ alkylsulfamoyloxy group, a carbamoyl group, a $C_{1-6}$ alkylcarbamoyl group, a di-$C_{1-6}$ alkylcarbamoyl group, a carbamoylamino group, a $C_{1-6}$ alkylcarbamoylamino group, a di-$C_{1-6}$ alkylcarbamoylamino group, a $C_{1-6}$ alkylcarbamoyl-$C_{1-6}$ alkylamino group, a di-$C_{1-6}$ alkylcarbamoyl-$C_{1-6}$ alkylamino group, a carbamoyloxy group, a $C_{1-6}$ alkylcarbamoyloxy group, a di-$C_{1-6}$ alkylcarbamoyloxy group, a $C_{1-6}$ alkylsulfonyl group, a $C_{1-6}$ alkylsulfonylamino group, and a $C_{1-6}$ alkylsulfonyloxy group.

Further, the invention provides the following:

(2) A nociceptin receptor antagonist containing a compound of formula [I] as the active ingredient thereof;

(3) A pharmaceutical composition comprising a compound of formula [I] and a pharmaceutically-acceptable additive;

(4) An analgesic; a reliever against tolerance to a narcotic analgesic such as morphine; a reliever against dependence on or addiction to a narcotic analgesic such as morphine; an analgesic enhancer; an antiobesitic or appetite suppressor; a treating or prophylactic agent for cognitive impairment and dementia/amnesia in aging, cerebrovascular diseases and Alzheimer's disease; an agent for treating developmental cognitive abnormality such as attention deficit hyperactivity disorder and learning disability; a remedy for schizophrenia; an agent for treating neurodegenerative diseases such as Parkinsonism and chorea; an anti-depressant or treating agent for affective disorder; a treating or prophylactic agent for diabetes insipidus; a treating or prophylactic agent for polyuria; or a remedy for hypotension; which contains a compound of formula [I] as the active ingredient thereof.

(5) A method for producing a compound of formula [I], which includes;

1) a sep of condensing a compound of a general formula [II]:

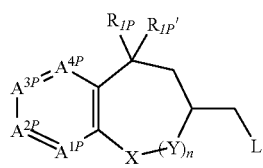

[II]

[wherein L represents a leaving group; $R_{1P}$ represents $R_1$ optionally having a protective group; $R_{1P}'$ represents $R_1'$ optionally having a protective group; $A^{1P}$ represents $A^1$ optionally having a protective group; $A^{2P}$ represents $A^2$ optionally having a protective group; $A^{3P}$ represents $A^1$ optionally having a protective group; $A^{4P}$ represents $A^4$ optionally having a protective group; X, Y and n have the same meanings as in (1)], with a compound of a general formula [III]:

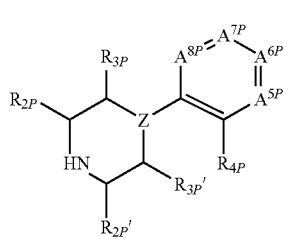

[III]

[wherein $R_{2P}$ represents $R_2$ optionally having a protective group; $R_{2P}'$ represents $R_2'$ optionally having a protective group; $R_{3P}$ represents $R_3$ optionally having a protective group; $R_{3P}'$ represents $R_3'$ optionally having a protective group; $R_{4P}$ represents $R_4$ optionally having a protective group; $A^{5P}$ represents $A^5$ optionally having a protective group; $A^{6P}$ represents $A^6$ optionally having a protective group; $A^{7P}$ represents $A^7$ optionally having a protective group; $A^{8P}$ represents $A^8$ optionally having a protective group; Z has the same meaning as in (1)];

2) when the compound obtained in the previous step has a protective group, a step of removing the protective group.

In this description;

"Halogen atom" includes a fluorine atom, a chlorine atom, a bromine atom and an iodine atom.

"Lower alkyl group" includes a linear alkyl group having from 1 to 6 carbon atoms, and a branched alkyl group having from 3 to 6 carbon atoms. Concretely, for example, it includes a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-amyl group, a 1-methylbutyl group, a 2-methylbutyl group, a 1,2-dimethylpropyl group, a 1-ethylpropyl group, an n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1-ethylbutyl group, a 1,1,2-trimethylpropyl group, a 1,2,2-trimethylpropyl group, a 1-ethyl-2-methylpropyl group, a 1-ethyl-1-methylpropyl group.

"Lower cycloalkyl group" includes a cycloalkyl group having from 3 to 6 carbon atoms. Concretely, for example, it includes a cyclopropyl group, a cyclobutyl group, a cyclopentyl group, and a cyclohexyl group.

"Oxo group" means a group (=O) that forms a carbonyl group (C=O) along with the carbon atom in an organic compound. For example, in case of $R_1$ or $R_1'$, $R_1$ and $R_1'$ together form a carbonyl group along with the carbon atom to which they bond.

"Lower alkyl group optionally substituted with a fluorine atom" includes a lower alkyl group, and a lower alkyl group in which a part or all of the hydrogen atoms are substituted with fluorine atoms. The latter fluorine atom-substituted lower alkyl group includes, for example, a fluoromethyl group, a difluoromethyl group, a trifluoromethyl group, a 2-fluoroethyl group, a 1,2-difluoroethyl group.

"Lower alkyloxy group optionally substituted with a fluorine atom" includes a group of an oxygen atom to which a lower alkyl group or a fluorine atom-substituted lower alkyl group bonds. Concretely, the lower alkyloxy group includes a methoxy group, an ethoxy group, an n-propyloxy group, an isopropyloxy group, a n-butoxy group, an isobutoxy group, a tert-butoxy group, an n-pentyloxy group; and the fluorine atom-substituted lower alkyloxy group includes, for example, a fluoromethoxy group, a difluoromethoxy group, a trifluoromethoxy group, a 1,2-difluoroethoxy group.

"Mono-lower alkylamino group" is a group derived from an amino group ($-NH_2$) by substituting one hydrogen atom of the amino group with a lower alkyl group. Concretely, for example, it includes a methylamino group, an ethylamino group, an n-propylamino group, an isopropylamino group, an n-butylamino group, a sec-butylamino group, and a tert-butylamino group.

"Di-lower alkylamino group" is a group derived from an amino group ($-NH_2$) by substituting two hydrogen atoms of the amino group with lower alkyl groups. Concretely, for example, it includes a dimethylamino group, a diethylamino group, an ethylmethylamino group, a di-(n-propyl)amino group, a methyl(n-propyl)amino group, a diisopropylamino group.

"Lower alkyloxycarbonyl group" is a group of a carbonyl group ($-CO-$) to which a lower alkyloxy group bonds, and includes an alkyloxycarbonyl group having from 1 to 6 carbon atoms. Concretely, for example, it includes a methoxycarbonyl group, an ethoxycarbonyl group, an n-propyloxycarbonyl group, an isopropyloxycarbonyl group, an n-butoxycarbonyl group, an isobutoxycarbonyl group, a tert-butoxycarbonyl group, an n-pentyloxycarbonyl group.

"(Lower alkyloxycarbonyl)amino group" is a group of an amino group ($-NH_2$) to which a lower alkyloxycarbonyl group bonds, and includes an alkyloxycarbonylamino group having from 1 to 6 carbon atoms. Concretely, for example, it includes a methoxycarbonylamino group, an ethoxycarbonylamino group, an n-propyloxycarbonylamino group, an isopropyloxycarbonylamino group, an n-butoxycarbonylamino group, an isobutoxycarbonylamino group, a tert-butoxycarbonylamino group, an n-pentyloxycarbonylamino group.

"(Lower alkyloxycarbonyl)-lower alkylamino group" is a group of a mono-lower alkylamino group to which a lower alkyloxycarbonyl group bonds in place of the hydrogen atom on the nitrogen atom thereof. Concretely, for example, it includes a (methoxycarbonyl)methylamino group, an (ethoxycarbonyl)methylamino group, an (n-propyloxycarbonyl)methylamino group.

"Lower alkylcarbonyl group" is a group of a carbonyl group (—CO—) to which a lower alkyl group bonds, and includes an alkylcarbonyl group having from 1 to 6 carbon atoms. Concretely, for example, it includes an acetyl group, a propionyl group, a butyryl group, an isobutyryl group, a valeryl group, an isovaleryl group, a pivaloyl group.

"Lower alkylcarbonylamino group" is a group derived from an amino group (—NH$_2$) by substituting one hydrogen atom thereof with a lower alkylcarbonyl group. Concretely, for example, it includes an acetamide group, a propionylamino group, an isobutyrylamino group, an valerylamino group, an isovalerylamino group, a pivaloylamino group.

"(Lower alkylcarbonyl)-lower alkylamino group" is a group of a mono-lower alkylamino group in which the hydrogen atom on the nitrogen atom is substituted with a lower alkylcarbonyl group. For example, it includes a (methylcarbonyl)methylamino group, an (ethylcarbonyl)methylamino group, an (n-propylcarbonyl)methylamino group.

"Lower alkylcarbonyloxy group" is a group of an oxygen atom to which a lower alkylcarbonyl group bonds. Concretely, for example, it includes an acetoxy group, a propionyloxy group, a valeryloxy group, an isovaleryloxy group, a pivaloyloxy group.

"Mono-lower alkylcarbamoyl group" is a group of a carbamoyl group (—CONH$_2$) in which one hydrogen atom is substituted with a lower alkyl group. Concretely, for example, it includes a methylcarbamoyl group, an ethylcarbamoyl group, an n-propylcarbamoyl group, an isopropylcarbamoyl group, an n-butylcarbamoyl group, a sec-butylcarbamoyl group, a tert-butylcarbamoyl group.

"Di-lower alkylcarbamoyl group" is a group of a carbamoyl group (—CONH$_2$) in which two hydrogen atoms are substituted with lower alkyl groups. Concretely, for example, it includes a dimethylcarbamoyl group, a diethylcarbamoyl group, an ethylmethylcarbamoyl group, a di-(n-propyl)carbamoyl group, a methyl(n-propyl)carbamoyl group, a diisopropylcarbamoyl group.

"Mono-lower alkylcarbamoylamino group" is a group of an amino group (—NH$_2$) in which one hydrogen atom is substituted with a mono-lower alkylcarbamoyl group. Concretely, for example, it includes a methylcarbamoylamino group, an ethylcarbamoylamino group, an n-propylcarbamoylamino group, an isopropylcarbamoylamino group, an n-butylcarbamoylamino group, a sec-butylcarbamoylamino group, a tert-butylcarbamoylamino group.

"Di-lower alkylcarbamoylamino group" is a group of an amino group (—NH$_2$) in which one hydrogen atom is substituted with a di-lower alkylcarbamoyl group. Concretely, for example, it includes a dimethylcarbamoylamino group, a diethylcarbamoylamino group, a di(n-propyl)carbamoylamino group, a diisopropylcarbamoylamino group, a di-(n-butyl)carbamoylamino group, a di-(sec-butyl)carbamoylamino group, a di(tert-butyl)carbamoylamino group.

"(Mono-lower alkylcarbamoyl)-lower alkylamino group" is a group of a mono-lower alkylamino group in which the hydrogen atom on the nitrogen atom is substituted with a mono-lower alkylcarbamoyl group. Concretely, for example, it includes a (monomethylcarbamoyl)methylamino group, a (monoethylcarbamoyl)methylamino group, a [mono(n-propyl)carbamoyl]methylamino group.

"(Di-lower alkylcarbamoyl)lower alkylamino group" is a group of a mono-lower alkylamino group in which the hydrogen atom on the nitrogen atom is substituted with a di-lower alkylcarbamoyl group. Concretely, for example, it includes a (dimethylcarbamoyl)methylamino group, a (diethylcarbamoyl)methylamino group, a [di(n-propyl)carbamoyl]methylamino group.

"Mono-lower alkylcarbamoyloxy group" is a group of an oxygen atom to which a mono-lower alkylcarbamoyl group bonds. Concretely, for example, it includes a methylcarbamoyloxy group, an ethylcarbamoyloxy group, an n-propylcarbamoyloxy group, an isopropylcarbamoyloxy group, an n-butylcarbamoyloxy group, a sec-butylcarbamoyloxy group, a tert-butylcarbamoyloxy group.

"Di-lower alkylcarbamoyloxy group" is a group of an oxygen atom to which a di-lower alkylcarbamoyl group bonds. Concretely, for example, it includes a dimethylcarbamoyloxy group, a diethylcarbamoyloxy group, an ethylmethylcarbamoyloxy group, a di-(n-propyl)carbamoyloxy group, a methyl(n-propyl)carbamoyloxy group, a diisopropylcarbamoyloxy group.

"Lower alkylsulfonyl group" is a group of a sulfonyl group (—SO$_2$) to which a lower alkyl group bonds. Concretely, for example, it includes a methylsulfonyl group, an ethylsulfonyl group, an n-propylsulfonyl group, an isopropylsulfonyl group, an n-butylsulfonyl group, a sec-butylsulfonyl group, a tert-butylsulfonyl group.

"Lower alkylsulfonylamino group" is a group of an amino group (—NH$_2$) in which one hydrogen atom is substituted with a lower alkylsulfonyl group. Concretely, for example, it includes a methylsulfonylamino group, an ethylsulfonylamino group, an n-propylsulfonylamino group, an isopropylsulfonylamino group, an n-butylsulfonylamino group, a sec-butylsulfonylamino group, a tert-butylsulfonylamino group.

"Mono-lower alkylsulfamoyl group" is a group of a sulfamoyl group (—SO$_2$NH$_2$) in which one hydrogen atom is substituted with a lower alkyl group. Concretely, for example, it includes a monomethylsulfamoyl group, a monoethylsulfamoyl group, a mono(n-propyl)sulfamoyl group, a monoisopropylsulfamoyl group, a mono(n-butyl)sulfamoyl group, a mono(sec-butyl)sulfamoyl group, a mono(tert-butyl)sulfamoyl group.

"Di-lower alkylsulfamoyl group" is a group of a sulfamoyl group (—SO$_2$NH$_2$) in which two hydrogen atoms are substituted with lower alkyl groups. Concretely, for example, it includes a dimethylsulfamoyl group, a diethylsulfamoyl group, a di(n-propyl)sulfamoyl group, a diisopropylsulfamoyl group, a di(n-butyl)sulfamoyl group, a di(sec-butyl)sulfamoyl group, a di(tert-butyl)sulfamoyl group.

"(Mono-lower alkylsulfamoyl)amino group" is a group of an amino group (—NH$_2$) in which one hydrogen atom is substituted with a mono-lower alkylsulfamoyl group. Concretely, for example, it includes a (monomethylsulfamoyl)amino group, a (monoethylsulfamoyl)amino group, a [mono(n-propyl)sulfamoyl]amino group, a (monoisopropylsulfamoyl)amino group, a [mono(n-butyl)sulfamoyl]amino group, a [(mono-sec-butyl)sulfamoyl]amino group, a [mono(tert-butyl)sulfamoyl]amino group.

"(Di-lower alkylsulfamoyl)amino group" is a group of an amino group (—NH$_2$) in which one hydrogen atom is substituted with a di-lower alkylsulfamoyl group. Concretely, for example, it includes a (dimethylsulfamoyl)amino group, a (diethylsulfamoyl)amino group, an (ethylmethylsulfamoyl)

amino group, a [di(n-propyl)sulfamoyl]amino group, a [methyl(n-propyl)sulfamoyl]amino group, a (diisopropylsulfamoyl)amino group.

"(Mono-lower alkylsulfamoyl)-lower alkylamino group" is a group of a mono-lower alkylamino group in which the hydrogen atom on the nitrogen atom is substituted with a mono-lower alkylsulfamoyl group. Concretely, for example, it includes a (monomethylsulfamoyl)methylamino group, a (monoethylsulfamoyl)methylamino group, a [mono(n-propyl)sulfamoyl]methylamino group.

"(Di-lower alkylsulfamoyl)-lower alkylamino group" is a group of a mono-lower alkylamino group in which the hydrogen atom on the nitrogen atom is substituted with a di-lower alkylsulfamoyl group. Concretely, for example, it includes a (dimethylsulfamoyl)methylamino group, a (diethylsulfamoyl)methylamino group, a [di(n-propyl)sulfamoyl]methylamino group.

The substituent selected from the group α includes a halogen atom, a hydroxyl group, a $C_{1-6}$ alkylcarbonyl group, a $C_{1-6}$ alkylcarbonyloxy group, a $C_{1-6}$ alkylcarbonylamino group, a $C_{1-6}$ alkylcarbonyl-$C_{1-6}$ alkylamino group, a $C_{1-6}$ alkyloxy group, a $C_{1-6}$ alkyloxycarbonyl group, a $C_{1-6}$ alkyloxycarbonylamino group, a $C_{1-6}$ alkyloxycarbonyl-$C_{1-6}$ alkylamino group, a $C_{1-6}$ alkylamino group, a di-$C_{1-6}$ alkylamino group, a sulfamoyl group, a $C_{1-6}$ alkylsulfamoyl group, a di-$C_{1-6}$ alkylsulfamoyl group, a sulfamoylamino group, a $C_{1-6}$ alkylsulfamoylamino group, a di-$C_{1-6}$ alkylsulfamoylamino group, a $C_{1-6}$ alkylsulfamoyl-$C_{1-6}$ alkylamino group, a di-$C_{1-6}$ alkylsulfamoyl-$C_{1-6}$ alkylamino group, a sulfamoyloxy group, a $C_{1-6}$ alkylsulfamoyloxy group, a di-$C_{1-6}$ alkylsulfamoyloxy group, a carbamoyl group, a $C_{1-6}$ alkylcarbamoyl group, a di-$C_{1-6}$ alkylcarbamoyl group, a carbamoylamino group, a $C_{1-6}$ alkylcarbamoylamino group, a di-$C_{1-6}$ alkylcarbamoylamino group, a $C_{1-6}$ alkylcarbamoyl-$C_{1-6}$ alkylamino group, a di-$C_{1-6}$ alkylcarbamoyl-$C_{1-6}$ alkylamino group, a carbamoyloxy group, a $C_{1-6}$ alkylcarbamoyloxy group, a di-$C_{1-6}$ alkylcarbamoyloxy group, a $C_{1-6}$ alkylsulfonyl group, a $C_{1-6}$ alkylsulfonylamino group, and a $C_{1-6}$ alkylsulfonyloxy group.

The compounds of the invention are described in detail hereinunder with reference to their examples.

In formula [I];

$A^1$, $A^2$, $A^3$ and $A^4$ each independently represent —C($R_5$)— or —N—, and at least one of $A^1$, $A^2$, $A^3$ and $A^4$ is —N—, preferably any one of them is —N—.

$R_5$ represents a hydrogen atom, a hydroxyl group, a fluorine atom, a chlorine atom, a $C_{1-6}$ alkyl group, a $C_{1-6}$ alkylamino group, a $C_{1-6}$ alkylcarbonyl group, a $C_{1-6}$ alkylcarbonylamino group, a $C_{1-6}$ alkylcarbonyl-($C_{1-6}$)alkylamino group, or a cyano group; preferably a hydrogen atom, a hydroxyl group, a fluorine atom, a chlorine atom, or a methyl group.

$A^1$, $A^2$, $A^3$ and $A^4$ concretely include the following examples:

$A^1$ is —N—; and $A^2$, $A^3$ and $A^4$ are —C($R_5$)—.

$A^2$ is —N—; and $A^1$, $A^3$ and $A^4$ are —C($R_5$)—.

$A^3$ is —N—; and $A^1$, $A^2$ and $A^4$ are —C($R_5$)—.

$A^4$ is —N—; and $A^1$, $A^2$ and $A^4$ are —C($R_5$)—.

Above all, preferred is a case where $A^4$ is —N—, and $A^1$, $A^2$ and $A^3$ are —C($R_5$)—; more preferred is a case where $A^4$ is —N—, and $A^1$, $A^2$ and $A^3$ each are —CH—, —CCl— or —C(CH$_3$)—.

$A^5$, $A^6$, $A^7$ and $A^8$ each independently represent —C($R_6$)— or —N—.

$R_6$ is, for example, a hydrogen atom, a halogen atom, a $C_{1-6}$ alkyl group optionally having a hydroxyl group, a halogeno-$C_{1-6}$ alkyl group, a $C_{1-6}$ alkyloxy group (especially in $A^6$, $A^7$), a $C_{1-6}$ alkyloxy-$C_{1-6}$ alkyl group, a $C_{1-6}$ alkylcarbonyl group, a cyano group, a formyl group, a $C_{1-6}$ alkyloxycarbonyl group, a $C_{1-6}$ alkylcarbonylamino group, a $C_{1-6}$ alkylcarbonyl-$C_{1-6}$ alkylamino group, or a $C_{1-6}$ alkylsulfonyl group.

$R_6$ is preferably a hydrogen atom, a fluorine atom, a chlorine atom, a methyl group, an ethyl group, an isopropyl group, a trifluoromethyl group, a methylcarbonyl group, a methoxymethyl group, a formyl group or a cyano group.

$A^5$, $A^6$, $A^7$ and $A^8$ concretely include the following examples:

$A^5$, $A^6$, $A^7$ and $A^8$ are —C($R_6$)—.

$A^5$ is —N—; and $A^6$, $A^7$ and $A^8$ are —C($R_6$)—.

$A^6$ is —N—; and $A^6$, $A^7$ and $A^8$ are —C($R_6$)—.

$A^7$ is —N—; and $A^5$, $A^6$ and $A^8$ are —C($R_6$)—.

$A^8$ is —N—; and $A^5$, $A^6$ and $A^7$ are —C($R_6$)—.

Their preferred examples are the following:

$A^5$, $A^6$, $A^7$ and $A^8$ are all —C($R_6$)—.

$A^7$ is —N—; and $A^5$, $A^6$ and $A^8$ are —C(R)—.

$A^5$ is —CH—;

$A^6$ is —CH— or —CF—;

$A^7$ is —CH—; and $A^8$ is —CH—, —CF—, —CCl—, —C(CH$_3$)—, —C(CN)—, —C(CHO)— or —C(CF$_3$)—.

$A^5$, $A^6$, $A^7$ and $A^8$ each are selected from a group consisting of —CH—, —CF—, —CCl—, —C(CH$_3$)—, —C(CN)—, —C(CHO)— and —C(CF$_3$)—.

$A_7$ is —N—; and $A^5$, $A^6$ and $A^8$ each are selected from a group consisting of —CH—, —CF—, —C(CH$_3$)—, —C(CN)—, —C(CHO)— and —C(CF$_3$)—.

$R_1$ and $R_1'$ each independently represent a hydrogen atom, a halogen atom, a hydroxyl group, a cyano group, a $C_{1-6}$ alkyloxy group, a $C_{1-6}$ alkyloxyalkyloxy group, a $C_{1-6}$ alkyloxycarbonyl group, a $C_{1-6}$ alkyloxycarbonylamino group, a $C_{1-6}$ alkylcarbonyl group, a $C_{1-6}$ alkylcarbonyloxy group, a $C_{1-6}$ alkylcarbonylamino group, a $C_{1-6}$ alkylsulfonyl group, a $C_{1-6}$ alkylsulfonylamino group, a $C_{1-6}$ alkylsulfonyl-$C_{1-6}$ alkylamino group, a carbamoylamino group, a ($C_{1-6}$ alkyl)carbamoylamino group, a di($C_{1-6}$ alkyl)carbamoylamino group, a pyrazolyl group, a triazolyl group, an oxazolyl group, or a $C_{1-6}$ alkyl group optionally having a substituent selected from the following group [α]; or $R_1$ and $R_1'$ together form an oxo group or a $C_{1-3}$ alkyleneketal group.

The substituent selected from the group [α] concretely includes the following:

A halogen atom such as a fluorine atom, a chlorine atom; a hydroxyl group; a $C_{1-6}$ alkylcarbonyl group such as a methylcarbonyl group, an ethylcarbonyl group; a $C_{1-6}$ alkylcarbonyloxy group such as a methylcarbonyloxy group, an ethylcarbonyloxy group; a $C_{1-6}$ alkylcarbonylamino group such as a methylcarbonylamino group, an ethylcarbonylamino group; a $C_{1-6}$ alkylcarbonyl-$C_{1-6}$ alkylamino group such as a methylcarbonylmethylamino group, an ethylcarbonylmethylamiono group; a $C_{1-6}$ alkyloxy group such as a methoxy group, an ethoxy group; a $C_{1-6}$ alkyloxycarbonyl group such as a methyloxycarbonyl group, an ethyloxycarbonyl group; a $C_{1-6}$ alkyloxycarbonylamino group such as a methyloxycarbonylamino group, an ethyloxycarbonylamino group; a $C_{1-6}$ alkyloxycarbonyl-$C_{1-6}$ alkylamino group such as methyloxycarbonylmethylamino group, an ethyloxycarbonylmethylamino group; a $C_{1-6}$ alkylamino group such as a methylamino group, an ethylamino group; a di-$C_{1-6}$ alkylamino group such as a dimethylamino group, a diethylamino group; a sulfamoyl group; a $C_{1-6}$ alkylsulfamoyl group such as a methylsulfamoyl group, an ethylsulfamoyl group; a di-$C_{1-6}$ alkylsulfamoyl group such as a dimethylsulfamoyl group, a diethylsulfamoyl group; a sulfamoylamino group; a $C_{1-6}$ alkylsulfamoylamino group such as methylsulfamoylamino group, an ethylsulfamoylamino group; a di-$C_{1-6}$ alkylsulfamoylamino group such as a dimethylsulfamoylamino group, a diethylsulfamoylamino group; a $C_{1-6}$ alkylsulfamoyl-$C_{1-6}$ alkylamino group such as a methylsulfamoylmethylamino group, an ethylsulfamoylmethylamino group; a di-$C_{1-6}$ alkylsulfamoyl-$C_{1-6}$ alkylamino group such as a dimethylsulfamoylmethylamino group, a diethylsulfamoylmethylamino group; a sulfamoyloxy group; a $C_{1-6}$ alkylsulfamoyloxy group such as a methylsulfamoyloxy group, an ethylsulfamoyloxy group; a di-$C_{1-6}$ alkylsulfamoyloxy group such as a dimethylsulfamoyloxy group, a diethylsulfamoyloxy group; a carbamoyl group; a $C_{1-6}$ alkylcarbamoyl group such as a methylcarbamoyl group, an ethylcarbamoyl group; a di-$C_{1-6}$ alkylcarbamoyl group such as a dimethylcarbamoyl group, a diethylcarbamoyl group; a carbamoylamino group; a $C_{1-6}$ alkylcarbamoylamino group such as a methylcarbamoylamino group, an ethylcarbamoylamino group; a di-$C_{1-6}$ alkylcarbamoylamino group such as a dimethylcarbamoylamino group, a diethylcarbamoylamino group; a $C_{1-6}$ alkylcarbamoyl-$C_{1-6}$ alkylamino group such as a methylcarbamoylmethylamino group, an ethylcarbamoylmethylamino group; a di-$C_{1-6}$ alkylcarbamoyl-$C_{1-6}$ alkylamino group such as a dimethylcarbamoylmethylamino group, a diethylcarbamoylmethylamino group; a carbamoyloxy group; a $C_{1-6}$ alkylcarbamoyloxy group such as a methylcarbamoyloxy group, an ethylcarbamoyloxy group; a di-$C_{1-6}$ alkylcarbamoyloxy group such as a dimethylcarbamoyloxy group, a diethylcarbamoyloxy group; a $C_{1-6}$ alkylsulfonyl group such as a methylsulfonyl group, an ethylsulfonyl group; a $C_{1-6}$ alkylsulfonylamino group such as a methylsulfonylamino group, an ethylsulfonylamino group; and a $C_{1-6}$ alkylsulfonyloxy group such as a methylsulfonyloxy group, an ethylsulfonyloxy group.

Concretely, examples of $R_1$ or $R_1'$ include a hydrogen atom, a fluorine atom, a chlorine atom, a hydroxyl group, a cyano group, a methyl group, an ethyl group, an isopropyl group, a t-butyl group, a methoxy group, an ethoxy group, an isopropyloxy group, a methyloxymethyloxy group, an ethyloxymethyloxy group, a methyloxycarbonyl group, an ethyloxycarbonyl group, a methyloxycarbonylamino group, an ethyloxycarbonylamino group, a methylcarbonyl group, an ethylcarbonyl group, a methylcarbonylamino group, an ethylcarbonylamino group, a methylsulfonyl group, an ethylsulfonyl group, a methylsulfonylamino group, an ethylsulfonylamino group, a pyrazolyl group, a triazolyl group, an oxazolyl group.

Examples of the group which $R_1$ and $R_1'$ together form include an oxo group, and an ethylene-ketal group.

Preferred examples of $R_1$ and $R_1'$ are a hydrogen atom, a hydroxyl group, a methyl group, a methoxy group, a methylsulfonylamino group, a methylcarbonylamino group, an oxo group and an ethylene-ketal group.

$R_2$ represents a hydrogen atom or a $C_{1-6}$ alkyl group optionally having a hydroxyl group, or $R_2$ and $R_2'$ or $R_3'$ together form a $C_{1-3}$ alkylene group or an oxy-$C_{1-3}$ alkylene group.

Examples of $R_2$ are a hydrogen atom, a methyl group, and an ethyl group.

Examples of the $C_{1-3}$ alkylene group or the oxy-$C_{1-3}$ alkylene group which $R_2$ and $R_2'$ or $R_3$ together form include —CH$_2$—, —CH$_2$CH$_2$—, —O—CH$_2$—, —CH$_2$—O—, —CH$_2$—O—CH$_2$—.

$R_2$ is preferably a hydrogen atom; and for the $C_{1-3}$ alkylene group or the oxy-$C_{1-3}$ alkylene group which $R_2$ and $R_2'$ or $R_3$ together form, preferred is —CH$_2$CH$_2$—.

$R_2'$ represents a hydrogen atom or a $C_{1-6}$ alkyl group optionally having a hydroxyl group, or $R_2'$ and $R_2$ or $R_3'$ together form a $C_{1-3}$ alkylene group or an oxy-$C_{1-3}$ alkylene group.

Examples of $R_2'$ are a hydrogen atom, a methyl group, and an ethyl group. Examples of the $C_{1-3}$ alkylene group or the oxy-$C_{1-3}$ alkylene group which $R_2'$ and $R_2$ or $R_3'$ together form include —CH$_2$—, —CH$_2$CH$_2$—, —O—CH$_2$—, —CH$_2$—O—, —CH$_2$—O—CH$_2$—.

$R_2'$ is preferably a hydrogen atom; and for the $C_{1-3}$ alkylene group or the oxy-$C_{1-3}$ alkylene group which $R_2'$ and $R_2$ or $R_3'$ together form, preferred is —CH$_2$CH$_2$—.

$R_3$ represents a hydrogen atom, a hydroxyl group, a halogen atom, a $C_{1-6}$ alkyloxy group, a $C_{1-6}$ alkylcarbonyl group, a $C_{1-6}$ alkyloxycarbonyl group, a $C_{1-6}$ alkylsulfonyl group, a $C_{1-6}$ alkylsulfonylamino group, a $C_{1-6}$ alkylsulfonylalkylamino group, a cyano group, or a $C_{1-6}$ alkyl group optionally having a substituent selected from the group [α]; or $R_3$ and $R_3'$ or $R_2'$ together form a $C_{1-3}$ alkylene group or an oxy-$C_{1-3}$ alkylene group.

Concretely, preferred examples of $R_3$ are a hydrogen atom, a hydroxyl group, a fluorine atom, a methoxy group, an ethoxy group, a methylcarbonyl group, an ethylcarbonyl group, a methoxycarbonyl group, an ethoxycarbonyl group, an isopropylmethylsulfonyl group, an ethylsulfonyl group, a methylsulfonylamino group, an ethylsulfonylamino group, a methylsulfonylmethylamino group, a cyano group, a methyl group, an ethyl group, a hydroxymethyl group, a fluoromethyl group, a trifluoromethyl group, a methylcarbonylmethyl group, a methylcarbonyloxymethyl group, a 2-hydroxyisopropyl group, a methoxycarbonylaminomethyl group, a methylsulfonylmethylaminomethyl group, a sulfamoylaminomethyl group, a dimethylsulfamoylamino group. Examples of the $C_{1-3}$ alkylene group or the oxy-$C_{1-3}$ alkylene group which $R_3$ and $R_2$ or $R_3'$ together form include —CH$_2$—, —CH$_2$CH$_2$—, —O—CH$_2$—, —CH$_2$—O—, —CH$_2$—O—CH$_2$—.

More preferred examples of $R_3$ are a hydrogen atom, a hydroxyl group, a fluorine atom, a methoxy group, a methyl group, a hydroxymethyl group, a fluoromethyl group, a methylsulfonylaminomethyl group, a methylsulfonylmethylaminomethyl group, a methoxycarbonylaminomethyl group, a dimethylsulfamoylaminomethyl group.

$R_3'$ represents a hydrogen atom, a hydroxyl group, a halogen atom, a $C_{1-6}$ alkyloxy group, a $C_{1-6}$ alkylcarbonyl group, a $C_{1-6}$ alkyloxycarbonyl group, a $C_{1-6}$ alkylsulfonyl group, a $C_{1-6}$ alkylsulfonylamino group, a $C_{1-6}$ alkylsulfonylaminoalkyl group, a cyano group, or a $C_{1-6}$ alkyl group optionally having a substituent selected from the group [α]; or $R_3'$ and $R_3$ or $R_2'$ together form a $C_{1-3}$ alkylene group or an oxy-$C_{1-3}$ alkylene group.

Concretely, preferred examples of $R_3'$ are a hydrogen atom, a hydroxyl group, a fluorine atom, a methoxy group, an ethoxy group, a methylcarbonyl group, an ethylcarbonyl group, a methoxycarbonyl group, an ethoxycarbonyl group, an isopropylmethylsulfonyl group, an ethylsulfonyl group, a methylsulfonylamino group, an ethylsulfonylamino group, a methylsulfonylmethylamino group, a cyano group, a methyl group, an ethyl group, a hydroxymethyl group, a fluoromethyl group, a trifluoromethyl group, a methylcarbonylmethyl group, a methylcarbonyloxymethyl group, a 2-hydroxyisopropyl group, a methoxycarbonylaminomethyl group, a methylsulfonylmethylaminomethyl group, a sulfamoylaminomethyl group, a dimethylsulfamoylaminomethyl group. Examples of the $C_{1-3}$ alkylene group or the oxy-$C_{1-3}$ alkylene group which $R_3'$ and $R_2'$ or $R_3$ together form are —$CH_2$—, —$CH_2CH_2$—, —O—$CH_2$—, —$CH_2$—O—, —$CH_2$—O—$CH_2$—.

More preferred examples of $R_3'$ are a hydrogen atom, a hydroxyl group, a fluorine atom, a methoxy group, a methyl group, a hydroxymethyl group, a fluoromethyl group, a methylsulfonylaminomethyl group, a methylsulfonylmethylaminomethyl group, a methoxycarbonylaminomethyl group, a dimethylsulfamoylaminomethyl group.

$R_4$ represents a hydrogen atom, a halogen atom, a $C_{1-6}$ alkyl group optionally having a hydroxyl group, a halogeno-$C_{1-6}$ alkyl group, a $C_{1-6}$ alkyloxy-$C_{1-6}$ alkyl group, a $C_{1-6}$ alkylcarbonyl group, a cyano group, a formyl group, a $C_{1-6}$ alkyloxycarbonyl group, a $C_{1-6}$ alkylcarbonylamino group, a $C_{1-6}$ alkylcarbonyl-$C_{1-6}$ alkylamino group or a $C_{1-6}$ alkylsulfonyl group; or when Z is —$C(R_7)$—, then $R_4$ and $R_7$ together form —$C(R_8)(R_8')$—O—, —$C(R_8)(R_8')$—CO—, —$C(R_8)(R_8')$—C($R_8)(R_8')$—, —O—CO—, —CO—O—, —CO—C($R_8)(R_8')$—, —O—$C(R_8)(R_8')$—, —$CH(R_8)$—N($R_9$)— or —N($R_9$)—$CH(R_8)$—.

Concretely, examples of $R_4$ include a hydrogen atom, a fluorine atom, a chlorine atom, a methyl group, an ethyl group, an acetyl group, an ethylcarbonyl group, a cyano group, a formyl group, a trichloromethyl group, a trifluoromethyl group, a methoxycarbonyl group, an ethoxycarbonyl group, a methylcarbonylamino group, a methylsulfonyl group.

Concretely, examples of the group which $R_4$ and $R_7$ together form when Z is —$C(R_7)$— include —$CH_2$—O—, —$CH(CH_3)$—O—, —$C(CH_3)_2$—O—, —$CH_2$—CO—, —$CH_2$—$CH_2$—, —$C(CH_3)_2$—$CH_2$—, —O—CO—, —CO—O—, —CO—$CH_2$—, —O—$CH_2$—, —O—$CH(CH_3)$—, —O—$C(CH_3)_2$—, —N($CH_3$)—$CH_2$—, as $R_4$-$R_7$. Preferred examples of $R_4$ are a hydrogen atom, a fluorine atom, a chlorine atom, a methyl group, an ethyl group, a cyano group, a formyl group, a trifluoromethyl group. Preferred examples of the group which $R_4$ and $R_7$ together form when Z is —$C(R_7)$— are —$CH_2$—O—, —$C(CH_3)_2$—O—, —$CH_2$—CO—, —$CH_2$—$CH_2$—, —O—CO—, —CO—O—, —CO—$CH_2$—, —O—$CH_2$— or —N($CH_3$)—$CH_2$—, as $R_4$-$R_7$. More preferably, $R_4$ is a hydrogen atom, a fluorine atom or a methyl group; pr $R_7$ and $R_4$ together form —$CH_2$—O—, —$CH(CH_3)$—O—, —$C(CH_3)_2$—O— or —N($CH_3$)—$CH_2$—, as $R_4$-$R_7$.

X represents —$CH_2$—, —$CH(OH)$—, —N(Ra)—, —O—, —S— or —$SO_2$—. Ra represents a hydrogen atom, a $C_{1-6}$ alkyl group, a $C_{1-6}$ alkyloxycarbonyl group, a carbamoyl group, a ($C_{1-6}$ alkyl)carbamoyl group, a di($C_{1-6}$ alkyl)carbamoyl group, a $C_{1-6}$ alkylsulfonyl group, a pyrazolyl group, a triazolyl group, or an oxazolyl group.

Concretely, examples of Ra include a hydrogen atom, a methyl group, an ethyl group, a methylcarbonyl group, a carbamoyl group, a methylcarbamoyl group, a pyrazolyl group, a triazolyl group, an oxazolyl group. Preferably, Ra is a hydrogen atom or a methyl group.

Concretely, examples of X include —$CH_2$—, —$CH(OH)$—, —O—, —NH—, —N($CH_3$)—, —N($C_2H_5$)—, —N($COCH_3$)—, —N($CONH_2$)—, —N($OCNHCH_3$)—, —S—, —$SO_2$—. Preferably, X is —$CH_2$—, —O— or —N($CH_3$)—, more preferably —$CH_2$—.

Z represents —$C(R_7)$— or —N—. $R_7$ represents a hydrogen atom, a halogen atom, a cyano group, a $C_{1-6}$ alkyl group, a $C_{1-6}$ alkyloxy group; or $R_7$ and $R_4$ together form —$C(R_8)(R_8')$—O—, —$C(R_8)(R_8')$—CO—, —$C(R_8)(R_8')$—$C(R_8)(R_8')$—, —O—CO—, —CO—O—, —CO—$C(R_8)(R_8')$—, —O—$C(R_8)(R_8')$—, —$CH(R_8)$—N($R_9$)— or —$CH(R_8)$—N($R_9$)—.

Concretely, examples of $R_7$ includes a hydrogen atom, a fluorine atom, a methyl group, an ethyl group. Preferably, $R_7$ is a hydrogen atom, a fluorine atom or a methyl group. Concretely, examples of the group which $R_7$ and $R_4$ together form include —$CH_2$—O—, —$CH(CH_3)$—O—, —$C(CH_3)_2$—O—, —$CH_2$—CO—, —$CH_2$—$CH_2$—, —$C(CH_3)_2$—$CH_2$—, —O—CO—, —CO—O—, —CO—$CH_2$—, —O—$CH_2$—, —O—$CH(CH_3)$—, —O—$C(CH_3)_2$—, —N($CH_3$)—$CH_2$—, as $R_4$-$R_7$. Preferably, the group is —$CH_2$—O—, —$C(CH_3)_2$—O—, —$CH_2$—CO—, —$CH_2$—$CH_2$—, —O—CO—, —CO—O—, —CO—$CH_2$—, —O—$CH_2$— or —N($CH_3$)—$CH_2$—, as $R_4$-$R_7$; more preferably, —$CH_2$—O—, —$CH(CH_3)$—O—, —$C(CH_3)_2$—O— or —N($CH_3$)—$CH_2$—.

$R_8$ and $R_8'$ are the same or different, each representing a hydrogen atom, a hydroxyl group, a $C_{1-6}$ alkyl group optionally having a hydroxyl group, or a $C_{1-6}$ alkylsulfonyl group.

Concretely, examples of $R_8$ and $R_8'$ include a hydrogen atom, a methyl group and an ethyl group, and preferred examples thereof are a hydrogen atom and a methyl group.

$R_9$ represents a hydrogen atom, a $C_{1-6}$ alkyl group, a $C_{1-6}$ alkylsulfonyl group, a $C_{1-6}$ alkyloxycarbonyl group, or a formyl group. Concretely, examples of $R_9$ include a hydrogen atom, a methyl group, an ethyl group, a methylsulfonyl group. Preferably, $R_9$ is a hydrogen atom or a methyl group.

Z is preferably —CH—, —CF— or —$C(CH_3)$—. When Z is —$C(R_7)$—, examples of the group which $R_7$ and $R_4$ together form are preferably those mentioned hereinabove.

Y represents —$CH_2$— or —N(Ra)—, and Ra has the same meaning as above.

Concretely, Y includes —$CH_2$—, —NH—, —N($CH_3$)—, —N($C_2H_5$)—, —N($COCH_3$)—, —N($CONH_2$)—, —N(OCNHCH_3)—, and is preferably —$CH_2$— or —NH—, more preferably —$CH_2$—.

Preferred examples of the combination of Y and n are n=0, or n=1 and Y is —$CH_2$—.

Preferred embodiments of the compounds of the invention are mentioned below.

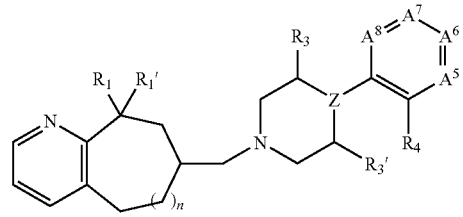

[I-1]

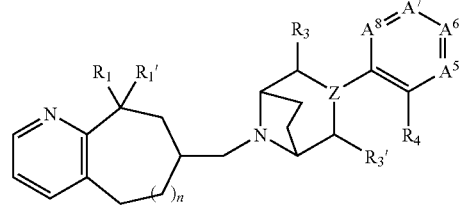

[I-2]

-continued
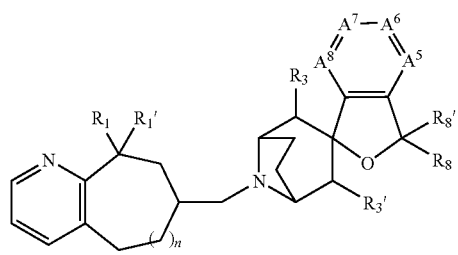
[I-3]
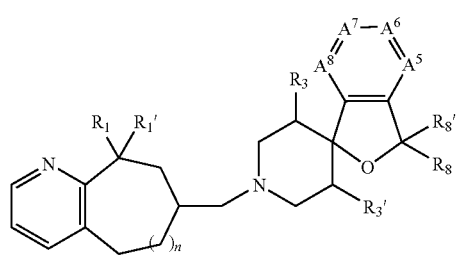
[I-4]
[wherein the symbols have the same meanings as above.]
Concretely, the compounds of the invention include the following examples.

TABLE 1-continued

| No. | Structural Formula |
|---|---|
| 14 | |
| 15 | |
| 16 | |

TABLE 2

| No. | Structural Formula |
|---|---|
| 17 | |
| 18 | |
| 19 | |
| 20 | |

TABLE 2-continued

| No. | Structural Formula |
|---|---|
| 21 | |
| 22 | |
| 23 | |
| 24 | |
| 25 | |
| 26 | |
| 27 | |
| 28 | |

TABLE 2-continued

| No. | Structural Formula |
|---|---|
| 29 | (structure) |
| 30 | (structure) |
| 31 | (structure) |
| 32 | (structure) |
| 33 | (structure) |
| 34 | (structure) |
| 35 | (structure) |
| 36 | (structure) |

TABLE 3

| No. | Structural Formula |
|---|---|
| 37 | (structure) |
| 38 | (structure) |
| 39 | (structure) |
| 40 | (structure) |
| 41 | (structure) |
| 42 | (structure) |

TABLE 3-continued

| No. | Structural Formula |
|---|---|
| 43 | |
| 44 | |
| 45 | |
| 46 | |
| 47 | |
| 48 | |

TABLE 3-continued

| No. | Structural Formula |
|---|---|
| 49 | |
| 50 | |
| 51 | |
| 52 | |
| 53 | |
| 54 | |

TABLE 4

| No. | Structural Formula |
|---|---|
| 55 | |
| 56 | |
| 57 | |
| 58 | |
| 59 | |
| 60 | |

TABLE 4-continued

| No. | Structural Formula |
|---|---|
| 61 | |
| 62 | |
| 63 | |
| 64 | |
| 65 | |
| 66 | |
| 67 | |
| 68 | |

TABLE 4-continued

| No. | Structural Formula |
|---|---|
| 69 | |
| 70 | |
| 71 | |
| 72 | |
| 73 | |
| 74 | |

Preferred examples of the compounds of the invention are:

(7R,9S)-7-(spiro[8-aza-biycyclo[3.2.1]octa-3,1'(3'H)-isobenzofuran]-8-ylmethyl)-6,7,8,9-tetrahydro-5H-cyclohepta[b]pyridin-9-ol;

(6R,8S)-6-(spiro[isobenzofuran-1-(3H),4'-piperidin]-1'-ylmethyl)-5,6,7,8-tetrahydroquinolin-8-ol);

(7R,9S)-7-[(3R*,4R*)-3-hydroxy-4-o-tolyl-piperidin-1-ylmethyl]-6,7,8,9-tetrahydro-5H-cyclohepta[b]pyridin-9-ol;

(7R,9S)-7-[(3R*,4R*)-(4-fluoro-o-tolyl)-3-hydroxypiperidin-1-ylmethyl]-6,7,8,9-tetrahydro-5H-cyclohepta[b]pyridin-9-ol;

(7R,9S)-7-(6'-aza-5'-fluoro-spiro[8-aza-bicyclo[3.2.1]-octa-3,1'(3'H)-isobenzofuran]-8-ylmethyl)-6,7,8,9-tetrahydro-5H-cyclohepta[b]pyridin-9-ol;

(6R,8S)-6-(3,3-dimethyl-spiro[isobenzofuran-1(3H),4'-piperidin]-1'-ylmethyl)-5,6,7,8-tetrahydroquinolin-8-ol;

(7R,9S)-7-(1-methylspiro-[2,3-dihydro-1H-indol-3,4'-piperidin]-1'-ylmethyl)-6,7,8,9-tetrahydro-5H-cyclohepta[b]pyridin-9-ol;

(6R,8S)-6-[4-(2-chlorophenyl)-4'-fluoropiperidin-1'-ylmethyl]-5,6,7,8-tetrahydroquinolin-8-ol;

(7R,9S)-7-[(3R*,4R*)-4-(2-chlorophenyl)-3-hydroxypiperidin-1-ylmethyl]-6,7,8,9-tetrahydro-5H-cyclohepta[b]pyridin-9-ol;

(7R,9S)-7-[(3R,4R)-4-(2-chloro-4-fluorophenyl)-3-hydroxypiperidin-1-ylmethyl]-6,7,8,9-tetrahydro-5H-cyclohepta[b]pyridin-9-ol;

(6R,8S)-6-[(3R,4R)-4-(2-chloro-4-fluorophenyl)-3-hydroxypiperidin-1-ylmethyl]-5,6,7,8-tetrahydroquinolin-8-ol;

(7R,9S)-7-[(3R*,4S*)-3-hydroxymethyl-4-phenyl-piperidin-1-ylmethyl]-6,7,8,9-tetrahydro-5H-cyclohepta[b]pyridin-9-ol;

(7R,9S)-7-[(3R*,4S*)-3-methyl-4-phenylpiperidin-1-ylmethyl]-6,7,8,9-tetrahydro-5H-cyclohepta[b]pyridin-9-ol;

N-{(7R,9S)-7-[(3R,4R)-4-(2-chloro-4-fluorophenyl)-3-hydroxypiperidin-1-ylmethyl]-6,7,8,9-tetrahydro-5H-cyclohepta[b]pyridin-9-yl}methanesulfonamide;

(6R,8S)-6-[(5'-fluoro-3',3'-dimethyl-3'H-6'-azaspiro[8-azabicyclo[3.2.1]octane-3,1'-isobenzofuran]-8-yl)methyl]-5,6,7,8-tetrahydroquinolin-8-ol; and (6R,8S)-6-[(1S*,2R*,3R*)-3-(2-chloro-4-fluorophenyl)-2-hydroxy-8-azabicyclo[3.2.1]octan-8-ylmethyl]-5,6,7,8-tetrahydroquinolin-8-ol.

More preferred examples of the compounds of the invention are:

(7R,9S)-7-[(3R*,4R*)-3-hydroxy-4-o-tolyl-piperidin-1-ylmethyl]-6,7,8,9-tetrahydro-5H-cyclohepta[b]pyridin-9-ol;

(7R,9S)-7-[(3R*,4R*)-(4-fluoro-o-tolyl)-3-hydroxypiperidin-1-ylmethyl]-6,7,8,9-tetrahydro-5H-cyclohepta[b]pyridin-9-ol;

(7R,9S)-7-(6'-aza-5'-fluoro-spiro[8-aza-bicyclo[3.2.1]-octa-3,1'(3'H)-isobenzofuran]-8-ylmethyl)-6,7,8,9-tetrahydro-5H-cyclohepta[b]pyridin-9-ol;

(7R,9S)-7-[(3R*,4R*)-4-(2-chlorophenyl)-3-hydroxypiperidin-1-ylmethyl]-6,7,8,9-tetrahydro-5H-cyclohepta[b]pyridin-9-ol;

(6R,8S)-6-[(3R,4R)-4-(2-chloro-4-fluorophenyl)-3-hydroxypiperidin-1-ylmethyl]-5,6,7,8-tetrahydroquinolin-8-ol;

N-{(7R,9S)-7-[(3R,4R)-4-(2-chloro-4-fluorophenyl)-3-hydroxypiperidin-1-ylmethyl]-6,7,8,9-tetrahydro-5H-cyclohepta[b]pyridin-9-yl}methanesulfonamide;

(6R,8S)-6-[(5'-fluoro-3',3'-dimethyl-3'H-6'-azaspiro[8-azabicyclo[3.2.1]octane-3,1'-isobenzofuran]-8-yl)methyl]-5,6,7,8-tetrahydroquinolin-8-ol; and (6R,8S)-6-[(1S*,2R*,3R*)-3-(2-chloro-4-fluorophenyl)-2-hydroxy-8-azabicyclo[3.2.1]octan-8-ylmethyl]-5,6,7,8-tetrahydroquinolin-8-ol.

The invention also provides compounds of a general formula [I-a]:

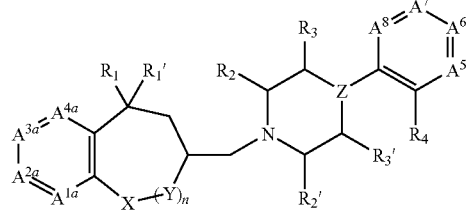

[wherein $A^{1a}$, $A^{2a}$, $A^{3a}$ and $A^{4a}$ each independently represent —C($R_5$)—, —N— or —N(O)—; provided that at least one of $A^{1a}$, $A^{2a}$, $A^{3a}$ and $A^{4a}$ is —N— or —N(O)—; and $A^5$, $A^6$, $A^7$, $A^8$, $R_1$, $R_1'$, $R_2$, $R_2'$, $R_3$, $R_3'$, $R_4$, $R_5$, X, Y, Z and n have the same meanings as above.]

Concretely, examples of the compounds of formula [I-a] are the following.

TABLE A

| No. | Structural Formula |
|---|---|
| 75 | |
| 76 | |
| 77 | |
| 78 | |
| 79 | |

TABLE A-continued

| No. | Structural Formula |
|---|---|
| 80 | |
| 81 | |
| 82 | |

Methods for Producing Compounds of Formula [I]

The compounds of formula [I] can be produced according to the following methods.

Production Method 1:

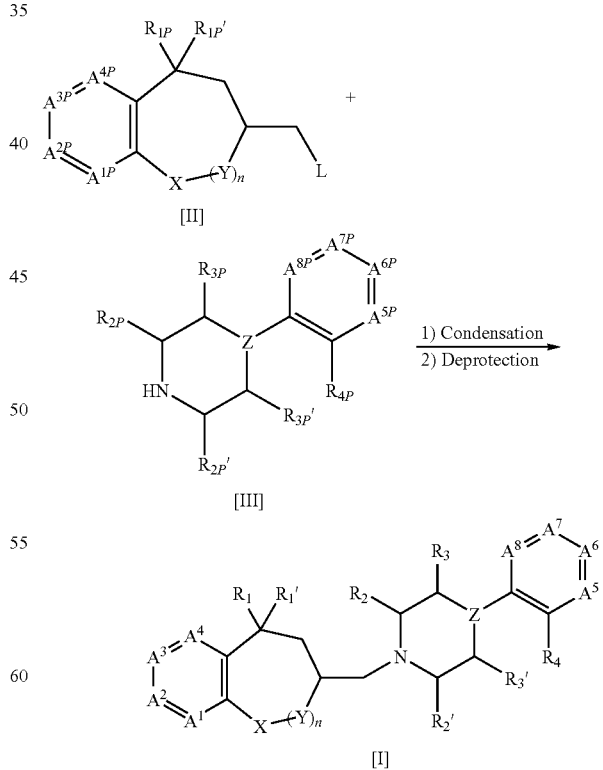

[In the formula, L represents a leaving group; $R_{1P}$ represents $R_1$ optionally having a protective group; $R_{1P}'$ represents $R_1'$ optionally having a protective group; $R_{2P}$ represents $R_2$ optionally having a protective group; $R_{2P}{}'$ represents $R_2{}'$ optionally having a protective group; $R_{3P}$ represents $R_3$ optionally having a protective group; $R_{3P}{}'$ represents $R_3{}'$ optionally having a protective group; $R_{4P}$ represents $R_4$ optionally having a protective group; $A^{1P}$ represents $A^1$ optionally having a protective group; $A^{2P}$ represents $A^2$ optionally having a protective group; $A^{3P}$ represents $A^3$ optionally having a protective group; $A^{4P}$ represents $A^4$ optionally having a protective group; $A^{5P}$ represents $A^5$ optionally having a protective group; $A^{6P}$ represents $A^6$ optionally having a protective group; $A^{7P}$ represents $A^7$ optionally having a protective group; $A^{8P}$ represents $A^8$ optionally having a protective group; $R_1, R_1{}', R_2, R_2{}', R_3, R_3{}', R_4, A^1, A^2, A^3, A^4, A^5, A^6, A^7, A^8, X, Y, Z$ and n have the same meanings as above.]

A compound of formula [II] is condensed with a compound of formula [III] preferably in a solvent, in the presence of a basic catalyst, and then optionally the protective group is removed (deprotection) to obtain a compound of formula [I].

Examples of the solvent include tetrahydrofuran (hereinafter referred to as "THF"), 1,4-dioxane (hereinafter referred to as "dioxane"), dimethylformamide (hereinafter referred to as "DMF"), dimethylsulfoxide (hereinafter referred to as "DMSO").

Examples of the basic catalyst include organic amines such as trimethylamine, triethylamine, diisopropylethylamine, N-methylmorpholine, pyridine; and inorganic amines such as sodium carbonate, sodium hydrogencarbonate, potassium carbonate, potassium hydrogencarbonate, lithium carbonate, sodium hydroxide, potassium hydroxide, lithium hydroxide. Preferred are triethylamine and diisopropylethylamine.

The amount of the basic catalyst may be, for example, from 1.0 to 10 equivalents per equivalent of the compound of formula [II], preferably from 2.0 to 5.0 equivalents.

The reaction temperature may be, for example, from room temperature to 150° C., preferably from 50 to 120° C.

For promoting the reaction, sodium iodide or potassium iodide may be added to the reaction system. In this case, the amount of the additive may be, for example, from 0.01 to 10 mols per mol of the compound of formula [II], preferably from 5.0 to 10 mols.

The amount of the compound of formula [III] to be used may be, for example, from 0.9 to 1.5 mols per mol of the compound of formula [II], preferably from 1.0 to 1.3 mols.

In case where the compound of formula [II] or the compound of formula [III] has a protective group, then the protective group may be removed after the condensation reaction. The deprotection may be attained in an conventional manner. For example, it may be attained according to the method described in a reference, *Protective Groups in Organic Synthesis*, by T. W. Greene, John Wiley & Sons (1981).

In the compounds, the oxo group, the hydroxyl group, the carboxyl group, the amino group and the formyl group may be protected.

The oxo-protective group includes, for example, acetals and ketals such as ethylene ketal, trimethylene ketal, dimethyl ketal.

The hydroxyl-protective group includes, for example, a substituted silyl group such as a trimethylsilyl group, a tert-butyldimethylsilyl group (hereinafter this may be referred to as "TBDMS"), a tert-butyldiphenylsilyl group; a lower alkoxymethyl group such as a methoxymethyl group, a 2-methoxyethoxymethyl group, a trimethylsilylethoxymethyl group; a tetrahydropyranyl group; an aralkyl group such as a benzyl group (hereinafter referred to as "Bn"), a p-methoxybenzyl group, a 2,3-dimethoxybenzyl group, an o-nitrobenzyl group, a p-nitrobenzyl group, a trityl group; an acyl group such as a formyl group, an acetyl group; and a benzoyl group (hereinafter referred to as "Bz"). Especially preferred are a methoxymethyl group, a tetrahydropyranyl group, a trityl group, a trimethylsilylethoxymethyl group, a tert-butyldimethylsilyl group and an acetyl group.

The carboxyl-protective group includes, for example, a lower alkyl group such as a methyl group, an ethyl group, a propyl group, an isopropyl group, a tert-butyl group; a lower alkenyl group such as a 2-propenyl group; an aralkyl group such as a benzyl group, a p-methoxybenzyl group, a p-nitrobenzyl group, a benzhydryl group. Especially preferred are a methyl group, an ethyl group, a tert-butyl group, a 2-propenyl group, a benzyl group, a p-methoxybenzyl group, a benzhydryl group.

The amino-protective group includes a benzyl group (hereinafter referred to as "Bn"), a tert-butyloxycarbonyl group (hereinafter referred to as "Boc"), a benzyloxycarbonyl group (hereinafter referred to as "Z"), a methanesulfonyl group.

In the compound of formula (II), the leaving group L includes, for example, a chlorine atom, a bromine atom, a benzenesulfonyloxy group, an o-toluenesulfonyloxy group, a m-toluenesulfonyloxy group, a p-toluenesulfonyloxy group, a methanesulfonyloxy group. Preferred are a p-toluenesulfonyloxy group and a methanesulfonyloxy group.

Production Method 2:

The compounds of formula (II) can be prepared according to the methods mentioned below or methods similar thereto or according to the methods described in Examples, depending on the position of the substituent in formula (II) and on the number n therein.

Production Method 2-1:

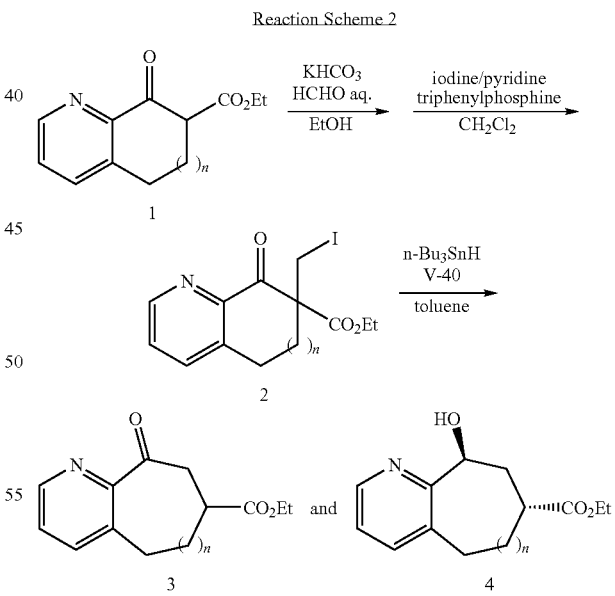

A compound 1 is reacted with a formalin solution, for example, at about 50° C. for about 4 hours in ethanol in the presence of potassium hydrogencarbonate for hydroxymethylation of the compound, and the resulting alcohol compound is reacted with iodine in methylene chloride in the presence of pyridine and triphenyl phosphine at room temperature for about 18 hours to obtain a compound 2. The compound 2 is heated in toluene in the presence of tributyltin hydride (this is referred to as "n-Bu₃SnH") and V-40 [this means 1,1'-azobis(cyclohexane-1-carbonitrile)], for example, at about 135° C. for about 4 hours to obtain a compound 3 and a compound 4 (note: when tributyltin hydride is increased, then 4 is predominantly obtained).

The compound 1 or its derivatives may be prepared according to the methods described in WO02/76950, WO03/70706; *Tetrahedron*, 1992, Vol. 48, p. 4038; *Tetrahedron Letters* 2001, 42(37), pp. 6593-6594; *Monatshefte Fuer Cheimie*, (1974), 105(1), pp. 179-86.

In case where a compound 1a:

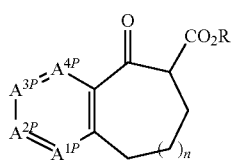

is used in place of the compound 1 in the above reaction, then the substituents in the side branches may be suitably protected before the reaction. For the type of the protective groups, referred to are *Protective Groups in Organic Synthesis*, by T. W. Greene, John Wiley & Sons (1981).

Production Method 2-2:

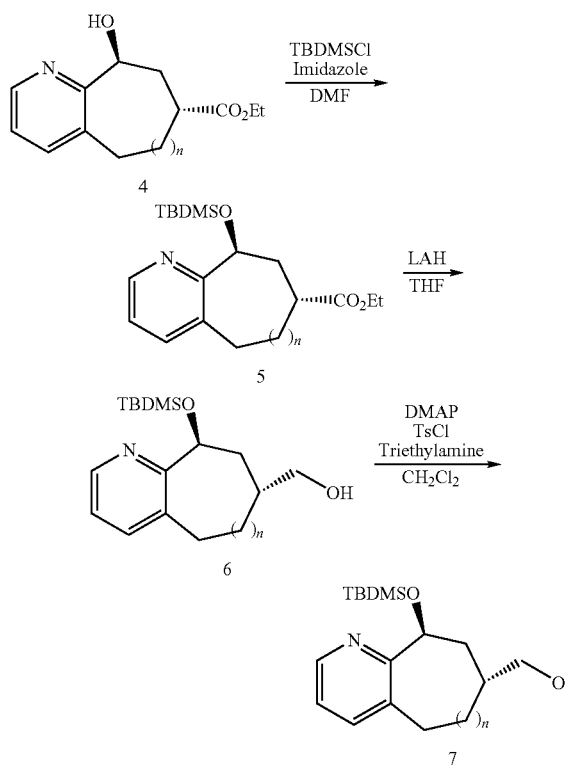

A compound 4 is reacted with t-butyldimethylchlorosilane (hereinafter this may be referred to as "TBDMSCl") in DMF in the presence of imidazole at room temperature for overnight to give a compound 5. The compound 5 is stirred in THF with lithium aluminium hydride (hereinafter referred to as "LAH") at room temperature for about 30 minutes to reduce the ester to give a compound 6. Next, the compound 6 is tosylated with tosyl chloride (hereinafter this may be referred to as "TsCl") at room temperature in methylene chloride in the presence of triethylamine and dimethylaminopyridine (hereinafter referred to as "DMAPP") to give a compound 7.

Production Method 2-3:

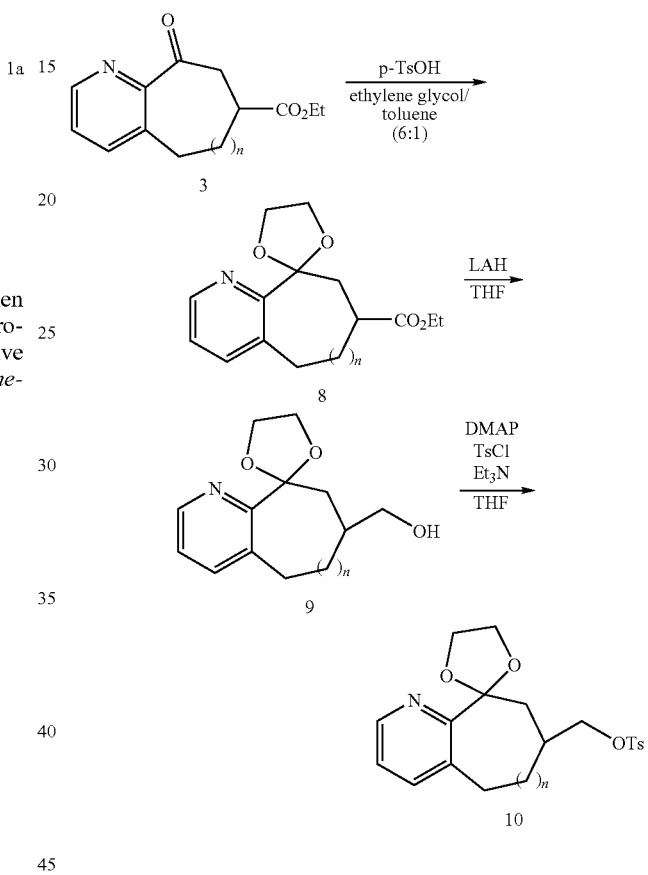

A compound 3 is ketalized with ethylene glycol in toluene in the presence of a catalyst, p-toluenesulfonic acid (hereinafter this may be referred to as "p-TsOH"), for example, at about 130° C. for overnight to give a compound 8. The compound 8 is reduced through hydrogenation with LAH in THF with cooling with ice for about 1 hour to give a compound 9. Then, the compound 9 is tolylated with TsCl in THF in the presence of triethylamine and DMAP, for example, at 50° C. to give a compound 10.

Production Method 2-4:

Reaction Scheme 5

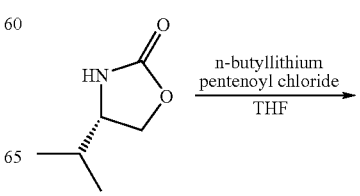

-continued

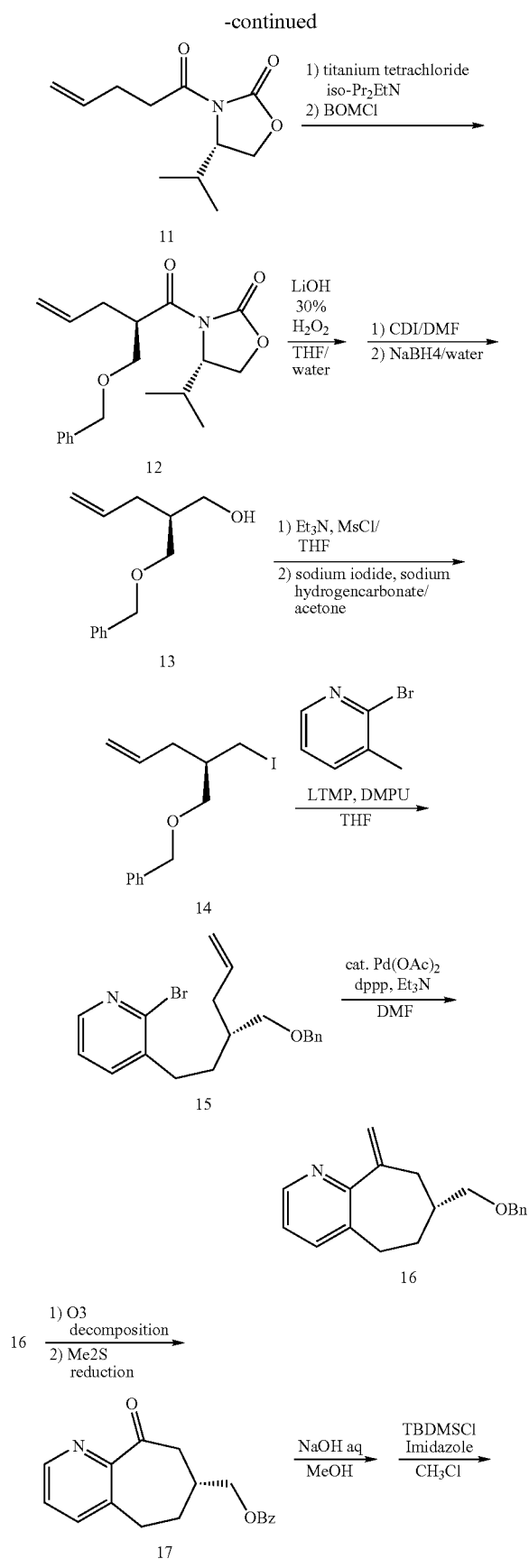

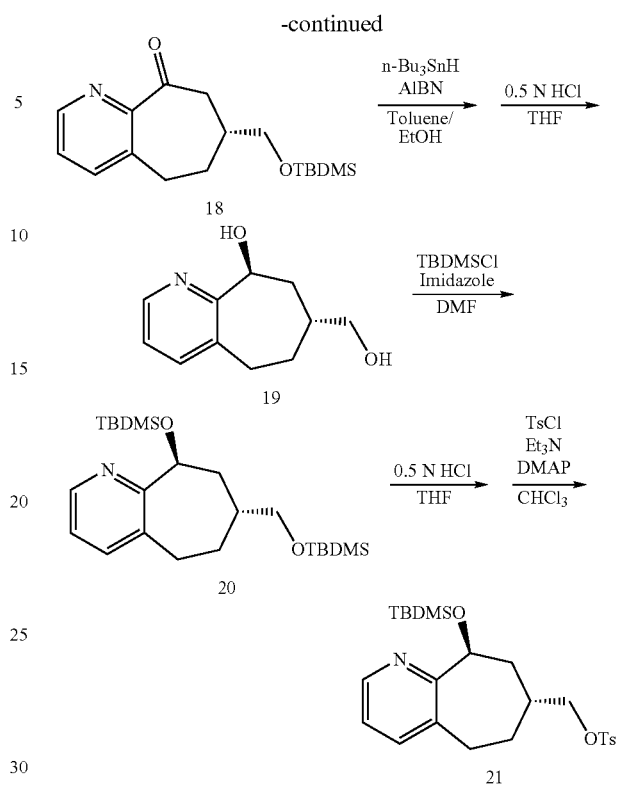

Commercially-available 4-isopropyl-2-oxazolidinone is reacted with pentenoyl chloride in THF in the presence of n-butyllithium at a temperature of from −78° C. to room temperature to give a compound 11. The compound 11 is reacted with benzyl chloromethyl ether (hereinafter referred to as "BOMCl") in methylene chloride in the presence of titanium tetrachloride and diisopropylethylamine at about 0° C. to give a compound 12. The compound 12 is hydrolyzed with aqueous alkaline hydrogen peroxide with cooling with ice, and the resulting carboxylic acid is converted into an imidazolide, using 1,1-carbonyldiimidazole (hereinafter referred to as "CDI"). Then, this is reduced through hydrogenation with sodium borohydride to give a compound 13. The compound 13 is mesylated and iodated in a known manner to give a compound 14. The compound 14 is reacted with a lithium reagent, which is prepared from lithium tetramethylpiperidide (hereinafter referred to as "LTMP") and 2-bromo-3-methylpyridine, in THF in the presence of 1,3-dimethyl-3,4,5,6-tetrahydro-2(1H)-pyrimidinone (hereinafter referred to as "DMPU") to obtain a compound 15. The compound 15 is cyclized in DMF in the presence of a catalytic amount of palladium acetate and 1,3-bis(diphenylphosphino) propane (hereinafter referred to as "dppp"), for example, at about 130° C. to obtain a compound 16. Next, the compound 16 is subjected to ozone decomposition in an known manner and then reduced with dimethyl sulfide to obtain a compound 17. The compound 17 is alkali-hydrolyzed with an aqueous solution of sodium hydroxide at the benzoyl group thereof, and then the resulting alcohol is t-butyldimethylsilylated in a known manner to give a compound 18. Then, the compound 18 is reacted with about 2.5 equivalents of tributyltin hydride in a mixed solvent of toluene/ethanol in the presence of about 0.25 equivalents of azoisobutyronitrile (hereinafter referred to as "AEBN"), for example, at 90° C., and then the product is treated with hydrochloric acid to obtain a compound 19. The compound 19 is again t-butyldimethylsilylated with t-butyldimethylsilyl chloride to give a compound 20, and the compound 20 is treated with hydrochloric acid to thereby deprotect only the primary alcohol-protective group, and the resulting product is tosylated in a known manner, for example, at about 50° C. for about 1 hour to give a compound 21.

Production Method 2-5:

Reaction Scheme 6

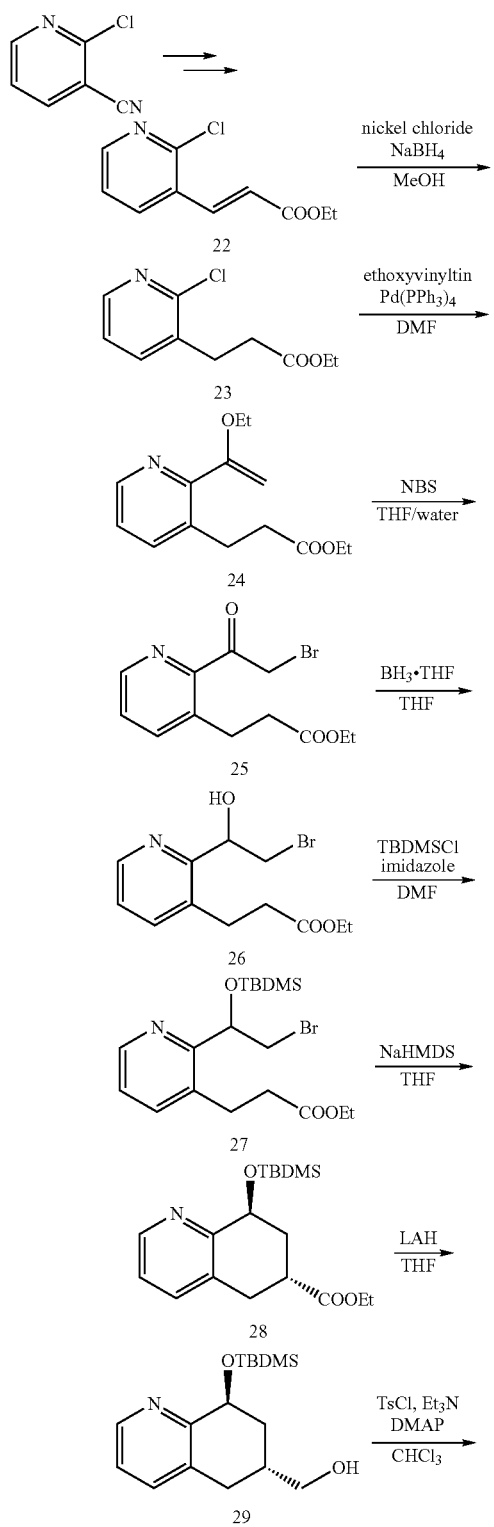

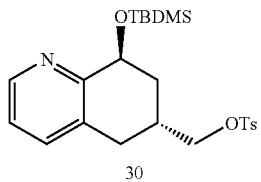

A compound 22 derived from 2-chloro-3-cyanopyridine in an ordinary manner is reduced through hydrogenation with sodium borohydride in methanol in the presence of nickel chloride, at room temperature for about 9 hours to obtain a compound 23. The compound 23 is reacted with ethoxyvinyltin in DMF in the presence of a catalyst, tetrakis(triphenylphosphine)palladium (hereinafter referred to as "Pd(PPh$_3$)$_4$"), for example at about 120° C. for about 6 hours to give a compound 24. The compound 24 is brominated with N-bromosuccinimide (hereinafter referred to as "NBS") in a mixed solvent of THF-water at room temperature for about 15 minutes to obtain a compound 25. Then, the compound 25 is reduced with borane in TBF at a temperature of from −10° C. to room temperature for about 1 hour to obtain a compound 26. The compound 26 is t-butyldimethylsilylated in a known method with t-butyldimethylsilyl chloride in DMF at room temperature for overnight to give a compound 27 and the compound 27 is cyclized, using sodium bistrimethylsilylamide (hereinafter referred to as "NaHMDS") in THF at −78 to 0° C., to give a compound 28. Then, the compound 28 is reduced through hydrogenation with LAH in THF at room temperature for about 15 minutes to give a compound 29 and the compound 29 is tosylated in chloroform, for example, at about 50° C. for 3.5 hours to obtain a compound 30.

The compound 7, the compound 10, the compound 21 and the compound 30 obtained in the above-mentioned methods correspond to the compounds of formula [II]. In case where the compounds of formula [II] have a leaving group except a tosyl group, for example, having a methanesulfonyl group, then the corresponding reagent, for example, methanesulfonyl chloride may be used to introduce the leaving group into the compounds in accordance with the reaction mentioned above.

Production Method 3:

The compounds of formula (III) can be prepared according to the methods mentioned below or methods similar thereto or according to the methods described in Examples. In addition, they may also be prepared also according to the methods described in WO02/88089.

Production Method 3-1:

Reaction Scheme 7

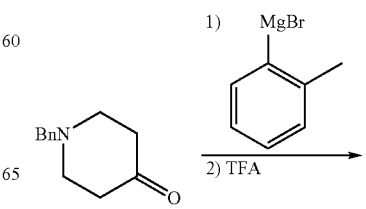

-continued

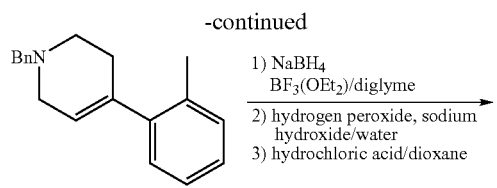

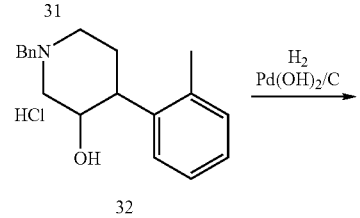

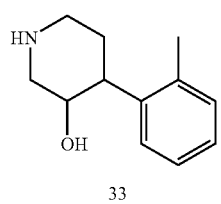

O-toluylmagnesium bromide and benzylpiperidone are reacted in THF, for example, about 0° C. for about 30 minutes, and the resulting addition product is reacted in trifluoroacetic acid (hereinafter referred to as "TFA"), for example, at about 80° C. for about 1 hour to give a compound 31. Next, the compound 31 is subjected to hydroboration with diborane, which is generated from boron trifluoride/diethyl ether complex (BF3.OEt2) and sodium borohydride, in diglyme, and then treated with aqueous alkaline hydrogen peroxide to give an alcohol compound, and thereafter a solution of hydrochloric acid/dioxane is added thereto to obtain a hydrochloride compound 32. Then, the compound 32 is hydrogenated with a catalyst, palladium hydroxide/carbon in a mixed solvent of methanol/ethanol in a hydrogen atmosphere, at the benzyl group of the compound to give a compound 33.

Production Method 3-2:

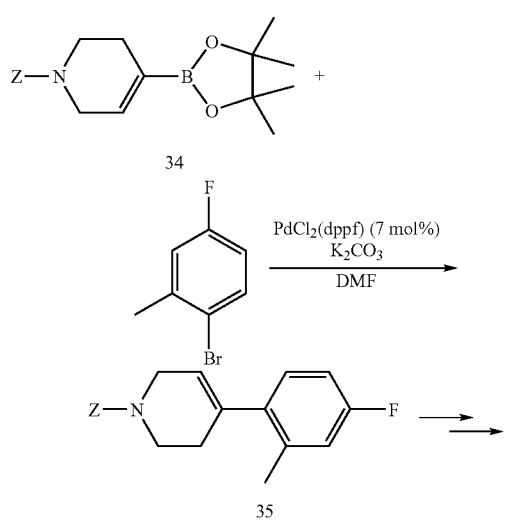

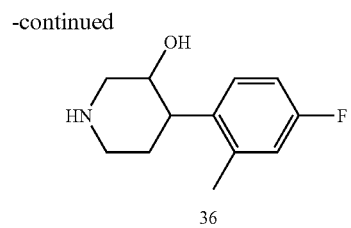

A compound 34 and 1-bromo-4-fluoro-2-methylbenzene are stirred in DMF, in the presence of 7 mol % of chloro[1,1'-bis(diphenylphosphino)ferrocene]palladium (hereinafter referred to as "PdCl₂(dppf)") and 3 equivalents of potassium carbonate, for example, at about 80° C. for about 6 hours to obtain a compound 35. Next, the compound 35 is reacted in the same manner as in Production Method 3-1 to give a compound 36.

The compound 34 can be prepared, for example, as follows: N-benzyloxycarbonylpiperidin-4-one is reacted with lithium bistrimethylsilylamide in THF at −78° C., and then N-phenylbis(trifluoromethanesulfonimide) is added thereto and stirred at −78 to 0° C. for about 2 hours to obtain 4-trifluoromethanesulfonyloxy-N-benzyloxycarbonyl-1,2,3,6-tetrahydropyridine. The resulting compound is reacted according to the method described in *J. Org. Chem.*, 62(19), pp. 6458-6459 (1997) to give the compound 34.

Production Method 3-3:

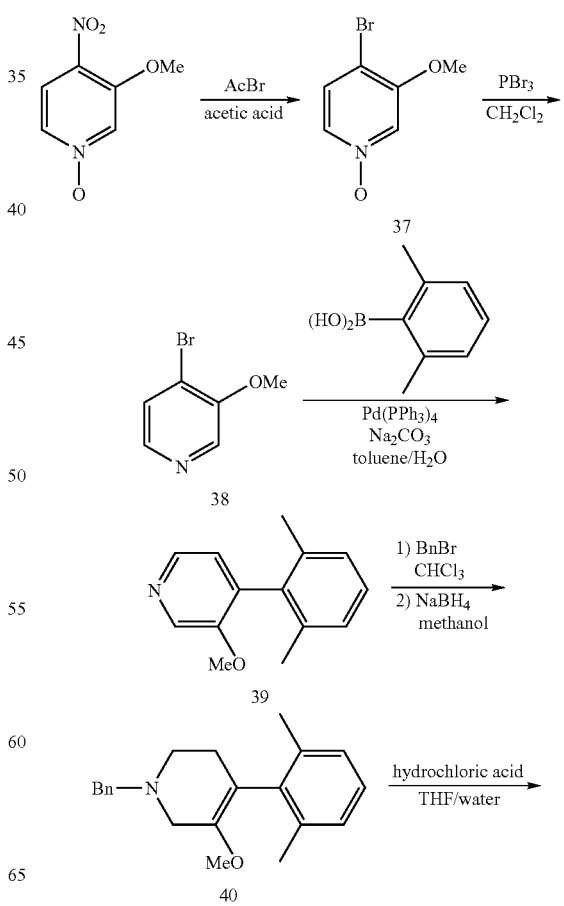

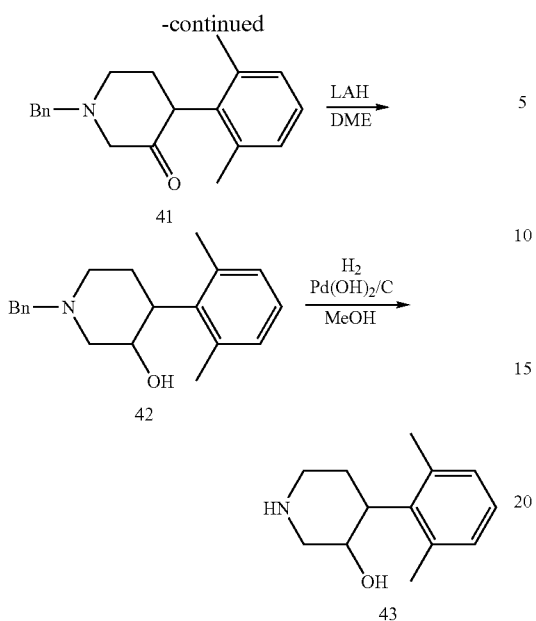

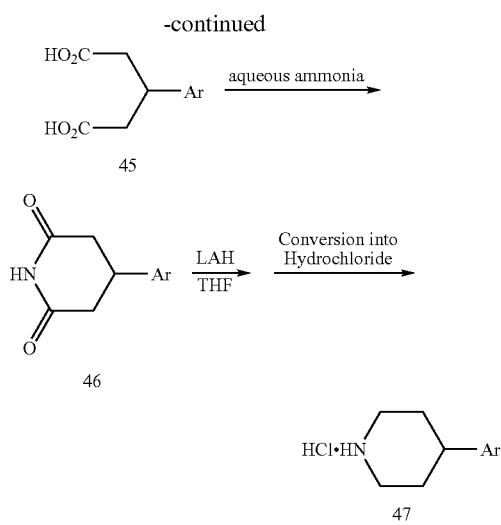

3-Methoxy-4-nitropyridine oxide is reacted with acetyl bromide (hereinafter referred to as "AcBr") in acetic acid, for example, at about 80° C. for about 2.5 hours to obtain a compound 37. The compound 37 is reacted with phosphorus tribromide (hereinafter referred to as "PBr$_3$") in methylene chloride, for example, at about 50° C. for about 2 hours to obtain a compound 38. The compound 38 is reacted with 2,6-dimethylphenylboronic acid in a mixed solvent of toluene and water, in the presence of tetrakis(triphenylphosphine)palladium (hereinafter referred to as "Pd(PPh$_3$)$_4$") and sodium carbonate, at about 110° C. for 2 days to obtain a compound 39. The compound 39 is benzylated with benzyl bromide (hereinafter referred to as "BnBr"), and the resulting compound is reduced through hydrogenation with sodium borohydride in methanol under the condition of cooling with ice to at room temperature for about 23 hours to obtain a compound 40. The compound 40 is reacted with hydrochloric acid in THF, for example, at about 90° C. for about 24 hours to obtain a compound 41. The compound 41 is reduced through hydrogenation with lithium aluminum hydride at a temperature of from room temperature to about 90° C. for about 6 hours to give a compound 42, and the compound 42 is hydrolyzed, using a catalyst, palladium hydroxide-carbon, in a hydrogen atmosphere at the benzyl group thereof to obtain a compound 43.

Production Method 3-4:

Reaction Scheme 10

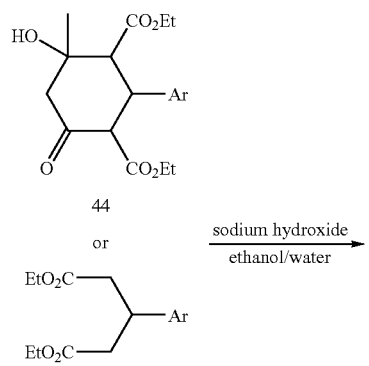

A compound 44 is alkali-hydrolyzed with an aqueous solution of sodium hydroxide at about 90° C. in a mixed solvent of ethanol/water to obtain a compound 45. The compound 45 may be obtained also by hydrolyzing the corresponding ester. The compound 45 is reacted under pressure in aqueous ammonia at about 190° C. for about 2 hours to obtain a compound 46. The compound 46 is reduced through hydrogenation with LAH in THF at about 70° C. in a known manner, and then converted into its hydrochloride with hydrochloric acid/dioxane to obtain a compound 47.

In Production Method 3-4, Ar includes, for example, the following:

Ar:

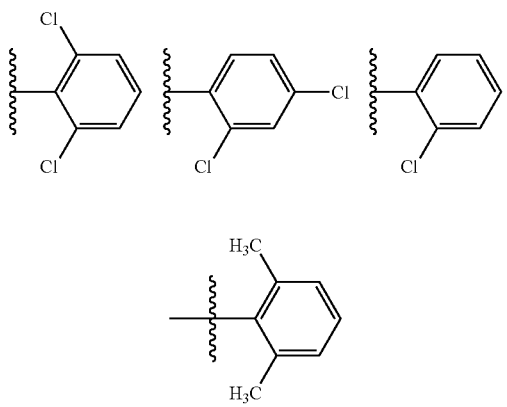

Production Method 4:

Production Method 4 is a method for producing the compounds of formula [III] where R$_2$ and R$_2$' or R$_3$' together form a C$_{1-3}$ alkylene group or an oxy-C$_{1-3}$ alkylene group. Apart from the methods mentioned below, the compounds may also be produced, for example, according to the methods described in *Tetrahedron*, 1998, Vol. 54, p. 8047; *J. Org. Chem.*, 1961, Vol. 26, p. 395; *Chem. Pharm. Bull.*, 1963, Vol. 11, p. 333.

Production Method 4-1:

Reaction Scheme 11

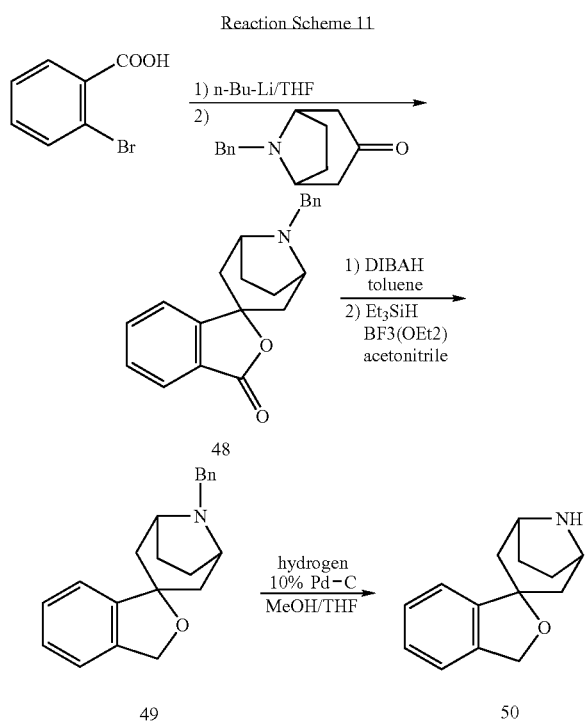

N-butyllithium is added to a THF solution of o-bromobenzoic acid at −78° C., and stirred for about 30 minutes at the temperature. Next, a THF solution of N-benzyl-azabicyclo[3.2.1]octan-3-one is added to the reaction liquid, and reacted at a temperature falling between −78° C. and −15° C. for about 3 hours to obtain a compound 48. The compound 48 is reduced into lactol, using diisobutylaluminium hydride (hereinafter referred to as "DIBAH") in toluene at −78° C. for about 1 hour, and the resulting lactol is reduced, using triethylsilane (hereinafter referred to as "Et₃SiH") and BF₃.OEt₂ in acetonitrile, to obtain a compound 49. Then, the compound 49 is hydrogenated at the benzyl group thereof, using a catalyst 10% palladium-carbon in a mixed solvent of methanol/THF in a hydrogen atmosphere, to give a compound 50.

Production Example 4-2:

Reaction Scheme 12

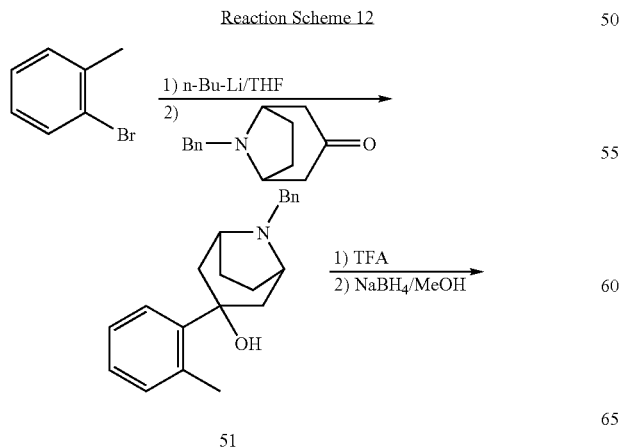

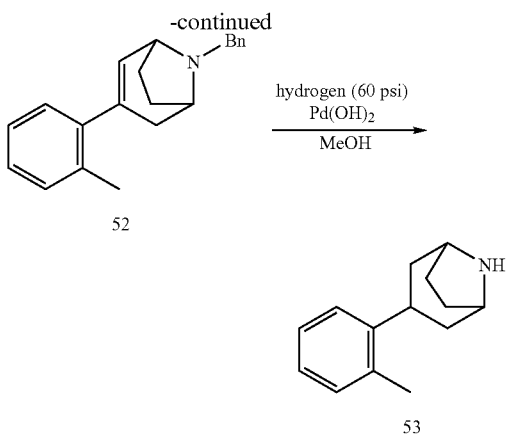

In the same manner as in Production Method 4-1, a compound 51 is obtained, for which, however, o-bromotoluene is used in place of o-bromobenzoic acid. Using TFA, the compound 51 is reacted under the same condition as in Production Method 3-1 to give a compound 52. The compound 52 contains the starting compound, N-benzyl-azabicyclo[3.2.1]octan-3-one in the reaction mixture thereof. Therefore, the reaction mixture is processed with sodium borohydride so as to selectively reduce N-benzyl-azabicyclo[3.2.1]octan-3-one alone into N-benzyl-azabicyclo-octan-3-ol, which is removed. Next, the resulting compound 52 is hydrogenated at the benzyl group thereof under hydrogen pressure (60 psi) using a catalyst palladium hydroxide-carbon to obtain a compound 53.

Production Method 4-3:

Reaction Scheme 13

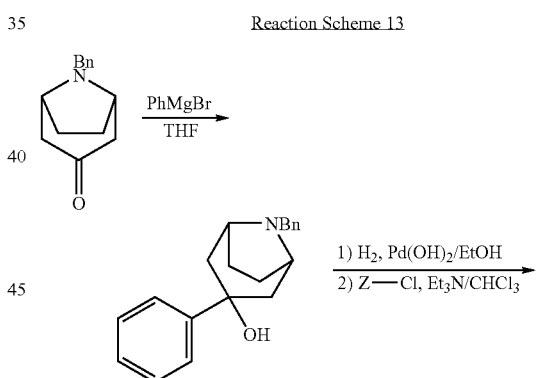

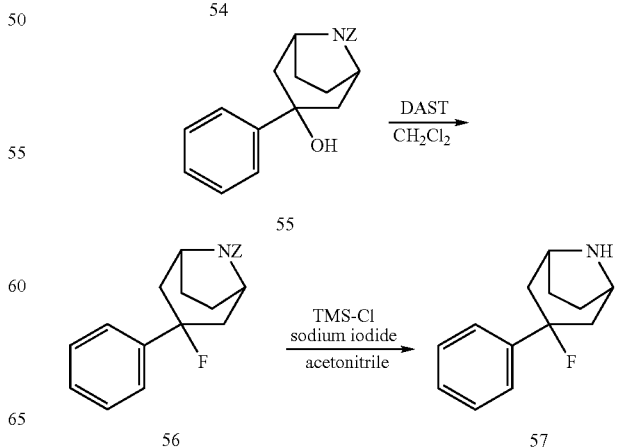

Phenylmagnesium bromide (hereinafter referred to as "PhMgBr") is added to a THF solution of N-benzyl-azabicyclo[3.2.1]-octan-3-one at about 0° C., and reacted, for example, for about 30 minutes to obtain a compound 54. Then, the compound 54 is hydrogenated in ethanol in a hydrogen atmosphere, using a catalyst palladium hydroxide-carbon, to remove the benzyl group from the compound, and the resulting product is benzyloxycarbonylated using carbobenzoxy chloride (hereinafter referred to as "Z—Cl")/triethylamine in amine-chloroform to give a compound 55. The resulting compound 55 is fluorinated in methylene chloride with diethylaminosulfite trifluoride (hereinafter referred to as "DAST") at −78° C. to obtain a compound 56. Then, the compound 56 is processed with trimethylchlorosilane (TMSCl) and sodium iodide in acetonitrile at room temperature to remove the benzyloxycarbonyl group from it to give a compound 57.

Production Method 4-4:

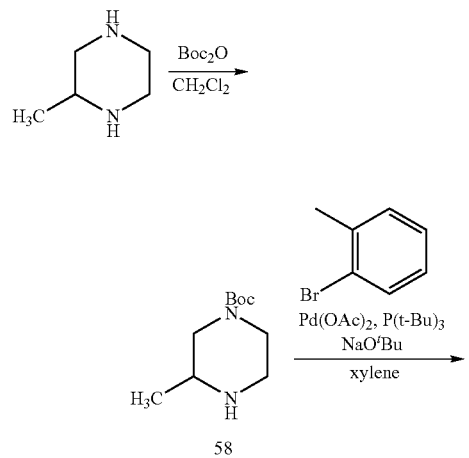

Reaction Scheme 14

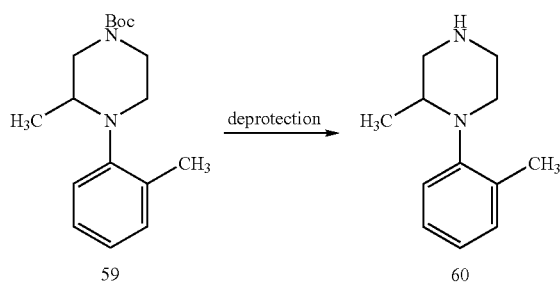

2-Methylpiperazine is processed with di-tert-butyl dicarbonate [hereinafter referred to as "(Boc)$_2$O"] at room temperature in methylene chloride to introduce a group Boc thereinto to give a compound 58. Then, the compound 58 is reacted with o-bromotoluene in xylene in the presence of a catalyst palladium acetate, for example, at about 120° C. in the presence of sodium t-butoxide and tributyl phosphine, to obtain a compound 59. Then, the compound 59 is deprotected with trifluoroacetic acid at room temperature to remove the group Boc to obtain a compound 60.

Production Method 5:

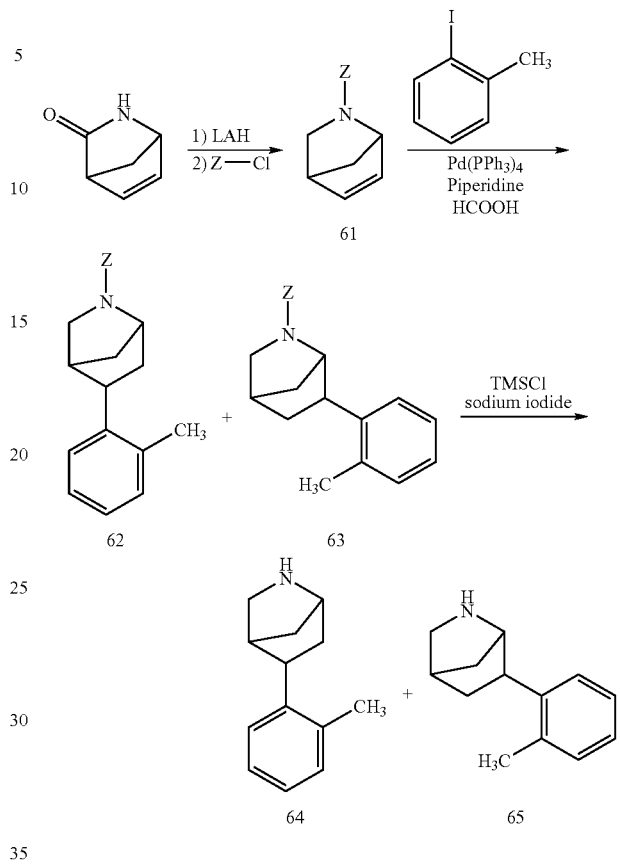

Reaction Scheme 15

Racemic 2-azabicyclo[2.2.1]-5-hepten-3-one is reduced with LAH in a mixture of THF/ether, and then its amino group is benzyloxycarbonylated with Z—Cl in an aqueous solution of sodium hydroxide at room temperature to give a compound 61. The compound 61 is reacted with o-iodotoluene in DMF in the presence of formic acid, piperidine and a catalyst tetrakis(triphenylphosphine)palladium, for example, at about 80° C. for about 4 hours to obtain a mixture of a compound 62 and a compound 63. Then, the benzyloxycarbonyl group is removed from these compound in the same manner as in Production Method 4-3 to obtain a compound 64 and a compound 65.

The compounds of the invention obtained according to the above-mentioned methods may be purified in a per-se known purification method so as to improve the purity of the compounds. The purification method includes, for example, column chromatography using an adsorption resin such as silica gel, alumina, purification with ion-exchange resin, liquid chromatography, solvent extraction, recrystallization, reprecipitation, and their combinations.

Some compounds of the invention may include optical isomers, and they may be used as their racemic mixtures. For example, they may be subjected to optical resolution through column chromatography with an optically-active filler filled in the column, and the racemic mixtures may be separated into individual isomers for use in the invention.

The compounds of the invention may be formed into pharmaceutically-acceptable salts in any ordinary method, or on the contrary, their salts may also be converted into free compounds. Examples of the pharmaceutically-acceptable salts of the compounds of the invention are base-addition salts of the compounds of formula (I) having a carboxyl group, in which a base is added to the carboxyl group; and acid addition salts of the compounds of formula (I) having an amino group or a nitrogen-containing hetero ring.

The acid-addition salts include inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

The base-addition salts include alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The usefulness of the compounds of the invention as medicines is verified, for example, as in the following Pharmacological Test Examples.

Pharmacological Test Example 1

Nociceptin Receptor Binding Inhibition Assay

A cDNA that codes for a human nociceptin receptor gene was cloned into an expression vector pCR3 (by Invitrogen) to prepare pCR3/ORL1. Next, pCR3/ORL1 was transfected in CHO cells using a transfectam (by Nippongene) to obtain a stable expression strain (CHO/ORL1 cells) having resistance against 1 mg/ml G418. Membrane fractions were prepared from this stable expression strain to carry out a receptor binding assay. 11 μg of the membrane fraction, 50 pM [$^{125}$I]Tyr$^{14}$-Nociceptin (by Amersham Pharmacia), 1 mg of wheat germ agglutinin SPA beads (PVT based, by Amersham Pharmacia) and each test compound were suspended in an NC buffer (50 mM Hepes, 10 mM sodium chloride, 1 mM magnesium chloride, 2.5 mM calcium chloride, 0.1% BSA, 0.025% bacitracin, pH 7.4) and incubated at 37° C. for 60 minutes, and then the radioactivity of the culture was determined. The binding activity to the nociceptin receptor was indicated by the 50% inhibition concentration (IC$_{50}$ value) of [$^{125}$I]Tyr$^{14}$-Nociceptin binding by each compound of the invention. The results were as shown in Table 5.

TABLE 5

| Example Compound | IC$_{50}$ value (nM) |
|---|---|
| Example 4 | 3.70 |
| Example 10 | 0.37 |
| Example 16 | 9.00 |
| Example 17 | 4.80 |
| Example 23 | 0.53 |
| Example 25 | 2.50 |
| Example 29 | 4.10 |
| Example 31 | 6.70 |
| Example 33 | 9.00 |
| Example 70 | 0.39 |
| Example 71 | 1.40 |

Pharmacological Test Example 2

Antagonism Against Nociceptin-elicited G Protein Activation

CHO cells which stably expressed a nociceptin receptor ORL1 were used to investigate the action of each test compound against nociceptin-elicited G protein activation. A membrane prepared from the CHO/ORL1 cells, 50 nM nociceptin, 200 pM GTPγ[$^{35}$S] (by NEN), 1.5 mg of wheat germ agglutinin SPA beads (by Amersham Pharmacia) and each test compound were mixed in a GDP buffer (20 mM Hepes, 100 mM sodium chloride, 10 mM magnesium chloride, 1 mM EDTA, 5 μM GDP, pH 7.4) and incubated at 25° C. for 150 minutes, and then the radioactivity of the culture was determined. The antagonism against the nociceptin-elicited G protein activation was shown by the 50% inhibition concentration (IC$_{50}$ value) of the test compound against GTPγ[$^{35}$S] binding. The results were as shown in Table 6.

TABLE 6

| Example Compound | IC$_{50}$ value (nM) |
|---|---|
| Example 4 | 1.80 |
| Example 10 | 0.08 |
| Example 16 | 2.50 |
| Example 17 | 1.30 |
| Example 23 | 1.20 |
| Example 25 | 4.20 |
| Example 29 | 4.70 |
| Example 31 | 2.10 |
| Example 33 | 5.90 |
| Example 70 | 0.32 |
| Example 71 | 0.68 |

Pharmacological Test Example 3

Antagonism Test

Using male ICR (CD-1) mice (weighing 20 to 40 g), antagonism to hypokinesis (suppression of motion) induced by a nociceptin agonist was observed. That is, the quantity of motion of each mouse in a 20 cm×30 cm×20 cm cage was measured with an infrared sensor. The test compound (1 to 10 mg/kg) as dissolved in either 0.5% methyl cellulose liquid or a solvent, and a nociceptin agonist (1 mg/kg) were administered to the test mice hypodermically, and the quantity of their motion for 60 minutes was measured. To the control group mice, the solvent only was administered. The evaluation was made by representing the quantity of motion of the mice administered with the test compound by percent, where the difference in the quantity of motion between the nociceptin agonist-administered group and that of the solvent-administered control group during the test time was set to be 100%. The results were as shown in Table 7.

TABLE 7

| Example Compound | Quantity of Motion (%) |
|---|---|
| Example 16 | >75% |
| Example 17 | >75% |
| Example 25 | >75% |
| Example 29 | >75% |
| Example 31 | >75% |
| Example 33 | >75% |

Pharmaceutical Composition Comprising Compound of Formula [I]

The compounds of the invention can be administered orally or parenterally. As formulated into pharmaceutical compositions suitable to administration, the compounds of the invention can be used for analgesics against diseases accompanied with pain such as cancerous pain, postoperative pain, migraine, gout, chronic rheumatism, chronic pain and neuralgia; relievers against tolerance to narcotic analgesics such as morphine; relievers against dependence on or addiction to narcotic analgesics such as morphine; analgesic enhancers; antiobesitics or appetite suppressors; treating or prophylactic agents for cognitive impairment and dementia/amnesia in aging, cerebrovascular diseases and Alzheimer's disease; agents for treating developmental cognitive abnormality such as attention deficit hyperactivity disorder and learning disability; remedies for schizophrenia; agents for treating neurodegenerative diseases such as Parkinsonism and chorea; anti-depressants or treating agents for affective disorder; treating or prophylactic agents for diabetes insipidus; treating or prophylactic agents for polyuria; remedies for hypotension.

In clinical use of the compounds of the invention, pharmaceutically-acceptable additives may be added thereto to formulate various preparations in accordance with the intended administration route thereof. Various additives generally used in the field of pharmaceutical compositions may be used herein, including, for example, gelatin, lactose, white sugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into solid preparations such as tablets, capsules, granules, powders and suppositories; and liquid preparations such as syrups, elixirs, injections. These preparations can be produced in any method known in the filed of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The preparations may contain the compound of the invention in an amount of from 1.0 to 100% by weight, preferably from 1.0 to 60% by weight of the preparation. The preparations may further contain any other therapeutically-effective compounds.

In case where the compounds of the invention are used for analgesics against diseases accompanied with pain such as cancerous pain, postoperative pain, migraine, gout, chronic rheumatism, chronic pain and neuralgia; relievers against tolerance to narcotic analgesics such as morphine; relievers against dependence on or addiction to narcotic analgesics such as morphine; analgesic enhancers; antiobesitics or appetite suppressors; treating or prophylactic agents for cognitive impairment and dementia/amnesia in aging, cerebrovascular diseases and Alzheimer's disease; agents for treating developmental cognitive abnormality such as attention deficit hyperactivity disorder and learning disability; remedies for schizophrenia; agents for treating neurodegenerative diseases such as Parkinsonism and chorea; anti-depressants or treating agents for affective disorder; treating or prophylactic agents for diabetes insipidus; treating or prophylactic agents for polyuria; remedies for hypotension, then their administration dose or frequency can be varied depending on the gender, the age, the body weight, the degree of symptoms of individual patients and the kind and the extent of the intended therapeutic effect. In general, the dose may be from 0.001 to 50 mg/kg/day, and it may be administered all at a time or may be administered in a few times as divided into a few portions. The dose is preferably from about 0.01 to about 25 mg/kg/day, more preferably from about 0.05 to about 10 mg/kg/day.

BEST MODE FOR CARRYING OUT THE INVENTION

The invention is described in detail with reference to the following Examples, to which, however, the invention should not be limited. Unless otherwise specifically indicated, the reagents used in the Examples are all commercial products. In silica gel column chromatography, Wako Pure Chemicals' Wakogel™ C-300 or Biotarge's KP-Sil™ Silica-prepacked Column were used. In preparative thin-layer chromatography, Merck's Kieselgel™ 60F$_{254}$, Art. 5744 was used. In basic silica gel column chromatography, Fuji Silicia's Chromatorex™ NH (100-250 mesh or 200-350 mesh) was used. In 1H-NMR, Varian's Gemini (200 MHz, 300 MHz), Mercury (400 MHz) and Inova (400 MHz) were used, in which tetramethylsilane was used as a standard substance. In mass spectrometry, Waters' Micromass ZQ was used for electrospray ionization (ESI) or atmospheric chemical ionization (APCI). The melting point was measured, using Yanako Instruments Development Laboratory's melting point microanalyzer, MP-J3.

Production Example 1

Production of ethyl 9-oxo-6,7,8,9-tetrahydro-5H-cyclohepta[b]pyridine-7-carboxylate 1) 8-Benzylidene-5,6,7,8-tetrahydroquinoline In a nitrogen atmosphere, 150 mL of benzaldehyde was added to acetic anhydride (180 mL) solution of 65 mL of 5,6,7,8-tetrahydroquinoline, and stirred at 170° C. for 12 hours. The reaction liquid was cooled to room temperature, and the excess reagent was evaporated off under reduced pressure. Then, aqueous saturated sodium hydroxide solution was added thereto, and extracted with ethyl acetate; and the ethyl acetate layer was washed with saturated saline water, and dried with anhydrous sodium sulfate. The solvent was evaporated off under reduced pressure, and the residue was crystallized from ethyl acetate/hexane to obtain 96.4 g of the entitled compound as a pale brown solid.

2) 6,7-Dihydro-5H-quinolin-8-one

In a nitrogen atmosphere, methanol (800 mL) solution of 51.4 g of the compound obtained in the above 1 was stirred for 10 hours with ozone jetted thereinto at −78° C. 25 mL of methyl sulfide was added to the reaction liquid, and heated up to room temperature, and the solvent was evaporated off under reduced pressure. Ethyl acetate and hexane were added to the resulting red oily substance, and a yellow solid was taken out through filtration. The resulting yellow solid was washed with ethyl acetate/hexane to obtain 30.9 g of the entitled compound as a white solid.

3) Ethyl 8-oxo-5,6,7,8-tetrahydroquinoline-7-carboxylate

In a nitrogen atmosphere, 2.97 g of 60% sodium hydride (oily) was added to diethyl carbonate (62 mL) solution of 9.11 g of the compound obtained in the above 2, and stirred at 130° C. for 1.5 hours. The reaction liquid was cooled to room temperature, water was added to the reaction liquid and extracted with chloroform, and the chloroform layer was washed with saturated saline water and then dried with anhydrous sodium sulfate. The solvent was evaporated off under reduced pressure, and the residue was separated and purified through silica gel column chromatography (chloroform/methanol=99/1) to obtain 11.6 g of the entitled compound as an orange solid.

4) Ethyl 7-iodomethyl-8-oxo-5,6,7,8-tetrahydroquinoline-7-carboxylate

In a nitrogen atmosphere, 12.0 g of potassium hydrogencarbonate and 25 mL of aqueous 35% formaldehyde solution were added in that order to ethanol (400 mL) solution of 21.9 g of the compound obtained in the above 3, and stirred at 50° C. for 4 hours. The reaction liquid was cooled to room temperature, the solvent was evaporated off under reduced pressure, and aqueous saturated sodium hydrogencarbonate solution was added thereto and extracted with chloroform. The chloroform layer was washed with saturated saline water, and dried with anhydrous sodium sulfate. The solvent was evaporated off under reduced pressure to obtain crude ethyl 7-hydroxymethyl-8-oxo-5,6,7,8-tetrahydroquinoline-7-carboxylate as a pale yellow oily substance.

In a nitrogen atmosphere, 24 mL of pyridine, 39.3 g of triphenyl phosphine and 19.0 g of iodine were added in that order to dichloromethane (400 mL) solution of the above-mentioned compound, and stirred at room temperature for 18 hours. Aqueous saturated sodium thiosulfate solution and aqueous saturated sodium hydrogencarbonate solution were added in that order to the reaction liquid, and extracted with chloroform. The chloroform layer was washed with saturated saline water, and dried with anhydrous sodium sulfate. The solvent was evaporated off under reduced pressure, and the residue was separated and purified through silica gel column chromatography (hexane/ethyl acetate=35/65) to obtain 25.0 g of the intended compound as a yellow oily substance.

5) Ethyl 9-oxo-6,7,8,9-tetrahydro-5H-cyclohepta[b]pyridine-7-carboxylate

In a nitrogen atmosphere, toluene (400 mL) solution of 25.0 g of the compound obtained in the above 4 was heated under reflux at 135° C., and toluene (400 mL) solution of 18.0 mL of tri-n-butyltin hydride and 1.50 g of V-40 (1,1'-azobis(cyclohexane)-1-carbonitrile) was dropwise added thereto an stirred for 2 days. The reaction liquid was cooled to room temperature, the solvent was evaporated off under reduced pressure, and hexane was added to the residue and extracted with acetonitrile. The solvent was evaporated off under reduced pressure, and the residue was separated and purified through silica gel column chromatography (hexane/ethyl acetate=30/70) to obtain 9.06 g of the entitled compound as an orange oily substance.

1H NMR (300 MHz, CDCl3) δ: 1.23 (3H, t, J=7.1 Hz), 2.12-2.20 (1H, m), 2.27-2.36 (1H, m), 2.88-2.96 (2H, m), 3.02-3.11 (3H, m), 4.11 (2H, q, J=7.2 Hz), 7.27-7.37 (1H, m), 7.59-7.62 (1H, m), 8.65-8.67 (1H, m)

ESI-MS Found: m/z 234.2 [M+H]+

Production Example 2

Production of methyl 9-oxo-6,7,8,9-tetrahydro-5H-cyclohepta[c]pridine-7-carboxylate 1) Methyl 4-methylnicotinate In a nitrogen atmosphere, 6.89 g of potassium carbonate and 4.6 mL of methyl iodide were added in that order to N,N-dimethylformamide (100 mL) solution of 6.86 g of 4-methylnicotinic acid, and stirred at room temperature for 3 hours. The solvent was evaporated off under reduced pressure, then aqueous sodium hydrogencarbonate solution was added to the residue and extracted with chloroform. The chloroform layer was washed with saturated saline water, and dried with anhydrous sodium sulfate. The solvent was evaporated off under reduced pressure, and the residue was separated and purified through silica gel column chromatography (hexane/ethyl acetate=50/50) to obtain 2.52 g of the entitled compound as a yellow oily substance.

2) Methyl 8-oxo-5,6,7,8-tetrahydroisoquinoline-7-carboxylate

In a nitrogen atmosphere, 9.8 mL of 1.50 M n-butyllithium/hexane solution was dropwise added to tetrahydrofuran (35 mL) solution of 2.1 mL of diisopropylamine at −78° C., and stirred at −78° C. for 30 minutes. Tetrahydrofuran (10 mL) solution of 1.63 g of the compound obtained in the above 1 was dropwise added to the reaction liquid, and stirred at −78° C. for 30 minutes. Next, tetrahydrofuran (5 mL) solution of 1.7 mL of methyl acrylate was dropwise added to the reaction liquid, and stirred at −78° C. for 1.5 hours. Further, aqueous 10% acetic acid solution was added to the reaction liquid, and heated up to room temperature, and then the solvent was evaporated off under reduced pressure. Aqueous saturated sodium hydrogencarbonate solution was added to the residue, and extracted with chloroform. The chloroform layer was washed with saturated saline water, and dried with anhydrous sodium sulfate. The solvent was evaporated off under reduced pressure, and the residue was separated and purified through silica gel column chromatography (chloroform/methanol=99/1) to obtain 1.60 g of the entitled compound as a yellow oily substance.

3) Methyl 7-iodomethyl-8-oxo-5,6,7,8-tetrahydroisoquinoline-7-carboxylate

The entitled compound was obtained in the same manner as in Production Example 1-4, for which, however, the compound obtained in the above 2 was used in place of ethyl 8-oxo-5,6,7,8-tetrahydroquinoline-7-carboxylate used in Production Example 1-4.

4) Methyl 9-oxo-6,7,8,9-tetrahydro-5H-cyclohepta[c]pyridine-7-carboxylate

The entitled compound was obtained in the same manner as in Production Example 1-5, for which, however, the compound obtained in the above 3 was used in place of ethyl 7-iodomethyl-8-oxo-5,6,7,8-tetrahydroquinoline-7-carboxylate used in Production Example 1-5.

1H NMR (300 MHz, CDCl3) δ: 2.11-2.19 (1H, m), 2.30-2.39 (1H, m), 2.90-3.15 (5H, m), 3.67 (3H, s), 7.16 (1H, d, J=5.0 Hz), 8.61 (1H, d, J=5.0 Hz), 8.87 (1H, s)

ESI-MS Found: m/z 220.2 [M#H]+

Production Example 3

Production of ethyl 5-oxo-6,7,8,9-tetrahydro-5H-cyclohepta[c]pyridine-7-carboxylate 1) 7,8-Dihydro-6H-isoquinolin-5-one oxime In a nitrogen atmosphere, tetrahydrofuran (125 mL) solution of 6.5 mL of 5,6,7,8-tetrahydroisoquinoline was added to tetrahydrofuran (100 mL) solution of 11.4 g of potassium tert-butoxide, and stirred at room temperature for 18 hours. Next, 17.5 mL of tert-butyl nitrite was dropwise added to the reaction liquid at 0° C., and stirred at room temperature for 18 hours. Saturated saline water was added to the reaction liquid, and extracted with ethyl acetate. The ethyl acetate layer was washed with saturated saline water, and dried with anhydrous sodium sulfate. The solvent was evaporated off under reduced pressure, and the residue was crystallized from water/ethanol to obtain 6.06 g of the entitled compound as a pale brown solid.

2) 7,8-Dihydro-6H-isoquinolin-5-one monohydrochloride

In a nitrogen atmosphere, 120 mL of 6 N hydrochloric acid was added to acetone (300 mL) solution of 6.06 g of the compound obtained in the above 1, and stirred at 80° C. for 12 hours. The reaction liquid was cooled to room temperature, concentrated under reduced pressure to remove the solvent, and the resulting dark red solid was taken out through filtration. This was washed with ethanol and dried to obtain 5.39 g of the entitled compound as a pale yellow solid.

3) Ethyl 5-oxo-5,6,7,8-tetrahydroisoquinoline-6-carboxylate

Aqueous saturated sodium hydrogencarbonate solution was added to 2.75 g of the compound obtained in the above 2, and extracted with chloroform. The chloroform layer was dried with anhydrous sodium sulfate. The solvent was evaporated off under reduced pressure to obtain crude 7,8-dihydro-6H-isoquinolin-5-one as a red oily substance. The resulting compound was reacted in the same manner as in Production Example 1-3 to obtain the entitled compound.

4) Ethyl 6-iodomethyl-5-oxo-5,6,7,8-tetrahydroisoquinoline-6-carboxylate

The entitled compound was obtained in the same manner as in Production Example 1-4, for which, however, the compound obtained in the above 3 was used in place of ethyl 8-oxo-5,6,7,8-tetrahydroquinoline-7-carboxylate used in Production Example 1-4.

5) Ethyl 5-oxo-6,7,8,9-tetrahydro-5H-cyclohepta[c]pyridine-7-carboxylate

The entitled compound was obtained in the same manner as in Production Example 1-5, for which, however, the compound obtained in the above 4 was used in place of ethyl 7-iodomethyl-8-oxo-5,6,7,8-tetrahydroquinoline-7-carboxylate used in Production Example 1-5.

1H NMR (300 MHz, CDCl3) δ: 1.22 (3H, t, J=7.1 Hz), 2.15-2.22 (1H, m), 2.28-2.37 (1H, m), 2.87-3.14 (5H, m), 4.11 (2H, q, J=7.1 Hz), 7.52 (1H, d, J=5.0 Hz), 8.57 (1H, s), 8.63 (1H, d, J=5.0 Hz)

ESI-MS Found: m/z 234.2 [M+H]+

Production Example 4

Production of ethyl 5-oxo-6,7,8,9-tetrahydro-5H-cyclohepta[b]pyridine-7-carboxylate

1) 7,8-Dihydro-6H-quinolin-5-one

In a nitrogen atmosphere, 24 mL of malonaldehyde tetraethyl acetal and 7.71 g of ammonium acetate were added in that order to xylene (80 mL) solution of 11.2 g of 1,3-cyclohexadione, and a reflux condenser tube fitted with a Dean-Stark water separator was attached to the reactor, and this was stirred at 160° C. for 18 hours. The reaction liquid was cooled to room temperature, the solvent was evaporated off under reduced pressure, the residue was extracted with chloroform, and the chloroform layer was washed with saturated saline water and dried with anhydrous sodium sulfate. The solvent was evaporated off under reduced pressure, and the residue was separated and purified through silica gel column chromatography (chloroform/methanol=97/3) to obtain 2.21 g of the entitled compound.

2) Ethyl 5-oxo-5,6,7,8-tetrahydroquinoline-6-carboxylate

The entitled compound was obtained in the same manner as in Production Example 1-3, for which, however, the compound obtained in the above 1 was used in place of 6,7-dihydro-5H-quinolin-1-one used in Production Example 1-3.

3) Ethyl 6-iodomethyl-5-oxo-5,6,7,8-tetrahydroquinoline-6-carboxylate

The entitled compound was obtained in the same manner as in Production Example 14, for which, however, the compound obtained in the above 2 was used in place of ethyl 8-oxo-5,6,7,8-tetrahydroquinoline-7-carboxylate used in Production Example 1-4.

4) Ethyl 5-oxo-6,7,8,9-tetrahydro-5H-cyclohepta[b]pyridine-7-carboxylate

The entitled compound was obtained in the same manner as in Production Example 1-5, for which, however, the compound obtained in the above 3 was used in place of ethyl 7-iodomethyl-8-oxo-5,6,7,8-tetrahydroquinoline-7-carboxylate used in Production Example 1-5.

1H NMR (300 MHz, CDCl3) δ: 1.23 (3H, t, J=7.1 Hz), 2.21-2.36 (2H, m), 2.92-3.30 (5H, m), 4.13 (2H, q, J=7.1 Hz), 7.27-7.31 (1H, m), 8.03-8.06 (1H, m), 8.62-8.64 (1H, m)

ESI-MS Found: m/z 234.1 [M+H]+

Production Example 5

Production of 4-o-tolylpiperidine monohydrochloride

1) 1-Benzyl-4-o-tolyl-1,2,3,6-tetrahydropyridine

In a nitrogen atmosphere, 75 mL of 1.50 M n-butyllithium/hexane solution was dropwise added to tetrahydrofuran (100 mL) solution of 12 mL of 2-bromotoluene at −78° C., and stirred at −78° C. for 30 minutes. Tetrahydrofuran (50 mL) solution of 18.5 mL of 1-benzyl-4-piperidone was dropwise added to the reaction liquid, and stirred at room temperature for 4 hours. Aqueous saturated ammonium chloride solution and aqueous saturated sodium hydrogencarbonate solution were added in that order to the reaction liquid, extracted with ether, and the ether layer was washed with saturated saline water and dried with anhydrous sodium sulfate. The solvent was evaporated off under reduced pressure to obtain crude 1-benzyl-4-o-tolylpiperidin-4-ol as a yellow oily substance.

In a nitrogen atmosphere, 100 mL of trifluoroacetic acid was added to the resulting compound and stirred at room temperature for 12 hours. The solvent was evaporated off under reduced pressure, and aqueous saturated sodium hydrogencarbonate solution was added thereto and extracted with ether. The ether layer was washed with saturated saline water and dried with anhydrous sodium sulfate. The solvent was evaporated off under reduced pressure, and the residue was separated and purified through silica gel column chromatography (hexane/ethyl acetate=85/15) to obtain 24.7 g of the entitled compound as a yellow oily substance.

2) 4-O-tolylpiperidine monohydrochloride 6.0 mL of formic acid and 12.0 g of 10% palladium-carbon catalyst were added in that order to ethanol (300 mL)-water (75 mL) solution of 24.7 g of the compound obtained in the above 1, and in a hydrogen atmosphere, this was stirred at room temperature under 3 atmospheres for 23 hours. The reaction system was purged with nitrogen, the catalyst was removed through filtration through Celite, and the solvent was evaporated off under reduced pressure. Aqueous saturated sodium hydrogencarbonate solution was added thereto and extracted with chloroform. The chloroform layer was washed with saturated saline water, and dried with anhydrous sodium sulfate. The solvent was evaporated off under reduced pressure to obtain crude 4-o-tolylpiperidine as a white solid. 4N hydrogen chloride-ethyl acetate solution was added to the compound, and stirred at room temperature, and the solvent was evaporated off under reduced pressure to obtain 10.7 g of the entitled compound as a white solid. The free amine of the compound was analyzed for assignment.

1H NMR (200 MHz, CDCl3) δ: 1.59-1.79 (4H, m), 2.35 (3H, s), 2.70-2.83 (3H, m), 3.17-3.23 (2H, m), 7.09-7.26 (4H, m)

ESI-MS Found: m/z 176.2 [M+H]+

Examples 1 to 4

Production of (7S*,9S*)-7-(4-o-tolylpiperidin-1-ylmethyl)-6,7,8,9-tetrahydro-5H-cyclohepta[b]pyridin-9-ol monofumarate; (7R*,9R*)-7-(4-o-tolylpiperidin-1-ylmethyl)-6,7,8,9-tetrahydro-5H-cyclohepta[b]pyridin-9-ol monofumarate: (7S,9R)-7-(4-o-tolylpiperidin-1-ylmethyl)-6,7,8,9-tetrahydro-5H-cyclohepta[b]pyridin-9-ol monofumarate; and (7R,9S)-7-(4-o-tolylpiperidin-1-ylmethyl)-6,7,8,9-tetrahydro-5H-cyclohepta[b]pyridin-9-ol monofumarate 1) 7-(4-O-tolylpiperidine-1-carbonyl)-5,6,7,8-tetrahydrocyclohepta[b]pyridin-9-one In a nitrogen atmosphere, 3.5 mL of 6 N hydrochloric acid was added to dioxane (1.5 mL) solution of 199 mg of the compound obtained in Production Example 1, and stirred at 110° C. for 2.5 hours. The reaction liquid was cooled to room temperature, the solvent was evaporated off under reduced pressure, and the residue was subjected to azeotropic distillation with toluene repeatedly twice to obtain crude 9-oxo-6,7,8,9-tetrahydro-5H-cyclohepta[b]pyridine-7-carboxylic acid monohydrochloride.

In a nitrogen atmosphere, 127 mg of 4-o-tolylpiperidine monohydrochloride obtained in Production Example 5 and 144 mg of 1-ethyl-3-(3'-dimethylaminopropyl)carbodiimide monohydrochloride were added in that order to pyridine (5.0 mL) solution of the compound obtained in the above, and stirred at room temperature for 8 hours. The solvent was evaporated off under reduced pressure, and aqueous saturated sodium hydrogencarbonate solution was added thereto and extracted with chloroform. The chloroform layer was washed with saturated saline water, and dried with anhydrous sodium sulfate. The solvent was evaporated off under reduced pressure, and the residue was separated and purified through silica gel column chromatography (chloroform/methanol=99/1) to obtain 142 mg of the entitled compound as a red amorphous substance.

2) (7RS,9RS)-7-(4-o-tolylpiperidin-1-ylmethyl)-6,7,8,9-tetrahydro-5H-cyclohepta[b]pyridin-9-ol and (7RS,9SR)-7-(4-o-tolylpiperidin-1-ylmethyl)-6,7,8,9-tetrahydro-5H-cyclohepta[b]pyridin-9-ol In a nitrogen atmosphere, 74.6 mg of lithiumaluminium hydride was added to tetrahydrofuran (4.0 mL) solution of 142 mg of the compound obtained in the above 1, at 0° C., and stirred at 70° C. for 2 hours. The reaction liquid was cooled to room temperature, and sodium sulfate 10-hydrate and chloroform were added in that order to the reaction liquid, and stirred at room temperature for 17 hours. The insoluble substance was separated through filtration, and the solvent of the filtrate was evaporated off under reduced pressure. The residue was separated and purified through preparative thin-layer chromatography (chloroform/methanol=95/5) to obtain 22.9 mg of (7RS,9RS)-7-(4-o-tolylpiperidin-1-ylmethyl)-6,7,8,9-tetrahydro-5H-cyclohepta[b]pyridin-9-ol as a colorless amorphous substance, and 12.9 mg of (7RS,9SR)-7-(4-o-tolylpiperidin-1-ylmethyl)-6,7,8,9-tetrahydro-5H-cyclohepta[b]pyridin-9-ol as a colorless amorphous substance.

(7RS,9RS) Form:

1H NMR (300 MHz, CDCl3) δ: 0.86-0.95 (1H, m), 1.06-1.22 (1H, m), 1.65-1.84 (4H, m), 2.02-2.20 (6H, m), 2.35 (3H, s), 2.35-2.42 (1H, m), 2.67-2.81 (3H, m), 2.99-3.03 (2H, m), 4.77-4.82 (1H, m) 5.99 (1H, brs), 7.08-7.28 (5H, m), 7.44-7.47 (1H, m), 8.36-8.39 (1H, m)

ESI-MS Found: m/z 351.3 [M+H]+

(7RS,9SR) Form:

1H NMR (300 MHz, CDCl3) δ: 1.58-1.87 (7H, m), 2.03-2.16 (4H, m), 2.34 (3H, s), 2.53-2.75 (4H, m), 2.84-2.89 (1H, m), 3.00-3.07 (2H, m), 4.93-4.97 (1H, m), 5.75 (1H, brs), 7.07-7.28 (5H, m), 7.43-7.46 (1H, m), 8.35-8.37 (1H, m)

ESI-MS Found: m/z 351.4 [M+H]+

3) (7S*,9S*)-7-(4-o-tolylpiperidin-1-ylmethyl)-6,7,8,9-tetrahydro-5H-cyclohepta[b]pyridin-9-ol monofumarate; and (7R*,9R*)-7-(4-o-tolylpiperidin-1-ylmethyl)-6,7,8,9-tetrahydro-5H-cyclohepta[b]pyridin-9-ol monofumarate 22.9 mg of the (7RS,9RS) form obtained in the above 2 was optically resolved in an optically-active column (Daicel's CHRALCEL OD column, 2 cm×25 cm; 0.1% diethylamine, hexane/isopropyl alcohol=9/1; flow rate, 15 mL/min). From the former fraction (retention time; 12.1 min), 7.9 mg of (7S*,9S*)-7-(4-o-tolylpiperidin-1-ylmethyl)-6,7,8,9-tetrahydro-5H-cyclohepta[b]pyridin-9-ol was obtained as a colorless amorphous substance; and from the latter fraction (retention time: 14.8 min), 8.0 mg of the (7R*,9R*) form was obtained as a colorless amorphous substance. (The two were not identified, and for convenience sake, one was referred to as (7S*,9S*) form and the other was as (7R*,9R*) form.)

An equimolar amount of fumaric acid, chloroform and methanol were added in that order to each of the two compounds, and stirred at room temperature. The solvent was evaporated off under reduced pressure to obtain a fumarate of the compound, both as a white solid. The free amine of the compound was analyzed for assignment.

Compound of Example 1

(7S*,9S*) Form

1H NMR and ESI-MS were the same as those of the racemate.

Compound of Example 2

(7R*,9R*) Form

1H NMR and ESI-MS were the same as those of the racemate.

4) (7S,9R)-7-(4-o-tolylpiperidin-1-ylmethyl)-6,7,8,9-tetrahydro-5H-cyclohepta[b]pyridin-9-ol monofumarate; and (7R,9S)-7-(4-o-tolylpiperidin-1-ylmethyl)-6,7,8,9-tetrahydro-5H-cyclohepta[b]pyridin-9-ol monofumarate 12.9 mg of the (7RS,9RS) form obtained in the above 2 was optically resolved in an optically-active column (Daicel's CHRALCEL OD column, 2 cm×25 cm; 0.1% diethylamine, hexane/isopropyl alcohol=9/1; flow rate, 15 mL/min). From the former fraction (retention time; 11.8 min), 4.5 mg of (7S,9R)-7-(4-o-tolylpiperidin-1-ylmethyl)-6,7,8,9-tetrahydro-5H-cyclohepta[b]pyridin-9-ol was obtained as a colorless amorphous substance; and from the latter fraction (retention time: 19.3 min), 4.6 mg of the (7R,9S) form was obtained as a colorless amorphous substance.

An equimolar amount of fumaric acid, chloroform and methanol were added in that order to each of the two compounds, and stirred at room temperature. The solvent was evaporated off under reduced pressure to obtain a fumarate of the compound, both as a white solid. The free amine of the compound was analyzed for assignment.

Compound of Example 3

(7S,9R) Form

1H NMR and ESI-MS were the same as those of the racemate.

Compound of Example 4

(7R,9S) Form

1H NMR and ESI-MS were the same as those of the racemate.

Example 5

Production of (7R*9R*)-7-(4-o-tolylpiperidin-1-ylmethyl)-6,7,8,9-tetrahydro-5H-cyclohepta[c]pyridin-9-ol monofumarate 1) 7-(4-O-tolylpiperidine-1-carbonyl)-5,6,7,8-tetrahydrocyclohepta[c]pyridin-9-one The entitled compound was obtained in the same manner as in 1 in Examples 1 to 4, for which, however, the compound obtained in Production Example 2 was used in place of ethyl 9-oxo-6,7,8,9-tetrahydro-5H-cyclohepta[b]pyridine-7-carboxylate used in 1 in Examples 1 to 4.

2) (7RS,9RS)-7-(4-o-tolylpiperidin-1-ylmethyl)-6,7,8,9-tetrahydro-5H-cyclohepta[c]pyridin-9-ol The entitled compound was obtained in the same manner as in 2 in Examples 1 to 4, for which, however, the compound obtained in the above 1 was used in place of 7-(4-o-tolylpiperidine-1-carbonyl)-5,6,7,8-tetrahydrocyclohepta[b]pyridin-9-one used in 2 in Examples 1 to 4.

1HNMR (300 MHz, CDCl3) δ: 0.94-1.10 (1H, m), 1.40-1.51 (1H, m), 1.71-1.88 (4H, m), 2.06-2.34 (7H, m), 2.34 (3H, s), 2.62-2.87 (3H, m), 2.99-3.06 (2H, m), 5.01 (1H, d, J=9.6 Hz), 7.00 (1H, d, J=4.9 Hz), 7.07-7.26 (4H, m), 8.38 (1H, d, J=4.7 Hz), 8.77 (1H, s)

ESI-MS Found: m/z 351.3 [M+H]+

3) (7R*,9R*)-7-(4-o-tolylpiperidin-1-ylmethyl)-6,7,8,9-tetrahydro-5H-cyclohepta[c]pyridin-9-ol monofumarate 86.2 mg of the racemate obtained in the above 2 was optically resolved in an optically-active column (Daicel's CHRALCEL OD column, 2 cm×25 cm; 0.1% diethylamine, hexane/isopropyl alcohol=6/4; flow rate, 15 mL/min). From the former fraction (retention time; 6.5 min), 10.1 mg of (7S*,9S*)-7-(4-o-tolylpiperidin-1-ylmethyl)-6,7,8,9-tetrahydro-5H-cyclohepta[c]pyridin-9-ol was obtained as a colorless amorphous substance; and from the latter fraction (retention time: 15.0 min), 28.6 mg of the (7R*,9R*) form was obtained as a colorless amorphous substance. (The two were not identified, and for convenience sake, one was referred to as (7S*,9S*) form and the other was as (7R*,9R*) form.)

An equimolar amount of fumaric acid, chloroform and methanol were added in that order to the resulting (7R*,9R*) form, and stirred at room temperature. The solvent was evaporated off under reduced pressure to obtain the entitled compound as a white solid. The free amine of the compound was analyzed for assignment.

1H NMR and ESI-MS were the same as those of the racemate.

Example 6

Production of (5S*,7R*)-7-(4-o-tolylpiperidin-1-ylmethyl)-6,7,8,9-tetrahydro-5H-cyclohepta[c]pyridin-5-ol monofumarate 1) 7-(4-O-tolylpiperidine-1-carbonyl)-6,7,8,9-tetrahydrocyclohepta[c]pyridin-5-one The entitled compound was obtained in the same manner as in 1 in Examples 1 to 4, for which, however, the compound obtained in Production Example 3 was used in place of ethyl 9-oxo-6,7,8,9-tetrahydro-5H-cyclohepta[b]pyridine-7-carboxylate used in 1 in Examples 1 to 4.

2) (5S*,7R*)-7-(4-o-tolylpiperidin-1-ylmethyl)-6,7,8,9-tetrahydro-5H-cyclohepta[c]pyridin-5-ol monofumarate 7-(4-O-tolylpiperidin-1-ylmethyl)-6,7,8,9-tetrahydro-5H-cyclohepta[c]pyridin-5-ol was obtained as a mixture of isomers thereof, in the same manner as in 2 in Examples 1 to 4, for which, however, the compound obtained in the above 1 was used in place of 7-(4-o-tolylpiperidine-1-carbonyl)-5,6,7,8-tetrahydrohepta[b]pyridin-9-one used in 2 in Examples 1 to 4.

49.7 mg of the mixture was separated in an optically-active column (Daicel's CHRALPAK AS column, 2 cm×25 cm; 0.1% diethylamine, hexane/isopropyl alcohol=9/1; flow rate, 15 mL/min). From the first fraction (retention time; 14.0 min), a mixture of two diastereomers was obtained; from the middle fraction (retention time; 20.2 min), 4.8 mg of (5R*,7S*)-7-(4-o-tolylpiperidin-1-ylmethyl)-6,7,8,9-tetrahydro-5H-cyclohepta[c]pyridin-5-ol was obtained as a colorless amorphous substance; and from the last fraction (retention time; 25.8 min), 10.3 mg of the (5S*,7S*) form was obtained as a colorless amorphous substance. The first fraction was separated in an optically-active column (Daicel's CHRALCEL OD column, 2 cm×25 cm; 0.1% diethylamine, hexane/isopropyl alcohol=8/2; flow rate, 15 mL/min). From the former fraction (retention time: 12.1 min), 2.7 mg of the (5S*,7R*) form was obtained as a colorless amorphous substance; and from the latter fraction (retention time: 14.9 min), 7.2 mg of the (5R*,7R*) form was obtained as a colorless amorphous substance. (The compounds were not identified, and for convenience sake, they were referred to as (5R*,7S*) form, (5S*,7S*) form, (5S*,7R*) form, (5R*,7R*) form.)

An equimolar amount of fumaric acid, chloroform and methanol were added in that order to the resulting (5S*,7R*) form, and stirred at room temperature. The solvent was evaporated off under reduced pressure to obtain the entitled compound as a white solid. The free amine of the compound was analyzed for assignment.

1H NMR (300 MHz, CDCl3) δ: 1.25-1.34 (3H, m), 1.55-2.42 (1H, m), 2.34 (3H, s), 2.69-2.89 (2H, m), 3.00-3.09 (3H, m), 4.96 (1H, dd, J=1.8, 8.0 Hz), 7.07-7.28 (5H, m), 8.33 (1H, s), 8.42 (1H, d, J=4.9 Hz)

ESI-MS Found: m/z 351.3 [M+H]+

Example 7

Production of (5R*,7R*)-7-(4-o-tolylpiperidin-1-ylmethyl)-6,7,8,9-tetrahydro-5H-cyclohepta[b]pyridin-5-ol monofumarate 1) 7-(4-O-tolylpiperidine-1-carbonyl)-6,7,8,9-tetrahydrocyclohepta[b]pyridin-5-one The entitled compound was obtained in the same manner as in 1 in Examples 1 to 4, for which, however, the compound obtained in Production Example 4 was used in place of ethyl 9-oxo-6,7,8,9-tetrahydro-5H-cyclohepta[b]pyridine-7-carboxylate used in 1 in Examples 1 to 4.

2) 7-(4-O-tolylpiperidin-1-ylmethyl)-6,7,8,9-tetrahydro-5H-cyclohepta[b]pyridin-5-ol The entitled compound was obtained in the same manner as in 2 in Examples 1 to 4, for which, however, the compound obtained in the above 1 was used in place of 7-(4-o-tolylpiperidine-1-carbonyl)-5,6,7,8-tetrahydrocyclohepta[b]pyridin-9-one used in 2 in Examples 1 to 4.

1H NMR (300 MHz, CDCl3) δ: 1.02-1.22 (1H, m), 1.32-1.43 (1H, m), 1.70-1.86 (4H, m), 2.01-2.2.34 (8H, m), 2.34 (3H, s), 2.65-2.76 (1H, m), 2.86-3.06 (3H, m), 3.13-3.20 (1H, m), 4.96 (1H, d, J=10.4 Hz), 7.07-7.26 (5H, m), 7.89-7.92 (1H, m), 8.32-8.34 (1H, m)

ESI-MS Found: m/z 351.3 [M+H]+

3) (5R*,7R*)-7-(4-o-tolylpiperidin-1-ylmethyl)-6,7,8,9-tetrahydro-5H-cyclohepta[b]pyridin-5-ol monofumarate 193 mg of the racemate obtained in the above 2 was optically resolved in an optically-active column (Daicel's CHRALCEL OD column, 2 cm×25 cm; 0.1% diethylamine, hexane/isopropyl alcohol=8/2; flow rate, 15 mL/min). From the former fraction (retention time; 10.1 min), 91.1 mg of (5S*,7S*)-7-(4-o-tolylpiperidin-1-ylmethyl)-6,7,8,9-tetrahydro-5H-cyclohepta[b]pyridin-5-ol was obtained as a colorless amorphous substance; and from the latter fraction (retention time: 18.1 min), 83.7 mg of the (5R*,7R*) form was obtained as a colorless amorphous substance. (The two were not identified, and for convenience sake, one was referred to as (5S*,7S*) form and the other was as (5R*,7R*) form.)

An equimolar amount of fumaric acid, chloroform and methanol were added in that order to the resulting (5R*,7R*) form, and stirred at room temperature. The solvent was evaporated off under reduced pressure to obtain the entitled compound as a white solid. The free amine of the compound was analyzed for assignment.

1HNMR and ESI-MS were the same as those of the racemate.

Example 8

Production of (7R*)-7-(4-o-tolylpiperidin-1-ylmethyl)-6,7,89-tetrahydro-5H-cyclohepta[b]pyridine monofumarate 28 mg of 20% palladium hydroxide-carbon catalyst and a few drops of 10% hydrochloric acid-methanol solution were added in that order to methanol (4.0 mL) solution of 18.2 mg of the compound obtained in Example 7, and in a hydrogen atmosphere, this was stirred at room temperature and under normal pressure for 20 hours. The reaction system was purged with nitrogen, and the catalyst was removed through filtration through Celite. The solvent was evaporated off under reduced pressure, aqueous saturated sodium hydrogencarbonate solution was added to the residue and extracted with chloroform. The chloroform layer was washed with saturated saline water, and dried with anhydrous sodium sulfate. The solvent was evaporated off under reduced pressure, and the residue was separated and purified through partitioning thin-layer chromatography (chloroform/methanol=9/1) to obtain 5.1 mg of (7R*)-7-(4-o-tolylpiperidin-1-ylmethyl)-6,7,8,9-tetrahydro-5H-cyclohepta[b]pyridine as a colorless amorphous substance.

An equimolar amount of fumaric acid, chloroform and methanol were added in that order to the above compound, and stirred at room temperature. The solvent was evaporated off under reduced pressure to obtain the entitled compound as a white solid. The free amine of the compound was analyzed for assignment.

1H NMR (300 MHz, CDCl3) δ: 1.03-1.26 (2H, m), 1.64-2.18 (1H, m), 2.34 (3H, s), 2.67-2.83 (3H, m), 2.97-3.17 (4H, m), 7.01-7.21 (4H, m), 7.26-7.28 (1H, m), 7.36-7.40 (1H, m), 8.29-8.31 (1H, m)

ESI-MS Found: m/z 335.3 [M+H]+

Production Example 6

Production of (7R,9S)-9-(tert-butyldimethylsilanyloxy)-6,7,8,9-tetrahydro-5H-cyclohepta[b]pyridin-7-ylmethyl toluene-4-sulfonate; and (7S,9R)-9-(tert-butyldimethylsilanyloxy)-6,7,8,9-tetrahydro-5H-cyclohepta[b]pyridin-7-ylmethyl toluene-4-sulfonate 1) Ethyl (7RS,9SR)-9-hydroxy-6,7,8,9-tetrahydro-5H-cyclohepta[b]pyridine-7-carboxylate Toluene (250 mL) solution of 13.74 g of the compound obtained in Production Example 1-4 (mixture with triphenylphosphine oxide) was heated under reflux at 130° C., while toluene (50 mL) solution of 13.5 mL of tri-n-butyltin hydride and 936 mg of V-40 (1,1'-azobis(cyclohexane)-1-carbonitrile) was dropwise added thereto little by little, and stirred for 1 hour. The reaction liquid was cooled to room temperature, the solvent was evaporated off under reduced pressure, hexane was added thereto and extracted with acetonitrile. The acetonitrile layer was concentrated, and the residue was separated and purified through silica gel column chromatography (hexane/ethyl acetate=1/1 to chloroform/methanol=100/1 to 10/1) to obtain 1.56 g of the entitled compound as a yellow oily substance.

2) Ethyl (7RS,9SR)-9-(tert-butyldimethylsilanyloxy)-6,7,8,9-tetrahydro-5H-cyclohepta[b]pyridine-7-carboxylate N,N-dimethylformamide (30 mL) solution of 1.55 g of the alcohol obtained in the above 1 and 1.35 g of imidazole was cooled with ice, and 1.99 g of tert-butyldimethylchlorosilane was added to the mixture. Then, this was heated up to room temperature, and stirred overnight. Water was added to the reaction liquid, and extracted with ethyl acetate. The organic layer was separated, and the residue was concentrated and purified through silica gel chromatography (hexane/ethyl acetate=20/1 to 5/1) to obtain 1.99 g of the entitled compound as a pale yellow oily substance.

3) (7RS,9SR)-9-(tert-butyldimethylsilanyloxy)-6,7,8, 9-tetrahydro-5H-cyclohepta[b]pyridine-7-methan-1-ol Tetrahydrofuran (40 mL) solution of 1.99 g of the product obtained in the above 2 was cooled with ice, and 432 mg of lithiumaluminium hydride was added to the resulting solution, and stirred at room temperature for 30 minutes. 4.32 g of sodium sulfate 10-hydrate was added to the reaction liquid little by little, and stirred overnight. 8.64 g of anhydrous sodium sulfate was added to the reaction suspension, and stirred at room temperature for 2 hours. The insoluble substance was removed through filtration, the filtrate was concentrated, and the residue was purified through silica gel chromatography (hexane/ethyl acetate=2/1 to 1/1) to obtain 1.65 g the entitled compound as a colorless oily substance.

4) (7R,9S)-9-(tert-butyldimethylsilanyloxy)-6,7,8,9-tetrahydro-5H-cyclohepta[b]pyridin-7-ylmethyl toluene-4-sulfonate; and (7S,9R)-9-(tert-butyldimethylsilanyloxy)-6,7,8,9-tetrahydro-5H-cyclohepta[b]pyridin-7-ylmethyl toluene-4-sulfonate Chloroform (30 mL) solution of 1.65 g of the compound obtained in the above 3, 656 mg of 4-dimethylaminopyridine and 1.50 mL of triethylamine was cooled with ice, and 2.05 g of p-toluenesulfonyl chloride was added to the resulting solution, and stirred overnight at room temperature. Water was added to the reaction liquid, and extracted with chloroform. The organic layer was concentrated, and the residue was separated and purified through silica gel chromatography (hexane/ethyl acetate=5/1 to 1/1) to obtain 2.32 g of the racemate of the entitled compound as a pale yellow oily substance. The resulting racemate was optically resolved in an optically-active column (Daicel's CHRALCEL OD column, 2 cm×25 cm; 0.1% diethylamine, hexane/isopropyl alcohol=95/5). From the former fraction (retention time; 12.0 min), 1.03 g of (7S,9R)-9-(tert-butyldimethylsilanyloxy)-6, 7,8,9-tetrahydro-5H-cyclohepta[b]pyridin-7-ylmethyl toluene-4-sulfonate was obtained as a yellow oily substance; and from the latter fraction (retention time: 18.0 min), 1.03 g of the (7R,9S) form was obtained as a yellow oily substance. (The absolute configuration of each compound was determined through asymmetric synthesis as in Production Example 7 mentioned below.)

Former Fraction, (7S,9R) Form:
Retention time, 6.2 min (optically-active column, Daicel's CHRALCEL OD column, 0.46 cm×25 cm; 0.1% diethylamine, hexane/isopropyl alcohol=9/1; flow rate, 1 mL/min).
1H NMR (300 MHz, CDCl3) δ: 0.01 (3H, s), 0.32 (3H, s), 1.10 (9H, s), 1.43 (1H, m), 1.71 (1H, t, J=13.2 Hz), 2.28 (2H, m), 2.72 (3H, s), 2.81 (1H, m), 2.93 (1H, m), 3.60 (1H, t, J=12.9 Hz), 4.15 (2H, m), 5.32 (1H, d, J=6.6 Hz), 7.34 (1H, dd, J=4.8, 7.4 Hz), 7.62 (3H, m), 8.05 (1H, d, J=8.2 Hz), 8.55 (1H, d, J=4.6 Hz)
ESI-MS Found: m/z 462 [M+H]+

Latter Fraction, (7R,9S) Form:
Retention time, 10.0 min (optically-active column, Daicel's CHRALCEL OD column, 0.46 cm×25 cm; 0.1% diethylamine, hexane/isopropyl alcohol=9/1; flow rate, 1 mL/min).

1H NMR and ESI-MS were the same as those of the (7S, 9R) form.

Production Example 7

Production of (7R,9S)-9-(tert-butyldimethylsilanyloxy)-6,7,8,9-tetrahydro-5H-cyclohepta[b]pyridin-7-ylmethyl toluene-4-sulfonate 1) (S)-4-isopropyl-3-(4-pentenoyl)-oxazolidin-2-one Tetrahydrofuran (2 L) solution of 108 g of (S)-4-isopropyl-oxazolidin-2-one was cooled in a dry ice bath at −70° C., 345 mL of 2.66 M n-butyllithium-hexane solution was added thereto, and the reaction liquid was stirred at −70° C. for 30 minutes. Next, 102 mL of 4-pentenoyl chloride was added thereto at −70° C., the reaction liquid was stirred for 30 minutes, and water was added thereto to stop the reaction. This was extracted with ethyl acetate, the organic layer was washed with aqueous saturated sodium deuteride solution, and dried with anhydrous sodium sulfate. The solvent was evaporated off under reduced pressure to obtain a crude product of the entitled compound.

2) (S)-3-[(2R)-2-benzyloxymethyl-4-pentenoyl]-4-isopropyl-oxazolidin-2-one

Dichloromethane (1 L) solution of the crude product obtained in the above 1 was cooled to 5° C., and 160 ml of diisopropylamine and 920 mL of 1 M titanium tetrachloride-dichloromethane solution were added thereto. 153 mL of benzyl chloromethyl ether was dropwise added to the mixture at 5° C., and after the addition, the reaction liquid was stirred with cooling with ice for 1.5 hours. Aqueous ammonium chloride solution was added to the reaction liquid, and extracted with chloroform. The organic layer was washed with saturated saline water and dried with anhydrous sodium sulfate. The solvent was evaporated off under reduced pressure to obtain a crude product of the entitled compound.

3) (R)-2-benzyloxymethyl-4-pentenecarboxylic acid

A mixture of 500 mL of tetrahydrofuran and 500 ml of water was cooled to 0° C., and 70 g of lithium hydroxide monohydrate and 330 mL of aqueous 30% hydrogen peroxide were added thereto in that order. The crude product obtained in the above 2 was dissolved in 1 L of tetrahydrofuran and 500 mL of water, and the resulting solution was gradually and dropwise added to the above mixture so that its inner temperature could be 15° C. or lower, and then this was stirred with cooling with ice for 2 hours. An aqueous solution of 530 g of sodium sulfite and an aqueous solution of 210 g of sodium hydrogencarbonate were added to it in that order, and then tetrahydrofuran was evaporated off under reduced pressure. Water was added to the mixture, and the aqueous layer was washed twice with chloroform. The aqueous layer was made acid with 6 N hydrochloric acid added thereto, and this was then extracted three times with chloroform. The organic layer was washed with saturated saline water, and dried with anhydrous sodium sulfate, and the solvent was evaporated off under reduced pressure to obtain 158 g of the entitled compound as a colorless oily substance.

4) (S)-2-benzyloxymethyl-4-penten-1-ol 157 g of the compound obtained in the above 3 was dissolved in 1.5 L of N,N-dimethylformamide, and cooled with ice. 140 g of 1,1'-carbonyldiimidazole was added to the solution, and the reaction liquid was stirred for 30 minutes with cooling with ice. 250 mL of an aqueous solution of 54 g of sodium borohydride was added to the reaction liquid with cooling with ice, and then the reaction was stopped with aqueous saturated ammonium chloride solution added thereto. This was extracted twice with diethyl ether, and the organic layer was washed with water and saturated saline water, and then dried with anhydrous sodium sulfate. The solvent was evaporated off under reduced pressure to obtain 114 g of the entitled compound as a colorless oily substance.

5) (R)-2-iodomethyl-4-pentenyloxymethylbenzene

Tetrahydrofuran (2.5 L) solution of 94 g of the compound obtained in the above 4 was cooled in an ice bath, and 128 mL of triethylamine and 42.7 mL of methanesulfonyl chloride were added thereto with its inner temperature kept not higher than 10° C. The reaction liquid was stirred in an ice bath for 30 minutes, and then water was added thereto, and tetrahydrofuran was evaporated off under reduced pressure. Diethyl ether and water were added to the residue for separation, and the organic layer was washed twice with 1 N hydrochloric acid, twice with aqueous saturated sodium hydrogencarbonate solution, and with saturated saline water, and then this was dried with anhydrous sodium sulfate. The solvent was evaporated off under reduced pressure, and the resulting crude product was dissolved in 600 mL of acetone. 7.7 g of sodium hydrogencarbonate and 345 g of sodium iodide were added to the solution, and stirred at room temperature for 2 days. Acetone was evaporated off under reduced pressure, and the residue was subjected to liquid-liquid separation with hexane and water added thereto. The organic layer was washed with saturated saline water, and dried with anhydrous sodium sulfate, and the solvent was evaporated off under reduced pressure to obtain 134 g of the entitled compound as a colorless oily substance.

6) 3-[(R)-3-benzyloxymethyl-5-hexenyl]-2-bromopyridine

Tetrahydrofuran (600 mL) solution of 32 mL of 2,2,6,6-tetramethylpiperidine was cooled to −70° C., and 78 mL of 2.66 M n-butyllithium-hexane solution was added thereto and heated up to 0° C. After stirred for 15 minutes, this was again cooled to −70° C., and 48.5 mL of DMPU was added thereto. 200 mL of tetrahydrofuran solution of 32.7 g of 2-bromo-3-picoline was added to the reaction liquid at −70° C., and stirred for 30 minutes. Tetrahydrofuran (200 mL) solution of 30 g of the iodine compound obtained in the above 5 was added to it with its inner temperature kept not higher than −60° C., and then the reaction liquid was stirred so that its inner temperature could be −30° C., taking 1.5 hours. Water was added to the reaction liquid all at a time to stop the reaction, and this was extracted with ethyl acetate. The organic layer was washed with water, aqueous saturated sodium hydrogencarbonate solution and saturated saline water, and dried with anhydrous sodium sulfate, and the solvent was evaporated off under reduced pressure. The resulting residue was purified through silica gel column chromatography (hexane/ethyl acetate=30/1 to 10/1) to obtain 21.0 g of the entitled compound as a pale yellow oily substance.

7) (R)-7-benzyloxymethyl-9-methylene-6,7,8,9-tetrahydro-5H-cyclohepta[b]pyridine 21.0 g of the compound obtained in the above 6 was dissolved in 1.2 L of N,N-dimethylformamide, and 40.4 mL of triethylamine, 1.30 g of palladium acetate and 3.60 g of 1,3-bisdiphenylphosphinopropane were added thereto, and the mixture was stirred overnight at 130° C. The reaction liquid was cooled to room temperature and extracted with diethyl ether, and the organic layer was washed with water and saturated saline water, and dried with anhydrous sodium sulfate. The solvent was evaporated off under reduced pressure, and the residue was purified through silica gel column chromatography (hexane/ethyl acetate=10/1 to 3/1) to obtain 13.0 g of the entitled compound as a brown oily substance.

8) (R)-7-tert-butyldimethylsilanyloxymethyl)-5,6,7,8-tetrahydro-5H-cyclohepta[b]pyridin-9-one 13.0 g of the compound obtained in the above 7 was dissolved in 500 mL of methanol, and cooled to −70° C. in a dry ice bath. The solution was stirred at an inner temperature of from −70 to −50° C. for 9 hours with ozone gas introduced thereinto. The excess ozone gas was removed by jetting nitrogen gas into it, and then the reaction liquid was heated up to −20° C., and 80 mL of dimethyl sulfide was added thereto. The mixture was heated up to room temperature and stirred for 1 hour at room temperature. The reaction mixture was concentrated under reduced pressure, diluted with ethyl acetate, and washed three times with water and then with saturated saline water. The organic layer was separated, dried with anhydrous magnesium sulfate, and the solvent was evaporated off under reduced pressure. The resulting crude product was dissolved in 400 mL of methanol, then 100 mL of aqueous 1 M sodium hydroxide solution was added thereto, and stirred at room temperature for 15 minutes. Methanol was evaporated off under reduced pressure, the residue was extracted with chloroform, and the organic layer was washed with aqueous saturated sodium hydrogencarbonate solution and saturated saline water, dried with anhydrous sodium sulfate, and concentrated under reduced pressure. The resulting crude product was dissolved in 300 mL of chloroform, and 4.23 g of imidazole and 9.36 g of tert-butyldimethylchlorosilane were added thereto, and the mixture was stirred at room temperature for 12 hours. The reaction liquid was washed with water and saturated saline water, dried with anhydrous sodium sulfate, and concentrated under reduced pressure. The resulting residue was purified through silica gel column chromatography to obtain 10.2 g of the entitled compound as a colorless oily substance.

9) (7R,9S)-7-hydroxymethyl-6,7,8,9-tetrahydro-5H-cyclohepta[b]pyridin-9-ol

Ethanol (300 mL) solution of 10.2 g of the compound obtained in the above 8 was heated up to 90° C., and 300 ml of toluene/ethanol (1:1) mixed solution of 22.4 mL of tributyltin hydride and 1.32 g of AIBN (2,2'-azobisisobutyronitrile) was added thereto. The reaction liquid was heated under reflux for 15 minutes, and the solvent was evaporated off under reduced pressure. 400 mL of tetrahydrofuran and 200 mL of 1 N hydrochloric acid were added to the resulting residue, and stirred at room temperature for 1 hour. Tetrahydrofuran was evaporated off under reduced pressure, and the remaining aqueous layer was washed twice with diethyl ether. The aqueous layer was make alkaline with aqueous 3 M sodium hydroxide solution added thereto, and extracted five times with chloroform. The organic layer was dried with anhydrous sodium sulfate, and the solvent was evaporated off. Diisopropyl ether was added to the resulting residue to obtain 4.00 g of the entitled compound as a white solid.

10) (7R,9S)-9-(tert-butyldimethylsilanyloxy)-6,7,8,9-tetrahydro-5H-cyclohepta[b]pyridine-7-methanol 7.05 g of imidazole and 9.33 g of tert-butyldimethylchlorosilane were added to 100 mL of N,N-dimethylformamide solution of 4.00 g of the compound obtained in the above 9, and stirred at room temperature for 24 hours. Water and ethyl acetate were added to the reaction liquid for separation, and the organic layer was washed with saturated saline water, dried with anhydrous magnesium sulfate, and then concentrated. 200 mL of tetrahydrofuran, 50 mL of water and 50 mL of 1 N hydrochloric acid were added to the residue, and stirred at room temperature for 1 hour. The reaction liquid was neutralized with aqueous saturated sodium hydrogencarbonate solution, and the solvent was evaporated off under reduced pressure. Aqueous sodium hydrogencarbonate solution and ethyl acetate were added to the residue for separation, and the aqueous layer was again extracted with ethyl acetate. The organic layers were combined, washed with saturated saline water, dried with anhydrous sodium sulfate, and concentrated to obtain 6.65 g of the entitled compound as a colorless solid.

11) (7R,9S)-9-(Tert-butyldimethylsilanyloxy)-6,7,8,9-tetrahydro-5H-cyclohepta[b]pyridin-7-ylmethyl toluene-4-sulfonate 9.30 g of the entitled compound was obtained in the same manner as in Production Example 6-4, for which, however, 5.43 g of the compound obtained in the above 10 was used. Through HPLC (Daicel's CHRALCEL OD column; 0.1% diethylamine, hexane/isopropyl alcohol=9/1), the compound had 94.8% ee.

Retention time, 10.0 min (optically-active column, Daicel's CHRALCEL OD column, 0.46 cm×25 cm; 0.1% diethylamine, hexane/isopropyl alcohol=9/1; flow rate, 1 mL/min).

1H NMR (300 MHz, CDCl3) δ: −0.28 (3H, s), 0.03 (3H, s), 0.81 (9H, s), 0.98-1.22 (1H, m), 1.39-1.50 (1H, m), 1.93-2.06 (1H, m), 2.42 (3H, s), 2.49-2.72 (2H, m), 3.28-3.37 (1H, m), 3.82-3.95 (2H, m), 5.02 (1H, d, J=7.6 Hz), 7.05 (1H, dd, J=6.2, 6.9 Hz), 7.32 (2H, d, J=8.2 Hz), 7.34 (1H, d, J=6.9 Hz), 7.77 (2H, d, J=8.2 Hz), 8.28 (1H, d, J=6.2 Hz)

ESI-MS Found: m/z 462.3 [M+H]+

Production Example 8

Production of spiro[8-aza-bicyclo[3.2.1]octa-3,1'(3'H)-isobenzofuran]monohydrochloride 1) 8-Aza-bicyclo[3.2.1]octan-3-one 25 g of tropinone was dissolved in 100 mL of chloroform, and 50 mL of chloroethyl chloroformate was added thereto, and stirred at room temperature for 6 hours. The reaction liquid was concentrated, and 100 mL of methanol was added thereto, and heated overnight under reflux. The reaction liquid was cooled to room temperature, and concentrated to obtain a crude product of the entitled compound.

2) Tert-butyl 3-oxo-8-aza-bicyclo[3.2.1]octane-8-carboxylate 9.0 g of the crude product obtained in the above 1 was dissolved in 20 mL of tetrahydrofuran, and 15 mL of di-tert-butyl dicarbonate was added thereto and stirred at room temperature for 1 hour. The reaction liquid was concentrated, and the resulting residue was separated and purified through silica gel column chromatography (hexane/ethyl acetate=5/1) to obtain 8.5 g of the entitled compound as a colorless oily substance.

3) Tert-butyl 3-hydroxy-3-(2-hydroxymethyl)phenyl-8-aza-bicyclo[3.2.1]octane-8-carboxylate 5.6 g of 2-bromobenzyl alcohol was dissolved in 20 mL of tetrahydrofuran, and 34.0 mL of 1.58 M n-butyllithium-hexane solution was added thereto at −78° C., and stirred for 10 minutes. Tetrahydrofuran (30 mL) solution of 6.0 g of the compound obtained in the above 2 was dropwise added to it, and stirred for 1 hour. The reaction liquid was heated up to room temperature, poured into aqueous saturated ammonium chloride solution, and extracted twice with ethyl acetate. The organic layer was washed with saline water, dewatered with anhydrous magnesium sulfate, filtered, and concentrated, and the resulting residue was separated and purified through silica gel column chromatography (hexane/ethyl acetate=1/1) to obtain 4.8 g of the entitled compound as a white solid.

4) Spiro[8-aza-bicyclo[3.2.1]octa-3,1'(3'H)-isobenzofuran]monohydrochloride 4.8 g of the compound obtained in the above 3 was dissolved in 40 mL of chloroform, and 1.76 g of 4-(dimethylamino)pyridine, 6.0 mL of triethylamine and 3.03 g of p-toluenesulfonyl chloride were added thereto in that order, and stirred at room temperature for 30 minutes. The reaction liquid was washed with aqueous saturated ammonium chloride solution and saline water in that order, dewatered with anhydrous magnesium sulfate, filtered and concentrated, and the resulting residue was separated and purified through silica gel column chromatography (hexane/ethyl acetate=5/1) to obtain 4.6 g of tert-butyl spiro[8-aza-bicyclo[3.2.1]octa-3,1'(3'H)-isobenzofuran]8-carboxylate as a colorless syrup. The compound was dissolved in 40 mL of methanol, and 10 mL of 4 N hydrogen chloride-dioxane solution was added thereto and stirred at room temperature for 3 hours. The reaction liquid was concentrated and dried to obtain 3.3 g of the entitled compound as a white solid.

1H NMR (300 MHz, CD3OD) δ: 2.05-2.68 (8H, m), 3.65 (1H, m), 4.11 (2H, s), 5.06 (2H, s), 7.17-7.32 (3H, m)

ESI-MS Found: m/z 216.1 [M+H]+

Examples 9 and 10

Production of (7R,9S)-7-(spiro[8-aza-bicyclo[3.2.1]octa-3,1'(3'H)-isobenzofuran]-8-ylmethyl)-6,7,8,9-tetrahydro-5H-cyclohepta[b]pyridin-9-ol; and (7S,9R)-7-(spiro[8-aza-bicyclo[3.2.1]octa-3,1'(3'H)-isobenzofuran]-8-ylmethyl)-6,7,8,9-tetrahydro-5H-cyclohepta[b]pyridin-9-ol 1) (7RS,9SR)-7-(spiro[8-aza-bicyclo[3.2.1]octa-3,1'(3'H)-isobenzofuran]-8-ylmethyl)-9-tert-butyldimethylsilyloxy-6,7,8,9-tetrahydro-5H-cyclohepta[b]pyridine 124 mg of sodium iodide and 0.21 mL of triethylamine were added in that order to N-methylpyrrolidone (1.0 mL) solution of 70 mg of (7RS,9SR)-9-(tert-butyldimethylsilanyloxy)-6,7,8,9-tetrahydro-5H-cyclohepta[b]pyridin-7-ylmethyl toluene-4-sulfonate obtained in Production Example 6 and 33 mg of spiro[8-aza-bicyclo[3.2.1]octa-3,1'(3'H)-isobenzofuran]monohydrochloride obtained in Production Example 8, and stirred in a nitrogen atmosphere at 90° C. for 5 hours. The reaction liquid was cooled to room temperature, and water, and aqueous saturated sodium hydrogencarbonate solution were added to the reaction liquid. This was extracted with ethyl acetate, and the ethyl acetate layer was washed with saturated saline water, and dried with anhydrous sodium sulfate. The solvent was evaporated off under reduced pressure, and the residue was separated and purified through silica gel column chromatography (hexane/ethyl acetate=19/1) to obtain 40 mg of the entitled compound as a white solid.

ESI-MS Found: m/z 505.3 [M+H]+

2) (7R,9S)-7-(spiro[8-aza-bicyclo[3.2.1]octa-3,1'(3'H)-isobenzofuran]-8-ylmethyl)-6,7,8,9-tetrahydro-5H-cyclohepta[b]pyridin-9-ol; and (7S,9R)-7-(spiro[8-aza-bicyclo[3.2.1]octa-3,1'(3'H)-isobenzofuran]-8-ylmethyl)-6,7,8,9-tetrahydro-5H-cyclohepta[b]pyridin-9-ol 1 mL of 1 M tetrabutylammonium fluoride-tetrahydrofuran solution was added to the compound obtained in the above 1, and stirred at 50° C. for 4 hours. Then, the reaction liquid was cooled to room temperature. Water was added to the reaction liquid, and extracted with ethyl acetate. The ethyl acetate layer was washed with saturated saline water, and dried with anhydrous sodium sulfate. The solvent was evaporated off under reduced pressure, and the residue was separated and purified through basic silica gel column chromatography (hexane/ethyl acetate=9/1 to 4/1) to obtain 19 mg of a racemate of the entitled compounds. The racemate was optically resolved in an optically-active column (Daicel's CHRALPAC AD column, 2 cm×25 cm; 0.1% diethylamine, hexane/isopropyl alcohol=9/1; flow rate, 20 mL/min). From the former fraction (retention time; 8.1 min), 6.4 mg of (7S,9R)-7-(spiro[8-aza-bicyclo[3.2.1]octa-3,1'(3'H)-isobenzofuran]-8-ylmethyl)-6,7,8,9-tetrahydro-5H-cyclohepta[b]pyridin-9-ol was obtained; and from the latter fraction (retention time; 9.8 min), 6.4 mg of the (7R,9S) form was obtained, both as a white powder.

Compound of Example 9

(7S,9R) Form

1H NMR (400 MHz, CDCl3) δ: 1.48-1.75 (1H, m), 1.75-1.90 (3H, m), 1.90-2.10 (4H, m), 2.10-2.32 (5H, m), 2.56-2.74 (3H, m), 2.83-3.00 (1H, m), 3.18-3.32 (2H, m), 4.93 (1H, d, J=7.7 Hz), 5.01 (2H, s), 5.45 (1H, s), 7.06-7.30 (5H, m), 7.44 (1H, d, J=7.3 Hz), 8.36 (1H, d, J=5.1 Hz)
ESI-MS Found: m/z 391.2 [M+H]+

Compound of Example 10

(7R,9S) Form

1H NMR and ESI-MS were the same as those of the compound of Example 9.

Production Example 9

Production of (7R*)-5,6,7,8-tetrahydrospiro[cyclohepta[b]pyridin-9,2'-[1,3]-dioxolan]-7-ylmethyl toluene-4-sulfonate; and (7S*)-5,6,7,8-tetrahydrospiro[cyclohepta[b]pyridin-9,2'-[1,3]-dioxolan]-7-ylmethyl toluene-4-sulfonate 1) Ethyl 5,6,7,8-tetrahydrospiro[cyclohepta[b]pyridin-9,2'-[1,3]-dioxolan]-7-carboxylate 6.76 g of ethyl 9-oxo-6,7,8,9-tetrahydro-5H-cyclohepta[b]pyridine-7-carboxylate obtained in Production Example 1 was dissolved in 200 mL of toluene, and 30 mL of ethylene glycol and 1.65 g of p-toluenesulfonic acid monohydrate were added thereto. The reaction mixture was heated under reflux for 12 hours in a Dean-Stark water separator. This was cooled to room temperature, neutralized with saturated sodium deuteride solution, and extracted with ethyl acetate. The organic layer was washed with saturated saline water, and concentrated. The residue was separated and purified through silica gel column chromatography (hexane/ethyl acetate) to obtain 5.39 g of the entitled compound as a pale yellow oily substance.

2) 5,6,7,8-Tetrahydrospiro[cyclohepta[b]pyridine-9,2'-[1,3]-dioxolane]-7-methanol In a nitrogen atmosphere, tetrahydrofuran (30.0 mL) solution of 3.68 g of lithiumaluminium hydride was cooled to 0° C., and tetrahydrofuran (30.0 mL) solution of 5.39 g of the compound obtained in the above 1 was dropwise added thereto. The reaction liquid was stirred at 0° C. for 1 hour, and then 3.7 mL of water, 3.7 mL of aqueous 1 M sodium hydroxide solution and 11.3 mL of water were added thereto. The reaction mixture was filtered through Celite, the filtrate was diluted with chloroform, and washed with water and saturated saline water. The organic layer was separated, dried with magnesium sulfate, and concentrated. 4.81 g of the thus-obtained crude product was used in the next reaction, without purification.

ESI-MS Found: m/z 236.3 [M+H]+

3) (7R*)-5,6,7,8-tetrahydrospiro[cyclohepta[b]pyridin-9,2'-[1,3]-dioxolan]-7-ylmethyl toluene-4-sulfonate; and (7S*)-5,6,7,8-tetrahydrospiro[cyclohepta[b]pyridin-9,2'-[1,3]-dioxolan]-7-ylmethyl toluene-4-sulfonate 750 mg of N,N-4-dimethylaminopyridine, 14.3 mL of triethylamine and 7.80 g of p-toluenesulfonic acid chloride were added to tetrahydrofuran (50.0 mL) solution of 4.81 g of the crude product obtained in the above 2, and the reaction liquid was stirred at 50° C. for 2 hours. The reaction liquid was cooled to room temperature, diluted with ethyl acetate, washed with saturated saline water, and dried with anhydrous magnesium sulfate. The solvent was evaporated off under reduced pressure, and the residue was separated and purified through silica gel column chromatography (hexane/ethyl acetate) to obtain 3.88 g of a racemate of the entitled compounds as a colorless-solid.

1HNMR (300 MHz, CDCl3) δ: 1.13-1.31 (1H, m), 1.68-1.75 (1H, m), 1.94-2.08 (2H, m), 2.43 (3H, s), 2.51-2.72 (2H, m), 3.19-3.30 (1H, m), 3.66 (1H, dd, J=3.0, 6.3 Hz), 3.88 (1H, d, J=4.2 Hz), 3.99 (1H, dd, J=3.0, 6.3 Hz), 4.12 (1H, dd, J=3.3, 6.3 Hz), 4.28 (1H, dd, J=3.3, 6.3 Hz), 7.10 (1H, dd, J=2.4, 6.2 Hz), 7.32 (1H, d, J=6.8 Hz), 7.39 (1H, d, J=6.2 Hz), 7.78 (1H, d, J=6.8 Hz), 8.40 (1H, d, J=2.4 Hz)

ESI-MS Found: m/z 390.1 [M+H]+

2.28 g of the racemate was optically resolved in an optically-active column (Daicel's CHRAPAK OD column, 2 cm×25 cm; 0.1% diethylamine, hexane/isopropyl alcohol=9/1; flow rate, 20 mL/min). From the former fraction, 1.10 g of (7R*)-5,6,7,8-tetrahydrospiro[cyclohepta[b]pyridin-9,2'-[1,3]-dioxolan]-7-ylmethyl toluene-4-sulfonate was obtained; and from the latter fraction, 1.13 g of the (7S*) form was obtained. (The two were not identified, and for convenience sake, one was referred to as 7R* form and the other was as 7S* form.)

Former Fraction, (7R*) Form:
Retention time, 10.2 min (optically-active column, Daicel's CHRALPAK OD column, 0.46 cm×25 cm; 0.1% diethylamine, hexane/isopropyl alcohol=9/1; flow rate, 1 mL/min).

Latter Fraction, (7S*) Form:
Retention time, 13.2 min (optically-active column, Daicel's CHRALPAK OD column, 0.46 cm×25 cm; 0.1% diethylamine, hexane/isopropyl alcohol=9/1; flow rate, 1 mL/min).

Example 11

Production of (7R*)-8-(5,6,7,8-tetrahydro-spiro[cyclohepta[b]pyridine-9,2'-[1,3]-dioxolan])-7-ylmethyl-spiro[8-aza-bicyclo[3.2.1]octa-3,1'(3'H)-isobenzofuran]monofumarate 172 mg of sodium iodide and 0.31 mL of triethylamine were added in that order to N-methylpyrrolidone (1.2 mL) solution of 84 mg of (7R*)-5,6,7,8-tetrahydrospiro[cyclohepta[b]pyridine-9,2'-[1,3]dioxolan]-7-ylmethyl toluene-4-sulfonate obtained in Production Example 9 and 53 mg of spiro[8-aza-bicyclo[3.2.1]octa-3,1'(3'H)-isobenzofuran] monohydrochloride obtained in Production Example 8, and stirred in a nitrogen atmosphere at 90° C. for 4 hours. The reaction liquid was cooled to room temperature, and water and aqueous saturated sodium hydrogencarbonate solution were added to the reaction liquid, and extracted with ethyl acetate. The ethyl acetate layer was washed with saturated saline water, and dried with anhydrous sodium sulfate. The solvent was evaporated off under reduced pressure, and the residue was separated and purified through silica gel column chromatography (chloroform/methanol=49/1) to obtain 67 mg of (7R*)-8-(5,6,7,8-tetrahydro-spiro[cyclohepta[b]pyridine-9,2'-[1,3]dioxolan])-7-ylmethyl-spiro[8-aza-bicyclo[3.2.1]octa-3,1'(3'H)-isobenzofuran] as a white powder.

An equimolar amount of fumaric acid and ethanol were added to 21.6 mg of the above compound, and the compound was dissolved therein. Then, the solvent was evaporated off under reduced pressure, and ethyl acetate/hexane was added to the residue to wash it. The wash was removed, and the residue was dried under reduced pressure to obtain 25 mg of the entitled compound as a white solid.

1H NMR (300 MHz, CD3OD) δ: 1.16-1.40 (1H, m), 1.84 (1H, dd, J=12.2, 13.3 Hz), 2.08-2.38 (6H, m), 2.46-2.63 (2H, m), 2.65-2.90 (4H, m), 3.04 (2H, d, J=6.6 Hz), 3.30-3.50 (1H, m), 4.01-4.20 (6H, m), 5.09 (2H, s), 6.69 (2H, s), 7.22-7.40 (5H, m), 7.64 (1H, d, J=7.4 Hz), 8.33 (1H, d, J=4.9 Hz)

ESI-MS Found: m/z 433.2 [M+H]+

Example 12

Production of (7R*)-7-(spiro[8-aza-bicyclo[3.2.1]octa-3,1'(3'H)-isobenzofuran]-8-ylmethyl)-6,7,8,9-tetrahydro-5H-cyclohepta[b]pyridin-9-one monofumarate 1.8 mL of 4 N hydrogen chloride-dioxane solution and 0.6 mL of water were added to 46 mg of the free amine compound obtained in Example 11, and heated under reflux for 14 hours. The reaction liquid was cooled to room temperature, neutralized with water and aqueous 1 M sodium hydroxide solution added thereto, and extracted with ethyl acetate. The ethyl acetate layer was washed with saturated saline water, and dried with anhydrous sodium sulfate, and the solvent was evaporated off under reduced pressure. The residue was separated and purified through silica gel column chromatography (chloroform/methanol=97/3) to obtain 38 mg of (7R*)-7-(spiro[8-aza-bicyclo[3.2.1]octa-3,1'(3'H)-isobenzofuran]-8-ylmethyl)-6,7,8,9-tetrahydro-5H-cyclohepta[b]pyridin-9-one as a brown oily substance. An equimolar amount of fumaric acid and ethanol were added to the compound to dissolve it, and the solvent was evaporated off under reduced pressure to obtain 49 mg of the entitled compound as a brown solid.

1H NMR (300 MHz, CD3OD) δ: 1.13-1.40 (1H, m), 1.65-1.85 (1H, m), 2.05-2.35 (4H, m), 2.35-2.80 (4H, m), 2.80-3.25 (4H, m), 3.51-3.80 (2H, m), 3.97-4.20 (3H, m), 5.08 (2H, s), 6.70 (21H, s), 7.18-7.42 (4H, m), 7.53 (1H, dd, J=4.6, 7.6 Hz), 7.87 (1H, d, J=7.6 Hz), 8.56 (1H, d, J=4.6 Hz)

ESI-MS Found: m/z 389.2 [M+H]+

Example 13

Production of (7R*,9S*)-7-(spiro[8-aza-bicyclo[3.2.1]octa-3,1'(3'H)-isobenzofuran]-8-ylmethyl)-9-methyl-6,7,8,9-tetrahydro-5H-cyclohepta[b]pyridin-9-ol monofumarate 70.1 mg of the free amine compound obtained in Example 12 was dissolved in 2 mL of tetrahydrofuran, and 180 mL of diethyl ether solution (3.0 M) of methylmagnesium bromide was added thereto at room temperature, and stirred for 30 minutes. The reaction liquid was poured into aqueous saturated ammonium chloride solution, extracted twice with ethyl acetate, and the organic layer was washed with saline water, dewatered with anhydrous magnesium sulfate, filtered and concentrated, and the resulting residue was separated and purified through silica gel column chromatography (aqueous 0.1% ammonia, chloroform/methanol=15/1) to obtain (7R*, 9S*)-7-(spiro[8-aza-bicyclo[3.2.1]octa-3,1'(3'H)-isobenzofuran]-8-ylmethyl)-9-methyl-6,7,8,9-tetrahydro-5H-cyclohepta[b]pyridin-9-ol. (Its stereochemical structure was not identified, and for convenience sake, it was referred to as (7R*,9S*) form.) The compound was dissolved in methanol, and an equimolar amount of fumaric acid was added thereto, concentrated, and dried to solidness under reduced pressure to obtain 31.2 mg of the entitled compound as a white solid. The free amine of the compound was analyzed for assignment.

1H NMR (300 MHz, CDCl3) δ: 1.48 (3H, s), 1.65-2.41 (1H, m), 2.64 (1H, m), 2.98 (1H, m), 3.17 (2H, brs), 3.60-3.80 (5H, m), 4.98 (2H, s), 7.08-8.41 (7H, m)

ESI-MS Found: m/z 405.2 [M+H]+

Production Example 10

Production of (6R,8S)-8-triethylsilanyloxy-5,6,7,8-tetrahydroquinolin-6-ylmethyl toluene-4-sulfonate 1) Ethyl 3-(2-chloropyridin-3-yl)acrylate In a nitrogen atmosphere, 121 mL of 1.01 M diisobutylaluminium hydride-hexane solution was dropwise added to toluene (280 mL) solution of 13.9 g of 2-chloronicotinonitrile at 0° C., and stirred at 0° C. for 1 hour. Ice and 420 mL of 2 N hydrochloric acid were added in that order at 0° C. to the reaction liquid, and stirred at room temperature for 1 hour. The reaction liquid was extracted with ethyl acetate, and the ethyl acetate layer was washed with saturated saline water, and dried with anhydrous sodium sulfate. The solvent was evaporated off under reduced pressure to obtain 10.4 g of crude 2-chloropyridine-3-carbaldehyde. In a nitrogen atmosphere, 1.54 g of 60% sodium hydride (oily) was added to tetrahydrofuran (80 mL) solution of 7.7 mL of triethyl phosphonoacetate at 0° C., and stirred at 0° C. for 20 minutes. Tetrahydrofuran (80 mL) solution of 5.48 g of the compound obtained was added to the reaction liquid at 0° C., and stirred at 0° C. for 1 hour. Aqueous saturated ammonium chloride solution was added to the reaction liquid, heated up to room temperature, and extracted with ethyl acetate. The ethyl acetate layer was washed with saturated saline water, and dried with anhydrous sodium sulfate. The solvent was evaporated off under reduced pressure, and the residue was crystallized (hexane/ethyl acetate), separated and purified to obtain 7.14 g of the entitled compound as a pale yellow solid.

2) Ethyl 3-(2-chloro-pyridin-3-yl)-propionate 13.6 g of cuprous chloride and 5.18 g of sodium borohydride were added to methanol/water (4:1) (500 mL) mixed solution of 29.9 g of the compound obtained in the above 1, with cooling with ice, and stirred at that temperature for 45 minutes. Confirming the disappearance of the starting compounds through thin-layer chromatography, 5.18 g of sodium borohydride was, as divided into two, added to it at two times, and stirred at that temperature, and then the reaction liquid was concentrated. The residue was diluted with ethyl acetate, washed with aqueous saturated ammonium chloride solution, and the ethyl acetate layer was dried with anhydrous sodium sulfate. The solvent was evaporated off under reduced pressure, and the residue was separated and purified through silica gel column chromatography (hexane/ethyl acetate=10/1) to obtain 26.3 g of the entitled compound as a pale yellow oily substance.

3) Ethyl 3-[2-(1-ethoxyvinyl)pyridin-3-yl]-propionate

In a nitrogen atmosphere, 43.4 mL of tributylethoxyvinyltin and 6.85 g of tetrakistriphenylphosphine palladium were added to N,N-dimethylformamide (400 mL) solution of 21.1 g of the compound obtained in the above 2, and stirred at 120° C. for 4 hours. The reaction liquid was cooled to room temperature, and the insoluble solid substance was removed through filtration through Celite. The filtrate was diluted with ethyl acetate, washed with aqueous saturated sodium chloride solution, and the ethyl acetate layer was dried with anhydrous sodium sulfate. The solvent was evaporated off under reduced pressure, and the residue was separated and purified through silica gel column chromatography (hexane/ethyl acetate=10/1) to obtain 22.9 g of the entitled compound as a brown oily substance.

4) Ethyl 3-[2-(2-bromoacetyl)-pyridin-3-yl]-propionate 20.6 g of N-bromosuccinic acid was added to tetrahydrofuran/water (15:1) (500 mL) mixed solution of 22.9 g of the compound obtained in the above 3, and stirred at room temperature for 20 minutes. The solvent was evaporated off under reduced pressure, and the residue was separated and purified through silica gel column chromatography (hexane/ethyl acetate=2/1) to obtain 18.9 g of the entitled compound as a gray oily substance.

5) Ethyl 3-[2-(1-hydroxyethyl)-pyridin-3-yl]-propionate

In a nitrogen atmosphere, 68.2 mL of 0.9 M borane-tetrahydrofuran complex-tetrahydrofuran solution was added to tetrahydrofuran (350 mL) solution of 18.4 g of the compound obtained in the above 4, at −18° C., and stirred at −18° C. for 40 minutes. Then, 300 ml of methanol was added to the reaction liquid, and stirred at room temperature for 1 hour. The solvent was evaporated off under reduced pressure, and the residue was separated and purified through silica gel column chromatography (hexane/ethyl acetate=5/1) to obtain 12.7 g of the entitled compound as a pale yellow oily substance.

6) Ethyl (6RS,8SR)-8-triethylsilanyloxy-5,6,7,8-tetrahydroquinoline-6-carboxylate 14.7 mL of triethylchlorosilane and 11.9 g of imidazole were added to N,N-dimethylformamide (260 mL) solution of 13.2 g of the compound obtained in the above 5, and stirred overnight at room temperature. The reaction liquid was diluted with ethyl acetate, and washed with aqueous saturated sodium chloride solution, and then the ethyl acetate layer was dried with anhydrous sodium sulfate. The solvent was evaporated off under reduced pressure, and the residue was separated and purified through silica gel column chromatography (hexane/ethyl acetate=20/1) to obtain 21.7 g of ethyl 3-[2-(2-bromo-1-triethylsilanyloxyethyl)-pyridin-3-yl]-propionate as a pale yellow oily substance. This contained reagent-derived impurities. In a nitrogen atmosphere, 52.4 mL of 1.0 M sodium bistrimethylsilylamide-tetrahydrofuran solution was added to tetrahydrofuran (300 mL) solution of 21.7 g of the above compound at −18° C., and stirred at −18° C. for 35 minutes. Still at −18° C. 26.2 ml of 1.0 M sodium bistrimethylsilylamide-tetrahydrofuran solution was added to it, and stirred for 80 minutes. Aqueous saturated ammonium chloride solution was added to the reaction liquid, and extracted with ethyl acetate. The ethyl acetate layer was washed with aqueous saturated ammonium chloride solution, and dried with anhydrous sodium sulfate. The solvent was evaporated off under reduced pressure, and the residue was separated and purified through silica gel column chromatography (hexane/ethyl acetate=20/1) to obtain 7.44 g of the entitled compound as a brown oily substance.

1H NMR (400 MHz, CDCl3) δ: 0.67 (6H, m), 0.93 (9H, m), 1.30 (3H, t, J=7.0 Hz), 1.92 (1H, m), 2.39 (1H, m), 2.93 (1H, m), 3.08 (1H, m), 3.28 (1H, m), 4.12 (2H, q, J=7.0 Hz), 4.87 (1H, t, J=3.1 Hz), 7.11 (1H, m), 7.40 (1H, m), 8.41 (1H, m)

ESI-MS Found: m/z 336.3 [M+H]+

This compound was produced also according to the method mentioned below.

At 60° C., ethanol (250 mL) solution of 500 g of ethyl 4-cyclohexanecarboxylate is added to ethanol (2.5 L) solution of 376 mL of propargylamine and 29.2 g of sodium tetrachloroaurate(III) dihydrate, and stirred overnight with reflux. The insoluble solid substance was removed through filtration through Celite, and the solvent was evaporated off under reduced pressure. The residue was separated and purified through silica gel column chromatography (hexane/ethyl acetate=1/1) to obtain 555 g of ethyl 5,6,7,8-tetrahydroquinoline-6-carboxylate as a brown oily substance. The compound contained impurities.

1H NMR (400 MHz, CDCl3) δ: 1.29 (3H, t, J=7.1 Hz), 2.00 (1H, m), 2.30 (1H, m), 2.77 (1H, m), 3.02 (4H, m), 4.19 (2H, q, J=7.1 Hz), 7.05 (1H, dd, J=4.7, 7.8 Hz), 7.40 (1H, d, J=7.8 Hz), 8.38 (1H, d, J=4 Hz).

At 0° C. 1.04 kg of metachloroperbenzoic acid was added to chloroform (6 L) solution of 689 g of the compound obtained in the above, and stirred at room temperature for 3 hours. 1:1 mixed solution of aqueous saturated sodium hydrogencarbonate solution and aqueous saturated sodium sulfite solution was added to the reaction liquid, and extracted with chloroform. The organic layer was washed with aqueous saturated sodium hydrogencarbonate solution and aqueous saturated sodium chloride solution, and dried with anhydrous sodium sulfate, and the solvent was evaporated off under reduced pressure to obtain ethyl 5,6,7,8-tetrahydroquinoline-6-carboxylate 1-oxide. The obtained compound was dissolved in 2 L of acetic anhydride, and stirred at 130° C. for 1 hour. The reaction liquid was distilled under reduced pressure, and diluted with aqueous saturated sodium hydrogencarbonate solution, and extracted with chloroform. The solvent was evaporated off under reduced pressure to obtain a mixture of ethyl (6RS,8SR)-8-acetoxy-5,6,7,8-tetrahydroquinoline-6-carboxylate and ethyl (6RS,8RS)-8-acetoxy-5,6,7,8-tetrahydroquinoline-6-carboxylate. At 0° C., ethanol (3.36 L) solution of 77.2 g of sodium was added to tetrahydrofuran (3 L) solution of the resulting mixture, and stirred at 0° C. for 1 hour. Aqueous saturated ammonium chloride solution was added to the reaction liquid, then extracted with chloroform, and the organic layer was dried with anhydrous sodium sulfate. The solvent was evaporated off under reduced pressure, and the residue was separated and purified through silica gel column chromatography (hexane/ethyl acetate=2/1) to obtain 336 g of ethyl (6RS,8SR)-8-hydroxy-5,6,7,8-tetrahydroquinoline-6-carboxylate as a brown oily substance. This compound contained impurities.

1H NMR (400 MHz, CDCl3) δ: 1.29 (3H, t, J=7.0 Hz), 2.23 (1H, m), 2.30 (1H, m), 3.00 (3H, m), 3.12 (1H, m), 4.19 (2H, q, J=7.0 Hz), 7.18 (1H, dd, J=4.7, 7.8 Hz), 7.50 (1H, d, J=7.8 Hz), 8.43 (1H, dd, J=1.2, 4.7 Hz)

At 0° C. 510 mL of chlorotriethylsilane, 634 mL of triethylamine and 18.6 g of N,N-dimethylaminopyridine were added to chloroform (5 L) solution of 336 g of the compound obtained in the above, and stirred at room temperature for 3 hours. Then, the reaction liquid was diluted with water, and extracted with chloroform. The organic layer was dried with anhydrous sodium sulfate, and the solvent was evaporated off under reduced pressure. The residue was separated and purified through silica gel column chromatography (hexane/ethyl acetate=20/1) to obtain 276 g of the entitled compound.

7) (6R,8S)-(8-triethylsilanyloxy-5,6,7,8-tetrahydroquinolin-6-yl)methanol and (6S,8R)-(8-triethylsilanyloxy-5,6,7,8-tetrahydroquinolin-6-yl)methanol 5.32 g of a racemate of the entitled compounds was obtained in the same manner as in Production Example 6-3, for which, however, the compound obtained in the above 6 was used in place of ethyl (7RS,9SR)-9-(tert-butyldimethylsilanyloxy)-6,7,8,9-tetrahydro-5H-cyclohepta[b]pyridine-7-carboxylate used in Production Example 6-3. The racemate was optically resolved in an optically-active column (Daicel's CHRALPAK AD column, 2 cm×25 cm; 0.1% diethylamine, hexane/isopropyl alcohol=50:1; flow rate, 20 mL/min). From the former fraction (retention time; 14.0 min), 2.05 g of (6R,8S)-(8-triethylsilanyloxy-5,6,7,8-tetrahydroquinolin-6-yl)methanol was obtained; and from the latter fraction (retention time; 18.0 min), 2.37 g of the (6S,8R) form was obtained.

Former Fraction, (6R,8S) Form:

1H NMR (400 MHz, CDCl3) δ: 0.66 (3H, m), 0.92 (9H, m), 1.60 (3H, m), 2.09 (1H, m), 2.50 (2H, m), 2.95 (1H, m), 3.67 (2H, m), 5.16 (1H, t, J=2.7 Hz), 7.09 (1H, m), 7.39 (1H, m), 8.40 (1H, m)

ESI-MS Found: m/z 294.3 [M+H]+

Latter Fraction, (6S,8R) Form:

1H NMR and ESI-MS were the same as those of the (6R, 8S) form.

8) (6R,8S)-8-Triethylsilanyloxy-5,6,7,8-tetrahydroquinolin-6-ylmethyl toluene-4-sulfonate 2.98 g of the entitled compound was obtained in the same manner as in Production Example 6-4, for which, however, the compound obtained in the above 7 was used in place of (7RS,9SR)-9-(tert-butyldimethylsilanyloxy)-6,7,8,9-tetrahydro-5H-cyclohepta[b]pyridine-7-methan-1-ol used in Production Example 6-4, and the product was not optically resolved.

1H NMR (400 MHz, CDCl3) δ: 0.60 (3H, m), 0.88 (3H, t, J=7.7 Hz), 1.59 (1H, m), 1.94 (1H, m), 2.45 (3H, s), 2.49 (1H, dd, J=5.1, 16.5 Hz), 2.67 (1H, m), 2.89 (1H, dd, J=5.1, 16.5 Hz), 4.01 (1H, dd, J=6.2, 9.5 Hz), 4.10 (1H, m), 4.82 (1H, t, J=2.9 Hz), 7.08 (1H, m), 7.34 (3H, m), 7.79 (2H, m), 8.38 (1H, m)

ESI-MS Found: m/z 448.3 [M+H]+

Production Example 11

Production of spiro[isobenzofuran-1(3H),4'-piperidine]monohydrochloride 1) 1-Benzyl-4-(2-hydroxymethylphenyl)piperidin-4-ol 1.83 g of the entitled compound was obtained as a pale yellow oily substance in the same manner as in Production Example 8-3, for which, however, 1-benzyl-4-piperidone was used in place of tert-butyl 3-oxo-8-aza-bicyclo[3.2.1]octane-8-carboxylate used in Production Example 8-3.

2) 1'-Benzyl-spiro[isobenzofuran-1(3H),4'-piperidine]monohydrochloride 227 g of the entitled compound was obtained as a white solid in the same manner as in Production Example 8-4, for which, however, the compound obtained in the above 1 was used in place of tert-butyl 3-hydroxy-3-(2-hydroxymethyl) phenyl-8-aza-bicyclo[3.2.1]octane-8-carboxylate used in Production Example 8-4.

The free amine of the compound was analyzed for assignment.

3) Spiro[isobenzofuran-1(3H),4'-piperidine]monohydrochloride 31.0 g of 20% palladium hydroxide-carbon catalyst was added to methanol (1 L) solution of 227 g of the compound obtained in the above 2, and stirred in a hydrogen atmosphere at room temperature under normal pressure for 21 hours. The reaction system was purged with nitrogen, and the catalyst was removed through filtration through Celite. Then, the solvent was concentrated under reduced pressure, and the resulting white solid was taken out through filtration, washed with isopropanol and dried under reduced pressure to obtain 93.2 g of the entitled compound as a white solid. The free amine of the compound was analyzed for assignment.

1H NMR (300 MHz, CDCl3) δ: 1.89-1.92 (2H, m), 2.46 (2H, td, J=4.8, 13.8 Hz), 3.39-3.54 (4H, m), 5.09 (2H, s), 7.22-7.33 (4H, m), 9.61 (1H, brs)

ESI-MS Found: m/z 189.9 [M]+

Example 14

Production of (6R,8S)-6-(spiro[isobenzofuran-1(3H), 4'-piperidin]-1'-ylmethyl)-5,6,7,8-tetrahydroquinolin-8-ol)mono-L-tartrate 13.8 mg of a free amine form of the entitled compound was obtained in the same manner as in Examples 9 to 10, for which, however, the compound obtained in Production Example 10 and the compound obtained in Production Example 11 were used in place of (7R,9S)-9-(tert-butyldimethylsilanyloxy)-6,7,8,9-tetrahydro-5H-cyclohepta[b]pyridin-7-ylmethyl toluene-4-sulfonate and spiro[8-aza-bicyclo [3.2.1]octa-3,1'(3'H)-isobenzofuran]monohydrochloride used in Examples 9 to 10, N,N-dimethylformamide was used in place of N-methylpyrrolidone, and the product was not optically resolved. An equimolar amount of L-tartaric acid and ethanol were added to the obtained free amine compound to dissolve it, and the solvent was evaporated off under reduced pressure. The residue was washed with ethyl acetate-hexane added thereto. The wash was removed, and the residue was dried under reduced pressure to obtain 18.9 mg of the entitled compound as a white solid.

1H NMR (400 MHz, CD3OD) δ: 1.73-1.88 (1H, m), 1.92-2.08 (2H, m), 2.56-2.2.80 (2H, m), 3.05-3.18 (1H, m), 3.18-

3.47 (4H, m), 3.55-3.68 (2H, m), 4.43 (2H, 4.80-4.95 (1H, m), 5.11 (2H, s), 7.24-7.30 (5H, m), 7.67 (1H, d, J=7.3 Hz), 8.42 (1H, d, J=4.4 Hz)

ESI-MS Found: m/z 351.3 [M+H]+

Production Example 12

Production of (3R*,4R*)-4-o-tolyl-piperidin-3-ol, and (3S*4S*)-4-o-tolyl-piperidin-3-ol 1) 1-Benzyl-4-o-tolyl-1,2,3,6-tetrahydropyridine 600 mL of 0.5 M o-tolylmagnesium bromide-tetrahydrofuran solution was cooled to 0° C., and 200 mL of tetrahydrofuran solution of 40.0 g of 1-benzylpiperidin-4-one was dropwise added thereto, over 10 minutes. Cooled with ice, the reaction mixture was stirred further for 30 minutes. Then, aqueous saturated ammonium chloride solution was added thereto to stop the reaction, and this was extracted three times with ethyl acetate. The organic layer was washed with saturated saline water, dried with anhydrous magnesium sulfate, and the solvent was evaporated off under reduced pressure. 300 mL of trifluoroacetic acid was added to the resulting residue, heated up to 80° C., and stirred for 2 hours. The reaction liquid was concentrated under reduced pressure, the residue was neutralized with aqueous saturated sodium hydrogencarbonate solution, and then extracted with ethyl acetate. The organic layer was washed with saturated saline water, dried with anhydrous magnesium sulfate, and the solvent was evaporated off under reduced pressure. The residue was separated and purified through silica gel column chromatography (hexane/ethyl acetate=20/1 to 10/1) to obtain 39.9 g of the entitled compound as a pale brown oily substance.

2) (3RS,4RS)-1-benzyl-4-o-tolyl-piperidin-3-ol monohydrochloride 39.9 g of the compound obtained in the above 1 was dissolved in 140 mL of diglyme, and 11.4 g of sodium borohydride, 44.1 mL of boron trifluoride/diethyl ether complex and 35 mL of diglyme were added to the resulting solution in that order. The reaction liquid was stirred at room temperature for 4 hours, and then cooled in an ice bath. This was treated carefully with 17 mL of water, and then 50 mL of aqueous 6 M sodium hydroxide solution and 45 mL of aqueous 30% hydrogen peroxide were added thereto. The resulting mixture was stirred at room temperature for 2 hours, and then extracted with ethyl acetate, and the organic layer was washed with saturated saline water, dried with anhydrous magnesium sulfate, and the solvent was evaporated off under reduced pressure. 50 mL of 4 N hydrogen chloride-dioxane solution and 500 mL of diisopropyl alcohol were added to the residue, and the resulting white powder was taken out through filtration, washed with diisopropyl ether, and dried under reduced pressure to obtain 41.5 g of the entitled compound as a white solid.

3) (3R*,4R*)-4-o-tolyl-piperidin-3-ol; and (3S*,4S*)-4-o-tolyl-piperidin-3-ol 10 g of 20% palladium hydroxide-carbon catalyst was added to a solution of 41.5 g of the compound obtained in the above 2 in a mixture of 500 mL of ethanol and 1 L of methanol, and in a hydrogen atmosphere, this was stirred overnight at room temperature and under normal pressure. The reaction mixture was filtered through Celite, and the solvent was concentrated under reduced pressure. The residue was made alkaline with aqueous sodium hydroxide solution, then extracted with ethyl acetate, and the organic layer was washed with saturated saline water, and dried with anhydrous magnesium sulfate. The solvent was evaporated off under reduced pressure to obtain 16.0 g of a racemate, (3RS,4RS)-4-o-tolyl-piperidin-3-ol of the entitled compounds as a pale yellow solid.

1H NMR (300 MHz, CDCl3) δ: 1.60-1.83 (2H, m), 2.39 (3H, s), 2.57-2.65 (2H, m), 2.81-2.93 (1H, m), 3.06-3.15 (1H, m), 3.35-3.43 (1H, m), 3.81-3.90 (1H, m), 7.10-7.32 (4H, m)

ESI-MS Found: m/z 192.1 [M+H]+

5.01 g of the racemate was optically resolved in an optically-active column (Daicel's CHRALPAK AD column; 0.1% diethylamine, hexane/isopropyl alcohol=4/1). From the former fraction, 2.31 g of (3S*,4S*)-4-o-tolyl-piperidin-3-ol was obtained; and from the latter fraction, 2.12 g of the (3R*,4R*) form was obtained. (The two were not identified, and for convenience sake, one was referred to as (3R*,4R*) form and the other was as (3S*,4S*) form.)

Former Fraction, (3S*,4S*) Form:

Retention time, 5.7 min (optically-active column, Daicel's CHRALPAK AD, 0.46 cm×25 cm; 0.1% diethylamine, hexane/ethanol=4/1; flow rate, 1 mL/min).

1H-NMR and ESI-MS were the same as those of the racemate.

Latter Fraction, (3R*,4R*) Form:

Retention time, 11.3 min (optically-active column, Daicel's CHRALPAK AD, 0.46 cm×25 cm; 0.1% diethylamine, hexane/ethanol=4/1; flow rate, 1 mL/min).

1H-NMR and ESI-MS were the same as those of the racemate.

Example 15

Production of (7R,9S)-7-[(3S*,4S*-3-hydroxy-4-o-tolyl-piperidin-1-ylmethyl]-6,7,8,9-tetrahydro-5H-cyclohepta[b]pyridin-9-ol mono-L-tartrate 14.4 mg of the entitled compound was obtained as a white solid in the same manner as in Example 14, for which, however, the compound obtained in Production Example 7 and (3S*,4S*)-4-o-tolyl-piperidin-3-ol obtained in Production Example 12 were used in place of (6R,8S)-8-triethylsilanyloxy-5,6,7,8-tetrahydroquinolin-6-ylmethyl toluene-4-sulfonate and spiro[isobenzofuran-1(3H),4'-piperidine] used in Example 14.

1H NMR (400 MHz, CD3OD) δ: 1.22-1.38 (1H, m), 1.52 (1H, dd, J=11.8, 12.5 Hz), 1.85-2.27 (3H, m), 2.35 (3H, s), 2.71-2.82 (3H, m), 2.89-3.07 (4H, m), 3.30-3.37 (1H, m), 3.55 (1H, d, J=12.5 Hz), 3.63 (1H, dd, J=3.3, 11.4 Hz), 4.19 (1H, dt, J=4.4, 10.3 Hz), 4.40 (2H, s), 5.01 (1H, d, J=7.6 Hz), 7.05 (1H, dd, J=7.3, 8.0 Hz), 7.08 (1H, d, J=8.0 Hz), 7.12 (1H, dd, J=7.2, 7.3 Hz), 7.20 (1H, dd, J=5.1, 7.0 Hz), 7.26 (1H, d, J=7.2 Hz), 7.55 (1H, d, J=7.0 Hz), 8.20 (1H, d, J=5.1 Hz)

ESI-MS Found: m/z 367.3 [M+H]+

Example 16

Production of (7R,9S)-7-[(3R*,4R*)-3-hydroxy-4-o-tolyl-piperidin-1-ylmethyl]-6,7,8,9-tetrahydro-5H-cyclohepta[b]pyridin-9-ol mono-L-tartrate A free amine form of the entitled compound was obtained in the same manner as in Example 15, for which, however, (3R*,4R*)-4-o-tolyl-piperidin-3-ol obtained in Production Example 12 were used in place of (3S*,4S*)-4-o-tolyl-piperidin-3-ol used in Example 15. The obtained free amine compound and the same amount of L-tartaric acid were mixed in ethanol, and crystallized from heptane added thereto to obtain the entitled compound as a white solid.

m.p.: 123-134° C.

1H NMR (400 MHz, CD3OD) δ: 1.23-1.35 (1H, m), 1.52-1.60 (1H, m), 1.89-2.11 (3H, m), 2.22-2.29 (1H, m), 2.35 (3H, s), 2.70-2.81 (3H, m), 2.91-3.04 (4H, m), 3.33-3.48 (1H, m), 3.58 (1H, d, J=11.5 Hz), 3.61 (1H, dd, J=4.8, 11.5 Hz), 4.19 (1H, dt, J=4.4, 10.6 Hz), 4.40 (2H, s), 5.01 (1H, d, J=6.6 Hz), 7.03 (1H, dd, J=7.3, 7.4 Hz), 7.11 (1H, d, J=7.4 Hz), 7.15 (1H, d, J=7.3 Hz), 7.20 (1H, dd, J=4.8, 7.3 Hz), 7.26 (1H, d, J=7.7 Hz), 7.56 (1H, dd, J=1.5, 7.3 Hz), 8.20 (1H, dd, J=1.5, 4.8 Hz)

ESI-MS Found: m/z 367.3 [M+H]+

Production Example 13

Production of (3R*,4R*)-4-(4-fluoro-o-tolyl)-3-hydroxypiperidine; and (3S*,4S*)-4-(4-fluoro-o-tolyl)-3-hydroxypiperidine 1) 1-Benzyl-4-(4-fluoro-o-tolyl)-1,2,3,6-tetrahydropyridine 1.83 g of the entitled compound was obtained as a pale yellow oily substance in the same manner as in Production Example 12-1, for which, however, a lithium reagent prepared from 2-bromo-5-fluorotoluene and n-butyllithium-hexane solution was used in place of o-tolylmagnesium bromide used in Production Example 12-1 and ether was used as the solvent.

2) (3RS,4RS)-1-benzyl-4-(4-fluoro-o-tolyl)-3-hydroxypiperidine monohydrochloride 922.9 mg of the entitled compound was obtained as a white solid in the same manner as in Production Example 12-2, for which, however, the compound obtained in the above 1 was used in place of 1-benzyl-4-o-tolyl-1,2,3,6-tetrahydropyridine used in Production Example 12-2.

3) (3R*,4R*)-4-(4-fluoro-o-tolyl)-piperidin-3-ol, and (3S*,4S*)-4-(4-fluoro-o-tolyl)-piperidin-3-ol 504 mg of a racemate of the entitled compounds was obtained as a pale yellow solid in the same manner as in Production Example 12-3, for which, however, the compound obtained in the above 2 was used in place of (3RS,4RS)-1-benzyl-4-o-tolyl-piperidin-3-ol monohydrochloride used in Example 12-3.

1H NMR (400 MHz, CD3OD) δ: 1.58-1.69 (1H, m), 1.78-1.82 (1H, m), 2.35 (3H, s), 2.61 (1H, t, J=11.4 Hz), 2.77 (1H, td, J=12.6, 2.7 Hz), 2.85-2.92 (1H, m), 3.11-3.14 (1H, m), 3.31-3.33 (1H, m), 3.83 (1H, td, J=10.3, 4.4 Hz), 6.84-6.91 (2H, m), 7.23-7.27 (1H, m)

APCI-MS Found: m/z 210.1 [M+H]+

504 mg of the racemate was optically resolved in an optically-active column (Daicel's CHRALPAK AD-H column, 2 cm×25 cm; 0.1% diethylamine, hexane/ethanol=9/1; flow rate, 15 mL/min). From the former fraction, 161 mg of (3S*,4S*)-4-(4-fluoro-o-tolyl)-3-hydroxypiperidine was obtained as a pale yellow solid; and from the latter fraction, 164 mg of the (3R*,4R*) form was obtained as a pale yellow solid. (The two were not identified, and for convenience sake, one was referred to as (3R*,4R*) form and the other was as (3S*,4S*) form.)

Former Fraction, (3S*,4S*) Form:

Retention time, 11.5 min (optically-active column, Daicel's CHRALPAK AD, 0.46 cm×25 cm; 0.1% diethylamine, hexane/ethanol=9/1; flow rate, 1 mL/min).

1H-NMR and APCI-MS were the same as those of the racemate.

Latter Fraction, (3R*,4R*) Form:

Retention time, 15.6 min (optically-active column, Daicel's CHRALPAK AD, 0.46 cm×25 cm; 0.1% diethylamine, hexane/ethanol=9/1; flow rate, 1 mL/min).

1H-NMR and APCI-MS were the same as those of the racemate.

Example 17

Production of (7R,9S)-7-[(3R*,4R*)-(4-fluoro-o-tolyl)-3-hydroxypiperidin-1-ylmethyl]-6,7,8,9-tetrahydro-5H-cyclohepta[b]pyridin-9-ol monohydrochloride A free amine form was obtained in the same manner as in Example 15, for which, however, (3R*,4R*)-4-(4-fluoro-o-tolyl)-piperidin-3-ol obtained in Production Example 13 was used in place of (3S*,4S*)-4-o-tolyl-piperidin-3-ol used in Example 15, and an optically-active column (Daicel's CHRALCEL OD column, 2 cm×25 cm; 0.1% diethylamine, hexane/isopropyl alcohol=19/1) was used for separation and purification of the crude product. The obtained free amine compound was dissolved in ethanol, and 1 equivalent amount of 1 N hydrochloric acid was added thereto, and the solvent was evaporated off under reduced pressure. The residue was again dissolved in ethanol, and heptane was added thereto for crystallization to obtain the entitled compound as a white solid.

m.p.: 212° C. (decomposition)

1H NMR (400 MHz, CD3OD) δ: 1.32 (1H, q, J=11.8 Hz), 1.58 (1H, t, J=12.5 Hz), 1.90-1.96 (2H, m), 2.10-2.15 (2H, m), 2.25-2.31 (2H, m), 2.41 (3H, s), 2.63-3.01 (8H, m), 3.39-3.59 (2H, m), 4.10 (1H, td, J=10.2, 4.3 Hz), 5.07 (1H, d, J=7.0 Hz), 6.94 (2H, d, J=9.0 Hz), 7.26-7.33 (2H, m), 7.64 (1H, d, J=7.4 Hz), 8.30 (1H, d, J=4.3 Hz)

APCI-MS Found: m/z 385.2 [M+H]+

Production Example 14

Production of (3RS,4RS)-3-methoxy-4-o-tolyl-piperidine

1) Benzyl (3RS,4RS)-3-hydroxy-4-o-tolyl-piperidine-1-carboxylate 227 mg of (3RS,4RS)-3-hydroxy-4-o-tolyl-piperidine hydrochloride obtained in Production Example 12 was dissolved in 45 mL of dioxane/water (4:5) mixture, and 405 mg of triethylamine and 269 mg of benzyl chloroformate were added thereto and stirred at room temperature for 4 hours. Aqueous sodium hydrogencarbonate solution was added to the reaction liquid, and extracted with ethyl acetate. The ethyl acetate layer was dried with magnesium sulfate. The solvent was evaporated off under reduced pressure, and the residue was separated and purified through silica gel column chromatography (hexane/ethyl acetate=4/1) to obtain 253.2 mg of the entitled compound as a pale yellow oily substance.

2) Benzyl (3RS,4RS)-3-methoxy-4-o-tolyl-piperidine-1-carboxylate

In a nitrogen atmosphere, 253.2 mg of the compound obtained in the above 1 was dissolved in 15 mL of tetrahydrofuran, and with cooling with ice, 85.6 mg of 60% sodium hydride (oily) was added thereto. This was stirred at room temperature for 30 minutes, and then 221 mg of methyl iodide was added thereto and stirred for 2 hours. 85.6 mg of 60% sodium hydride (oily) and 221 mg of methyl iodide were added thereto, and stirred further for 2 hours. Then, with cooling with ice, aqueous saturated sodium hydrogencarbonate solution was added to it, and extracted with ethyl acetate. The ethyl acetate layer was dried with magnesium sulfate, and the solvent was evaporated off under reduced pressure. The residue was separated and purified through silica gel column chromatography (hexane/ethyl acetate=4/1) to obtain 264.1 mg of the entitled compound as a pale yellow oily substance.

3) Production of (3RS,4RS)-3-methoxy-4-o-tolyl-piperidine 168.1 mg of the entitled compound was obtained as a white solid in the same manner as in Production Example 12-3, for which, however, the compound obtained in the above 2 was used in place of (3RS,4RS)-1-benzyl-4-o-tolyl-piperidin-3-ol monohydrochloride used in Production Example 12-3.

1H NMR (400 MHz, CDCl3) δ: 1.96 (1H, d, J=13.9 Hz), 2.20-2.34 (1H, m), 2.36 (3H, S), 2.74 (1H, t, J=11.4 Hz), 2.92-3.04 (2H, m), 3.11 (3H, s), 3.58 (1H, d, J=12.5 Hz), 3.81 (1H, dd, J=12.1, 4.0 Hz), 3.92 (1H, td, J=10.3, 4.4 Hz), 7.11-7.23 (3H, m), 7.32 (1H, d, J=8.1 Hz)

ESI-MS Found: m/z 206.1 [M+H]+

Examples 18 and 19

Production of (7R,9S)-7-[(3R*,4R*)-3-methoxy-4-o-tolyl-piperidin-ylmethyl]-6,7,8,9-tetrahydro-5H-cyclohepta[b]pyridin-9-ol mono-L-tartrate; and (7R,9S)-7-[(3S*,4S*)-3-methoxy-4-o-tolyl-piperidin-1-ylmethyl]-6,7,8,9-tetrahydro-5H-cyclohepta[b]pyridin-9-ol mono-L-tartrate A diastereomer mixture of the entitled compounds was obtained in the same manner as in Example 15, for which, however, the compound obtained in Production Example 14 was used in place of (3S*,4S*)-4-o-tolyl-piperidin-3-ol used in Example 15, and the step of converting the product into a salt with L-tartaric acid was omitted. The obtained diastereomer mixture was separated in an optically-active column (Daicel's CHRALPAK AD column, 2 cm×25 cm; 0.1% diethylamine, hexane/isopropyl alcohol=19/1; flow rate, 20 mL/min). From the former fraction, (7R,9S)-7-[(3S*,4S*)-3-methoxy-4-o-tolyl-piperidin-1-ylmethyl]-6,7,8,9-tetrahydro-5H-cyclohepta[b]pyridin-9-ol was obtained; and from the latter fraction, the (3R*,4R*) form was obtained. (The two were not identified, and for convenience sake, one was referred to as (3R*,4R*) form and the other was as (3S*,4S*) form.) The two compounds were separately dissolved in methanol, and an equimolar amount of L-tartaric acid was added thereto, and the solvent was evaporated off to obtain 8.8 mg of (7R,9S)-7-[(3R*,4R*)-3-methoxy-4-o-tolyl-piperidin-1-ylmethyl]-6,7,8,9-tetrahydro-5H-cyclohepta[b]pyridin-9-ol mono-L-tartrate, and 12.5 mg of (7R,9S)-7-[(3S*,4S*)-3-methoxy-4-o-tolyl-piperidin-1-ylmethyl]-6,7,8,9-tetrahydro-5H-cyclohepta[b]pyridin-9-ol mono-L-tartrate, both as a white solid.

Compound of Example 18

(3S*,4S*) Form

Retention time 11.0 min (optically-aceive column; Daicel's CHRALPAK AD column, 0.46 cm×25 cm; 0.1% diethylamine, hexane/isopropyl alcohol=19/1; flow rate 1 mL/min)

1H NMR (400 MHz, CD3OD) δ: 1.34 (1H, q, J=12.0 Hz), 1.56-1.62 (1H, m), 1.91-1.96 (1H, m), 2.05-2.16 (2H, m), 2.28 (1H, dd, J=6.8, 13.2 Hz), 2.36 (3H, s), 2.69-2.83 (3H, m), 2.94 (1H, dt, J=2.9, 12.5 Hz), 3.01-3.10 (3H, m), 3.13 (3H, s), 3.34-3.40 (1H, m), 3.58 (1H, d, J=12.5 Hz), 3.81-3.87 (2H, m), 4.45 (2H, s), 5.05 (1H, d, J=7.3 Hz), 7.07-7.32 (5H, m), 7.60-7.62 (1H, m), 8.21-8.21 (1H, m)

ESI-MS Found: m/z 381.4 [M+H]+

Compound of Example 19

(3R*,4R*) Form

Retention time 12.6 min (optically-aceive column; Daicel's CHRALPAK AD column, 0.46 cm×25 cm; 0.1% diethylamine, hexane/isopropyl alcohol=19/1; flow rate 1 mL/min)

1H NMR (400 MHz, CD3OD) δ: 1.34 (1H, q, J=12.2 Hz), 1.59 (1H, t, J=12.8 Hz), 1.91-2.14 (3H, m), 2.27-2.32 (1H, m), 2.36 (3H, s), 2.68-2.81 (3H, m), 2.92 (1H, td, J=12.5, 2.9 Hz), 3.04-3.09 (3H, m), 3.14 (3H, s), 3.34-3.40 (1H, m), 3.58 (1H, d, J=11.7 Hz), 3.79-3.88 (2H, m), 4.45 (2H, s), 5.05 (1H, d, J=7.3 Hz), 7.07-7.32 (5H, m), 7.61 (1H, d, J=8.1 Hz), 8.25 (1H, dd, J=5.1, 1.1 Hz)

ESI-MS Found: m/z 381.4 [M+H]+

Production Example 15

Production of (3R*,4R*)-3-fluoro-4-o-tolylpiperidine monohydrochloride

1) Tert-butyl (3R*,4R*)-3-hydroxy-4-o-tolylpiperidine-1-carboxylate

In a nitrogen atmosphere, 0.28 mL of di-tert-butyl dicarbonate was added to chloroform (4.0 mL) solution of 190 mg of (3R*,4R*)-4-o-tolyl-piperidin-3-ol obtained in Production Example 12-3, and stirred at room temperature for 15 hours. Aqueous saturated sodium hydrogencarbonate solution was added to the reaction liquid, extracted with chloroform, and the chloroform layer was washed with saturated saline water and dried with anhydrous sodium sulfate. The solvent was evaporated off under reduced pressure, and the residue was separated and purified through silica gel column chromatography (hexane/ethyl acetate=75/25) to obtain 352 mg of the entitled compound as a colorless oily substance.

2) Tert-butyl (3R*,4R*)-3-fluoro-4-o-tolylpiperidine-1-carboxylate; and tert-butyl (3S*,4R*)-3-fluoro-4-o-tolylpiperidine-1-carboxylate In a nitrogen atmosphere, 0.53 mL of diethylaminosulfur trifluoride was added to chloroform (10 mL) solution of 352 mg of the compound obtained in the above 1, at 0° C., and stirred at room temperature for 3 hours. Aqueous saturated sodium hydrogencarbonate solution was added to the reaction liquid, extracted with chloroform, and the chloroform layer was washed with saturated saline water, and dried with anhydrous sodium sulfate. The solvent was evaporated off under reduced pressure, and the residue was separated and purified through silica gel column chromatography (ethyl acetate/hexane=6/94) to obtain 149 mg of tert-butyl (3R*,4R*)-3-fluoro-4-o-tolylpiperidine-1-carboxylate as a pale yellow oily substance, and 90 mg of tert-butyl (3S*,4R*)-3-fluoro-4-o-tolylpiperidine-1-carboxylate as a pale yellow oily substance. (The two were not identified, and for convenience sake, one was referred to as (3R*,4R*) form and the other was as (3S*,4R*) form.)

(3R*,4R*) Form:

1H NMR (400 MHz, CDCl3) δ: 1.49 (9H, s), 1.62-1.74 (1H, m), 1.78-1.88 (1H, m), 2.37 (3H, s), 2.71-2.89 (2H, m), 3.03-3.14 (1H, m), 4.06-4.29 (1H, m), 4.45-4.70 (2H, m), 7.07-7.28 (4H, m)

ESI-MS Found: m/z 316.2 [M+Na]+

(3S*,4R*) Form:

1H NMR (400 MHz, CDCl3) δ: 1.47 (9H, s), 1.75-1.87 (1H, m), 2.16-2.24 (1H, m), 2.40 (3H, s), 2.70-2.96 (2H, m), 3.04-3.17 (1H, m), 4.01-4.34 (2H, m), 4.76-4.97 (1H, m), 7.13-7.26 (4H, m)

ESI-MS Found: m/z 316.2 [M+Na]+

3) (3R*,4R*)-3-fluoro-4-o-tolylpiperidine monohydrochloride

In a nitrogen atmosphere, 5.0 mL of 4 N hydrogen chloride-dioxane solution was added to 149 mg of the (3R*,4R*) form obtained in the above 2, and stirred at room temperature for 1 hour. Then, the solvent was evaporated off under reduced pressure to obtain 106 mg of the entitled compound as a white solid.

1H NMR (400 MHz, CD3OD) δ: 1.91-2.01 (1H, m), 2.08-2.11 (1H, m), 2.38 (3H, s), 3.15-3.24 (2H, m), 3.37-3.48 (2H, m), 3.72-3.77 (1H, m), 4.85-5.03 (1H, m), 7.14-7.30 (4H, m)

ESI-MS Found: m/z 194.2 [M+H]+

Example 20

Production of (7R,9S)-7-[(3R*,4R*)-3-fluoro-4-o-tolylpiperidin-1-ylmethyl]-6,7,8,9-tetrahydro-5H-cyclohepta[b]pyridin-9-ol mono-L-tartrate The entitled compound was obtained as a white solid in the same manner as in Example 15, for which, however, the compound obtained in Production Example 15 was used in place of (3S*,4S*)-4-o-tolyl-piperidin-3-ol used in Example 15. The free amine of the compound was analyzed for assignment.

1H NMR (400 MHz, CDCl3) δ: 1.62-1.84 (5H, m), 2.04-2.18 (4H, m), 2.36 (3H, s), 2.55-2.72 (3H, m), 2.84-2.99 (3H, m), 3.32-3.37 (1H, m), 4.67-4.85 (1H, m), 4.94-4.96 (1H, m), 5.40 (1H, brs), 7.11-7.32 (5H, m), 7.43-7.46 (1H, m), 8.35-8.37 (1H, m)

ESI-MS Found: m/z 369.2 [M+H]+

Production Example 16

Production of 5'-aza-spiro[8-aza-bicyclo[3.2.1]octa-3,1'(3'H)isobenzofuran]

1) 8-Benzyl-8-aza-bicyclo[3.2.1]octan-3-one 25 g of tropinone was dissolved in 100 mL of chloroform, and 50 mL of chloroethyl chloroformate was added thereto and stirred at room temperature for 6 hours. The reaction liquid was concentrated, 100 mL of methanol was added thereto, and heated overnight under reflux. The reaction liquid was cooled to room temperature and concentrated, and the resulting crude product was dissolved in 80 mL of N-methylpyrrolidone. 43 mL of benzyl bromide and 99 g of potassium carbonate were added thereto and stirred overnight at room temperature. The reaction liquid was poured into water, and extracted three times with ethyl acetate. The organic layer was washed with water and saturated saline water, dried with anhydrous magnesium sulfate, and the solvent was evaporated off under reduced pressure to obtain 29.5 g of the entitled compound as a pale yellow liquid.

2) 5'-Azaspiro[8-benzyl-8-aza-bicyclo[3.2.1]octa-3,1'(3'H)isobenzofuran-3'-one]

6.6 mL of 2,2,6,6-tetramethylpiperidine was dissolved in 10 mL of tetrahydrofuran, and at −78° C. 24.7 mL of 1.58 M n-butyllithium-hexane solution was added thereto, and stirred at room temperature for 30 minutes. At −78° C., this was dropwise added to tetrahydrofuran (10 mL) solution of 1.32 g of nicotinic acid, and stirred for 30 minutes. Tetrahydrofuran (10 mL) solution of 2.1 g of the compound obtained in the above 1 was dropwise added to it, and stirred further for 30 minutes. 50 mL of 2 N hydrochloric acid was added thereto, and stirred at room temperature for 1 hour. This was extracted once with ethyl acetate, and the aqueous layer was made to have a pH of about 9 with aqueous 5 M sodium hydroxide solution added thereto, and extracted twice with ethyl acetate. The organic layer was dried with anhydrous magnesium sulfate, the solvent was evaporated off under reduced pressure, and the resulting residue was separated and purified through silica gel column chromatography (chloroform/methanol=9/1) to obtain 1.4 g of the entitled compound as a pale yellow solid.

3) 5'-Aza-spiro[8-benzyl-8-aza-bicyclo[3.2.1]octa-3,1'(3'H)isobenzofuran]

1.2 g of the compound obtained in the above 2 was dissolved in 10 mL of tetrahydrofuran, and at −78° C. 10.3 mL of 1.0 M diisopropylaluminium hydride-toluene solution was added thereto. After stirred for 1 hour, this was heated up to room temperature, and a large excess amount of sodium sulfate 10-hydrate was added thereto and stirred for 4 hours. This was filtered, extracted with ethyl acetate, washed with saturated sodium chloride, and dewatered with anhydrous magnesium sulfate. This was filtered and concentrated, and the resulting compound was dissolved in 20 mL of acetonitrile, then 17.3 mL of triethylsilane and 4.6 mL of boron trifluoride/diethyl ether complex were added thereto in that order, and heated under reflux for 1 hour. The reaction liquid was concentrated, diluted with chloroform, and then washed with aqueous 4 M sodium hydroxide solution, aqueous saturated sodium hydrogencarbonate solution and saline water in that order. The organic layer was dried with anhydrous magnesium sulfate, the solvent was evaporated off under reduced pressure, and the resulting residue was separated and purified through silica gel column chromatography (chloroform/methanol=9/1) to obtain 703 mg of the entitled compound as a white solid.

4) 5'-Aza-spiro[8-aza-bicyclo[3.2.1]octa-3,1'(3'H)isobenzofuran]

703 mg of the compound obtained in the above 3 was dissolved in 5 mL of methanol, 100 mg of 20% palladium hydroxide-carbon catalyst was added thereto, and in a hydrogen atmosphere, this was stirred overnight at room temperature and under normal pressure. The reaction liquid was filtered through Celite, 10% hydrochloric acid-methanol solution was added to the filtrate and concentrated, whereby the compound was converted into its hydrochloride. This was dissolved in water, washed with ethyl acetate, and the aqueous layer was made to have a pH of about 9 with aqueous 5 M sodium hydroxide solution added thereto, then extracted three times with chloroform, and dried with anhydrous magnesium sulfate. Then, the solvent was evaporated off under reduced pressure to obtain 232 mg of the entitled compound as a white solid.

1H NMR (300 MHz, CDCl3) δ: 1.75-2.32 (8H, m), 3.63 (3H, brs), 5.07 (2H, s), 7.10 (1H, m), 8.49 (2H, m)

ESI-MS Found: m/z 217.2 [M+H]

Example 21

Production of (7R,9S)-7-(5'-aza-spiro[8-aza-bicyclo[3.2.1]octa-3,1'(3'H)-isobenzofuran]-8-ylmethyl)-6,7,8,9-tetrahydro-5H-cyclohepta[b]pyridin-9-ol mono-L-tartrate 34.5 mg of the entitled compound was obtained as a white solid in the same manner as in Example 15, for which, however, the compound obtained in Production Example 16 was used in place of (3S*,4S*)-4-o-tolyl-piperidin-3-ol used in Example 15. The free amine of the compound was analyzed for assignment.

1H NMR (300 MHz, CDCl3) δ: 1.60-2.30 (13H, m), 2.58-2.73 (3H, m), 2.84-2.97 (2H, m), 3.27 (2H, brs), 4.96 (1H, m), 5.07 (2H, s), 7.10-8.50 (6H, m)

ESI-MS Found: m/z 392.2 [M+H]+

Production Example 17

6'-Aza-spiro[8-aza-bicyclo[3.2.1]octa-3,1'(3'H)isobenzofuran]

646 mg of the entitled compound was obtained as a white solid in the same manner as in Production Example 16, for which, however, isonicotinic acid was used in place of nicotinic acid used in Production Example 16.

1H NMR (300 MHz, CDCl3) δ: 1.79 (2H, m), 1.98 (2H, m), 2.10 (2H, m), 2.35 (2H, m), 3.66 (2H, s), 5.04 (2H, s), 7.18 (1H, d, J=5.0 Hz), 8.46 (1H, s), 8.49 (1H, d, J=5.0 Hz)

ESI-MS Found: m/z 217 [M+H]+

Example 22

Production of (7R,9S)-7-(6'-aza-spiro[8-aza-bicyclo[3.2.1]octa-3,1'(3'H)-isobenzofuran]-8-ylmethyl)-6,7,8,9-tetrahydro-5H-cyclohepta[b]pyridin-9-ol mono-L-tartrate 625 mg of the entitled compound was obtained as a white solid in the same manner as in Example 15, for which, however, the compound obtained in Production Example 16 was used in place of (3S*,4S*)-4-o-tolyl-piperidin-3-ol used in Example 15. The free amine of the compound was analyzed for assignment.

1H NMR (300 MHz, CDCl3) δ: 1.72 (2H, m), 1.89 (4H, m), 2.17 (4H, m), 2.60 (2H, m), 2.67 (1H, m), 2.90 (1H, m), 3.24 (2H, m), 4.95 (1H, d, J=10.8 Hz), 4.99 (2H, s), 5.43 (1H, bs), 7.14 (2H, m), 7.45 (1H, d, J=7.6 Hz), 8.36 (1H, d, J=5.2 Hz), 8.43 (1H, s), 8.46 (1H, d, J=5.2 Hz)

ESI-MS Found: m/z 392 [M+H]+

Production Example 18

Production of 6'-aza-5'-fluoro-spiro[8-aza-bicyclo[3.2.1]-octa-3,1'(3'H)-isobenzofuran]

1) 3-Chloro-2-fluoropyridine 107.3 g of 2,3-dichloropyridine was dissolved in 270 mL of N-methylpiperidone, and 268.25 g of cesium fluoride was added thereto, and stirred in a nitrogen atmosphere at 180° C. for 23 hours. One L of water was added to the solution, and filtered through Celite, and the filtrate was extracted twice with diethyl ether. The organic layers were combined, washed with saturated saline water, and dried with sodium sulfate. The solvent was evaporated off under reduced pressure, and the residue was purified through distillation (91 to 95° C./15 mmHg) to obtain 76.14 g of the entitled compound as a colorless liquid.

2) 3-Chloro-2-fluoroisonicotinic acid

In a nitrogen atmosphere, 97 mL of diisopropylamine was dissolved in 1.2 L of tetrahydrofuran, and at −70° C. 239 mL of 2.66 M n-butyllithium-hexane solution was dropwise added thereto. The solution was stirred for 30 minutes, and then tetrahydrofuran (300 mL) solution of 76.14 g of the compound obtained in the above 1 was dropwise added thereto at −70° C. This was stirred for 1 hour, and dry ice was added to the reaction solution, heated up to room temperature, and 1 L of water and diethyl ether were added thereto. Its pH was controlled to 10 with aqueous 4 M sodium hydroxide solution added to it. Then, its pH was controlled to 1 to 2 with concentrated hydrochloric acid added to it, and this was extracted three times with diethyl ether. The organic layers were combined, washed with saturated saline water, and dried with sodium sulfate. The solvent was evaporated off under reduced pressure, the residue was crystallized from etherhexane to obtain 55.9 g of the entitled compound as a pale yellow solid.

3) Production of 6'-aza-5'-fluoro-spiro(8-aza-bicyclo[3.2.1]-octa-3,1'(3'H)-isobenzofuran)

80 mg of the entitled compound was obtained as a white solid in the same manner as in Production Example 16, for which, however, the compound obtained in the above 2 was used in place of nicotinic acid used in Production Example 16.

1H NMR (300 MHz, CDCl3) δ: 2.04 (2H, m), 2.27 (2H, m), 2.48 (2H, m), 2.88 (2H, m), 4.13 (2H, brs), 5.02 (2H, s), 6.71 (1H, s), 8.42 (1H, s)

ESI-MS Found: m/z 235.3 [M+H]+

Example 23

Production of (7R,9S)-7-(6'-aza-5'-fluoro-spiro[8-aza-bicyclo[3.2.1]-octa-3,1'(3'H)-isobenzofuran]-8-ylmethyl)-6,7,8,9-tetrahydro-5H-cyclohepta[b]pyridin-9-ol mono-L-tartrate 25 mg of the entitled compound was obtained as a white solid in the same manner as in Example 15, for which, however, the compound obtained in Production Example 18 was used in place of (3S*,4S*)-4-o-tolyl-piperidin-3-ol used in Example 15, and the residue was again dissolved in ethanol and heptane and added thereto to solidify it.

m.p.: 133-141° C.

1H NMR (300 MHz, CD3OD) δ: 1.37 (1H, m), 1.62 (1H, t, J=13.0 Hz), 2.10-2.33 (6H, m), 2.08-2.85 (6H, m), 3.05 (2H, d, J=6.9 Hz), 3.38 (1H, m), 4.12 (2H, brs), 4.42 (2H, s), 5.05 (1H, d, J=7.5 Hz), 5.11 (2H, s), 6.99 (1H, brs), 7.22 (1H, m), 7.61 (1H, d, J=7.6 Hz), 8.15 (1H, brs), 8.26 (1H, d, J=4.3 Hz)

ESI-MS Found: m/z 410.4 [M+H]+

Production Example 19

Production of 6'-aza-7'-fluoro-spiro[8-aza-bicyclo[3.2.1]-octa-3,1'(3'H)-isobenzofuran]

1) 2-Fluoroisonicotinic acid 20 g of 2-fluoro-4-methylpyridine was suspended in 500 mL of water, and 100 g of potassium permanganate was added thereto and stirred at 115° C. for 20 hours. The reaction solution was filtered through Celite while hot, and then the filtrate was concentrated under reduced pressure until the amount of the solvent became ⅓. The solution was neutralized with aqueous sodium hydroxide solution, and then aqueous hydrochloric acid solution was added thereto until its pH became 2. The formed white solid was taken out through filtration, and the filtrate was extracted twice with ethyl acetate, washed with saturated saline water and dried with sodium sulfate. The solvent was evaporated off under reduced pressure, and the resulting white solid was combined with the solid taken out through filtration to obtain 9.51 g of the entitled compound.

2) (2-Fluoropyridin-4-yl)-methanol

With cooling with ice, 538 mg of lithiumaluminium hydride was added to tetrahydrofuran (18 mL) solution of 500 mg of the compound obtained in the above 1, and stirred for 10 minutes. Sodium sulfate 10-hydrate was added to the solution to stop the reaction, extracted three times with ethyl acetate, and then dried with sodium sulfate. The solvent was evaporated off under reduced pressure, and the resulting residue was separated and purified through silica gel column chromatography (chloroform/methanol=20/1) to obtain 234 mg of the entitled compound as a pale yellow solid.

3) 6'-Aza-7'-fluoro-spiro[8-aza-bicyclo[3.2.1]-octa-3,1'(3'H)-isobenzofuran]

109 mg of the entitled compound was obtained as a white solid in the same manner as in Production Example 11, for which, however, the compound obtained in the above 2 and the compound obtained in Production Example 16-1 were used in place of 2-bromobenzyl alcohol and 1-benzyl-4-piperidone used in Production Example 11, and lithium tetramethylpiperidide prepared from 2,2,6,6-tetramethylpiperidine and n-butyllithium-hexane solution was used in place of n-butyllithium-hexane solution.

1H NMR (300 MHz, CDCl3) δ: 2.02 (2H, m), 2.31 (2H, m), 2.52 (2H, m), 2.83 (2H, m), 4.24 (2H, m), 5.11 (2H, s), 7.08 (1H, m), 8.17 (1H, m)

ESI-MS Found: m/z 235.1 [M+H]+

Example 24

Production of (7R,9S)-7-(6'-aza-7'-fluoro-spiro[8-aza-bicyclo[3.2.1]-octa-3,1'(3'H)-isobenzofuran]-8-ylmethyl)-6,7,8,9-tetrahydro-5H-cyclohepta[b]pyridin-9-ol mono-L-tartrate 41 mg of the entitled compound was obtained as a white solid in the same manner as in Example 15, for which, however, the compound obtained in Production Example 19 was used in place of (3S*,4S*)-4-o-tolyl-piperidin-3-ol used in Example 15.

1H NMR (300 MHz, CD3OD) δ: 1.24-1.45 (1H, m), 1.64 (1H, t, J=13.5 Hz), 2.09-2.36 (6H, m), 2.60-2.85 (6H, m), 3.12 (2H, brs), 3.39 (1H, t, J=12.4 Hz), 4.12 (2H, rbs), 4.39 (2H, s), 5.06 (1H, d, J=6.9 Hz), 5.20 (2H, s), 7.22-7.33 (2H, m), 7.61 (1H, d, J=7.3 Hz), 8.15 (1H, d, J=4.9 Hz), 8.27 (1H, d, J=4.8 Hz)

ESI-MS Found: m/z 410.4 [M+H]+

Production Example 20

Production of 3,3-dimethyl-spiro[isobenzofuran-1(3H),4'-piperidine]

1) 2-(2-Bromo-phenyl)-propan-2-ol

In a nitrogen atmosphere, 49.5 mL of 3.0 M methylmagnesium bromide-diethyl ether solution was dropwise added to tetrahydrofuran (200 mL) solution of 10.7 g of methyl 2-bromobenzoate with cooling with ice. This was stirred at that temperature for 15 minutes, and then stirred at room temperature for 6 days. Aqueous saturated ammonium chloride solution was added to the reaction liquid, and extracted with diethyl ether. The diethyl ether layer was washed with saturated saline water, and then dried with anhydrous magnesium sulfate. The solvent was evaporated off under reduced pressure, and the residue was separated and purified through silica gel column chromatography (hexane/ethyl acetate=9/1) to obtain 7.4 g of the entitled compound.

2) 1-Benzyl-4-[2-(1-hydroxy-1-methyl-ethyl)-phenyl]piperidin-4-ol 2.62 g of the entitled compound was obtained in the same manner as in Production Example 11-1, for which, however, the compound obtained in the above 1 was used in place of 2-bromobenzyl alcohol used in Production Example 11-1.

3) 1-Benzyl-3,3-dimethyl-spiro[isobenzofuran-1(3H),4'-piperidine]

12 mL of 2 N sulfuric acid was added to 2.62 g of the compound obtained in the above 2, and stirred at 100° C. for 3.5 hours. With cooling with ice, the reaction liquid was neutralized with aqueous 2 M sodium hydroxide solution added thereto, and extracted with ethyl acetate. The ethyl acetate layer was washed with saturated saline water, and dried with anhydrous magnesium sulfate. The solvent was evaporated off under reduced pressure, and the residue was separated and purified through silica gel column chromatography (hexane/ethyl acetate=4/1) to obtain 1.93 g of the entitled compound.

4) 3,3-Dimethyl-spiro[isobenzofuran-1(3H),4'-piperidine]

1.34 g of the entitled compound was obtained in the same manner as in Production Example 11-3, for which, however, 1.93 g of the compound obtained in the above 3 was used and the product was not washed with isopropyl alcohol.

1H NMR (200 MHz, CDCl3) δ: 1.49 (6H, s), 1.70-1.92 (2H, m), 2.30-2.65 (2H, m), 3.30-3.73 (4H, m), 7.02-7.53 (4H, m)

ESI-MS Found: m/z 218.2 [M+H]+

Example 25

Production of (6R,8S)-6-(3,3-dimethyl-spiro[isobenzofuran-1(3H),4'-piperidin]-1'-ylmethyl)-5,6,7,8-tetrahydro-quinolin-8-ol mono-L-tartrate 7.0 mg of the entitled compound was obtained as a white solid in the same manner as in Example 14, for which, however, the compound obtained in Production Example 20 was used in place of spiro[isobenzofuran-1(3H),4'-piperidine] used in Example 14.

1H NMR (300 MHz, CD3OD) δ: 1.52 (6H, s), 1.71-1.90 (3H, m), 2.27-2.37 (1H, m), 2.45-2.83 (4H, m), 3.10-3.22 (1H, m), 3.22-3.49 (4H, m), 3.61-3.73 (2H, m), 4.48 (2H, s), 4.80-4.87 (1H, m), 7.18-7.40 (5H, m), 7.66-7.73 (1H, m), 8.38-8.47 (1H, m)

ESI-MS Found: m/z 379.2 [M+H]+

Production Example 21

Production of (1RS,3'RS)-3'-[(tert-butyldimethylsilyl)oxy]methyl)-spiro[isobenzofuran-1(3H),4'-piperidine]

1) 1-Benzyl-3-(tert-butyldimethylsilyloxymethyl)-piperidin-4-one 0.82 g of imidazole and 0.72 g of tert-butyldimethylchlorosilane were added to N,N-dimethylformamide (10 mL) solution of 1.0 g of methyl 1-benzyl-4-hydroxy-1,2,5,6-tetrahydropyridine-3-carboxylate, and stirred at room temperature for 0.5 hours, and then methanol was added thereto. The reaction solution was diluted with ethyl acetate, washed with water and saturated saline water in that order, dried with anhydrous sodium sulfate, and the solvent was evaporated off under reduced pressure. The resulting residue was dissolved in 30 mL of diethyl ether, and with cooling with ice, 0.30 g of lithiumaluminium hydride was added thereto, and stirred at that temperature for 1.5 hours, and then methanol was added thereto. The reaction solution was diluted with ethyl acetate, then washed with water and saturated saline water in that order, dried with anhydrous sodium sulfate, and the solvent was evaporated off under reduced pressure. High-polarity side products were removed from the resulting residue through silica gel column chromatography (chloroform/methanol=10/1), and the residue was dissolved in 10 mL of N,N-dimethylformamide, and 0.41 g of imidazole and 0.72 g of tert-butyldimethylchlorosilane were added thereto, and stirred at room temperature for 10 minutes. Water was added to the reaction solution, and diluted with ethyl acetate. Then, this was washed with water and saturated saline water in that order, dried with anhydrous sodium sulfate, and the solvent was evaporated off under reduced pressure. The residue was separated and purified through silica gel column chromatography (hexane/ethyl acetate=10/1 to 4/1) to obtain 566 mg of the entitled compound as a pale yellow oily substance.

2) (1RS,3'RS)-3'-[(tert-butyldimethylsilyl)oxy]methyl)-spiro[isobenzofuran-1(3H),4'-piperidine]

130 mg of the entitled compound was obtained as a colorless oily substance in the same manner as in Production Example 11, for which, however, the compound obtained in the above 1 was used in place of 4-benzylpiperidone used in Production Example 11.

1H NMR (300 MHz, CDCl$_3$) δ: −0.13 (6H, s), 0.79 (9H, s), 1.70-1.90 (1H, m), 2.05-2.25 (1H, m), 2.38-2.52 (1H, m), 2.93-3.06 (1H, m), 3.20-3.37 (3H, m), 3.50-3.60 (1H, m), 4.99 (1H, d, J=11.0 Hz), 5.08 (1H, d, J=11.0 Hz), 7.18-7.32 (1H, m)

Example 26 AND 27

Production of (7R,9S)-7-((1R*,3'R*)-3'-hydroxymethyl-spiro[isobenzofuran-1(3H),4'-piperidin]-1'-ylmethyl)-6,7,8,9-tetrahydro-5H-cyclohepta[b]pyridin-9-ol; and (7R,9S)-7-((1S*,3'S*)-3'-hydroxymethyl-spiro[isobenzofuran-1(3H),4'-piperidin]-1'-ylmethyl)-6,7,8,9-tetrahydro-5H-cyclohepta[b]pyridin-9-ol A diastereomer mixture of the entitled compounds was obtained in the same manner as in Example 15, for which, however, the compound obtained in Production Example 21 was used in place of (3S*,4S*)-4-o-tolyl-piperidin-3-ol used in Example 15, and the step of converting the product into a salt with L-tartaric acid was omitted. The obtained diastereomer mixture was separated in an optically-active column (Daicel's CHRALPAK AD, 2 cm×25 cm; 0.1% diethylamine, hexane/isopropyl alcohol=2/1; flow rate, 20 mL/min). From the former fraction, 10 mg of (7R,9S)-7-((1R*,3'R*)-3'-hydroxymethyl-spiro[isobenzofuran-1(3H),4'-piperidin]-1'-ylmethyl)-6,7,8,9-tetrahydro-5H-cyclohepta[b]pyridin-9-ol was obtained; and from the latter fraction, 10 mg of the (1S*,3'S*) form was obtained. (The two were not identified, and for convenience sake, one was referred to as (1R*,3'R*) form and the other was as (1S*,3'S*) form.)

Compound of Example 26

(1R*,3'R*) Form

Retention time: 6.5 min (optically-active column; Daicel's CHRALPAK AD column, 0.46 cm×25 cm; 0.1% diethylamine, hexane/isopropyl alcohol=2/1; flow rate, 1 mL/min)

1H NMR (300 MHz, CDCl$_3$) δ: 1.55-2.00 (5H, m), 2.10-2.32 (3H, m), 2.35-2.74 (5H, m), 2.78-2.96 (2H, m), 3.00-3.11 (1H, m), 3.41 (1H, dd, J=3.8, 11.0 Hz), 3.49 (1H, dd, J=5.0, 11.2 Hz), 4.96 (1H, d, J=9.9 Hz), 5.07 (2H, s), 5.40 (1H, bs), 7.10-7.34 (5H, m), 7.45 (1H, d, J=7.3 Hz), 8.36 (1H, d, J=4.9 Hz)

ESI-MS Found: m/z 395.3 [M+H]+

Compound of Example 27

(1S*,3'S*) Form

Retention time: 11.7 min (optically-active column; Daicel's CHRALPAK AD column, 0.46 cm×25 cm; 0.1% diethylamine, hexane/isopropyl alcohol=2/1; flow rate, 1 mL/min)

1H NMR (300 MHz, CDCl$_3$) δ: 1.60-2.13 (5H, m), 2.13-2.32 (3H, m), 2.36-2.75 (5H, m), 2.80-2.95 (2H, m), 3.05 (1H, dd, J=4.0, 11.6 Hz), 3.40 (1H, dd, J=4.0, 11.2 Hz), 3.49 (1H, dd, J=5.0, 11.2 Hz), 4.96 (1H, dd, J=2.6, 10.8 Hz), 5.07 (2H, s), 7.10-7.34 (5H, m), 7.45 (1H, d, J=7.4 Hz), 8.36 (1H, d, J=4.9 Hz)

ESI-MS Found: m/z 395.3 [M+H]+

Production Example 22

Production of 1-methyl-spiro[2,3-dihydro-1H-indole-3,4'-piperidine]

1) 1'-Methyl-spiro[2,3-dihydro-1H-indole-3,4'-piperidine]

In a nitrogen atmosphere, 3.8 mL of 65% sodium-bis(2-methoxyethoxy)aluminium hydride-toluene solution was added to toluene (20 mL) solution of 1 g of benzyl 1-methanesulfonyl-spiro[2,3-dihydro-1H-indole-3,4'-piperidine]-1'-carboxylate (prepared according to the method described in Tetrahedron, 1997, 53, 10983-10992), and refluxed for 3 hours. The reaction liquid was cooled to 0° C., poured into aqueous 1 M sodium hydroxide solution at that temperature, and extracted with ethyl acetate. The ethyl acetate layer was washed with saturated saline water, and dried with anhydrous magnesium sulfate. The solvent was evaporated off under reduced pressure, and the residue was separated and purified through silica gel column chromatography (aqueous 1% ammonia, chloroform/methanol=5/1) to obtain 0.32 g of the entitled compound.

2) 1,1'-Dimethyl-spiro[2,3-dihydro-1H-indole-3,4'-piperidine]

With cooling with ice, 187 mg of sodium cyanoborohydride was added to methanol (10 mL) solution of 0.30 g of the compound obtained in the above 1. Its pH was controlled to 4 to 5 with 1% hydrochloric acid added thereto, and 3 mL of 37% formaldehyde solution was added thereto and stirred at room temperature for 7.5 hours. The solvent was evaporated off under reduced pressure, and the residue was diluted with ethyl acetate, washed with aqueous 1 M sodium hydroxide solution and saturated saline water, and dried with anhydrous magnesium sulfate. The solvent was evaporated off under reduced pressure, and the residue was separated and purified through silica gel column chromatography (chloroform/methanol=10/1) to obtain 243 mg of the entitled compound.

3) 1-Methylspiro[2,3-dihydro-1H-indole-3,4'-piperidine]

1.21 mL of 1-chloroethyl chloroformate was added to dichloroethane (7 mL) solution of 243 mg of the compound obtained in the above 2, and refluxed for 15 hours. The solvent and superfluous reagents were evaporated off, and the resulting residue was dissolved in 7 mL of methanol and refluxed for 3 hours. The solvent was evaporated off, and the residue was diluted with ethyl acetate, washed with aqueous 2 M sodium hydroxide solution and saturated water, and dried with anhydrous magnesium sulfate. The solvent was evaporated off under reduced pressure, and the residue was separated and purified through preparative thin-layer chromatography (aqueous 1% ammonia, chloroform/methanol=15/1) to obtain 64 mg of the entitled compound.

ESI-MS Found: m/z 203.2 [M+H]+

Example 28

Production of (7R,9S)-7-(1-methylspiro-[2,3-dihydro-1H-indole-3,4'-piperidin]-1'-ylmethyl)-6,7,8,9-tetrahydro-5H-cyclohepta[b]pyridin-9-ol mono-L-tartrate 12.6 mg of the entitled compound was obtained as a white solid in the same manner as in Example 15, for which, however, the compound obtained in Production Example 22 was used in place of (3S*,4S*)-4-o-tolyl-piperidin-3-ol obtained in Example 15.

1H NMR (300 MHz, CD3OD) δ: 1.29-1.63 (2H, m), 1.88-1.99 (2H, m), 2.04-2.18 (1H, m), 2.18-2.32 (3H, m), 2.71-2.90 (1H, m), 2.77 (3H, s), 3.04-3.22 (4H, m), 3.25-3.42 (2H, m), 3.33 (2H, s), 3.53-3.67 (2H, m), 4.42 (2H, s), 5.01-5.09 (1H, m), 6.50-6.72 (2H, m), 7.02-7.15 (2H, m), 7.20-7.28 (1H, m), 7.57-7.63 (1H, m), 8.22-8.30 (1H, m)

ESI-MS Found: m/z 378.3 [M+H]+

Production Example 23

Production of 4-(2-chlorophenyl)-4-fluoropiperidine

1) Benzyl 4-(2-chlorophenyl)-4-hydroxypiperidine-1-carboxylate 9.74 g of the entitled compound was obtained as a pale yellow oily substance in the same manner as in Production Example 8-3, for which, however, benzyl 4-oxopiperidine-1-carboxylate was used in place of tert-butyl 3-oxo-8-aza-bicyclo-[3.2.1]octane-8-carboxylate used in Production Example 8-3, and 2-chlorophenylmagnesium bromide was used in place of the lithium reagent prepared from 2-bromobenzyl alcohol and n-butyllithium.

2) Benzyl 4-(2-chlorophenyl)-4-fluoropiperidine-1-carboxylate

In a nitrogen atmosphere, 5.26 mL of diethylaminosulfur trifluoride was added to chloroform (160 mL) solution of 5.51 g of benzyl 4-(2-chlorophenyl)-4-hydroxypiperidine-1-carboxylate at −78° C., and stirred for 1 hour at −78° C. Water was added to the reaction liquid, and extracted with chloroform. The chloroform layer was dried with anhydrous sodium sulfate. The solvent was evaporated off under reduced pressure, and the residue was dissolved in 150 mL of acetone/water (2:1) mixture. 15.9 mL of aqueous 0.05 M osmium tetroxide solution and 3.73 g of N-methylmorpholine N-oxide were added thereto, and stirred overnight at room temperature. The reaction liquid was diluted with ethyl acetate, washed with aqueous sodium hydrogencarbonate solution, and dried with anhydrous sodium sulfate. The solvent was evaporated off under reduced pressure, and the residue was separated and purified through silica gel column chromatography (hexane/ethyl acetate=10/1) to obtain 2.11 g of the entitled compound as a colorless oily substance.

3) 4-(2-Chlorophenyl)-4-fluoropiperidine 1.53 mL of trimethylchlorosilane and 1.82 g of sodium iodide were added to acetonitrile (50 mL) solution of 2.11 g of benzyl 4-(2-chlorophenyl)-4-fluoropiperidine-1-carboxylate, and stirred at room temperature for 30 minutes. 0.77 mL of trimethylchlorosilane and 0.91 g of sodium iodide were further added thereto, and stirred for 10 minutes. Then, the reaction liquid was diluted with ethyl acetate, and back-extracted with 1 M hydrochloric acid. Sodium hydroxide was added to the aqueous layer so that the system was made basic, and then extracted with chloroform, and dried with anhydrous sodium sulfate. The solvent was evaporated off under reduced pressure, and the residue was separated and purified through silica gel column chromatography (chloroform/methanol=10/1) to obtain 992 mg of the entitled compound as a colorless oily substance.

1H NMR (400 MHz, CD3OD) δ: 2.17 (2H, m), 2.95 (2H, m), 3.35 (2H, m), 3.51 (2H, m), 7.34 (3H, m), 7.59 (1H, m)

ESI-MS Found: m/z 214.2 [M+H]+

Example 29

Production of (6R,8S)-6-[4-(2-chlorophenyl)-4-fluoropiperidin-1-ylmethyl]-5,6,7,8-tetrahydroquinolin-8-ol mono-L-tartrate 70.0 mg of the entitled compound was obtained as a white solid in the same manner as in Example 14, for which, however, the compound obtained in Production Example 23 was used in place of spiro[isobenzofuran-1(3H),4'-piperidine] monohydrochloride used in Example 14.

1H NMR (400 MHz, CD3OD) δ: 1.30 (1H, m), 1.56 (1H, m), 2.08 (1H, m), 2.23 (3H, m), 2.77 (2H, m), 3.01 (4H, m), 3.30 (4H, m), 4.40 (2H, s), 5.01 (1H, m), 7.20 (1H, m), 7.32 (2H, m), 7.41 (1H, m), 7.56 (1H, m), 7.61 (1H, dd, J=1.8, 8.7 Hz), 8.21 (1H, dd, J=1.5, 5.1 Hz)

ESI-MS Found: m/z 375.2 [M+H]+

Production Example 24

Production of 3-fluoro-3-phenyl-8-aza-bicyclo[3.2.1]octane 1) 8-Benzyl-3-phenyl-8-aza-bicyclo[3.2.1]octan-3-ol 2.80 g of the entitled compound was obtained as a white powder in the same manner as in Production Example 8-3, for which, however, benzyl 3-oxo-8-aza-bicyclo[3.2.1]octane-8-carboxylate and phenylmagnesium bromide were used in place of tert-butyl 3-oxo-8-aza-bicyclo[3.2.1]octane-8-carboxylate and the lithium reagent prepared from and 2-bromobenzyl alcohol and n-butyllithium-hexane solution used in Production Example 8-3.

2) Benzyl 3-hydroxy-3-phenyl-8-azabicyclo[3.2.1]octane-8-carboxylate

A crude 3-phenyl-8-aza-bicyclo[3.2.1]octan-3-ol was obtained in the same manner as in Production Example 12-3, for which, however, the compound obtained in the above 1 was used and ethanol was used as the solvent. Then, in the same manner as in Production Example 14-1 but using the compound obtained herein and using chloroform as the solvent, 248 mg of the entitled compound was obtained as a yellow oily substance.

3) Benzyl 3-fluoro-3-phenyl-8-azabicyclo[3.2.1]octane-8-carboxylate 91.7 mg of the entitled compound was obtained as a yellow oily substance in the same manner as in Production Example 23-2, for which, however, the compound obtained in the above 2 was used in place of benzyl 4-(2-chlorophenyl)-4-hydroxypiperidine-1-carboxylate used in Production Example 23-2, and methylene chloride was used as the solvent.

4) 3-Fluoro-3-phenyl-8-azabicyclo[3.2.1]octane 30.3 mg of an a hardly-separable compound of 3-fluoro-3-phenyl-8-azabicyclo[3.2.1]octane and 3-phenyl-8-azabicyclo[3.2.1]oct-2-ene was obtained in the same manner as in Production Example 23-3, for which, however, the compound obtained in the above 3 was used in place of benzyl 4-(2-chlorophenyl)-4-fluoropiperidine-1-carboxylate used in Production Example 23-3.

Example 30

Production of (7R,9S)-7-(3-fluoro-3-phenyl-8-azabicyclo[3.2.1]oct-8-ylmethyl)-6,7,8,9-tetrahydro-5H-cyclohepta[b]pyridin-9-ol mono-L-tartrate 5.84 mg of the entitled compound was obtained as a white powder in the same manner as in Example 15, for which, however, the compound obtained in Production Example 24 was sued in place of (3S*,4S*)-4-o-tolyl-piperidin-3-ol used in Example 15.

1H NMR (400 MHz, CD3OD) δ: 1.24 (5H, m), 1.60 (1H, m), 2.32 (8H, m), 2.79 (4H, m), 3.04 (2H, m), 5.01 (1H, m), 7.27 (4H, m), 7.46 (2H, m), 7.56 (1H, m), 8.22 (1H, m)
ESI-MS Found: m/z 381.3 [M+H]+

Production Example 25

Production of (3R*,4R*)-4-(2-chlorophenyl)piperidin-3-ol

1) Tert-butyl 4-(4,4,5,5-tetramethyl-[1.3.2]dioxaborolan-2-yl)-3,6-dihydro-2H-pyridine-1-carboxylate In a nitrogen atmosphere, 75 mL of 1.0 M lithium bis(trimethylsilyl)amide-tetrahydrofuran solution was dropwise added to tetrahydrofuran (250 mL) solution of 9.96 g of tert-butyl 4-oxo-piperidine-1-carboxylate at −78° C., and stirred at −78° C. for 30 minutes. At −78° C., tetrahydrofuran (75 mL) solution of 17.9 g of N-phenylbis(trifluoromethanesulfonimide) was dropwise added to the reaction liquid, and stirred at 0° C. for 2 hours. Aqueous saturated ammonium chloride solution was added to the reaction liquid, extracted with ethyl acetate, and the ethyl acetate layer was washed with saturated saline water, and dried with anhydrous sodium sulfate. The solvent was evaporated off under reduced pressure to obtain crude tert-butyl 4-trifluoromethanesulfonyloxy-3,6-dihydro-2H-pyridine-1-carboxylate as an orange oily substance.

In a nitrogen atmosphere, 12.7 g of bis(pinacolate)diboron, 14.7 g of potassium acetate, 1.39 g of 1,1'-bis(diphenylphosphino)ferrocene and 1.83 g of [1.1'-bis(diphenylphosphino)ferrocene]palladium were added in that order to dioxane (400 mL) solution of the above compound, and stirred at 80° C. for 22 hours. The reaction liquid was filtered through Celite, the solvent was evaporated off under reduced pressure, and the residue was separated and purified through silica gel column chromatography (hexane/ethyl acetate=85/15) to obtain 15.2 g of the entitled compound as a yellow oily substance.

2) Tert-butyl 4-(2-chlorophenyl)-3,6-dihydro-2H-pyridine-1-carboxylate

In a nitrogen atmosphere, 1.72 mL of 1-chloro-2-iodobenzene, 5.31 g of potassium carbonate and 474 mg of chloro[1,1'-bis(diphenylphosphino)ferrocene]palladium were added in that order to N,N-dimethylformamide (51 mL) solution of 3.95 g of the compound obtained in the above 1, and stirred at 80° C. for 17 hours. Aqueous saturated sodium hydrogencarbonate solution was added to the reaction liquid, extracted with ethyl acetate, and the ethyl acetate layer was washed with saturated saline water and dried with anhydrous sodium sulfate. The solvent was evaporated off under reduced pressure, and the residue was separated and purified through silica gel column chromatography (hexane/ethyl acetate=90/10) to obtain 1.61 g of the entitled compound as a pale yellow oily substance.

3) (3R*,4R*)-4-(2-chlorophenyl)piperidin-3-ol

Tert-butyl (3RS,4RS)-4-(2-chlorophenyl)-3-hydroxypiperidine-1-carboxylate was obtained as a colorless amorphous substance in the same manner as in Production Example 12-2, for which, however, the compound obtained in the above 2 was used in place of 1-benzyl-4-o-tolyl-1,2,3,6-tetrahydropyridine used in Production Example 12-2 and the step of converting the product into its hydrochloride was omitted. In a nitrogen atmosphere, 4 N hydrogen chloride-dioxane solution was added to the above compound, and stirred at room temperature for 1.5 hours. The solvent was evaporated off under reduced pressure, aqueous saturated sodium hydrogencarbonate solution was added to the residue, and extracted with ethyl acetate. The ethyl acetate layer was washed with saturated saline water, and dried with anhydrous sodium sulfate. The solvent was evaporated off under reduced pressure to obtain (3RS,4RS)-4-(2-chlorophenyl)piperidin-3-ol as a white solid.

186 mg of the obtained racemate was optically resolved in an optically-active column (Daicel's CHRALPAK AD-H column, 2 cm×25 cm; 0.1% diethylamine, hexane/ethanol=8/2; flow rate, 20 mL/min). From the former fraction (retention time; 7.0 min), 71.3 mg of (3S*,4S*)-4-(2-chlorophenyl)piperidin-3-ol was obtained as a white solid; and from the latter fraction (retention time; 11.5 min), 68.2 mg of the (3R*,4R*) form was obtained as a white solid. (The two were not identified, and for convenience sake, one was referred to as (3R*,4R*) form and the other was as (3S*,4S*) form.) Former fraction, (3S*,4S*) form:

1H NMR (400 MHz, CDCl3) δ: 1.52-1.64 (1H, m), 1.86-1.91 (1H, m), 2.61 (1H, dd, J=9.7, 11.5 Hz), 2.71 (1H, td,

J=2.7, 12.1 Hz), 3.05-3.10 (1H, m), 3.16-3.22 (1H, m), 3.38 (1H, ddd, J=1.0, 4.4, 11.4 Hz), 3.87 (1H, td, J=4.6, 10.1 Hz), 7.14-7.18 (1H, m), 7.24-7.29 (1H, m), 7.33-7.38 (2H, m)
ESI-MS Found: m/z 212.1 [M+H]+

Latter Fraction, (3R*,4R*) Form:
1H NMR and ESI-MS were the same as those of the (3S*,4S*) form.

Example 31

Production of (7R,9S)-7-[(3R*,4R*)-4-(2-chlorophenyl)-3-hydroxypiperidin-1-ylmethyl]-6,7,8,9-tetrahydro-5H-cyclohepta[b]pyridin-9-ol monohydrochloride The entitled compound was obtained as a white solid in the same manner as in Example 17, for which, however, the compound, (3R*,4R*) form obtained in Production Example 25 was used in place of (3R*,4R*)-4-(4-fluoro-o-tolyl)piperidin-3-ol used in Example 17, and the optically-active column was not used for the separation and purification of the crude product, but the residue was again dissolved in ethanol and heptane was added thereto for crystallization of the product.

m.p.: 214° C. (decomposition)

The free amine of the compound was analyzed for the following assignment.

1H NMR (400 MHz, CDCl3) δ: 1.45-1.90 (6H, m), 2.03 (1H, t, J=10.1 Hz), 2.10-2.17 (3H, m), 2.58 (2H, d, J=7.3 Hz), 2.64-2.70 (1H, m), 2.84-2.93 (2H, m), 3.06-3.12 (1H, m), 3.21-3.25 (1H, m), 3.97-4.03 (1H, m), 4.93 (1H, dd, J=2.6 Hz, 10.3 Hz), 5.36 (1H, brs), 7.09-7.18 (2H, m), 7.23-7.29 (1H, m), 7.35-7.38 (2H, m), 7.41-7.50 (1H, m), 8.33-8.35 (1H, m)
ESI-MS Found: m/z 387.2 [M+H]+

Production Example 26

Production of (3R,4R)-4-(2-chloro-4-fluorophenyl)piperidin-3-ol

1) Tert-butyl 4-(2-chloro-4-fluorophenyl)-3,6-dihydro-2H-pyridine-1-carboxylate 16.7 g of the entitled compound was obtained as a green oily substance in the same manner as in Production Example 25-2, for which, however, 1-chloro-5-fluoro-2-iodobenzene was used in place of 1-chloro-2-iodobenzene used in Production Example 25-2.

2) (3R,4R)-4-(2-chloro-4-fluorophenyl)piperidin-3-ol 3.62 g of the entitled compound was obtained as a pale orange solid from the latter fraction (retention time: 14.8 min) in the same method as in Production Example 25-3, for which, however, tert-butyl 4-(2-chloro-4-fluorophenyl)-3,6-dihydro-2H-pyridine-1-carboxylate was used in place of tert-butyl 4-(2-chlorophenyl)-3,6-dihydro-2H-pyridine-1-carboxylate used in Production Example 25-3, and an optically-active column (Daicel's CHRALPAK AD column, 2 cm×25 cm; 0.1% diethylamine, hexane/ethanol=9/1; flow rate, 20 mL/min) was sued for the optical resolution.

1H NMR (300 MHz, CDCl$_3$) δ: 1.80 (1H, d, J=13.0 Hz), 2.11 (1H, m), 2.55 (1H, t, J=11.0 Hz), 2.70 (1H, t, J=12.3 Hz), 3.13 (1H, d, J=12.5 Hz), 3.36 (2H, m), 4.23 (1H, bs), 6.99 (1H, m), 7.19 (2H, m)
ESI-MS Found: m/z 230 [M+H]+

Example 32

Production of (7R,9S)-7-[(3R,4R)-4-(2-chloro-4-fluorophenyl-3-hydroxypiperidin-1-ylmethyl]-6,7,8,9-tetrahydro-5H-cyclohepta[b]pyridin-9-ol mono-L-tartrate The entitled compound was obtained as a white solid in the same manner as in Example 15, for which, however, the compound obtained in Production Example 26 was used in place of (3S*,4S*)-4-o-tolyl-piperidin-3-ol used in Example 15. The free amine of the compound was analyzed for assignment.

1H NMR (400 MHz, CDCl3) δ: 1.51-1.87 (6H, m), 2.00-2.05 (1H, m), 2.09-2.16 (3H, m), 2.52-2.61 (2H, m), 2.64-2.70 (1H, m), 2.83-2.92 (2H, m), 3.00-3.07 (1H, m), 3.20-3.25 (1H, m), 3.92-4.14 (1H, m), 4.91-4.94 (1H, m), 5.37 (1H, brs), 6.97-7.01 (1H, m), 7.08-7.13 (2H, m), 7.31-7.34 (1H, m), 7.41-7.43 (1H, m), 8.33-8.34 (1H, m)
ESI-MS Found: m/z 405.2 [M+H]+

Example 33

Production of (6R,8S)-6-[(3R,4R)-4-(2-chloro-4-fluorophenyl)-3-hydroxypiperidin-1-ylmethyl]-5,6,7,8-tetrahydroquinolin-8-ol monohydrochloride A free amine form was obtained in the same manner as in Example 14, for which, however, the compound obtained in Production Example 26 was used in place of spiro[isobenzofuran-1(3H),4'-piperidine]monohydrochloride used in Example 14. The obtained amine compound was dissolved in ethanol, 1 equivalent of 1 N hydrochloric acid was added thereto, and the solvent was evaporated off under reduced pressure. The residue was again dissolved in ethanol, and heptane was added thereto for crystallization to obtain the entitled compound as a white solid.

m.p.: 218° C. (decomposition)

1H NMR (300 MHz, CD3OD) δ: 1.65-1.81 (1H, m), 1.83-2.09 (2H, m), 2.20-2.31 (1H, m), 2.49-2.78 (3H, m), 2.80-2.96 (1H, m), 3.00-3.18 (3H, m), 3.18-3.34 (1H, m), 3.45-3.72 (2H, m), 4.20-4.35 (1H, m), 4.47 (2H, s), 4.75-5.00 (1H, m), 7.02-7.16 (1H, m), 7.16-7.33 (2H, m), 7.40-7.52 (1H, m), 7.60-7.71 (1H, m), 8.35-8.43 (1H, m)
ESI-MS Found: m/z 391.1 [M+H]+

Production Example 27

Production of (3R*,4R*)-4-(2-chloro-6-fluorophenyl)piperidin-3-ol

1) Tert-butyl 4-(2-chloro-6-fluorophenyl)-3,6-dihydro-2H-pyridine-1-carboxylate 3.87 g of the entitled compound was obtained as a pale yellow oily substance in the same manner as in Production Example 25-2, for which, however, 1-chloro-3-fluoro-2-iodobenzene was used in place of the compound used in Production Example 25-2.

2) Tert-butyl (3RS,4RS)-4-(2-chloro-6-fluorophenyl)-3-hydroxypiperidine-1-carboxylate 0.33 mL of boron trifluoride-diethyl ether complex was added to ether/tetrahydrofuran (5:1) (6 mL) solution of 553 mg of N,N'-bis(monoisopinocamphenylborane)-N,N,N',N'-tetramethylethylenediamine, and stirred at room temperature for 1.5 hours. Ether (2 mL) solution of 318 mg of the compound obtained in the above 1 was added to the resulting suspension, and stirred overnight at 50° C. The reaction liquid was restored to room temperature, and 0.22 mL of ethanol, 0.11 mL of water, 0.41 mL of aqueous 5 M sodium hydroxide solution and 0.35 mL of aqueous 30% hydrogen peroxide were gradually added thereto, and stirred overnight at room temperature. Water was added to the reaction liquid, and extracted with ethyl acetate. The organic layer was concentrated, and the residue was separated and purified through silica gel column chromatography (hexane/ethyl acetate=5/1 to 3/1) to obtain 186 mg of the entitled compound as a colorless oily substance.

3) (3R*,4R*)-4-(2-chloro-6-fluorophenyl)piperidin-3-ol

In a nitrogen atmosphere, 4 N hydrogen chloride-dioxane solution was added to 186 mg of the above compound, and stirred at room temperature for 1.5 hours. The solvent was evaporated off under reduced pressure, and aqueous saturated sodium hydrogencarbonate solution was added to the residue and extracted with ethyl acetate. The ethyl acetate layer was washed with saturated saline water, and dried with anhydrous sodium sulfate. The solvent was evaporated off under reduced pressure to obtain (3RS,4RS)-4-(2-chloro-6-fluorophenyl)piperidin-3-ol as a white solid. 77 mg of the thus-obtained racemate was optically resolved in an optically-active column (Daicel's CHRALPAK AD column, 2 cm×25 cm; 0.1% diethylamine, hexane/ethanol=8/2; flow rate, 20 mL/min). From the latter fraction (retention time: 17.2 min), 47 mg of the entitled compound was obtained as a pale orange solid. (The stereochemistry of the product was not identified, and for convenience sake, one was referred to as (3R*,4R*) form and the other was as (3S*,4S*) form.)
ESI-MS Found: m/z 230 [M+H]+

Example 34

Production of (7R,9S)-7-[(3R*,4R*)-4-(2-chloro-6-fluorophenyl)-3-hydroxypiperidin-1-ylmethyl]-6,7,8,9-tetrahydro-5H-cyclohepta[b]pyridin-9-ol mono-L-tartrate 40 mg of the entitled compound was obtained as a white solid in the same manner as in Example 15, for which, however, the compound obtained in Production Example 27 was used in place of (3S*,4S*)-4-o-tolyl-piperidin-3-ol used in Example 15. The free amine of the compound was analyzed for assignment.
1H NMR (300 MHz, CDCl$_3$) δ: 1.68 (4H, s), 1.92 (1H, t, J=10.4 Hz), 2.14 (4H, m), 2.61 (3H, m), 2.88 (2H, m), 3.20 (2H, m), 4.33 (1H, m), 4.95 (1H, d, J=11.0 Hz), 5.35 (1H, brs), 6.97 (1H, m), 7.16 (3H, m), 7.45 (1H, d, J=7.1 Hz), 8.36 (1H, d, J=4.7 Hz)
ESI-MS Found: m/z 405 [M+H]+

Production Example 28

Production of (3R*,4R*)-4-(2-chloro-4-fluorophenyl)-3-methoxypiperidine

1) Tert-butyl (3R*,4R*)-4-(2-chloro-4-fluorophenyl)-3-hydroxypiperidine-1-carboxylate The entitled compound was obtained in the same manner as in Production Example 8-2, for which, however, the compound obtained in Production Example 26-2 was used in place of 8-aza-bicyclo[3.2.1]octan-3-one used in Production Example 8-2.

2) Tert-butyl (3R*,4R*)-4-(2-chloro-4-fluorophenyl)-3-methoxypiperidine-1-carboxylate The entitled compound was obtained in the same manner as in Production Example 14-2, for which, however, the compound obtained in the above 1 was used in place of (3RS,4RS)-1-benzyloxycarbonyl-3-hydroxy-4-o-tolylpiperidine used in Production Example 14-2.

3) (3R*,4R*)-4-(2-chloro-4-fluorophenyl)-3-methoxypiperidine

In a nitrogen atmosphere, 4 N hydrogen chloride-dioxane solution was added to the compound obtained in the above 2, and stirred at room temperature for 2 hours. The solvent was evaporated off under reduced pressure, and aqueous saturated sodium hydrogencarbonate solution was added to the residue and extracted with ethyl acetate. The ethyl acetate layer was washed with saturated saline water, and dried with anhydrous sodium sulfate. The solvent was evaporated off under reduced pressure to obtain the entitled compound as a pale yellow oily substance.
1H NMR (400 MHz, CDCl3) δ: 1.51 (1H, ddd, J=4.2, 12.3, 25.4 Hz), 1.73-1.89 (1H, m), 2.52 (1H, dd, J=9.9, 11.0 Hz), 2.70 (1H, td, J=2.7, 12.1 Hz), 3.04-3.08 (1H, m), 3.10-3.23 (1H, m), 3.22 (3H, s), 3.45 (1H, td, J=4.3, 10.0 Hz), 3.54 (1H, dd, J=4.2, 11.2 Hz), 6.96-7.01 (1H, m), 7.10-7.13 (1H, m), 7.25-7.28 (1H, m)
ESI-MS Found: m/z 244.1 [M+H]+

Example 35

Production of (6R,8S)-6-[(3R*,4R*)-4-(2-chloro-4-fluorophenyl)-3-methoxypiperidin-1-ylmethyl]-5,6,7,8-tetrahydroquinolin-8-ol mono-L-tartrate The entitled compound was obtained as a white solid in the same manner as in Example 14, for which, however, the compound obtained in Production Example 28 was used in place of spiro[isobenzofuran-1(3H),4'-piperidine] used in Example 14. The free amine of the compound was analyzed for assignment.
1H NMR (400 MHz, CDCl3) δ: 1.62-1.68 (1H, m), 1.82-1.95 (3H, m), 2.08-2.20 (2H, m), 2.41-2.47 (4H, m), 2.90-3.10 (3H, m), 3.20 (3H, s), 3.36-3.39 (1H, m), 3.55 (1H, td, J=4.3, 10.1 Hz), 3.94 (1H, brs), 4.89 (1H, brs), 6.94-6.99 (1H, m), 7.08-7.11 (1H, m), 7.15 (1H, brs), 7.24-7.28 (1H, m), 7.46-7.48 (1H, m), 8.40 (1H, brs)
ESI-MS Found: m/z 405.2 [M+H]+

Production Example 29

Production of (3RS,4RS)-4-(2-fluoro-4-methylpiperidin-5-yl)-3-methoxypiperidine 1) 2-Amino-5-bromo-4-methylpyridine In a nitrogen atmosphere, 1.08 g of 2-amino-4-methylpyridine was dissolved in 75 mL of tetrahydrofuran, and tetrahydrofuran (75 mL) solution of 3.20 g of pyridinium hydrobromide perbromide was dropwise added thereto at room temperature, over 1.5 hours. After the addition, this was stirred at room temperature for 40 minutes, and 100 mL of aqueous saturated sodium sulfite solution was added to the reaction mixture. This was extracted with ethyl acetate, and the ethyl acetate layer was dried with magnesium sulfate. The solvent was evaporated off under reduced pressure, and the residue was separated and purified through silica gel column chromatography (hexane/ethyl acetate=4/1 to ethyl acetate) to obtain 1.00 g of the entitled compound as a white solid.

2) 5-Bromo-2-fluoro-4-methylpyridine

In a nitrogen atmosphere, nitrosium tetrafluoroborate was suspended in 20 mL of chloroform, and with cooling with ice, chloroform (20 mL) solution of 748 mg of the compound obtained in the above 1 was added thereto. This was stirred at 0° C. for 30 minutes, and the reaction liquid was restored to room temperature, and then stirred for 1.5 hours. The solvent was evaporated off under reduced pressure, and the residue was dissolved in 30 mL of dimethylsulfoxide, and stirred overnight at 150° C. This was restored to room temperature, and the reaction liquid was made basic with saturated sodium hydrogencarbonate added thereto, and then extracted with ether. The ether layer was dried with magnesium sulfate. The solvent was evaporated off, and the residue was separated and purified through silica gel column chromatography (hexane/ethyl acetate=2/1) to obtain 318.8 mg of the entitled compound as a yellow oily substance.

3) Benzyl 4-(4,4,5,5-tetramethyl-[1,3,2]dioxaborolan-2-yl)-3,6-dihydro-2H-pyridine-1-carboxylate 6.83 g of the entitled compound was obtained as an orange oily substance in the same manner as in Production Example 25-1, for which, however, benzyl 4-oxy-1-carboxylate was used in place of tert-butyl 4-oxo-piperidine-1-carboxylate used in Production Example 25-1.

4) Benzyl 4-(2-fluoro-4-methylpyridin-5-yl)-3,6-dihydro-2H-pyridine-1-carboxylate 188 mg of the entitled compound was obtained as a colorless amorphous substance in the same manner as in Production Example 25-2, for which, however, 5-bromo-2-fluoro-4-methylpyridine and benzyl 4-(4,4,5,5-tetramethyl-[1,3,2]dioxaborolan-2-yl)-3,6-dihydro-2H-pyridine-1-carboxylate obtained in the above 2 and 3 were used in place of 1-chloro-2-iodobenzene and tert-butyl 4-(4,4,5,5-tetramethyl-[1,3,2]dioxaborolan-2-yl)-3,6-dihydro-2H-pyridine-1-carboxylate used in Production Example 25-2.

5) Benzyl (3RS,4RS)-4-(2-fluoro-4-methylpyridin-5-yl)-3-methoxypiperidine-1-carboxylate 48.8 mg of a mixture of (3RS,4RS)-1-benzyloxycarbonyl-4-(2-fluoro-4-methylpyridin-5-yl)-3-hydroxypiperidine and 1-benzyloxycarbonyl-4-(2-fluoro-4-methylpiperidin-5-yl)-4-hydroxypiperidine was obtained as a colorless amorphous compound in the same manner as in Production Example 12-2, for which, however, the compound obtained in the above 4 was used in place of 1-benzyl-4-o-tolyl-1,2,3,6-tetrahydropyridine used in Production Example 12-2, and the step of converting the product into its hydrochloride was omitted. The thus-obtained mixture was processed in the same manner as in Production Example 14-2 to obtain 19.4 mg of the entitled compound as a colorless amorphous substance.

6) Production of (3RS,4RS)-4-(2-fluoro-4-methylpyridin-5-yl)-3-methoxypiperidine 13.6 mg of the entitled compound was obtained as a colorless amorphous substance in the same manner as in Production Example 12-3, for which, however, the compound obtained in the above 5 was used in place of (3RS,4RS)-1-benzyl-4-o-tolyl-piperidin-3-ol monohydrochloride used in Production Example 12-3.

1H NMR (400 MHz, CDCl3) δ: 1.91-1.94 (1H, m), 2.07-2.22 (1H, m), 2.39 (3H, s), 2.60-2.74 (1H, m), 2.84-2.93 (2H, m), 3.17 (3H, s), 3.40-3.46 (1H, m), 3.68-3.78 (2H, m), 6.72 (1H, s), 8.11 (1H, s)

ESI-MS Found: m/z 225.2 [M+H]+

Examples 36 and 37

Production of (7R,9S)-7-[(3R*,4R*)-4-(2-fluoro-4-methylpyridin-5-yl)-3-methoxypiperidin-1-ylmethyl]-6,7,8,9-tetrahydro-5H-cyclohepta[b]pyridin-9-ol mono-L-tartrate; and (7R,9S)-7-[(3S*,4S*)-4-(2-fluoro-4-methylpyridin-5-yl)-3-methoxypiperidin-1-ylmethyl]-6,7,8,9-tetrahydro-5H-cyclohepta[b]pyridin-9-ol mono-L-tartrate A diastereomer mixture of the entitled compounds was obtained in the same manner as in Example 15, for which, however, the compound obtained in Production Example 29 was used in place of (3S*,4S*)-4-o-tolyl-piperidin-3-ol used in Example 15 and the step of converting the product into its L-tartrate was omitted. 5.0 mg of the obtained diastereomer mixture was separated in an optically-active column (Daicel's CHRALCEL OD column, 2 cm×25 cm; 0.1% diethylamine, hexane/isopropyl alcohol=4/1; flow rate, 20 mL/min). From the former fraction, 1.7 mg of (7R,9S)-7-[(3R*,4R*)-4-(2-fluoro-4-methylpyridin-5-yl)-3-methoxypiperidin-1-ylmethyl]-6,7,8,9-tetrahydro-5H-cyclohepta[b]pyridin-9-ol was obtained as a colorless amorphous substance; and from the latter fraction, 2.2 mg of the (3S*,4S*) form was obtained as a colorless amorphous substance. (The two were not identified, and for convenience sake, one was referred to as (3R*,4R*) form and the other was as (3S*,4S*) form.)

The two compounds were separately dissolved in methanol, an equimolar amount of L-tartaric acid was added thereto, and the solvent was evaporated off to obtain 2.4 mg of (3R*,4R*) form and 3.1 mg of (3S*,4S*) form, respectively, both as a white solid.

Compound of Example 36

(3R*,4R*) Form

Retention time, 7.8 min (optically-active column; Daicel's CHRALCEL OD column, 0.46 cm×25 cm; 0.1% diethylamine, hexane/isopropyl alcohol=4/1; flow rate, 1 mL/min)

1H NMR (400 MHz CD3OD) δ: 1.28-1.36 (1H, m), 1.58 (1H, t, J=12.5 Hz), 1.97-2.15 (3H, m), 2.25-2.31 (1H, m), 2.43 (3H, s), 2.57 (1H, t, J=10.6 Hz), 2.71-2.81 (3H, m), 2.92 (2H, d, J=7.3 Hz), 2.99-3.05 (1H, m), 3.32-3.39 (1H, m), 3.49 (1H, d, J=12.5 Hz), 3.73-3.80 (2H, m), 4.47 (2H, s), 5.05 (1H, d, J=6.6 Hz), 6.90 (1H, s), 7.25 (1H, dd, J=5.1, 7.3 Hz), 7.61 (1H, d, J=7.3 Hz), 8.09 (1H, s), 8.26 (1H, d, J=4.4 Hz)

ESI-MS Found: m/z 400.2 [M+H]+

Compound of Example 37

(3S*,4S*) Form

Retention time, 11.7 min (optically-active column; Daicel's CHRALCEL OD column, 0.46 cm×25 cm; 0.1% diethylamine, hexane/isopropyl alcohol=4/1; flow rate, 1 mL/min)

1H NMR (400 MHz, CD3OD) δ: 1.27-1.36 (1H, m), 1.58 (1H, t, J=12.5 Hz), 1.96-2.00 (1H, m), 2.05-2.15 (2H, m), 2.24-2.29 (1H, m), 2.43 (3H, s), 2.51-2.59 (1H, m), 2.71-2.81 (3H, m), 2.88-3.05 (3H, m), 3.20 (3H, s), 3.32-3.38 (1H, m), 3.49 (1H, d, J=11.7 Hz), 3.71-3.80 (2H, m), 4.46 (2H, s), 5.05

(1H, d, J=6.6 Hz), 6.90 (1H, s), 7.25 (1H, dd, 5.1, 7.3 Hz), 7.61 (1H, d, J=7.3 Hz), 8.09 (1H, s), 8.26 (1H, d, J=4.4 Hz)
ESI-MS Found: m/z 400.2 [M+H]+

Production Example 30

Production of 4-(2-cyanophenyl)piperidine

1) Benzyl 4-(2-cyanophenyl)-3,6-dihydro-2H-pyridine-1-carboxylate 784 mg of the entitled compound was obtained as a pale yellow solid in the same manner as in Production Example 29-4, for which, however, 2-bromobenzonitrile was used in place of 5-bromo-2-fluoro-4-methylpyridine used in Production Example 29-4.

2) 4-(2-Chyanophenyl)piperidine 22 mg of the entitled compound was obtained as a pale yellow oily substance in the same manner as in Production Example 12-3, for which, however, the compound obtained in the above 1 was used in place of (3RS,4RS)-1-benzyl-4-o-tolyl-piperidin-3-ol monohydrochloride used in Production Example 12-3.
ESI-MS Found: m/z 187 [M+H]+

Example 38

Production of (7R,9S)-7-[4-(2-cyanophenyl)piperidin-1-ylmethyl]-6,7,8,9-tetrahydro-5H-cyclohepta[b]pyridin-9-ol 3 mg of the entitled compound was obtained as a pale yellow oily substance in the same manner as in Example 15, for which, however, the compound obtained in Production Example 30 was used in place of (3S*,4S*)-4-o-tolyl-piperidin-3-ol used in Example 15, and the step of converting the product into its L-tartrate was omitted.
1H NMR (300 MHz, CDCl3) δ: 1.67 (2H, m), 1.79 (5H, m), 2.15 (4H, m), 2.62 (3H, m), 2.88 (1H, m), 3.00 (2H, m), 4.95 (1H, d, J=9.1 Hz), 5.36 (1H, bs), 7.13 (1H, m), 7.32 (1H, m), 7.43 (2H, m), 7.57 (2H, m), 8.36 (1H, d, J=5.0 Hz)
ESI-MS Found: m/z 362 [M+H]+

Production Example 31

Production of methyl (3R*,4S*)-4-o-tolyl-piperidine-3-carboxylate; and methyl (3S*,4R*)-4-o-tolyl-piperidine-3-carboxylate 1) Methyl (3RS,4SR)-1-methyl-4-o-tolyl-piperidine-3-carboxylate In a nitrogen atmosphere, diethyl ether (20 mL) solution of 1.80 g of arecoline (prepared by processing a hydrobromide with aqueous saturated sodium hydrogencarbonate solution and converting the product into its free form) was gradually added to diethyl ether (180 mL) solution of 11.6 mL of 2.0 M o-tolylmagnesium bromide-diethyl ether solution at −40° C., and stirred at that temperature for 2 hours. The reaction liquid was heated up to −20° C., then poured into water with ice, and 1 N hydrochloric acid was added thereto. This was subjected to liquid-liquid separation, and the aqueous layer was made alkaline with aqueous ammonia added thereto. Then, this was extracted with diethyl ether, and the diethyl layer was dried with anhydrous magnesium sulfate. The solvent was evaporated off under reduced pressure, and the residue was separated and purified through silica gel column chromatography (chloroform/methanol=50/1) to obtain 1.40 g of a product. In a nitrogen atmosphere, 0.64 g of potassium tert-butoxide was added to tetrahydrofuran (50 mL) solution of 1.40 g of the product, with cooling with ice, and then stirred at room temperature for 1 hour. Aqueous saturated sodium hydrogencarbonate solution was added to the reaction liquid, and extracted with ethyl acetate. The ethyl acetate layer was washed with saturated saline water, and then dried with anhydrous magnesium sulfate. The solvent was evaporated off under reduced pressure, and the residue was separated and purified through silica gel column chromatography (chloroform/methanol=50/1) to obtain 0.92 g of the entitled compound.

2) Methyl (3R*,4S*)-4-o-tolyl-piperidine-3-carboxylate; and methyl (3S*,4R*)-4-o-tolyl-piperidine-3-carboxylate 287 mg of methyl (3RS,4SR)-4-o-tolyl-piperidine-3-carboxylate was obtained in the same manner as in Production Example 22-3, for which, however, the compound obtained in the above 1 was used in place of 1,1'-dimethyl-spiro[2,3-dihydro-1H-indole-3,4'-piperidine] used in Production Example 22-3.
1H NMR (200 MHz, CDCl3) δ: 1.38-1.61 (1H, m), 1.70-1.85 (1H, m), 2.37 (3H, s), 2.70-2.94 (3H, m), 3.11-3.26 (2H, m), 3.26-3.45 (1H, m), 3.42 (3H, s), 7.00-7.21 (4H, m)
ESI-MS Found: m/z 234.3 [M+H]+

101 mg of the above racemate was optically resolved in an optically-active column (Daicel's CHRALCEL OD column, 2 cm×25 cm; 0.1% diethylamine, hexane/isopropyl alcohol=9/1; flow rate, 15 mL/min). From the former fraction (retention time; 14.5 min), 51 mg of methyl (3S*,4R*)-4-o-tolyl-piperidine-3-carboxylate was obtained; and from the latter fraction (retention time; 17.0 min), 47 mg of the (3R*, 4S*) form was obtained. (The two were not identified, and for convenience sake, one was referred to as (3R*,4S*) form and the other was as (3S*,4R*) form.)

Former Fraction, (3S*,4R*) Form:
1H NMR and ESI-MS were the same as those of the racemate.

Latter Fraction, (3R*,4S*) Form:
1H NMR and ESI-MS were the same as those of the racemate.

Examples 39 and 40

Production of (7R,9S)-7-[(3R*,4S*-3-methoxycarbonyl-4-o-tolyl-piperidin-1-ylmethyl]-6,7,8,9-tetrahydro-5H-cyclohepta[b]pyridin-9-ol; and (7R,9S)-7-[(3S*,4R*)-3-methoxycarbonyl-4-o-tolyl-piperidin-1-ylmethyl]-6,7,8,9-tetrahydro-5H-cyclohepta[b]pyridin-9-ol 1) (7R,9S)-9-tert-butyldimethylsilanyloxy-7-[(3RS,4SR)-3-methoxycarbonyl-4-o-tolyl-piperidin-1-ylmethyl]-6,7,8,9-tetrahydro-5H-cyclohepta[b]pyridine 174 mg of the entitled compound was obtained in the same manner as in Example 15, for which, however, methyl (3RS, 4SR)-4-o-tolyl-piperidine-3-carboxylate before optical resolution obtained in Production Example 31 was used in place of (3S*,4S*)-4-o-tolyl-piperidin-3-ol used in Example 15, and the step of treating the product with tetrabutylammonium fluoride and the step of converting the product into its L-tartrate were omitted.

2) (7R,9S)-7-[(3S*,4R*)-3-methoxycarbonyl-4-o-tolyl-piperidin-1-ylmethyl]-6,7,8,9-tetrahydro-5H-cyclohepta[b]pyridin-9-ol; and (7R,9S)-7-[(3R*,4S*)-3-methoxycarbonyl-4-o-tolyl-piperidin-1-ylmethyl]-6,7,8,9-tetrahydro-5H-cyclohepta[b]pyridin-9-ol A diastereomer mixture of the entitled compounds was obtained in the same manner as in 2 in Examples 9 and 10, for which, however, the compound obtained in the above 1 was used in place of (7RS,9SR)-7-(spiro[8-aza-bicyclo[3.2.1]octa-3,1'(3'H)-isobenzofuran]-8-ylmethyl)-9-tert-butyldimethylsilyloxy-6,7,8,9-tetrahydro-5H-cyclohepta[b]pyridine used in 2 in Examples 9 and 10. The resulting diastereomer mixture was separated in an optically-active column (Daicel's CHRALPAK AD column, 2 cm×25 cm, two columns connected; 0.1% diethylamine, hexane/isopropyl alcohol=29/1; flow rate, 20 mL/min). From the former fraction (retention time; 62.6 min), 4.8 mg of (7R,9S)-7-[(3S*,4R*)-3-methoxycarbonyl-4-o-tolyl-piperidin-1-ylmethyl]-6,7,8,9-tetrahydro-5H-cyclohepta[b]pyridin-9-ol was obtained as a colorless amorphous substance; and from the latter fraction (retention time; 66.2 min), 2.3 mg of the (3R*,4S*) form was obtained as a colorless amorphous substance. (The two were not identified, and for convenience sake, one was referred to as (3S*,4R*) form and the other was as (3R*,4S*) form.)

Compound of Example 39

(3S*,4R*) Form

1H NMR (200 MHz, CDCl3) δ: 1.50-1.94 (5H, m), 2.06-2.33 (4H, m), 2.38 (3H, s), 2.53-2.92 (4H, m), 2.92-3.23 (4H, m), 3.43 (3H, s), 4.89-5.00 (1H, m), 5.20-5.60 (1H, brd), 7.00-7.30 (5H, m), 7.40-7.50 (1H, m), 8.33-8.41 (1H, m)
ESI-MS Found: m/z 409.3 [M+H]+

Compound of Example 40

(3R*,4S*) Form

1H NMR (200 MHz, CDCl3) δ: 1.49-1.92 (5H, m), 2.05-2.29 (4H, m), 2.38 (3H, s), 2.51-3.24 (8H, m), 3.42 (3H, s), 4.88-5.00 (1H, m), 5.18-5.62 (1H, brd), 7.01-7.31 (5H, m), 7.40-7.50 (1H, m), 8.32-8.41 (1H, m)
ESI-MS Found: m/z 409.4 [M+H]+

Examples 41 and 42

Production of (7R,9S)-7-[(3R*,4S*)-3-hydroxymethyl-4-o-tolyl-piperidin-1-ylmethyl]-6,7,8,9-tetrahydro-5H-cyclohepta[b]pyridin-9-ol; and (7R,9S)-7-[(3S*,4R*)-3-hydroxymethyl-4-o-tolyl-piperidin-1-ylmethyl]-6,7,8,9-tetrahydro-5H-cyclohepta[b]pyridin-9-ol With cooling with ice, 7.6 mg of lithiumaluminium hydride was added to tetrahydrofuran (3 mL) solution of 70 mg of the compound obtained in 1 in Examples 39 and 40, and stirred at room temperature for 30 minutes. Aqueous 1 M sodium hydroxide solution was added to the reaction liquid, extracted with ethyl acetate, and the ethyl acetate layer was washed with saturated saline water and dried with anhydrous magnesium sulfate. The solvent was evaporated off under reduced pressure, and the residue was separated and purified through silica gel column chromatography (chloroform/methanol=20/1) to obtain 45 mg of (7R,9S)-9-tert-butyldimethylsilanyloxy-7-[(3RS,4SR)-3-hydroxymethyl-4-o-tolyl-piperidin-1-ylmethyl]-6,7,8,9-tetrahydro-5H-cyclohepta[b]pyridine.

The compound was processed in the same manner as in 2 in Examples 9 and 10, and 4.3 mg of the resulting diastereomer mixture was separated in an optically-active column (Daicel's CHRALCEL OD column, 2 cm×25 cm; 0.1% diethylamine, hexane/isopropyl alcohol=17/3; flow rate, 15 mL/min). From the former fraction (retention time; 15.9 min), 2.4 mg of (7R,9S)-7-[(3S*,4R*)-3-hydroxymethyl-4-o-tolyl-piperidin-1-ylmethyl]-6,7,8,9-tetrahydro-5H-cyclohepta[b]pyridin-9-ol was obtained as a colorless amorphous substance; and from the latter fraction (retention time; 20.2 min), 1.8 mg of the (3R*,4S*) form was obtained as a colorless amorphous substance. (The two were not identified, and for convenience sake, one was referred to as (3R*,4S*) form and the other was as (3S*,4R*) form.)

Compound of Example 41

(3S*,4R*) Form

1H NMR (200 MHz, CDCl3) δ: 1.40-2.29 (10H, m), 2.32 (3H, s), 2.51-2.74 (4H, m), 2.81-3.10 (2H, m), 3.18-3.32 (2H, m), 3.38-3.48 (1H, m), 4.90-5.00 (1H, m), 7.04-7.35 (5H, m), 7.40-7.50 (1H, m), 8.32-8.40 (1H, m)
ESI-MS Found: m/z 381.2 [M+H]+

Compound of Example 42

(3R*,4S*) Form

1H NMR (200 MHz, CDCl3) δ: 1.40-2.29 (10H, m), 2.32 (3H, s), 2.50-2.77 (4H, m), 2.80-3.07 (2H, m), 3.18-3.33 (2H, m), 3.38-3.50 (1H, m), 4.90-5.00 (1H, m), 7.04-7.32 (5H, m), 7.40-7.50 (1H, m), 8.32-8.40 (1H, m)
ESI-MS Found: m/z 381.4 [M+H]+

Examples 43 and 44

Production of (7R,9S)-7-[(3R*,4S*)-3-(1-hydroxy-1-methyl-ethyl)-4-o-tolyl-piperidin-1-ylmethyl]-6,7,8,9-tetrahydro-5H-cyclohepta[b]pyridin-9-ol mono-L-tartrate; and (7R,9S)-7-[(3S*,4R*)-3-(1-hydroxy-1-methyl-ethyl)-4-o-tolyl-piperidin-1-ylmethyl]-6,7,8,9-tetrahydro-5H-cyclohepta[b]pyridin-9-ol mono-L-tartrate In a nitrogen atmosphere, 87 μL of 3.0 M methylmagnesium bromide-diethyl ether solution was added to tetrahydrofuran (2 mL) solution of 68 mg of the compound obtained in 1 in Examples 39 and 40, with cooling with ice, and stirred at room temperature for 45 minutes. 87 μL of methylmagnesium bromide solution was added to the reaction liquid at room temperature, and stirred for 30 minutes. Further, 175 μL of methylmagnesium bromide solution was added to the reaction liquid at room temperature, and stirred for 1 hour. Aqueous 1 M sodium hydroxide solution was added to the reaction liquid, and extracted with ethyl acetate, and the ethyl acetate layer was washed with saturated saline water and dried with anhydrous magnesium sulfate. The solvent was evaporated off under reduced pressure, and the residue was separated and purified through partitioning thin-layer chromatography (chloroform/methanol=20/1) to obtain 31 mg of (7R,9S)-7-[(3RS,4SR)-3-(1-hydroxy-1-methyl-ethyl)-4-o-tolyl-piperidin-1-ylmethyl]-9-tert-butyldimethylsilanyloxy-6,7,8,9-tetrahydro-5H-cyclohepta[b]pyridine.

The compound was processed in the same manner as in 2 in Examples 9 and 10, and 18 mg of the resulting diastereomer mixture was separated in an optically-active column (Daicel's CHRALCEL OD column, 2 cm×25 cm; 0.1% diethylamine, hexane/isopropyl alcohol=9/1; flow rate, 15 mL/min). From the former fraction (retention time; 15.5 min), 6.4 mg of (7R,9S)-7-[(3S*,4R*)-3-(1-hydroxy-1-methyl-ethyl)-4-o-tolyl-piperidin-1-ylmethyl]-6,7,8,9-tetrahydro-5H-cyclohepta[b]pyridin-9-ol was obtained; and from the latter fraction (retention time; 19.2 min), 7.3 mg of the (3R*,4S*) form was obtained. (The two were not identified, and for convenience sake, one was referred to as (3R*,4S*) form and the other was as (3S*,4R*) form.)

An equimolar amount of L-tartaric acid and ethanol were added to the above compound to dissolve it, and the solvent was evaporated off under reduced pressure. The residue was washed with ethyl acetate/hexane added thereto. The wash was removed, and the residue was dried under reduced pressure to obtain (7R,9S)-7-[(3S*,4R*)-3-(1-hydroxy-1-methyl-ethyl)-4-o-tolyl-piperidin-1-ylmethyl]-6,7,8,9-tetrahydro-5H-cyclohepta[b]pyridin-9-ol mono-L-tartrate and (7R,9S)-7-[(3R*,4S*)-3-(1-hydroxy-1-methyl-ethyl)-4-o-tolyl-piperidin-1-ylmethyl]-6,7,8,9-tetrahydro-5H-cyclohepta[b]pyridin-9-ol mono-L-tartrate, both as a white solid.

Compound of Example 43

(3S*,4R*) Form

1H NMR (200 MHz, CD3OD) δ: 0.79 (3H, s), 1.00 (3H, s), 1.23-1.69 (2H, m), 1.81-2.33 (4H, m), 2.39 (3H, s), 2.53-2.91 (3H, m), 2.91-3.24 (5H, m), 3.30-3.48 (1H, m), 3.56-3.72 (1H, m), 3.90-4.07 (1H, m), 4.42 (2H, s), 5.00-5.10 (1H, m), 7.01-7.38 (5H, m), 7.57-7.67 (1H, m), 8.23-8.31 (1H, m)
ESI-MS Found: m/z 409.4 [M+H]+

Compound of Example 44

(3R*,4S*) Form

1H NMR (200 MHz, CD3OD) δ: 0.78 (3H, s), 1.00 (3H, s), 1.21-1.69 (2H, m), 1.82-2.38 (4H, m), 2.40 (3H, s), 2.55-3.20 (8H, m), 3.30-3.47 (1H, m), 3.57-3.71 (1H, m), 3.91-4.09 (1H, m), 4.42 (2H, s), 5.00-5.10 (1H, m), 7.01-7.38 (5H, m), 7.58-7.67 (1H, m), 8.21-8.31 (1H, m)
ESI-MS Found: m/z 409.4 [M+H]+

Example 45

Production of (7R,9S)-7-[(3R*,4S*)-3-acetyl-4-o-tolyl-piperidin-1-ylmethyl]-6,7,8,9-tetrahydro-5H-cyclohepta[b]pyridin-9-ol 1) (7R,9S)-9-tert-butyldimethylsilanyloxy-7-[(3R*,4S*)-3-methoxycarbonyl-4-o-tolyl-piperidin-1-ylmethyl]-6,7,8,9-tetrahydro-5H-cyclohepta[b]pyridine 58 mg of the entitled compound was obtained in the same manner as in Example 15, for which, however, methyl (3R*,4S*)-4-o-tolyl-piperidine-3-carboxylate obtained in Production Example 31 was used in place of (3S*,4S*)-4-o-tolyl-piperidin-3-ol used in Example 15, and the step of treating the product with tetrabutylammonium fluoride and the step of converting the product into its L-tartrate were omitted.

2) (7R,9S)-7-[(3R*,4S*)-3-acetyl-4-o-tolyl-piperidin-1-ylmethyl]-6,7,8,9-tetrahydro-5H-cyclohepta[b]pyridin-9-ol 2.9 mg of lithium hydroxide was added to ethanol (3 mL) solution of 58 mg of the compound obtained in the above 1, and refluxed for 17 hours. Then, 2 ml of aqueous 2 M sodium hydroxide solution was added thereto, and refluxed further for 2 hours. The solvent was evaporated off, and the resulting residue was dissolved in 2 mL of diethyl ether. In a nitrogen atmosphere, 40 μL of 1.20 M methyllithium-diethyl ether solution was added to it at 0° C., and stirred at 0° C. for 45 minutes and then at room temperature for 1 hour. Next, 40 μL of 1.20 M methyllithium-diethyl ether solution was further added to it at 0° C., and stirred at room temperature for 40 minutes. Aqueous saturated sodium hydrogencarbonate solution was added to the reaction liquid, and extracted with ethyl acetate. The ethyl acetate layer was washed with saturated saline water, and dried with anhydrous magnesium sulfate. The solvent was evaporated off under reduced pressure, and the residue was separated and purified through preparative thin-layer chromatography (chloroform/methanol=20/1) to obtain 5 mg of (7R,9S)-7-[(3S*,4R*)-3-acetyl-4-o-tolyl-piperidin-1-ylmethyl]-9-tert-butyldimethylsilanyloxy-6,7,8,9-tetrahydro-5H-cyclohepta[b]pyridine. The obtained compound was processed in the same manner as in 2 in Examples 9 and 10 to obtain 2.2 mg of the entitled compound as a colorless amorphous substance.

1H NMR (200 MHz, CDCl3) δ: 1.50-1.83 (7H, m), 1.82 (3H, s), 2.05-2.26 (4H, m), 2.32 (3H, s), 2.48-2.74 (2H, m), 2.79-3.32 (4H, m), 4.90-5.00 (1H, m), 5.20-5.55 (1H, brd), 7.05-7.31 (5H, m), 7.41-7.50 (1H, m), 8.34-8.41 (1H, m)
ESI-MS Found: m/z 393.1 [M+H]+

Production Example 32

Methyl (3RS,4SR)-4-phenyl-piperidine-3-carboxylate monohydrochloride 210.9 mg of the entitled compound was obtained as a white solid in the same manner as in Production Example 31-1, for which, however, phenylmagnesium bromide was used in place of o-tolylmagnesium bromide used in Production Example 31-1, and the resulting produce was processed in the same manner as in Production Example 8-1.

1H NMR (300 MHz, CDCl3) δ: 2.02-2.07 (1H, m), 2.35-2.49 (1H, m), 2.95-3.16 (3H, m), 3.39-3.48 (4H, m), 3.65-3.77 (2H, m), 7.22-7.34 (5H, m)
ESI-MS Found: m/z 220.3 [M+H]+

Examples 46 and 47

Production of (7R,9S)-7-[(3R*,4S*)-3-hydroxymethyl-4-phenyl-piperidin-1-ylmethyl]-6,7,8,9-tetrahydro-5H-cyclohepta[b]pyridin-9-ol; and (7R,9S)-7-[(3S*,4R*)-3-hydroxymethyl-4-phenyl-piperidin-1-ylmethyl]-6,7,8,9-tetrahydro-5H-cyclohepta[b]pyridin-9-ol 1) (7R,9S)-7-[(3RS,4SR)-3-methoxycarbonyl-4-phenyl-piperidin-1-ylmethyl]-9-tert-butyldimethylsilanyloxy-6,7,8,9-tetrahydro-5H-cyclohepta[b]pyridine 120 mg of the entitled compound was obtained as a colorless amorphous substance in the same manner as in Example 15, for which, however, the compound obtained in Production Example 32 was used in place of (3S*,4S*)-4-o-tolyl-piperidin-3-ol used in Example 15 and the step of treating the product with tetrabutylammonium fluoride and the step of converting the product into its L-tartrate were omitted.
ESI-MS Found: m/z 509.4 [M+H]+

2) (7R,9S)-7-[(3R*,4S*)-3-hydroxymethyl-4-phenyl-piperidin-1-ylmethyl]-6,7,8,9-tetrahydro-5H-cyclohepta[b]pyridin-9-ol; and (7R,9S)-7-[(3S*,4R*)-3-hydroxymethyl-4-phenyl-piperidin-1-ylmethyl]-6,7,8,9-tetrahydro-5H-cyclohepta[b]pyridin-9-ol 40.4 mg of a diastereomer mixture of the entitled compounds was obtained in the same manner as in Examples 41 and 42, for which, however, the compound obtained in the above 1 was used in place of (7R,9S)-7-[(3RS,4SR)-3-methoxycarbonyl-4-o-tolyl-piperidin-1-ylmethyl]-9-tert-butyldimethylsilanyloxy-6,7,8,9-tetrahydro-5H-cyclohepta[b]pyridine used in Examples 41 and 42. The diastereomer mixture was separated in an optically-active column (Daicel's CHRALCEL OD column, 2 cm×25 cm; 0.1% diethylamine, hexane/isopropyl alcohol=17/3; flow rate, 15 mL/min). From the former fraction (retention time; 16.3 min), 14.9 mg of (7R,9S)-7-[(3S*,4R*)-3-hydroxymethyl-4-phenyl-piperidin-1-ylmethyl]-6,7,8,9-tetrahydro-5H-cyclohepta[b]pyridin-9-ol was obtained as a colorless amorphous substance; and from the latter fraction (retention time; 22.6 min), 14.8 mg of the (3R*,4S*) form was obtained as a colorless amorphous substance. (The two were not identified, and for convenience sake, one was referred to as (3R*,4S*) form and the other was as (3S*,4R*) form.)

The two compounds were separately dissolved in methanol, and an equimolar amount of L-tartaric acid was added thereto, and the solvent was evaporated off to obtain 17.4 mg of (7R,9S)-7-[(3S*,4R*)-3-hydroxymethyl-4-phenyl-piperidin-1-ylmethyl]-6,7,8,9-tetrahydro-5H-cyclohepta[b]pyridin-9-ol mono-L-tartrate and 18.0 mg of (7R,9S)-7-[(3R*,4S*)-3-hydroxymethyl-4-phenyl-piperidin-1-ylmethyl]-6,7,8,9-tetrahydro-5H-cyclohepta[b]pyridin-9-ol mono-L-tartrate, both as a white solid.

Compound of Example 46

(3S*,4R*) Form

1H NMR (300 MHz, CD3OD) δ: 1.35 (1H, q, J=12.8 Hz), 1.60 (1H, t, J=12.5 Hz), 1.98-2.39 (5H, m), 2.68-3.24 (8H, m), 3.30-3.43 (2H, m), 3.69-3.83 (2H, m), 4.45 (2H, s), 5.06 (1H, d, J=7.5 Hz), 7.21-7.36 (6H, m), 7.63 (1H, d, J=7.5 Hz), 8.27 (1H, d, J=4.5 Hz)

ESI-MS Found: m/z 367.1 [M+H]+

Compound of Example 47

(3R*,4S*) Form

1H NMR (300 MHz, CD3OD) δ: 1.35 (1H, q, J=12.4 Hz), 1.56-1.65 (1H, m), 1.98-2.43 (5H, m), 2.67-3.24 (8H, m), 3.30-3.43 (2H, m), 4.45 (2H, s), 5.06 (1H, d, J=6.8 Hz), 7.21-7.36 (6H, m), 7.62 (1H, d, J=7.6 Hz), 8.27 (1H, d, J=5.2 Hz)

ESI-MS Found: m/z 367.1 [M+H]+

Production Example 33

Production of
(3RS,4SR)-3-fluoromethyl-4-o-tolylpiperidine 1) (3RS,4SR)-(1-methyl-4-o-tolylpiperidin-3-yl)methanol In a nitrogen atmosphere, 152 mg of lithiumaluminium hydride was added to tetrahydrofuran (20 mL) solution of 500 mg of methyl (3RS,4SR)-1-methyl-4-o-tolylpiperidine-3-carboxylate obtained in Production Example 31-1, at 0° C., and stirred at 0° C. for 30 minutes. 0.15 mL of water, 0.15 mL of aqueous 15% sodium hydroxide solution and 0.46 mL of water were added to the reaction liquid in that order, and stirred at room temperature for 1 hour. This was diluted with ethyl acetate, and dried with anhydrous sodium sulfate, and the insoluble substance was removed through filtration through Celite. The filtrate was distilled under reduced pressure, and the residue was separated and purified through silica gel column chromatography (chloroform/methanol=70/30) to obtain 470 mg of the entitled compound as a pale yellow oily substance.

2) (3RS,4SR)-3-fluoromethyl-1-methyl-4-o-tolylpiperidine

The entitled compound was obtained in the same manner as in Production Example 15-2, for which, however, the compound obtained in the above 1 was used in place of tert-butyl (3R*,4R*)-3-hydroxy-4-o-tolylpiperidine-1-carboxylate used in Production Example 15-2.

3) (3RS,4SR)-3-fluoromethyl-4-o-tolylpiperidine

The compound obtained in the above 2 was processed in the same manner as in Production Example 22-3, using it in place of 1,1'-dimethyl-spiro[2,3-dihydro-1H-indole-3,4'-piperidine] used in Production Example 22-3; and the resulting crude product was separated and purified through basic silica gel column chromatography (hexane/ethyl acetate=7/3) to obtain the entitled compound as a yellow oily substance.

1H NMR (400 MHz, CDCl3) δ: 1.63-1.79 (2H, m), 2.05-2.14 (1H, m), 2.32 (3H, s), 2.70-2.77 (2H, m), 2.83 (1H, td, J=4.0, 11.7 Hz), 3.15-3.20 (1H, m), 3.36 (1H, dd, J=3.0, 12.3 Hz), 3.95-4.23 (2H, m), 7.08-7.26 (4H, m)

ESI-MS Found: m/z 208.1 [M+H]+

Examples 48 and 49

Production of (7R,9S)-7-[(3R*,4S*)-3-fluoromethyl-4-o-tolylpiperidin-1-ylmethyl]-6,7,8,9-tetrahydro-5H-cyclohepta[b]pyridin-9-ol mono-L-tartrate; and (7R,9S)-7-[(3S*,4R*)-3-fluoromethyl-4-o-tolylpiperidin-1-ylmethyl]-6,7,8,9-tetrahydro-5H-cyclohepta[b]pyridin-9-ol mono-L-tartrate 25.5 mg of a diastereomer mixture of the entitled compounds was obtained in the same manner as in Example 15, for which, however, the compound obtained in Production Example 33 was used in place of (3S*,4S*)-4-o-tolyl-piperidin-3-ol used in Example 15 and the step of converting the product into its L-tartrate was omitted. The diastereomer mixture was separated in an optically-active column (Daicel's CHRALPAK AD column, 2 cm×25 cm; 0.1% diethylamine, hexane/isopropyl alcohol=95/5; flow rate, 20 mL/min). From the former fraction (retention time; 12.5 min), 7.2 mg of (7R,9S)-7-[(3S*,4R*)-3-fluoromethyl-4-o-tolylpiperidin-1-ylmethyl]-6,7,8,9-tetrahydro-5H-cyclohepta[b]pyridin-9-ol was obtained as a colorless amorphous substance; and from the latter fraction (retention time; 13.3 min), 10.4 mg of the (3R*,4S*) form was obtained as a colorless amorphous substance. (The two were not identified, and for convenience sake, one was referred to as (3R*,4S*) form and the other was as (3S*,4R*) form.)

An equimolar amount of L-tartaric acid, chloroform and methanol were added in that order to each of the two compounds, and stirred at room temperature. The solvent was evaporated off under reduced pressure to obtain (7R,9S)-7-[(3S*,4R*)-3-fluoromethyl-4-o-tolylpiperidin-1-ylmethyl]-6,7,8,9-tetrahydro-5H-cyclohepta[b]pyridin-9-ol mono-L-tartrate and (7R,9S)-7-[(3R*,4S*)-3-fluoromethyl-4-o-tolylpiperidin-1-ylmethyl]-6,7,8,9-tetrahydro-5H-cyclohepta[b]pyridin-9-ol mono-L-tartrate, both as a white solid. The free amine of the compound was analyzed for assignment.

Compound of Example 48

(3S*,4R*) Form

1H NMR (400 MHz, CDCl3) δ: 1.62-1.86 (5H, m), 2.02-2.31 (5H, m), 2.31 (3H, s), 2.57 (1H, d, J=7.3 Hz), 2.64-2.71 (2H, m), 2.85-2.92 (1H, m), 3.00-3.02 (1H, m), 3.14-3.18

(1H, m), 3.95-4.22 (2H, m), 4.93-4.96 (1H, m), 5.41 (1H, brs), 7.06-7.25 (5H, m), 7.42-7.44 (1H, m), 8.33-8.35 (1H, m)
ESI-MS Found: m/z 383.3 [M+H]+

Compound of Example 49

(3R*,4S*) Form

1H NMR (400 MHz, CDCl3) δ: 1.62-1.86 (5H, m), 2.04-2.29 (5H, m), 2.31 (3H, s), 2.56-2.58 (2H, m), 2.65-2.72 (2H, m), 2.85-2.92 (1H, m), 2.97-3.00 (1H, m), 3.16-3.20 (1H, m), 3.95-4.22 (2H, m), 4.93-4.96 (1H, m), 5.40 (1H, brs), 7.06-7.25 (5H, m), 7.42-7.44 (1H, m), 8.33-8.35 (1H, m)
ESI-MS Found: m/z 383.3 [M+H]+

Production Example 34

Production of
(3RS,4SR)-3-methyl-4-o-tolylpiperidine 1) (3RS,4SR)-1,3-dimethyl-4-o-tolylpiperidine At 0° C. 0.45 mL of triethylamine and 0.17 mL of methanesulfonyl chloride were added to chloroform (5 mL) solution of 237 mg of (3SR,4RS)-(1-methyl-4-o-tolylpiperidin-3-yl)-methanol obtained in Production Example 33-1. This was stirred at 0° C. for 50 minutes, diluted with ethyl acetate, washed with aqueous saturated sodium hydrogencarbonate solution, and dried with anhydrous sodium sulfate, and the solvent was evaporated off under reduced pressure to obtain 321 mg of 1-methyl-4-o-tolylpiperidin-3-ylmethyl methanesulfonate.

In a nitrogen atmosphere, 5.4 mL of 1.0 M lithium triethylborohydride-tetrahydrofuran solution was added to tetrahydrofuran (5 mL) solution of 321 mg of the above compound at 0° C., and stirred overnight at room temperature. This was diluted with ethyl acetate, washed with aqueous saturated sodium hydrogencarbonate solution, and dried with anhydrous sodium sulfate. The solvent was evaporated off under reduced pressure, and the residue was separated and purified through silica gel column chromatography (hexane/ethyl acetate=2/1) to obtain 166 mg of the entitled compound as a colorless oily substance.

2) Production of
(3RS,4SR)-3-methyl-4-o-tolylpiperidine 132 mg of the entitled compound was obtained in the same manner as in Production Example 22-3, for which, however, the compound obtained in the above 1 was used in place of 1,1'-dimethyl-spiro[2,3-dihydro-1H-indole-3,4'-piperidine] used in Production Example 22-3.
1H NMR (400 MHz, CD3OD) δ: 0.57 (3H, d, J=6.6 Hz), 1.54 (3H, m), 1.82 (1H, m), 2.25 (3H, s), 2.29 (1H, m), 2.53 (1H, m), 2.65 (1H, m), 3.02 (1H, m), 7.04 (4H, m)
ESI-MS Found: m/z 190.2 [M+H]+

Examples 50 and 51

Production of (7R,9S)-7-[(3R*,4S*)-3-methyl-4-o-tolylpiperidin-1-ylmethyl]-6,7,8,9-tetrahydro-5H-cyclohepta[b]pyridin-9-ol mono-L-tartrate; and (7R, 9S)-7-[(3S*,4R*)-3-methyl-4-o-tolylpiperidin-1-ylmethyl]-6,7,8,9-tetrahydro-5H-cyclohepta[b] pyridin-9-ol mono-L-tartrate 27.6 mg of a diastereomer mixture of the entitled compounds was obtained as a colorless amorphous substance in the same manner as in Example 15, for which, however, the compound obtained in Production Example 34 was used in place of (3S*,4S*)-4-o-tolyl-piperidin-3-ol used in Example 15, and the step of converting the product into its L-tartrate was omitted. The diastereomer mixture was separated in an optically-active column (Daicel's CHRALPAK AD column, 2 cm×25 cm; 0.1% diethylamine, hexane/ethanol=33/1). From the former fraction, 8.1 mg of (7R,9S)-7-[(3R*,4S*)-3-methyl-4-o-tolylpiperidin-1-ylmethyl]-6,7,8,9-tetrahydro-5H-cyclohepta[b]pyridin-9-ol was obtained as a colorless amorphous substance; and from the latter fraction, 8.4 mg of the (3S*,4R*) form was obtained as a colorless amorphous substance. (The two were not identified, and for convenience sake, one was referred to as (3R*,4S*) form and the other was as (3S*,4R*) form.)

The two compounds were separately dissolved in methanol, an equimolar amount of L-tartaric acid was added thereto, and the solvent was evaporated off under reduced pressure to obtain 11.9 mg of the (3R*,4S*) form and 10.9 mg of the (3S*,4R*) form, both as a white solid.

Compound of Example 50

(3R*,4S*) Form

Retention time, 17.4 min (optically-active column, Daicel's CHRALPAK AD column, 0.46 cm×25 cm; 0.1% diethylamine, hexane/ethanol=50/1; flow rate, 1 mL/min)
1H NMR (400 MHz, CD3OD) δ: 0.78 (3H, d, J=6.6 Hz), 1.35 (1H, q, J=12.5 Hz), 1.60 (1H, t, J=12.5 Hz), 1.94-2.15 (3H, m), 2.25 (2H, m), 2.36 (3H, s), 2.76-2.89 (4H, m), 3.08-3.16 (3H, m), 3.40 (1H, t, J=12.8 Hz), 3.63-3.72 (2H, m), 4.45 (2H, s), 5.06 (1H, d, J=6.6 Hz), 7.08-7.27 (5H, m), 7.61 (1H, d, J=7.3 Hz), 8.26 (1H, d, J=4.4 Hz)
APCI-MS Found: m/z 365.2 [M+H]+

Compound of Example 51

(3S*,4R*) Form

Retention time, 18.8 min (optically-active column, Daicel's CHRALPAK AD column, 0.46 cm×25 cm; 0.1% diethylamine, hexane/ethanol=50/1; flow rate, 1 mL/min)
1H NMR (400 MHz, CD3OD) δ: 0.78 (3H, d, J=6.6 Hz), 1.34 (1H, q, J=12.0 Hz), 1.60 (1H, t, J=12.8 Hz), 1.92-2.14 (3H, m), 2.25-2.36 (2H, m), 2.36 (3H, s), 2.76-2.87 (4H, m), 3.06-3.15 (3H, m), 3.39 (1H, t, J=13.2 Hz), 3.64-3.70 (2H, m), 4.42 (2H, s), 5.05 (1H, d, J=6.6 Hz), 7.07-7.26 (5H, m), 7.60 (1H, d, J=6.6 Hz), 8.25 (1H, dd, J=1.0, 4.4 Hz)
APCI-MS Found: m/z 365.2 [M+H]+

Production Example 35

Production of
(3RS,4SR)-4-phenyl-3-methylpiperidine 1) (3RS,4SR)-(1-methyl-4-phenyl-piperidin-3-yl) methanol 136.7 mg of the entitled compound was obtained as a colorless oily substance in the same manner as in Production Example 33-1, for which, however, used was methyl (3SR, 4RS)-1-methyl-4-phenyl-piperidine-3-carboxylate that had been obtained in Production Example 32 in which the process after the treatment with 1-chloroethyl chloroformate had been omitted.

2) (3RS,4SR)-3-methyl-4-phenylpiperidine monohydrochloride

A product was obtained in the same manner as in Production Example 34-1, for which, however, the compound obtained in the above 1 was used in place of (3RS,4SR)-(1-methyl-4-o-tolylpiperidin-3-yl)-methanol used in Production Example 34-1; and the product was processed in the same manner as in Production Example 8-1 to obtain 76.4 mg of the entitled compound as a white solid.

1H NMR (400 MHz, CDCl3) δ: 0.75 (3H, d, J=6.2 Hz), 1.97-2.02 (1H, m), 2.23-2.38 (3H, m), 2.61-2.79 (1H, m), 2.95-2.97 (1H, m), 3.53-3.63 (2H, m), 7.19-7.45 (5H, m)

ESI-MS Found: m/z 176.3 [M+H]+

Examples 52 and 53

Production of (7R,9S)-7-[(3R*,4S*)-3-methyl-4-phenylpiperidin-1-ylmethyl]-6,7,8,9-tetrahydro-5H-cyclohepta[b]pyridin-9-ol mono-L-tartrate; and (7R,9S)-7-[(3S*,4R*)-3-methyl-4-phenylpiperidin-1-ylmethyl]-6,7,8,9-tetrahydro-5H-cyclohepta[b]pyridin-9-ol mono-L-tartrate 46.4 mg of a diastereomer mixture of the entitled compounds was obtained in the same manner as in Example 15, for which, however, the compound obtained in Production Example 34 was used in place of (3S*,4S*)-4-o-tolyl-piperidin-3-ol used in Example 15 and the step of converting the product into its L-tartrate was omitted. The diastereomer mixture was separated in an optically-active column (Daicel's CHRALCEL OD column, 2 cm×25 cm; 0.1% diethylamine, hexane/isopropyl alcohol=19/1). From the former fraction, 20.3 mg of (7R,9S)-7-[(3S*,4R*)-3-methyl-4-phenylpiperidin-1-ylmethyl]-6,7,8,9-tetrahydro-5H-cyclohepta[b]pyridin-9-ol was obtained as a colorless amorphous substance; and from the latter fraction, 21.0 mg of the (3R*,4S*) form was obtained as a colorless amorphous substance. (The two were not identified, and for convenience sake, one was referred to as (3R*,4S*) form and the other was as (3S*,4R*) form.)

The two compounds were separately dissolved in methanol, and an equimolar amount of L-tartaric acid was added thereto, and the solvent was evaporated off to obtain 28.8 mg of the (3S*,4R*) form and 30.0 mg of the (3R*,4S*) form, both as a white solid.

Compound of Example 52

(3S*,4R*) Form

Retention time, 12.0 min (optically-active column; Daicel's CHRALCEL OD column, 0.46 cm×25 cm; 0.1% diethylamine, hexane/isopropyl alcohol=19/1; flow rate, 1 mL/min)

1H NMR (300 MHz, CD3OD) δ: 0.76 (3H, d, J=6.3 Hz), 1.28-1.36 (1H, m), 1.55-1.63 (1H, m), 1.94-2.44 (6H, m), 2.73-2.84 (3H, m), 3.00-3.14 (3H, m), 3.31-3.42 (1H, m), 3.62-3.72 (2H, m), 4.43 (2H, s), 5.06 (1H, d, J=6.3 Hz), 7.20-7.35 (6H, m), 7.60-7.63 (1H, m), 8.25-8.27 (1H, m)

ESI-MS Found: m/z 351.1 [M+H]+

Compound of Example 53

(3R*,4S*) Form

Retention time, 15.1 min (optically-active column; Daicel's CHRALCEL OD column, 0.46 cm×25 cm; 0.1% diethylamine, hexane/isopropyl alcohol=19/1; flow rate, 1 mL/min)

1H NMR (300 MHz, CD3OD) δ: 0.75 (3H, d, J=6.4 Hz), 1.28-1.38 (1H, m), 1.55-1.63 (1H, m), 1.94-2.47 (6H, m), 2.72-2.88 (3H, m), 3.00-3.16 (3H, m), 3.31-3.42 (1H, m), 3.60-3.79 (2H, m), 4.43 (2H, s), 5.06 (1H, d, J=6.8 Hz), 7.19-7.35 (6H, m), 7.60-7.65 (1H, m), 8.25-8.27 (1H, m)

ESI-MS Found: m/z 351.1 [M+H]+

Production Example 36

Production of (3RS,4SR)-3-methoxymethyl-4-o-tolyl-piperidine 1) (3RS,4SR)-(1-benzyl-4-o-tolyl-piperidin-3-yl)-methanol 540 mg of potassium carbonate and 0.25 mL of benzyl bromide were added to N,N-dimethylformamide (7 mL) solution of 453 mg of methyl (3RS,4SR)-4-o-tolyl-piperidine-3-carboxylate obtained in Production Example 31, and stirred at 70° C. for 1.5 hours. Then, this was restored to room temperature, aqueous saturated sodium hydrogencarbonate solution was added thereto and extracted with ether. The ether layer was washed with saturated saline water, and dried with anhydrous sodium sulfate, and the solvent was evaporated off under reduced pressure. The residue was separated and purified through silica gel column chroamtography (hexane/ethyl acetate=9/1) to obtain 463 mg of methyl (3RS,4SR)-1-benzyl-4-o-tolyl-piperidine-3-carboxylate. The compound was processed in the same manner as in Production Example 33-1 to obtain 360 mg of the entitled compound.

2) (3RS,4SR)-3-methoxymethyl-4-o-tolyl-piperidine 43 mg of (3RS,4SR)-1-benzyl-3-methoxymethyl-4-o-tolyl-piperidine was obtained in the same manner as in Production Example 14-2, for which, however, the compound obtained in the above 1 was used in place of benzyl (3RS,4SR)-3-hydroxy-4-o-tolyl-piperidine-1-carboxylate used in Production Example 14-2. The obtained compound was dissolved in 3 ml of methanol, then 20 mg of 10% palladium-carbon catalyst (AD) was added thereto. In a hydrogen atmosphere, this was stirred at room temperature under normal pressure for 15 hours. The reaction system was purged with nitrogen, and the catalyst was removed through filtration through Celite. The solvent was evaporated off under reduced pressure to obtain 28 mg of the entitled compound.

1H NMR (200 MHz, CDCl3) δ: 1.69-1.83 (2H, m), 2.00-2.21 (1H, m), 2.32 (3H, s), 2.58-3.02 (4H, m), 3.02-3.28 (5H, m), 3.33-3.50 (1H, m), 7.02-7.32 (4H, m)

ESI-MS Found: m/z 220.3 [M+H]+

Examples 54 and 55

Production of (7R,9S)-7-[(3R*,4S*)-3-methoxymethyl-4-o-tolyl-piperidin-1-ylmethyl]-6,7,8,9-tetrahydro-5H-cyclohepta[b]pyridin-9-ol mono-L-tartrate; and (7R,9S)-7-[(3S*,4R*)-3-methoxymethyl-4-o-tolyl-piperidin-1-ylmethyl]-6,7,8,9-tetrahydro-5H-cyclohepta[b]pyridin-9-ol mono-L-tartrate 27.6 mg of a diastereomer mixture of the entitled compounds was obtained in the same manner as in Example 15, for which, however, the compound obtained in Production Example 36 was used in place of (3S*,4S*)-4-o-tolyl-piperidin-3-ol used in Example 15 and the step of converting the product into its L-tartrate was omitted.

The diastereomer mixture was separated in an optically-active column (Daicel's CHRALPAK AD column, 2 cm×25 cm, two columns connected; 0.1% diethylamine, hexane/isopropyl alcohol=29/1; flow rate, 20 mL/min). From the former fraction (retention time; 32.0 min), 11 mg of (7R,9S)-7-[(3R*,4S*)-3-methoxymethyl-4-o-tolyl-piperidin-1-ylmethyl]-6,7,8,9-tetrahydro-5H-cyclohepta[b]pyridin-9-ol was obtained; and from the latter fraction (retention time; 34.4 min), 13 mg of the (3S*,4R*) form was obtained. (The two were not identified, and for convenience sake, one was referred to as (3R*,4S*) form and the other was as (3S*,4R*) form.)

The two compounds were separately dissolved in methanol, and an equimolar amount of L-tartaric acid was added thereto, and the solvent was evaporated off to obtain their tartrates both as a white solid.

Compound of Example 54

(3R*,4S*) Form

1H NMR (200 MHz, CD3OD) δ: 1.22-1.43 (1H, m), 1.50-1.69 (1H, m), 1.88-2.35 (4H, m), 2.36 (3H, s), 2.42-2.66 (1H, m), 2.70-2.96 (2H, m), 2.96-3.48 (11H, m), 3.62-3.82 (2H, m), 4.43 (2H, s), 5.00-5.11 (1H, m), 7.03-7.31 (5H, m), 7.57-7.67 (1H, m), 8.21-8.30 (1H, m)

ESI-MS Found: m/z 395.4 [M+H]+

Compound of Example 55

(3S*,4R*) Form

1H NMR (200 MHz, CD3OD) δ: 1.21-1.43 (1H, m), 1.50-1.69 (1H, m), 1.87-2.33 (4H, m), 2.34 (3H, s), 2.40-2.62 (1H, m), 2.69-2.96 (2H, m), 2.96-3.48 (11H, m), 3.60-3.83 (2H, m), 4.42 (2H, s), 5.01-5.11 (1H, m), 7.03-7.31 (5H, m), 7.58-7.67 (1H, m), 8.21-8.30 (1H, m)

ESI-MS Found: m/z 395.4 [M+H]+

Production Example 37

Production of (3S*,4S*)-3-aminomethyl-1-benzyl-4-o-tolyl-piperidine 1) (3R*4S*)-(1-benzyl-4-o-tolyl-piperidin-3-yl)-methanol The entitled compound was obtained in the same manner as in Production Example 36-1, for which, however, methyl (3R*,4S*)-4-o-tolyl-piperidine-3-carboxylate obtained in Production Example 31 was used in place of methyl (3RS,4SR)-4-o-tolyl-piperidine-3-carboxylate used in Production Example 36-1.

2) (3R*,4S*)-3-azido-1-benzyl-4-o-tolyl-piperidine

340 µL of triethylamine and 142 µL of methanesulfonyl chloride were added to chloroform (7 mL) solution of 0.36 g of the compound obtained in the above 1, and stirred at room temperature for 1 hour. Aqueous saturated sodium hydrogencarbonate solution was added to the reaction liquid, and extracted with chloroform, and the chloroform layer was washed with saturated saline water and dried with anhydrous magnesium sulfate. The solvent was evaporated off under reduced pressure, and the residue was dissolved in 5 mL of N,N-dimethylformamide. 198 mg of sodium azide was added thereto and stirred at 80° C. for 2 hours. Aqueous 1 M sodium hydroxide solution was added to the reaction liquid, and extracted with ethyl acetate. The ethyl acetate layer was washed with saturated saline water, and dried with anhydrous magnesium sulfate. The solvent was evaporated off under reduced pressure, and the residue was separated and purified through silica gel column chromatography (hexane/ethyl acetate=3/1) to obtain 393 mg of the entitled compound.

3) (3S*,4S*)-3-aminomethyl-1-benzyl-4-o-tolyl-piperidine 0.8 mL of water and 322 mg of triphenyl phosphine were added to tetrahydrofuran (8 mL) solution of 393 mg of the compound obtained in the above 2, and refluxed for 2 hours. The solvent was evaporated off under reduced pressure, and the residue was separated and purified through silica gel column chromatography (aqueous 1% ammonia, chloroform/methanol=10/1) to obtain 353 mg of the entitled compound.

1H NMR (200 MHz, CDCl3) δ: 1.65-2.12 (5H, m), 2.20-2.37 (1H, m), 2.30 (3H, s), 2.42-2.60 (2H, m), 2.91-3.04 (1H, m), 3.21-3.32 (1H, m), 3.50-3.72 (2H, m), 7.00-7.41 (9H, m)

ESI-MS Found: m/z 295.3 [M+H]+

Production Example 38

Production of (3R*,4S*)-3-(methanesulfonylamino-methyl)-4-o-tolyl-piperidine 1) (3R*,4S*)-1-benzyl-3-(methanesulfonylamino-methyl)-4-o-tolyl-piperidine 217 µL of triethylamine and 72 µL of methanesulfonyl chloride were added to chloroform (3 mL) solution of 183 mg of the compound obtained in Production Example 37, and stirred at room temperature for 40 minutes. Aqueous saturated sodium hydrogencarbonate solution was added to the reaction liquid, and extracted with chloroform. The chloroform layer was washed with saturated saline water and dried with anhydrous magnesium sulfate. The solvent was evaporated off under reduced pressure, and the residue was separated and purified through silica gel column chromatography (chloroform/methanol=50/1) to obtain 194 mg of the entitled compound.

2) (3R*,4S*)-3-(methanesulfonylamino-methyl)-4-o-tolyl-piperidine 194 mg of the compound obtained in the above 1 was dissolved in 7 mL of methanol, and 70 mg of 10% palladium-carbon catalyst (AD) was added thereto. In a hydrogen atmosphere, this was stirred at room temperature under normal pressure for 15 hours. The catalyst was removed through filtration, and the solvent was evaporated off under reduced pressure to obtain 175 mg of the entitled compound.

1H NMR (200 MHz, CDCl3) δ: 1.49-1.83 (2H, m), 1.99-2.21 (1H, m), 2.32 (3H, m), 2.42-2.94 (5H, m), 2.74 (3H, s), 3.10-3.23 (1H, m), 3.41-3.54 (1H, m), 7.07-7.31 (4H, m)

ESI-MS Found: m/z 283.3 [M+H]+

Example 56

Production of (7R,9S)-7-[(3R*,4S*)-3-(methanesulfonylamino-methyl)-4-o-tolyl-piperidin-1-ylmethyl]-6,7,8,9-tetrahydro-5H-cyclohepta[b]pyridin-9-ol mono-L-tartrate 68 mg of the entitled compound was obtained as a white solid in the same manner as in Example 15, for which, however, the compound obtained in Production Example 38 was used in place of (3S*,4S*)-4-o-tolyl-piperidin-3-ol used in Example 15.

1H NMR (400 MHz, CDCl3) δ: 1.50-1.84 (6H, m), 2.02-2.28 (4H, m), 2.32 (3H, s), 2.48-2.94 (10H, m), 2.99 (1H, bd, J=11.4 Hz), 3.22-3.28 (1H, m), 4.08-4.16 (1H, m), 4.94 (1H, dd, J=2.2, 10.6 Hz), 7.07-7.28 (5H, m), 7.43 (1H, d, J=7.7 Hz), 8.34 (1H, d, J=4.8 Hz)

ESI-MS Found: m/z 458.3 [M+H]+

Example 57

Production of (7R,9S)-7-[(3R*,4S*)-3-(methane-sulfonyl-methyl-amino-methyl)-4-o-tolyl-piperidin-1-ylmethyl]-6,7,8,9-tetrahydro-5H-cyclohepta[b]pyridin-9-ol mono-L-tartrate 1) (7R,9S)-9-tert-butyldimethylsilanyloxy-7-[(3R*,4S*)-3-(methanesulfonyl-methyl-amino-methyl)-4-o-tolyl-piperidin-1-ylmethyl]-6,7,8,9-tetrahydro-5H-cyclohepta[b]pyridine In a nitrogen atmosphere, 18 mg of 60% sodium hydride (oily) was added to tetrahydrofuran (6 mL) solution of 130 mg of the compound obtained in Example 56 but not treated with tetrabutylammonium fluoride, with cooling with ice, and stirred at room temperature for 1 hour. Then, 16 μL of iodomethane was added to it and stirred at room temperature for 1 hour. Next, 13 μL of iodomethane was further added thereto, and stirred at room temperature for 3 hours. Aqueous 1 M sodium hydroxide solution was added to the reaction liquid, and extracted with ethyl acetate. The ethyl acetate layer was washed with saturated saline water, and dried with anhydrous magnesium sulfate. The solvent was evaporated off under reduced pressure, and the residue was separated and purified through partitioning thin-layer chromatography (chloroform/methanol=20/1) to obtain 80 mg of the entitled compound.

2) (7R,9S)-7-[(3R*,4S*)-3-(methanesulfonyl-methyl-amino-methyl)-4-o-tolyl-piperidin-1-ylmethyl]-6,7,8,9-tetrahydro-5H-cyclohepta[b]pyridin-9-ol mono-L-tartrate The compound obtained in the above 1 was processed in the same manner as in 2 of Examples 9 and 10 but not processed for optical resolution, and ethanol and an equimolar amount of L-tartaric acid were added to the resulting compound to dissolve it. Then, the solvent was evaporated off under reduced pressure to obtain 13 mg of the entitled compound as a white solid.

1H NMR (200 MHz, CD3OD) δ: 1.25-1.70 (2H, m), 1.87-2.22 (3H, m), 2.22-2.40 (1H, m), 2.35 (3H, s), 2.51-3.03 (6H, m), 2.70 (6H, s), 3.03-3.21 (4H, m), 3.21-3.44 (1H, m), 3.67-3.91 (2H, m), 4.41-4.50 (2H, m), 5.01-5.11 (1H, m), 7.04-7.42 (5H, m), 7.57-7.67 (1H, m), 8.20-8.30 (1H, m)

ESI-MS Found: m/z 472.2 [M+H]+

Production Example 39

Production of methyl (3R*,4S*)-(4-o-tolyl-piperidin-3-ylmethyl)carbamate

1) Methyl (3S*,4S*)-(1-benzyl-4-o-tolyl-piperidin-3-ylmethyl)carbamate

111 μL of triethylamine and 37 μL of methyl chlorocarbonate were added to chloroform (2 mL) solution of 93 mg of (3S*,4S*)-3-aminomethyl-1-benzyl-4-o-tolyl-piperidine obtained in Production Example 37, and stirred at room temperature for 50 minutes. Aqueous 1 M sodium hydroxide solution was added to the reaction liquid, and extracted with ethyl acetate. The ethyl acetate layer was washed with saturated saline water, and dried with anhydrous sodium sulfate. The solvent was evaporated off under reduced pressure, and the residue was separated and purified through preparative thin-layer chromatography (chloroform/methanol=20/1) to obtain 78 mg of the entitled compound.

2) Methyl (3R*,4S*)-(4-o-tolyl-piperidin-3-ylmethyl)carbamate 78 mg of the compound obtained in the above 1 was dissolved in 3 mL of methanol, and 80 mg of 10% palladium-carbon catalyst (AD) was added thereto. In a hydrogen atmosphere, this was stirred at room temperature under normal pressure for 27 hours. The reaction system was purged with nitrogen, and the catalyst was removed through filtration through Celite. The solvent was evaporated off to obtain 56 mg of the entitled compound.

1H NMR (200 MHz, CD3OD) δ: 1.79-2.00 (2H, m), 2.31 (3H, s), 2.30-2.54 (1H, m), 2.73-3.02 (4H, m), 3.02-3.22 (1H, m), 3.38-3.63 (5H, m), 7.02-7.33 (4H, m)

ESI-MS Found: m/z 263.2 [M+H]+

Example 58

Production of (7R,9S)-7-[(3S*,4S*)-3-(methocarbonylamino-methyl)-4-o-tolyl-piperidin-1-ylmethyl]-6,7,8,9-tetrahydro-5H-cyclohepta[b]pyridin-9-ol mono-L-tartrate 23 mg of the entitled compound was obtained as a white solid in the same manner as in Example 15, for which, however, the compound obtained in Production Example 39 was used in place of (3S*,4S*)-4-o-tolyl-piperidin-3-ol used in Example 15.

1H NMR (200 MHz, CD3OD) δ: 1.27-1.70 (2H, m), 1.88-2.45 (3H, m), 2.35 (3H, s), 2.51-3.05 (7H, m), 3.05-3.21 (3H, m), 3.26-3.46 (3H, m), 3.57 (3H, s), 3.62-3.81 (2H, m), 4.46 (2H, s), 5.01-5.10 (1H, m), 7.03-7.38 (5H, m), 7.58-7.67 (1H, m), 8.22-8.31 (1H, m)

ESI-MS Found: m/z 438.4 [M+H]+

Production Example 40

Production of (3R*,4S*)-3-(dimethylsulfamoylamino-methyl)-4-o-tolyl-piperidine 1) (3R*,4S*)-1-benzyl-3-(dimethylsulfamoylamino-methyl)-4-o-tolyl-piperidine 39 μL of triethylamine and 18 μL of dimethylsulfamoyl chloride were added to chloroform (1 mL) solution of 41 mg of (3S*,4S*)-3-aminomethyl-1-benzyl-4-o-tolyl-piperidine obtained in Production Example 37, and stirred at room temperature for 2.5 hours. 39 μL of triethylamine and 18 μL of dimethylsulfamoyl chloride were further added to the reaction liquid, and stirred at room temperature for 1 hour. Still further, 39 μL of triethylamine and 18 μL of dimethylsulfamoyl chloride were added to the reaction liquid, and stirred at room temperature for 1 hour. Aqueous 1 M sodium hydroxide solution was added to the reaction liquid, and extracted with ethyl acetate. The ethyl acetate layer was washed with saturated saline water, and dried with anhydrous magnesium sulfate. The solvent was evaporated off under reduced pressure, and the residue was separated and purified through preparative thin-layer chromatography (chloroform/methanol=10/1) to obtain 27 mg of the entitled compound.

2) Production of (3R*,4S*)-3-(dimethylsulfamoylamino-methyl)-4-o-tolyl-piperidine 27 mg of the compound obtained in the above 1 was dissolved in 3 mL of methanol, and 30 mg of 10% palladium-carbon catalyst (AD) was added thereto. In a hydrogen atmosphere, this was stirred at room temperature under normal pressure for 25 hours. The reaction system was purged with nitrogen, and the catalyst was removed through filtration through Celite. The solvent was evaporated off to obtain 23 mg of the entitled compound.

1H NMR (200 MHz, CDCl3) δ: 1.73-2.21 (2H, m), 2.30 (3H, s), 2.61 (6H, s), 2.59-3.00 (6H, m), 3.00-3.20 (1H, m), 3.50-3.63 (1H, m), 3.98-4.12 (1H, m), 7.05-7.40 (4H, m)

ESI-MS Found: m/z 312.1 [M+H]+

Example 59

Production of (7R,9S)-7-[(3R*,4S*)-3-(dimethylsulfamoylamino-methyl)-4-o-tolyl-piperidin-1-ylmethyl]-6,7,8,9-tetrahydro-5H-cyclohepta[b]pyridin-9-ol mono-L-tartrate 13 mg of the entitled compound was obtained as a white solid in the same manner as in Example 15, for which, however, the compound obtained in Production Example 40 was used in place of (3S*,4S*)-4-o-tolyl-piperidin-3-ol used in Example 15.

1H NMR (300 MHz, CD3OD) δ: 1.28-1.68 (2H, m), 1.91-2.18 (3H, m), 2.23-2.35 (1H, m), 2.35 (3H, s), 2.61 (6H, s), 2.63-2.97 (7H, m), 3.02-3.19 (3H, m), 3.34-3.45 (1H, m), 3.64-3.96 (2H, m), 4.45 (2H, s), 5.03-5.12 (1H, m), 7.09-7.36 (5H, m), 7.60-7.68 (1H, m), 8.25-8.31 (1H, m)

ESI-MS Found: m/z 487.3 [M+H]+

Production Example 41

Production of (±)-5-exo-o-tolyl-2-aza-bicyclo[2.2.1]-heptane

1) Benzyl 2-aza-bicyclo[2.2.1]-5-heptene-2-carboxylate

Diethyl ether/tetrahydrofuran (4:1) (25 mL) mixed suspension of 606 mg of 2-aza-bicyclo[2.2.1]-5-hepten-3-one was added to diethyl ether (50 mL) solution of 1.06 g of lithiumaluminium hydride, with cooling with ice. The reaction mixture was heated under reflux for 5.5 hours. This was cooled to room temperature, and 1.0 mL of water, 1.0 mL of aqueous 3 M sodium hydroxide solution and 3.0 mL of water were added thereto to stop the reaction. 0.95 mL of benzyl chloroformate was added to the resulting suspension, and stirred at room temperature for 1 hour. The reaction mixture was filtered through Celite, and ethyl acetate and water were added to the filtrate to separate it. The organic layer was washed with saturated saline water, and dried with anhydrous magnesium sulfate. The solvent was evaporated off under reduced pressure, and the residue was purified through silica gel column chromatography (hexane/ethyl acetate=15/1 to 6/1) to obtain 1.25 g of the entitled compound as an oily substance.

2) (±)-5-Exo-o-tolyl-2-aza-bicyclo[2.2.1]-heptane 287 mg of tetrakistriphenylphosphine palladium, 0.95 mL of 2-iodotoluene, 0.86 mL of piperidine and 0.28 mL of formic acid were added to N,N-dimethylformamide (8.0 mL) solution of 570 mg of the compound obtained in the above 1, and the mixture was stirred in a hydrogen atmosphere at 80° C. for 4 hours. Water was added to the reaction liquid, and extracted with ethyl acetate. The organic layer was washed with water and saturated saline water, and dried with anhydrous magnesium sulfate. The solvent was evaporated off under reduced pressure to obtain 865 mg of a crude product. The crude product was dissolved in 20 mL of acetonitrile, and at room temperature, 1.86 g of sodium iodide and 1.58 mL of trimethylchlorosilane were added thereto, and stirred for 10 minutes. 1 N hydrochloric acid was added to the reaction liquid, and extracted twice with ethyl acetate. The aqueous layer was made alkaline with 3 M sodium hydroxide, and then extracted with chloroform. The organic layer was washed with saturated saline water, dried with anhydrous magnesium sulfate, and purified through basic silica gel column chromatography (chloroform/methanol=200/1) to obtain 111 mg of the entitled compound as an oily substance.

1H NMR (300 MHz, CDCl3) δ: 1.53 (1H, d, J=10.2 Hz), 1.64 (1H, ddd, J=2.4, 4.8, 18.6 Hz), 1.68 (1H, d, J=10.2 Hz), 1.88-2.01 (1H, brs), 2.02-2.11 (1H, m), 2.31 (3H, s), 2.59 (1H, s), 2.79 (1H, d, J=11.4 Hz), 3.00-3.08 (2H, m), 3.57 (1H, s), 7.09-7.25 (4H, m)

ESI-MS Found: m/z 188.1 [M+H]+

Examples 60 and 61

Production of (7R,9S)-7-{(5R*)-exo-5-o-tolyl-2-azabicyclo[2.2.1]hept-2-ylmethyl}-6,7,8,9-tetrahydro-5H-cyclohepta[b]pyridin-9-ol mono-L-tartrate; and (7R,9S)-7-{(5S*)-exo-5-o-tolyl-2-azabicyclo[2.2.1]hept-2-ylmethyl}-6,7,8,9-tetrahydro-5H-cyclohepta[b]pyridin-9-ol mono-L-tartrate 100 m of a diastereomer mixture of the entitled compounds was obtained as a colorless amorphous in the same manner as in Example 15, for which, however, the compound obtained in Production Example 41 was used in place of (3S*,4S*)-4-o-tolyl-piperidin-3-ol used in Example 15 and the step of converting the product into its L-tartrate was omitted.

The diastereomer mixture was separated in an optically-active column (Daicel's CHRALPAK AD column, 2 cm×25 cm, two columns combined; 0.1% diethylamine, hexane/ethanol=9/1; flow rate, 20 mL/min). From the former fraction (retention time; 14.6 min), 51.5 mg of (7R,9S)-7-{(5S*)-exo-5-o-tolyl-2-azabicyclo[2.2.1]hept-2-ylmethyl}-6,7,8,9-tetrahydro-5H-cyclohepta[b]pyridin-9-ol was obtained, and from the latter fraction (retention time; 16.2 min), 45.0 mg of the (5R*) form was obtained, both as a white solid. (The two were not identified, and for convenience sake, one was referred to as (5R*) form and the other was as (5S*) form.) The two compounds were separately dissolved in methanol, an equimolar amount of L-tartaric acid was added thereto, and the solvent was evaporated off to obtain their tartrates both as a white solid.

Compound of Example 60

(5S*) Form

1H NMR (300 MHz, CD3OD) δ: 1.24-1.40 (1H, m), 1.53-1.62 (1H, m), 1.83-1.91 (1H, m), 2.04-2.12 (3H, m), 2.23-2.37 (1H, m), 2.33 (3H, s), 2.55-2.90 (4H, m), 3.10-3.43 (6H, m), 4.19-4.23 (1H, brs), 4.40 (2H, s), 5.05 (1H, d, J=6.6 Hz), 7.10-7.29 (5H, m), 7.61 (1H, d, J=7.0 Hz), 8.27 (1H, d, J=4.3 Hz)

ESI-MS Found: m/z 363.4 [M+H]+

Compound of Example 61

(5R*) Form

1H NMR (300 MHz, CD3OD) δ: 1.24-1.40 (1H, m), 1.53-1.62 (1H, m), 1.83-1.93 (1H, m), 2.09-2.30 (4H, m), 2.33 (3H, s), 2.55-2.90 (4H, m), 3.03-3.48 (6H, m), 4.19-4.23 (1H, brs), 4.40 (2H, s), 5.05 (1H, d, J=6.5 Hz), 7.10-7.29 (5H, m), 7.61 (1H, d, J=7.3 Hz), 8.27 (1H, d, J=4.7 Hz)

ESI-MS Found: m/z 363.4 [M+H]+

Production Example 42

Production of (R)-2-methyl-1-(2-methylphenyl)piperazine

1) (R)-1-tert-butoxycarbonyl-3-methylpiperazine

In a nitrogen atmosphere, 115 mL of di-tert-butyl dicarbonate was dropwise added to chloroform (500 mL) solution of 50.0 g of (R)-2-methylpiperazine, over 1 hour. The reaction liquid was washed with water, and dried with anhydrous magnesium sulfate. The solvent was evaporated off under reduced pressure, and the residue was separated and purified through silica gel column chromatography (hexane/ethyl acetate=2/1) to obtain 63.5 g of the entitled compound as a colorless oily substance.

2) (R)-2-methyl-1-(2-methylphenyl)piperazine

In a nitrogen atmosphere, 15 mg of palladium acetate, 0.061 mL of tert-butyl phosphine, 1.08 mL of 2-bromotoluene and sodium tert-butoxide were added to xylene (9 mL) solution of 1.50 g of the compound obtained in the above 1, and stirred at 120° C. for 18 hours. The reaction liquid was cooled to room temperature, diluted with chloroform, washed with water, and dried with anhydrous magnesium sulfate. The solvent was evaporated off under reduced pressure, and the residue was separated through silica gel column chromatography (hexane/ethyl acetate=20/1) to obtain crude (R)-1-tert-butoxycarbonyl-3-methyl-4-(2-methylphenyl)piperazine. 1 mL of trifluoroacetic acid was added to chloroform (1 mL) solution of the compound, and stirred at room temperature for 30 minutes. The solvent of the reaction liquid was evaporated off under reduced pressure, and 1.5 mL of 1 N hydrochloric acid was added to the residue, and washed with ether. The aqueous layer was made alkaline with aqueous saturated sodium hydrogencarbonate solution added thereto, and then extracted with chloroform. The chloroform layer was dried with anhydrous magnesium sulfate, and concentrated under reduced pressure, and the residue was separated and purified through NH silica gel column chromatography (hexane/ethyl acetate=1/1) to obtain 206 mg of the entitled compound as a brown solid.

1H NMR (400 MHz, CDCl3) δ: 0.80 (3H, d, J=6.0 Hz), 2.30 (3H, S), 2.60-2.69 (2H, m), 2.85 (1H, m), 2.97-3.00 (2H, m), 3.03-3.10 (2H, m), 7.01 (1H, m), 7.09-7.19 (3H, m)

Example 62

Production of (7R,9S)-7-[(R)-3-methyl-4-(2-methylphenyl)piperazin-1-ylmethyl]-6,7,8,9-tetrahydro-5H-cyclohepta[b]pyridin-9-ol mono-L-tartrate 33 m of the entitled compound was obtained as a white solid in the same manner as in Example 15, for which, however, the compound obtained in Production Example 42 was used in place of (3S*,4S*)-4-o-tolyl-piperidin-3-ol used in Example 15.

1H NMR (400 MHz, CD3OD) δ: 0.88 (3H, d, J=6.0 Hz), 1.36 (1H, m), 1.59 (1H, m), 2.12 (1H, m), 2.30 (1H, m), 2.32 (3H, s), 2.72-2.88 (3H, m), 2.98-3.16 (5H, m), 3.38 (1H, m), 3.42-3.57 (3H, m), 4.23 (2H, s), 5.04 (1H, d, J=6.4 Hz), 7.06 (1H, dd, J=1.8, 7.0 Hz), 7.15-7.28 (4H, m), 7.60 (1H, d, J=7.6 Hz), 8.25 (1H, d, J=4.0 Hz)

ESI-MS Found: m/z 366.4 [M+H]+

Production Example 43

Production of (6RS,8SR)-8-(tert-butyldimethylsilanyloxy)-2-chloro-5,6,7,8-tetrahydroquinolin-6-ylmethyl toluene-4-sulfonate

1) 3-(Bromomethyl)-2,6-dichloropyridine

Tetrahydrofuran (100 mL) solution of 6.16 g of 2,6-dichloronicotinic acid and 6.25 g of carbonyldiimidazole was cooled with ice, and 3.64 g of sodium borohydride was added thereto and stirred overnight at room temperature. Water with ice was added to the reaction liquid, and extracted with ethyl acetate. The organic layer was concentrated, and the residue was separated and purified through silica gel column chromatography (hexane/ethyl acetate=3/1) to obtain 3.68 g of the entitled compound as a white solid.

2) Ethyl 3-(2,6-dichloro-3-pyridin-3-yl)-propionate

Tetrahydrofuran (100 mL) solution of 38.0 mL of 1.0 M lithium hexamethyldisilazide-tetrahydrofuran solution was cooled to −78° C., and 3.71 mL of ethyl acetate was added to the solution and stirred for 30 minutes. Tetrahydrofuran (8 mL) solution of 4.58 g of the compound obtained in the above 1 was added to the solution, and stirred at −78° C. for 1 hour. Water was added to the reaction liquid, and extracted with ethyl acetate. The organic layer was concentrated, and the residue was separated and purified through silica gel column chromatography (hexane/ethyl acetate=10/1) to obtain 2.82 g of the entitled compound as a yellow oily substance.

3) Ethyl 2-(2,6-dichloropyridin-3-ylmethyl)pent-4-enoate

Tetrahydrofuran (70 mL) solution of 13.7 mL of 1.0 M lithium hexamethyldisilazide-tetrahydrofuran solution was cooled to −78° C., and tetrahydrofuran (5 mL) solution of 2.82 g of the compound obtained in the above 2 was added to the solution, and stirred for 30 minutes. Further, 1.18 mL of allyl bromide was added to the reaction liquid, and gradually heated up to −5° C., over 4 hours. Water was added to the reaction liquid, and extracted with ethyl acetate. The organic layer was concentrated, and the residue was separated and purified through silica gel chromatography (hexane/ethyl acetate=10/1) to obtain 1.87 g of the entitled compound as a yellow oily substance.

4) Ethyl 2-chloro-8-methylene-5,6,7,8-tetrahydro-quinoline-6-carboxylate

N,N-dimethylformamide (50 mL) solution of 1.87 g of the compound obtained in the above 3, 1.80 g of tetrabutylammonium chloride, 511 mg of triphenyl phosphine, 1.91 g of potassium acetate and 146 mg of palladium acetate was stirred at 130° C. for 12 hours. Water was added to the reaction liquid, and extracted with ethyl acetate. The organic layer was concentrated, and the residue was separated and purified through silica gel chromatography (hexane/ethyl acetate=10/1 to 5/1) to obtain 345 mg of the entitled compound as a yellow oily substance.

5) Ethyl 2-chloro-8-oxo-5,6,7,8-tetrahydroquinoline-6-carboxylate

Methanol (50 mL) solution of 345 mg of the compound obtained in the above 4 was cooled to −50° C., and ozone gas was jetted into the solution with stirring for 30 minutes. 2 mL of dimethyl sulfide was added to the reaction liquid, and heated up to room temperature. The reaction liquid was concentrated, and the residue was separated and purified through silica gel chromatography (hexane/ethyl acetate=3/1 to 1/1) to obtain 251 mg of the entitled compound as a white solid.

6) Ethyl (6RS,8SR)-8-tert-butyldimethylsilanyloxy-2-chloro-5,6,7,8-tetrahydroquinoline-6-carboxylate Ethyl (6RS,8SR)-2-chloro-8-hydroxy-5,6,7,8-tetrahydroquinoline-6-carboxylate was obtained in the same manner as in Production Example 6-1, for which, however, the compound obtained in the above 5 was used in place of ethyl 7-iodomethyl-8-oxo-5,6,7,8-tetrahydroquinoline-7-carboxylate used in Production Example 6-1. The compound was processed in the same manner as in Production Example 6-2 to obtain 34 mg of the entitled compound as a white solid.

7) (6RS,8SR)-8-[(tert-butyldimethylsilanyloxy)-2-chloro-5,6,7,8-tetrahydroquinolin-6-yl]methanol 53 mg of the entitled compound was obtained as a colorless oily substance in the same manner as in Production Example 6-3, for which, however, the compound obtained in the above 6 was used in place of ethyl (7RS,9SR)-9-(tert-butyldimethylsilanyloxy)-6,7,8,9-tetrahydro-5H-cyclohepta[b]pyridine-7-carboxylate used in Production Example 6-3.

8) (6RS,8SR)-8-(tert-butyldimethylsilanyloxy)-2-chloro-5,6,7,8-tetrahydroquinolin-6-ylmethyl toluene-4-sulfonate 73 mg of the entitled compound was obtained as a colorless oily substance in the same manner as in Production Example 6-4, for which, however, the compound obtained in the above 7 was sued in place of (7RS,9SR)-9-(tert-butyldimethylsilanyloxy)-6,7,8,9-tetrahydro-5H-cyclohepta[b]pyridine-7-methan-1-ol used in Production Example 6-4 and the product was not subjected to optical resolution.

1H NMR (300 MHz, CDCl3) δ: 0.02 (3H, s), 0.19 (3H, s), 0.83 (9H, s), 1.59 (1H, m), 1.92 (1H, m), 2.46 (1H, m), 2.47 (1H, s), 2.59 (1H, m), 2.86 (1H, m), 4.07 (2, m), 4.78 (1H, m), 7.14 (1H, d, J=8.0 Hz), 7.36 (3H, m), 7.82 (2H, d, J=8.3 Hz)

ESI-MS Found: m/z 482 [M]+

Example 63

Production of (6R*,8S*)-2-chloro-6-(4-o-tolylpiperidin-1-ylmethyl)-5,6,7,8-tetrahydroquinolin-8-ol 13 mg of a racemic mixture of the entitled compound was obtained as a pale yellow oily substance in the same manner as in Example 14, for which, however, the compound obtained in Production Example 43 was used in place of (6R,8S)-8-triethylsilanyloxy-5,6,7,8-tetrahydroquinolin-6-ylmethyl toluene-4-sulfonate sued in Example 14 and the step of converting the product into its L-tartrate was omitted. The mixture was optically resolved in an optically-active column (Daicel's CHRALPAK AD column, 2 cm×25 cm; 0.1% diethylamine, hexane/isopropanol=9/1; flow rate, 20 mL/min). From the former fraction (retention time; 10.8 min), 7.0 mg of (6R*,8S*)-2-chloro-6-(4-o-tolylpiperidin-1-ylmethyl)-5,6,7,8-tetrahydroquinolin-8-ol was obtained as a pale yellow oily substance. (The absolute configuration was not identified, and for convenience sake, it was referred to as (6R*,8S*) form.)

1H NMR (300 MHz, CDCl3) δ: 1.77 (6H, m), 2.11 (3H, m), 2.34 (3H, s), 2.42 (4H, s), 2.72 (1H, m), 3.03 (3H, m), 4.80 (1H, m), 7.17 (5H, m), 7.45 (1H, d, J=8.2 Hz)

ESI-MS Found: m/z 371 [M+H]+

Production Example 44

Production of (6R*,8S*)8-(tert-bulyldimethylsilanyloxy)-3-chloro-5,6,7,8-tetrahydroquinolin-6-ylmethyl-toluene-4-sulfonate

1) Methyl 2,5-dichloronicotinate

With cooling with ice, 32 mL of 50% sodium hydroxide solution and 13.9 g of 2-hydroxynicotinic acid were added to 170 mL of 5% sodium chlorite, and stirred for 21 hours with heating up to room temperature. Then, aqueous (5 mL) solution of 1.40 g of sodium sulfite and 50 mL of concentrated hydrochloric acid were added to the reaction liquid to stop the reaction. The precipitated solid was taken out through filtration, washed with water and a small amount of acetone, and then dried overnight with heating at 65° C. under reduced pressure. 100 mL of thionyl chloride and 6.8 mL of N,N-dimethylformamide were added to the obtained white solid to dissolve it, and heated under reflux for 3 hours. Then, the reaction liquid was cooled to room temperature. Thionyl chloride was evaporated off under reduced pressure, and 80 mL of methanol was added to the resulting residue, and the solvent was again evaporated off under reduced pressure. Aqueous saturated sodium hydrogencarbonate solution was added to the residue, and extracted with ethyl acetate. The ethyl acetate layer was washed with saturated saline water, and dried with anhydrous sodium sulfate. The solvent was evaporated off under reduced pressure, and the residue was separated and purified through silica gel column chromatography (hexane/ethyl acetate=9/1) to obtain 9.33 g of the entitled compound as a pale brown solid.

2) (6S*,8R*)-[8-(tert-butyldimethylsilanyloxy)-3-chloro-5,6,7,8-tetrahydroquinolin-6-yl]methanol and (6R*,8S*)-[8-(tert-butyldimethylsilanyloxy)-2-chloro-5,6,7,8-tetrahydroquinolin-6-yl]methanol 119 mg of a racemate of the entitled compounds was obtained as a colorless oily substance in the same manner as in Production Example 10-1 to 10-7, for which, however, the compound obtained in the above 1 was used in place of 2-chloronicotinonitrile used in Production Example 10-1 and tert-butyldimethylchlorosilane was used in place of triethylchlorosilane used in Production Example 10-6. The racemic mixture was optically resolved in an optically-active column (Daicel's CHRALPAK AD-H column, 2 cm×25 cm; 0.1% diethylamine, hexane/isopropanol=39/1; flow rate, 20 mL/min). From the former fraction (retention time; 8.8 min), 60 mg of (6R*,8S*)-[8-(tert-butyldimethylsilanyloxy)-3-chloro-5,6,7,8-tetrahydroquinolin-6-yl]methanol was obtained, and from the latter fraction (retention time; 10.8 min), 47.0 mg of the (6S*,8R*) form was obtained, both as a colorless oily substance. (The two were not identified, and for convenience sake, one was referred to as (6R*,8S*) form and the other was as (6S*,8R*) form.)

3) (6R*,8S*)-8-(Tert-butyldimethylsilanyloxy)-3-chloro-5,6,7,8-tetrahydroquinolin-6-ylmethyl toluene-4-sulfonate 82 mg of the entitled compound was obtained as a colorless oily substance in the same manner as in Production Example 6-4, for which, however, the (6R*,8S*) compound obtained in the above 2 was used in place of (7RS,9SR)-9-(tert-butyldimethylsilanyloxy)-6,7,8,9-tetrahydro-5H-cyclohepta[b]pyridine-7-methan-1-ol used in Production Example 6-4, and the product was not subjected to optical resolution.

1H NMR (400 MHz, CDCl3) δ: −0.01 (3H, s), 0.16 (3H, s), 0.81 (9H, s), 1.54-1.62 (1H, m), 1.89-1.97 (1H, m), 2.46 (3H, s), 2.48 (1H, dd, J=11.0, 16.1 Hz), 2.55-2.68 (1H, m), 2.85 (1H, dd, J=4.4, 16.1 Hz), 3.98-4.11 (2H, m), 4.79 (1H, t, J=2.9 Hz), 7.36-7.33 (3H, m), 7.79 (2H, d, J=8.8 Hz), 8.33 (1H, d, J=2.9 Hz)

ESI-MS Found: m/z 482.0 [M+H]+

Example 64

Production of (6R*,8S*)-3-chloro-6-(4-o-tolylpiperidin-1-ylmethyl)-5,6,7,8-tetrahydroquinolin-8-ol mono-L-tartrate 18 mg of the entitled compound was obtained as a white solid in the same manner as in Example 14, for which, however, the (6R*,8S*) compound obtained in Production Example 44 and the compound obtained in Production Example 5 were used in place of (6R,8S)-8-triethylsilanyloxy-5,6,7,8-tetrahydroquinolin-6-ylmethyl toluene-4-sulfonate and spiro[isobenzofuran-1(3H),4'-piperidine]monohydrochloride used in Example 14.

1H NMR (400 MHz, CD3OD) δ: 1.72-1.84 (1H, m), 1.94-2.12 (4H, m), 2.20-2.29 (1H, m), 2.37 (3H, s), 2.51-2.73 (2H, m), 3.01-3.20 (6H, m), 3.61-3.72 (2H, m), 4.40 (2H, s), 4.78-4.83 (1H, m), 7.05-7.27 (4H, m), 7.69 (1H, d, J=2.3 Hz), 8.40 (1H, d, J=2.3 Hz)

ESI-MS Found: m/z 371.2 [M+H]+

Production Example 45

Production of (6R*,8S*)-8-(tert-butyldimethylsilanyloxy)-2-methyl-5,6,7,8-tetrahydroquinolin-6-ylmethyl toluene-4-sulfonate 1) (6R*,8S*)-[8-(tert-butyldimethylsilanyloxy)-2-methyl-5,6,7,8-tetrahydroquinolin-6-yl]methanol and (6S*,8R*)-[8-(tert-butyldimethylsilanyloxy)-2-methyl-5,6,7,8-tetrahydroquinolin-6-yl]methanol A racemate of the entitled compounds was obtained as a colorless oily substance in the same manner as in 1 to 7 in Production Example 10, for which, however, methyl 2-methylnicotinate was used in place of 2-chloronicotinonitrile used in Production Example 10-1.

ESI-MS Found: m/z 308.4 [M+H]+

The racemic mixture was optically resolved in an optically-active column (Daicel's CHRALPAK AD column, 2 cm×25 cm, two columns combined; 0.1% diethylamine, hexane/isopropanol=40/1; flow rate, 20 mL/min). From the former fraction (retention time; 20.8 min), 91 mg of (6R*,8S*)-[8-(tert-butyldimethylsilanyloxy)-2-methyl-5,6,7,8-tetrahydroquinolin-6-yl]methanol was obtained, and from the latter fraction (retention time; 23.3 min), 88 mg of the (6S*,8R*) form was obtained, both as a colorless oily substance. (The two were not identified, and for convenience sake, one was referred to as (6R*,8S*) form and the other was as (6S*,8R*) form.)

2) (6R*,8S*)-8-(Tert-butyldimethylsilanyloxy)-2-methyl-5,6,7,8-tetrahydroquinolin-6-ylmethyl toluene-4-sulfonate 125 mg of the entitled compound was obtained as a colorless oily substance in the same manner as in Production Example 6-4, for which, however, the (6R*,8S) compound obtained in the above 1 was used in place of (7RS,9SR)-9-(tert-butyldimethylsilanyloxy)-6,7,8,9-tetrahydro-5H-cyclohepta[b]pyridine-7-methan-1-ol used in Production Example 6-4, and the product was not subjected to optical resolution.

1H NMR (300 MHz, CDCl3) δ: −0.05 (3H, s), 0.18 (3H, s), 0.82 (9H, s), 1.58 (1H, td, J=12.3, 3.2 Hz), 1.93 (1H, m), 2.43 (1H, m), 2.60 (1H, m), 2.82 (1H, m), 4.02 (2H, dd, J=9.6, 5.2 Hz), 4.09 (2H, dd, J=9.6, 5.2 Hz), 4.78 (1H, d, J=2.8 Hz), 6.95 (1H, d, J=7.7 Hz), 7.24 (1H, d, J=7.9 Hz), 7.35 (2H, d, J=7.9 Hz), 7.81 (2H, d, J=8.3 Hz)

ESI-MS Found: m/z 462.2 [M+H]+

Example 65

Production of (6R*8S*)-2-methyl-6-(4-o-tolylpiperidin-1-ylmethyl)-5,6,7,8-tetrahydroquinolin-8-ol 24 mg of the entitled compound was obtained as a white solid in the same manner as in Example 14, for which, however, the compound obtained in Production Example 45 and the compound obtained in Production Example 5 were used in place of (6R,8S)-8-triethylsilanyloxy-5,6,7,8-tetrahydroquinolin-6-ylmethyl toluene-4-sulfonate and spiro[isobenzofuran-1(3H),4'-piperidine]monohydrochloride used in Example 14.

1H NMR (300 MHz, CD3OD) δ: 1.75 (1H, m), 1.95 (2H, m), 2.36 (3H, s), 2.50 (3H, s), 2.50-2.76 (2H, m), 3.02-3.32 (6H, m), 3.73 (2H, m), 4.43 (2H, s), 4.80 (1H, m), 7.05-7.28 (5H, m), 7.55 (1H, d, J=8.2 Hz)

ESI-MS Found: m/z 351.3 [M+H]+

Production Example 46

Production of (7R)-9-oxo-6,7,8,9-tetrahydro-5H-pyrido[2,3-c]azepin-7-ylmethyl toluene-4-sulfonate, and (7S)-9-oxo-6,7,8,9-tetrahydro-5H-pyrido[2,3-c]azepin-7-ylmethyl toluene-4-sulfonate 1) Ethyl 7-azido-8-oxo-5,6,7,8-tetrahydroquinoline-7-carboxylate In a nitrogen atmosphere, 7.4 mL of bromine was dropwise added to ethanol (480 mL) solution of 26.1 g of the compound obtained in Production Example 1-3 and 46.9 g of cesium carbonate, and stirred at room temperature for 30 minutes. The reaction liquid was cooled to room temperature, and water and aqueous sodium hydrogencarbonate solution were added in that order to the reaction liquid, and extracted with chloroform. The chloroform layer was washed with saturated saline water, and dried with anhydrous sodium sulfate. The solvent was evaporated off under reduced pressure to obtain crude ethyl 7-bromo-8-oxo-5,6,7,8-tetrahydroquinoline-7-carboxylate as a yellow oily substance. In a nitrogen atmosphere, 9.36 g of sodium azide was added to dimethyl sulfoxide (240 mL) solution of the above compound, and stirred at room temperature for 1 hour. Water and aqueous sodium hydrogencarbonate solution were added in that order to the reaction liquid, an extracted with ethyl acetate. The ethyl acetate layer was washed with saturated saline water, and dried with anhydrous sodium sulfate. The solvent was evaporated off under reduced pressure, and the residue was separated and purified through silica gel column chromatography (hexane/ethyl acetate=30/70) to obtain 29.4 g of the entitled compound as an orange oily substance.

2) Ethyl 9-oxo-6,7,8,9-tetrahydro-5H-pyrido[2,3-c]azepine-7-carboxylate

The entitled compound was obtained in the same manner as in Production Example 1-5, for which, however, the compound obtained in the above 1 was used in place of ethyl 7-iodomethyl-8-oxo-5,6,7,8-tetrahydroquinoline-7-carboxylate used in Production Example 1-5.

3) (7S)-7-hydroxymethyl-5,6,7,8-tetrahydro-9H-pyrido[2,3-c]azepin-9-one, and (7R)-7-hydroxymethyl-5,6,7,8-tetrahydro-9H-pyrido[2,3-c]azepin-9-one In a nitrogen atmosphere, 13 mL of methanol was dropwise added at 90° C. to tert-butyl alcohol (52 mL) solution of 3.04 g of the compound obtained in the above 2 and 1.23 g of sodium borohydride, and stirred at 90° C. for 2 hours. The reaction liquid was cooled to room temperature, water was added to the reaction liquid, and the solvent was evaporated off under reduced pressure. The residue was diluted with methanol, and dried with anhydrous sodium sulfate. The solvent was evaporated off under reduced pressure, and the residue was separated and purified through silica gel column chromatography (chloroform/methanol=90/10) to obtain 1.42 g of a racemate of the entitled compounds.

1H NMR (300 MHz, CDCl3) δ: 1.82-1.95 (1H, m), 2.12-2.23 (1H, m), 2.71-2.78 (1H, m), 2.96-3.07 (1H, m), 3.29-3.36 (1H, m), 3.71-3.85 (2H, m), 4.80 (1H, brs), 7.32-7.36 (1H, m), 7.58-7.61 (1H, m), 8.37 (1H, brs), 8.60-8.62 (1H, m)
ESI-MS Found: m/z 193.1 [M+1H]+

1.42 g of the obtained racemate was optically resolved in an optically-active column (Daicel's C ALPAK AS column, 2 cm×25 cm; 0.1% diethylamine, hexane/ethanol=6/4; flow rate, 20 mL/min). From the former fraction (retention time; 4.7 min), 645 mg of (7S)-7-hydroxymethyl-5,6,7,8-tetrahydropyrido[2,3-c]azepin-9-one was obtained, and from the latter fraction (retention time; 6.3 min), 637 mg of the (7R) form was obtained. (The absolute configuration of each compound was determined through asymmetric synthesis as in Production Example 48 mentioned below.)

Former Fraction, (7S) Form:
Retention time, 6.1 min (optically-active column, Daicel's CHRALPAK AS column, 0.46 cm×25 cm; 0.1% diethylamine, hexane/ethanol=3/2; flow rate, 1 mL/min)

Latter Fraction, (7R) Form:
Retention time, 9.1 min (optically-active column, Daicel's CHRALPAK AS column, 0.46 cm×25 cm; 0.1% diethylamine, hexane/ethanol=3/2; flow rate, 1 mL/min)

4) (7S)-9-oxo-6,7,8,9-tetrahydro-5H-pyrido[2,3-c]azepin-7-ylmethyl toluene-4-sulfonate The entitled compound was obtained as a colorless oily substance in the same manner as in Production Example 6-4, for which, however, (7S)-7-hydroxymethyl-5,6,7,8-tetrahydro-9H-pyrido[2,3-c]azepin-9-one obtained in the above 3 was used in place of (7RS,9SR)-9-(tert-butyldimethylsilanyloxy)-6,7,8,9-tetrahydro-5H-cyclohepta[b]pyridine-7-methan-1-ol used in Production Example 6-4, and the product was not subjected to optical resolution.

1H NMR (300 MHz, CDCl3) δ: 1.86-1.96 (1H, m), 2.06-2.14 (1H, m), 2.45 (3H, s), 2.71-2.77 (1H, m), 2.94-3.05 (1H, m), 3.43-3.50 (1H, m), 4.08-4.19 (2H, m), 6.67 (1H, brs), 7.32-7.37 (3H, m), 7.54-7.57 (1H, m), 7.77-7.80 (2H, m), 8.64-8.66 (1H, m)
ESI-MS Found: m/z 347.2 [M+H]+

Production Example 47

Production of (7R)-7-hydroxymethyl-5,6,7,8-tetrahydro-9H-pyrido[2,3-c]azepin-9-one 1) Tert-butyl (4R)-2,2-dimethyl-4-vinyloxazolidine-3-carboxylate 543 mg of the entitled compound was obtained as a colorless oily substance, using methyl (S)-3-(tert-butoxycarbonyl)-2,2-dimethyl-4-oxazolidinecarboxylate and according to the method described in a reference (Synthesis, 1994, 1463-1466).

2) Methyl 3-bromopyridine-2-carboxylate 1.01 g of 3-bromo-2-cyanopyridine was added to methanol (18 mL) solution of 1.55 g of sodium methoxide, and in a nitrogen atmosphere, this was stirred at room temperature for 1.5 hours and then at 70° C. for 2.5 hours. The reaction liquid was cooled to room temperature, and 30 mL of 2 N hydrochloric acid was added thereto and stirred at room temperature for 4 hours. Then, aqueous saturated sodium hydrogencarbonate solution was added to the reaction liquid, and extracted with ethyl acetate. The ethyl acetate layer was washed with saturated saline water, and dried with anhydrous sodium sulfate, and the solvent was evaporated off under reduced pressure. The residue was separated and purified through silica gel column chromatography (hexane/ethyl acetate=9/1 to 4/1) to obtain 135 mg of the entitled compound as a colorless oily substance.

3) Methyl 3-[2-{(4S)-3-tert-butoxycarbonyl-2,2-dimethyloxazolidin-4-yl}-ethyl]-pyridine-2-carboxylate In a nitrogen atmosphere, 2.3 mL of 0.5 M 9-borabicyclo[3,3,1]nonane-tetrahydrofuran solution was added to tetrahydrofuran (2.9 mL) solution of 130 mg of the compound obtained in the above 1, with cooling with ice, and stirred at that temperature for 15 minutes. Then, this was restored to room temperature, and further stirred for 1 hour. 0.39 mL of aqueous 3 M potassium phosphate solution, 42 mg of chloro[1,1'-bis(diphenylphosphino)ferrocene]palladium, and N,N-dimethylformamide (5.8 mL) solution of 135 mg of the compound obtained in the above 2 were added in that order to the reaction liquid, and stirred in a nitrogen atmosphere at room temperature for 15 hours. Then, aqueous saturated sodium hydrogencarbonate solution was added to the reaction liquid, and extracted with ethyl acetate. The ethyl acetate layer was washed with saturated saline water, and dried with anhydrous sodium sulfate. The solvent was evaporated off under reduced pressure, and the residue was separated and purified through silica gel column chromatography (hexane/ethyl acetate=4/1) to obtain 173 mg of the entitled compound as a pale brown oily substance.

4) (7R)-7-hydroxymethyl-5,6,7,8-tetrahydro-9H-pyrido[2,3-c]azepin-9-one 1 mL of 10% hydrogen chloride-methanol solution was added to 16 mg of the compound obtained in the above 3, and stirred at room temperature for 18 hours, and the solvent was evaporated off under reduced pressure. The residue was dissolved in 0.22 mL of acetonitrile, and 62 μL of triethylamine was added thereto and stirred under heat at 80° C. for 12 hours, and then left cooled to room temperature. The solvent was evaporated off under reduced pressure, and the residue was separated and purified through basic silica gel column chromatography (ethyl acetate/methanol=99/1 to 19/1) to obtain 7.4 mg of the entitled compound as a white solid. Through BPLC (Daicel's CHRALPAK AS column, 0.46 cm×25 cm; 0.1% diethylamine, hexane/ethanol=3/2; flow rate, 1 mL/min), the compound had 98.7% ee.

Retention time, 9.1 min (optically-active column, Daicel's CHRALPAK AS column, 0.46 cm×25 cm; 0.1% diethylamine, hexane/ethanol=3/2; flow rate, 1 mL/min)
ESI-MS Found: m/z 192.9 [M+H]+

Example 66

Production of (7S)-7-(4-o-tolylpiperidin-1-ylmethyl)-6,7,8,9-tetrahydro-5H-pyrido[2,3-c]azepine

1) (7S)-7-(4-o-tolylpiperidin-1-ylmethyl)-5,6,7,8-tetrahydro-9H-pyrido[2,3-c]azepin-9-one 181 mg of the entitled compound was obtained as a white solid in the same manner as in Example 11, for which, however, the compound obtained in Production Example 46 and the compound obtained in Production Example 5 were used in place of (7R*)-5,6,7,8-tetrahydro[cyclohepta[b]pyridine-9,2'-[1,3]dioxolan]-7-ylmethyl toluene-4-sulfonate and spiro[8-aza-bicyclo[3.2.1]octa-3,1'(3'H)-isobenzofuran]hydrochloride used in Example 11, and the step of converting the product into its fumarate was omitted.

2) (7S)-7-(4-o-tolylpiperidin-1-ylmethyl)-6,7,8,9-tetrahydro-5H-pyrido[2,3-c]azepine In a nitrogen atmosphere, 2 mL of 1.0 M lithiumaluminium hydride-tetrahydrofuran solution was added to tetrahydrofuran (2 mL) solution of 180 mg of the compound obtained in the above 1, and stirred at room temperature for 30 minutes. Then, 76 μL of water, 76 μL of aqueous 4 M sodium hydroxide solution and 230 μL of water were added thereto to stop the reaction. Ethyl acetate was added to the reaction liquid, and the insoluble substance was taken out through filtration through Celite, and the insoluble substance was well washed with ethyl acetate. The filtrate and the wash were combined, and the solvent was evaporated off under reduced pressure. The residue was separated and purified through basic silica gel column chromatography (hexane/ethyl acetate=3/2) to obtain 73 mg of the entitled compound as a pale yellow solid.

1H NMR (400 MHz, CDCl3) δ: 1.25-1.37 (1H, m), 1.68-1.90 (5H, m), 1.97-2.05 (1H, m), 2.21-2.30 (2H, m), 2.33 (3H, s), 2.38 (1H, dd, J=10.3, 12.5 Hz), 2.65-2.75 (1H, m), 2.82 (1H, ddd, J=2.0, 6.8, 14.8 Hz), 2.87-3.01 (2H, m), 3.05 (1H, tt, J=2.9, 10.3 Hz), 3.09-3.16 (1H, m), 4.06 (1H, d, J=13.9 Hz), 4.22 (1H, d, J=13.9 Hz), 7.00-7.20 (4H, m), 7.23-7.28 (1H, m), 7.40 (1H, dd, J=1.5, 7.9 Hz), 8.29 (1H, dd, J=1.5, 5.1 Hz)

ESI-MS Found: m/z 336.3 [M+H]+

Production Example 48

Production of 8-oxo-6,7,8,9-tetrahydro-5H-pyrido[2,3-b]azepin-7-ylmethyl toluene-4-sulfonate

1) 5,6,7,9-Tetrahydro-8H-pyrido[2,3-b]azepin-8-one 0.94 g of hydroxylammonium chloride and 1.1 g of sodium acetate were added in that order to ethanol/water (2:1) (45 mL) solution of 1.0 g of the compound obtained in Production Example 1-2, and stirred at 110° C. for 1 hour. The reaction liquid was cooled to room temperature, added to water, and extracted with chloroform. The chloroform layer was dried with anhydrous sodium sulfate, and the solvent was evaporated off under reduced pressure to obtain 1.1 g of a crude product, 6,7-dihydro-5H-quinolin-8-one oxime. 5 mL of triethylamine and 0.5 mL of methanesulfonyl chloride were added in that order to methylene chloride (20 mL) solution of 1.0 g of the obtained compound. The reaction liquid was stirred for 1 hour, then added to water, and extracted with chloroform. The chloroform layer was dried with anhydrous sodium sulfate, the solvent was evaporated off under reduced pressure. High-polarity side products were removed from the resulting residue through silica gel column chromatography (chloroform/methanol=10/1).

5.0 g of potassium acetate was added to ethanol/water (1:2) (90 mL) solution of the obtained compound, and stirred overnight at 110° C. The reaction liquid was cooled to room temperature, ethanol was evaporated off under reduced pressure, and the residue was extracted with ethyl acetate. The ethyl acetate layer was dried with anhydrous sodium sulfate, the solvent was evaporated off under reduced pressure, and the residue was separated and purified through silica gel column chromatography (chloroform/methanol=10/1) to obtain 430 mg of the entitled compound.

2) 7-Hydroxymethyl-5,6,7,9-tetrahydro-8H-pyrido[2,3-b]azepin-8-one

At −78° C. 4.5 mL of 2.0 M lithium diisopropylamide-tetrahydrofuran solution and 300 mg of paraformaldehyde were added to tetrahydrofuran (30 mL) solution of 367 mg of the compound of the above 1, and gradually heated up to room temperature. At room temperature, this was stirred overnight, and then water was added to the reaction liquid and extracted with ethyl acetate. The ethyl acetate layer was dried with anhydrous sodium sulfate, the solvent was evaporated off under reduced pressure, and the residue was separated and purified through partitioning thin-layer chromatography (chloroform/methanol=10/1) to obtain 111 mg of the entitled compound.

3) 8-Oxo-6,7,8,9-tetrahydro-5H-pyrido[2,3-b]azepin-7-ylmethyl toluene-4-sulfonate The entitled compound was obtained in the same manner as in Production Example 6-4, for which, however, the compound obtained in the above 2 was used in place of (7RS, 9SR)-9-(tert-butyldimethylsilanyloxy)-6,7,8,9-tetrahydro-5H-cyclohepta[b]pyridine-7-methan-1-ol used in Production Example 6-4, and the product was not subjected to optical resolution.

1H NMR (300 MHz, CDCl$_3$) δ: 1.94-2.08 (1H, m), 2.35-2.50 (4H, m), 2.65-2.95 (3H, m), 4.10 (1H, dd, J=7.6, 10.0 Hz), 4.32 (1H, dd, J=5.9, 9.9 Hz), 7.08 (1H, dd, J=4.9, 7.5 Hz), 7.32 (2H, d, J=8.4 Hz), 7.56 (1H, dd, J=1.6, 7.5 Hz), 7.76 (2H, dd, J=2.0, 8.6 Hz), 8.35 (1H, dd, J=1.7, 4.9 Hz), 8.92 (1H, brs)

ESI-MS Found: m/z 347.2 [M+H]+

Example 67

Production of (7RS)-7-(4-o-tolylpiperidin-1-ylmethyl)-5,6,7,9-tetrahydropyrido[2,3-b]azepine

1) (7RS)-7-(4-o-tolylpiperidin-1-ylmethyl)-5,6,7,9-tetrahydro-8H-pyrido[2,3-b]azepin-8-one 15 mg of the compound obtained in Production Example 5 was added to N,N-dimethylformamide (2 mL) solution of 19.7 mg of the compound obtained in Production Example 48, and stirred overnight at 90° C. Water was added to the reaction liquid, and extracted with ethyl acetate. The ethyl acetate layer was dried with anhydrous sodium sulfate, the solvent was evaporated off under reduced pressure, and the residue was separated and purified through preparative thin-layer chromatography (chloroform/methanol 4/1) to obtain 1.2 mg of the entitled compound and 16.6 mg of 7-methylene-5,6,7,9-tetrahydro-8H-pyrido[2,3-b]azepin-8-one. 16.6 mg of the obtained 7-methylene-5,6,7,9-tetrahydro-8H-pyrido[2,3-b]azepin-8-one was dissolved in 2 mL of N,N-dimethylformamide, and 20 mg of 4-o-tolylpiperidine monohydrochloride was added thereto and stirred at 90° C. for 0.5 hours. The reaction solution was concentrated under reduced pressure, and the residue was separated and purified through preparative thin-layer chromatography (chloroform/methanol=4/1) to obtain 12.1 mg of the entitled compound.

2) (7RS)-7-(4-o-tolylpiperidin-1-ylmethyl)-5,6,7,9-tetrahydro-5H-pyrido[2,3-b]azepine Excess lithiumaluminium hydride was added to tetrahydrofuran (2 mL) solution of 10.1 mg of the compound of above 1, and stirred at room temperature for 22 hours. Water was added to the reaction liquid, and extracted with chloroform. The chloroform layer was dried with anhydrous sodium sulfate, the solvent was evaporated off under reduced pressure, and the residue was separated and purified through preparative thin-layer chromatography (chloroform/methanol=4/1) to obtain 7.4 mg of the entitled compound.

1H NMR (300 MHz, CDCl$_3$) δ: 1.58-1.87 (6H, m), 1.93-2.38 (9H, m), 2.62-3.14 (7H, m), 3.48-3.58 (1H, m), 4.70-4.76 (1H, m), 6.63-6.70 (1H, m), 7.04-7.33 (5H, m), 7.92-7.96 (1H, m)

ESI-MS Found: m/z 336.3 [M+H]+

Production Example 49

Production of (7R,9S)-9-methanesulfonylamino-6,7,8,9-tetrahydro-5H-cyclohepta[b]pyridin-7-ylmethyl toluene-4-sulfonate

1) (7R,9R)-7-(tert-butyldimethylsilanyloxy)-5,6,7,8-tetrahydrocyclohepta[b]pyridin-9-ol 4.25 g of manganese dioxide was added to chloroform (22 mL) solution of 850 mg of the compound obtained in Production Example 7-9, and stirred in a nitrogen atmosphere at room temperature for 6 hours. Then, the insoluble substance was removed through filtration through Celite. The Celite layer was washed with ethyl acetate, and the filtrate and the wash were combined, and the solvent was evaporated off under reduced pressure. The residue was separated and purified through silica gel column chromatography (hexane/ethyl acetate=3/2 to 2/3) to obtain 798 mg of (7R)-7-hydroxymethyl-5,6,7,8-tetrahydrocyclohepta[b]pyridin-9-one as a colorless oily substance.

798 mg of the obtained compound was dissolved in 2 mL of N,N-dimethylformamide, and 1.14 g of imidazole and 3.07 g of tert-butyldimethylchlorosilane were added thereto and stirred at room temperature for 7 hours. Then, the reaction liquid was diluted with water and extracted with ethyl acetate. The ethyl acetate layer was washed with saturated saline water, and dried with anhydrous sodium sulfate, and the solvent was evaporated off under reduced pressure. The residue was separated and purified through silica gel column chromatography (hexane/ethyl acetate=7/3 to 3/2) to obtain 708 mg of (7R)-7-(tert-butyldimethylsilanyloxy)-5,6,7,8-tetrahydrocyclohepta[b]pyridin-9-one as a colorless oily substance.

708 mg of the obtained compound was dissolved in 12 mL of methanol, and with cooling with ice, 178 mg of sodium borohydride was added thereto and stirred at that temperature for 30 minutes. Aqueous saturated ammonium chloride solution was added to it, and restored to room temperature. The reaction liquid was diluted with water, and extracted with ethyl acetate. The ethyl acetate layer was washed with saturated saline water, and dried with anhydrous sodium sulfate, and the solvent was evaporated off under reduced pressure. The residue was separated and purified through silica gel column chromatography (hexane/ethyl acetate=9/1 to 4/1) to obtain 471 mg of the entitled compound as a colorless oily substance.

2) (7R,9S)-9-azido-7-(tert-butyldimethylsilanyloxy)-6,7,8,9-tetrahydro-5H-cyclohepta[b]pyridine With cooling with ice, 0.77 mL of triethylamine and 0.29 mL of methanesulfonyl chloride were added to ethyl acetate (9.2 mL) solution of 566 mg of the compound obtained in the above 1, and stirred at that temperature for 40 minutes. Then, the reaction liquid was diluted with water, and extracted with ethyl acetate. The ethyl acetate layer was washed with saturated saline water, and dried with anhydrous sodium sulfate, and the solvent was evaporated off under reduced pressure. The resulting residue was dissolved in 9 mL of N,N-dimethylformamide, 598 mg of sodium azide was added thereto, and stirred in a nitrogen atmosphere at 90° C. for 3 hours. Then, the reaction liquid was cooled to room temperature, diluted with water, and extracted with ethyl acetate. The ethyl acetate layer was washed with saturated saline water, dried with anhydrous sodium sulfate, and the solvent was evaporated off under reduced pressure. The residue was separated and purified through silica gel column chromatography (hexane/ethyl acetate=33/1 to 19/1) to obtain 421 mg of the entitled compound as a colorless oily substance.

3) N-[(7R,9S)-7-(tert-butyldimethylsilanyloxymethyl)-6,7,8,9-tetrahydro-5H-cyclohepta[b]pyridin-9-yl]methanesulfonamide 400 mg of 10% palladium-carbon catalyst was added to ethyl acetate (6.4 mL) solution of 421 mg of the compound obtained in the above 2, and stirred in a hydrogen atmosphere at room temperature under normal pressure for 2 hours. Then, the reaction system was purged with nitrogen, and the catalyst was removed through filtration through Celite. The Celite layer was washed with ethyl acetate and methanol. The filtrate and the wash were combined, and the solvent was evaporated off under reduced pressure to obtain 303 mg of crude (7R,9S)-7-(tert-butyldimethylsilanyloxymethyl)-6,7,8,9-tetrahydro-5H-cyclohepta[b]pyridin-9-ylamine. 50 mg of the obtained compound was dissolved in 1.0 mL of ethyl acetate, and with cooling with ice, 69 μL of triethylamine and 25 μL of methanesulfonyl chloride were added in that order to it, and stirred at that temperature for 1 hour. The reaction liquid was diluted with water, and extracted with ethyl acetate. The ethyl acetate layer was washed with saturated saline water, dried with anhydrous sodium sulfate, and the solvent was evaporated off under reduced pressure. The residue was separated and purified through silica gel column chromatography (hexane/ethyl acetate=65/35) to obtain 50 mg of the entitled compound as a colorless oily substance.

4) N-[(7R,9S)-7-hydroxymethyl-6,7,8,9-tetrahydro-5H-cyclohepta[b]pyridin-9-yl]methanesulfonamide 0.65 mL of 1.0 M tetrabutylammonium fluoride-tetrahydrofuran solution was added to 50 mg of the compound obtained in the above 3 to dissolve it, then stirred at room temperature for 4 hours, and the solvent was evaporated off under reduced pressure. The residue was separated and purified through basic silica gel column chromatography (hexane/ethyl acetate=1/4 to ethyl acetate) to obtain 33 mg of the entitled compound as a pale brown oily substance.

5) (7R,9S)-9-methanesulfonylamino-6,7,8,9-tetrahydro-5H-cyclohepta[b]pyridin-7-ylmethyl toluene-4-sulfonate 39 mg of the entitled compound was obtained as a white solid in the same manner as in Production Example 6-4, for which, however, the compound obtained in the above 4 was used in place of (7RS,9SR)-9-(tert-butyldimethylsilanyloxy)-6,7,8,9-tetrahydro-5H-cyclohepta[b]pyridine-7-methan-1-ol used in Production Example 6-4, and the product was not subjected to optical resolution.

1H NMR (400 MHz, CDCl$_3$) δ: 1.71-1.97 (4H, m), 2.08 (1H, ddd, J=4.7, 8.2, 14.0 Hz), 2.47 (3H, s), 2.74 (1H, td, J=5.7, 15.2 Hz), 2.87 (3H, s), 2.90-3.00 (1H, m), 4.01 (1H, dd, J=5.9, 10.0 Hz), 4.10 (1H, dd, J=7.4, 10.0 Hz), 4.75-4.82 (1H, m), 6.65 (1H, brs), 7.19 (1H, dd, J=4.9, 7.5 Hz), 7.37 (2H, d, J=8.0 Hz), 7.47 (1H, dd, J=1.6, 7.5 Hz), 7.80 (2H, d, J=8.0 Hz), 8.38 (1H, dd, J=1.6, 4.9 Hz)

ESI-MS Found: m/z 347.2 [M+H]+

Example 68

Production of N-{(7R,9S)-7-[(3R,4R)-4-(2-chloro-4-fluorophenyl)-3-hydroxypiperidin-1-ylmethyl]-6,7,8,9-tetrahydro-5H-cyclohepta[b]pyridin-9-yl]methane-sulfonamide mono-L-tartrate 23 mg of the entitled compound was obtained as a white solid in the same manner as in Example 11, for which, however, the compound obtained in Production Example 49 and (3R,4R)-4-(2-chloro-4-fluorophenyl)piperidin-3-ol obtained in Production Example 26 were used in place of (7R*)-5,6,7,8-tetrahydrospiro[cyclohepta[b]pyridin-9,2'-[1,3]-dioxolan]-7-ylmethyl toluene-4-sulfonate and spiro[8-aza-bicyclo[3.2.1]octa-3,1'(3'H)-isobenzofuran]monohydrochloride used in Example 11, L-tartaric acid was used in place of fumaric acid, and the residue obtained through the reaction was again dissolved in ethanol and heptane was added thereto for solidification of the product.

m.p.: 119-128° C.

1H NMR (400 MHz, CD3OD) δ: 1.25-1.46 (2H, m), 1.65-1.78 (2H, m), 1.89-2.06 (2H, m), 2.21-2.51 (4H, m), 2.65-2.76 (2H, m), 2.87-2.95 (1H, m), 2.91 (3H, s), 3.05-3.18 (2H, m), 3.22-3.41 (2H, m), 4.03-4.11 (1H, m), 4.42 (2H, s), 7.10 (1H, td, J=2.5, 8.6 Hz), 7.21 (1H, dd, J=2.5, 8.6 Hz), 7.27 (1H, dd, J=4.9, 7.6 Hz), 7.43 (1H, dd, J=6.2, 8.6 Hz), 7.62 (1H, d, J=7.6 Hz), 8.33 (1H, dd, J=1.2, 4.9 Hz)

ESI-MS Found: m/z 482.1 [M+H]+

Production Example 50

Production of 3',3'-dimethyl-3'H-6'-azaspiro[8-azabicyclo[3.2.1]octane-3,1'-isobenzofuran]

1) Benzyl 3'-oxo-3'H-6'-azaspiro[8-azabicyclo[3.2.1]octane-3,1'-isobenzofuran]-8-carboxylate 2.0 g of 7.5% palladium-carbon was added to methanol (150 mL) solution of 3.13 g of 8-benzyl-3'H-6'-azaspiro[8-azabicyclo[3.2.1]octane-3,1'-isobenzofuran]-3'-one obtained in the course of Production Example 17, and stirred in a hydrogen atmosphere at room temperature under normal pressure for 2 hours. The reaction solution was filtered through Celite, and the solvent was evaporated off under reduced pressure.

2.1 mL of triethylamine and 1.7 mL of benzyl chloroformate were added in that order to chloroform (100 mL) solution of the residue obtained in the above, and stirred at room temperature for 15 hours. The reaction solution was diluted with chloroform, washed with water and saturated saline water in that order, and dried with anhydrous magnesium sulfate. The solvent was evaporated off under reduced pressure. The residue was separated and purified through silica gel column chromatography (hexane/ethyl acetate=4/1 to 1/1) to obtain 2.3 g of the entitled compound as a white solid.

2) Benzyl 3'-methoxy-3'-methyl-3'H-6'-azaspiro[8-azabicyclo[3.2.1]octane-3,1'-isobenzofuran]-8-carboxylate In a nitrogen atmosphere, 14 mL of 0.89 M methylmagnesium bromide-tetrahydrofuran solution was dropwise added to tetrahydrofuran (50 mL) solution of the compound obtained in the above 1, at 0° C., and stirred at 0° C. for 45 minutes. Water was added to the reaction liquid, and extracted with chloroform. The chloroform layer was washed with saturated saline water, dried with anhydrous sodium sulfate, and the solvent was evaporated off under reduced pressure.

0.56 mL of methyl iodide and sodium hydride (oily, 60 to 72%) were added in that order to tetrahydrofuran (40 mL) solution of the residue obtained in the above, and stirred at 40° C. for 2 hours. The reaction solution was diluted with chloroform, then washed with aqueous saturated sodium bicarbonate solution and saturated saline water in that order, dried with anhydrous sodium sulfate, and the solvent was evaporated off under reduced pressure. The residue was separated and purified through silica gel column chromatography (hexane/ethyl acetate=2/1 to 1/1) to obtain 1.17 g of the entitled compound as a pale yellow oily substance.

3) Benzyl 3',3'-dimethyl-3'H-6'-azaspiro[8-azabicyclo[3.2.1]octane-3,1'-isobenzofuran]-8-carboxylate In a nitrogen atmosphere, 6 mL of 1.0 M dimethylzinc-hexane solution was dropwise added to methylene chloride (20 mL) solution of the compound obtained in the above 2, at −78° C., and stirred at −78° C. for 10 minutes. 6 mL of 1.0 M titanium chloride-methylene chloride solution was dropwise added to the reaction liquid, and restored to room temperature, over 30 minutes. Then, aqueous saturated sodium hydrogencarbonate solution was added to it. The reaction solution was diluted with chloroform, then washed with water and saturated saline water in that order, and dried with anhydrous sodium sulfate. Then, the solvent was evaporated off under reduced pressure. The residue was separated and purified through silica gel column chromatography (hexane/ethyl acetate=2/1 to 1/1) to obtain 0.74 g of the entitled compound as a white solid.

4) 3',3'-Dimethyl-3'H-6'-azaspiro[8-azabicyclo[3.2.1]octane-3,1'-isobenzofuran]

0.5 g of 7.5% palladium-carbon was added to methanol (20 mL) solution of the compound obtained in the above 3, and stirred in a hydrogen atmosphere at room temperature under normal pressure for 2 hours. The reaction solution was filtered through Celite, and the solvent was evaporated off under reduced pressure. The obtained white solid was recrystallized from chloroform-isopropyl ether to obtain 444 mg of the entitled compound as a white solid.

1H NMR (400 MHz, CD$_3$OD) δ: 1.58 (6H, s), 2.12-2.22 (4H, m), 2.52 (2H, dd, J=3.0, 12.0 Hz), 2.72 (2H, d, J=6.0 Hz), 4.20 (2H, bs), 7.42 (1H, d, J=5.0 Hz), 8.48 (1H, s), 8.54 (1H, d, J=5.0 Hz)

ESI-MS Found: m/z 245.2 [M+H]+

Example 69

Production of (6R,8S)-6-[(3',3'-dimethyl-3'H-6'-azaspiro[8-azabicyclo[3.2.1]octane-3,1'-isobenzofuran]-8-yl)methyl]-5,6,7,8-tetrahydroquinolin-8-ol The entitled compound was obtained as a white solid in the same manner as in Example 14, for which, however, the compound obtained in Production Example 50 was used in place of spiro[isobenzofuran-1(3H),4'-piperidine]monohydrochloride used in Example 14, and the product was not converted into its L-tartrate.

1H NMR (400 MHz, CDCl3) δ: 1.43 (6H, s), 1.75-1.93 (5H, m), 2.10-2.37 (7H, m), 2.44-2.57 (2H, m), 3.06 (1H, dd, J=16.7, 4.7 Hz), 3.22 (2H, d, J=20.8 Hz), 4.85 (1H, t, J=4.4 Hz), 6.98 (1H, d, J=4.7 Hz), 7.13 (1H, dd, J=7.6, 4.7 Hz), 7.48 (1H, d, J=7.3 Hz), 8.41-8.37 (2H, m), 8.44 (1H, d, J=5.0 Hz)

ESI-MS Found: m/z 406.2 [M+H]+

Production Example 51

Production of 5'-fluoro-3',3'-dimethyl-3'H-6'-azaspiro[8-azabicyclo[3.2.1]octane-3,1'-isobenzofuran]

The entitled compound was obtained as a white solid in the same manner as in Production Example 50, for which, however, 8-benzyl-4'-chloro-5'-fluoro-3'H-6'-azaspiro[8-azabicyclo[3.2.1]octane-3,1'-isobenzofuran]-3'-one obtained in the course of Production Example 18 was used in place of 8-benzyl-3'-H-6'-azaspiro[8-azabicyclo[3.2.1]octane-3,1'-isobenzofuran]-3'-one used in Production Example 50.

1H NMR (400 MHz, CD3OD) δ: 1.52 (6H, s), 2.05 (2H, d, J=13.5 Hz), 2.22-2.32 (2H, m), 2.61 (2H, d, J=7.4 Hz), 2.89 (2H, d, J=15.3 Hz), 4.19 (2H, bs), 7.42 (1H, d, J=2.5 Hz), 8.37 (1H, s)

ESI-MS Found: m/z 263.3 [M+H]+

Example 70

Production of (6R,8S)-6-[(5'-fluoro-3',3'-dimethyl-3'H-6'-azaspiro[8-azabicyclo[3.2.1]octane-3,1'-isobenzofuran]-8-yl)methyl]-5,6,7,8-tetrahydroquinolin-8-ol mono-L-tartrate The entitled compound was obtained in the same manner as in Example 14, for which, however, the compound obtained in Production Example 51 was used in place of spiro[isobenzofuran-1(3H),4'-piperidine]monohydrochloride used in Example 14, and the residue was again dissolved in ethanol and heptane was added thereto for solidification of the product.

m.p.: 126-141° C.

The free amine of the compound was analyzed for the following assignment.

1H NMR (400 MHz CDCl3) δ: 1.48 (6H, s), 1.80-2.39 (13H, m), 2.47-2.56 (2H, m), 3.05-3.09 (1H, m), 3.24-3.28 (2H, m), 4.90 (1H, t, J=4.3 Hz), 6.59 (1H, d, J=2.2 Hz), 7.16 (1H, dd, J=7.6, 4.9 Hz), 7.52 (1H, d, J=7.4 Hz), 7.96 (2H, s), 8.41 (1H, d, J=4.3 Hz)

ESI-MS Found: m/z 424.2 [M+H]+

Production Example 52

Production of (1S*,2R*,3R*)-3-(2-chloro-4-fluorophenyl)-8-azabicyclo[3.2.1]octan-2-ol 1) Tert-butyl 3-(2-chloro-4-fluorophenyl)-8-azabicyclo[3.2.1]oct-2-ene-8-carboxylate 11.8 g of the entitled compound was obtained as a pale yellow oily substance in the same manner as in 1 and 2 in Production Example 25, for which, however, the compound obtained in Production Example 8-2 was used in place of tert-butyl 4-oxo-piperidine-1-carboxylate used in Production Example 25-1.

2) 3-(2-Chloro-4-fluorophenyl)-8-methyl-8-azabicyclo[3.2.1]oct-2-ene

In a nitrogen atmosphere, tetrahydrofuran (175 mL) suspension of 11.8 g of the compound obtained in the above 1 and 5.31 g of lithiumaluminium hydride was refluxed for 2 hours. The reaction liquid was cooled with ice, and 5.5 mL of water, 5.5 mL of aqueous 4 M sodium hydroxide solution, and 16.5 mL of water were added thereto in that order. The insoluble substance was removed through filtration, and the solvent was evaporated off under reduced pressure. The residue was separated and purified through basic silica gel column chromatography (hexane to hexane/ethyl acetate=4/1) to obtain 1.65 g of the entitled compound as a white solid.

3) (1SR,2RS,3RS)-3-(2-chloro-4-fluorophenyl)-8-methyl-8-azabicyclo[3.2.1]octan-2-ol In a nitrogen atmosphere, 102 mL of 1.07 M borane-tetrahydrofuran solution was dropwise added to tetrahydrofuran (22 mL) solution of 5.49 g of the compound obtained in the above 2, at room temperature, and heated under reflux for 12 hours. The reaction liquid was then cooled to room temperature, and 36 mL of water, 145 mL of aqueous 6 M sodium hydroxide solution and 145 mL of aqueous 30% hydrogen peroxide were added thereto, and stirred at 80° C. for 3 hours. The reaction liquid was cooled to room temperature, and 400 mL of aqueous 1 M sodium thiosulfate solution was added thereto, and extracted with ethyl acetate. The ethyl acetate layer was washed with saturated saline water, dried with anhydrous sodium sulfate, and the solvent was evaporated off under reduced pressure. The residue was separated and purified through basic silica gel column chromatography (hexane/ethyl acetate=10/0 to 0/10) to obtain 1.85 g of the entitled compound as a white solid.

4) (1SR,2RS,3RS)-3-(2-chloro-4-fluorophenyl)-8-methyl-8-azabicyclo[3.2.1]oct-2-yl acetate 5.2 mL of triethylamine, 1.4 mL of acetic anhydride, and 153 mg of dimethylaminopyridine were added in that order to chloroform (62 mL) solution of the compound obtained in the above 3, and stirred at room temperature for 2 hours. Aqueous saturated sodium hydrogencarbonate solution was added to the reaction liquid, extracted with ethyl acetate, and the ethyl acetate layer was washed with saturated saline water and dried with anhydrous sodium sulfate. The solvent was evaporated off under reduced pressure. The residue was separated and purified through basic silica gel column chromatography (hexane to hexane/ethyl acetate=7/3) to obtain 3.93 g of the entitled compound as a colorless oily substance.

5) (1S*,2R*,3R*)-3-(2-chloro-4-fluorophenyl)-8-azabicyclo[3.2.1]octan-2-ol (1SR,2RS,3RS)-3-(2-chloro-4-fluorophenyl)-8-azabicyclo[3.2.1]octan-2-ol was obtained as a white solid in the same manner as in Production Example 22-3, for which, however, the compound obtained in the above 4 was used in place of 1,1'-dimethyl-spiro[2,3-dihydro-1H-indole-3,4'-piperidine] used in Production Example 22-3. 1.27 g of the obtained racemate was optically resolved in an optically-active column (Daicel's CHRALPAK AD column, 5 cm×50 cm; 0.1% diethylamine, hexane/ethanol=75/25; flow rate, 150 mL/min). From the former fraction, 1.54 g of (1R*,2S*,3S*)-3-(2-chloro-4-fluorophenyl)-8-azabicyclo[3.2.1]octan-2-ol was obtained as a pale yellow solid; and from the latter fraction, 1.14 g of the (1S*,2R*,3R*) form was obtained as a white solid. (The two were not identified, and for convenience sake, one was referred to as (1R*,2S*,3S*) form and the other was as (1S*,2R*,3R*) form.)

Former Fraction, (1R*,2S*,3S*) Form:

Retention time, 2.8 min (optically-active column, Daicel's CHRALPAK AD column, 0.46 cm×25 cm; 0.1% diethylamine, hexane/ethanol=75/25; flow rate, 1 mL/min)

1H NMR (400 MHz, CD3OD) δ: 1.51-1.62 (1H, m), 1.72-1.86 (3H, m), 1.91-2.05 (1H, m), 2.10-2.22 (1H, m), 3.27-3.38 (1H, m), 3.53-3.64 (2H, m), 4.03 (1H, dd, J=3.5, 10.2 Hz), 7.08 (1H, ddd, J=2.7, 8.3, 8.6 Hz), 7.18 (1H, dd, J=2.7, 8.6 Hz), 7.46 (1H, dd, J=6.1, 8.6 Hz).

ESI-MS Found: m/z 256.1 [M+H]+

Latter Fraction, (1S*,2R*,3R*) Form:

Retention time, 11.7 min (optically-active column, Daicel's CHRALPAK AD column, 0.46 cm×25 cm; 0.1% diethylamine, hexane/ethanol=75/25; flow rate, 1 mL/min)

1H NMR and ESI-MS were the same as those of the racemate.

Example 71

Production of (6R,8S)-6-[(1S*,2R*,3R*)-3-(2-chloro-4-fluorophenyl)-2-hydroxy-8-azabicyclo[3.2.1]octan-8-ylmethyl]-5,6,7,8-tetrahydroquinolin-8-ol monohydrochloride 1.04 g of the entitled compound was obtained as a white solid in the same manner as in Example 14, for which, however, the compound obtained in Production Example 52 was used in place of spiro[isobenzofuran-1(3H),4'-piperidine] monohydrochloride used in Example 14, 4 N hydrogen chloride-ethyl acetate was used in place of L-tartaric acid, the residue was again dissolved in ethanol and heptane was added thereto for crystallization of the product.

m.p.: 238° C. (decomposition) 1H NMR (400 MHz, CD3OD) δ: 1.83-1.94 (1H, m), 2.03-2.18 (3H, m), 2.24-2.35 (2H, m), 2.41-2.53 (2H, m), 2.67-2.77 (2H, m), 3.15-3.29 (3H, m), 3.45-3.55 (1H, m), 4.02-4.09 (1H, m), 4.16-4.23 (1H, m), 4.48-4.56 (1H, m), 4.87-4.92 (1H, m), 7.15 (1H, ddd, J=2.7, 8.3, 8.8 Hz), 7.26 (1H, dd, J=2.7, 8.8 Hz), 7.42 (1H, dd, J=4.9, 7.8 Hz), 7.61 (1H, dd, J=5.9, 8.8 Hz), 7.80 (1H, d, J=7.8 Hz), 8.48 (1H, d, J=4.9 Hz).

ESI-MS Found: m/z 417.2 [M+H]+

INDUSTRIAL APPLICABILITY

The compounds exhibit an antagonism to binding of nociceptin to a nociceptin receptor ORL1 (opioid receptor-like-1 receptor) and are useful as an analgesic against diseases accompanied with pains such as cancerous pain, postoperative pain, migraine, gout, chronic rheumatism, chronic pain and neuralgia; a reliever against tolerance to a narcotic analgesic such as morphine; a reliever against dependence on or addiction to a narcotic analgesic such as morphine; an analgesic enhancer; an antiobesitic or appetite suppressor; a treating or prophylactic agent for cognitive impairment and dementia/amnesia in aging, cerebrovascular diseases and Alzheimer's disease; an agent for treating developmental cognitive abnormality such as attention deficit hyperactivity disorder and learning disability; a remedy for schizophrenia; an agent for treating neurodegenerative diseases such as Parkinsonism and chorea; an anti-depressant or treating agent for affective disorder; a treating or prophylactic agent for diabetes insipidus; a treating or prophylactic agent for polyuria; a remedy for hypotension.

The invention claimed is:
1. A compound of the formula I:

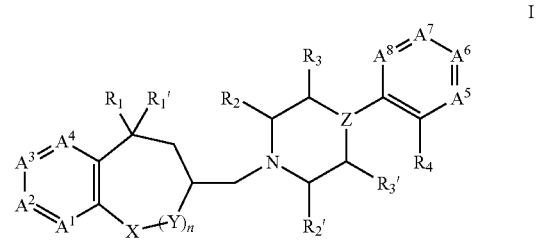

wherein:
$A^1$, $A^2$, $A^3$ and $A^4$ each independently represent —C($R_5$)— or —N—, provided that only one of $A^1$, $A^2$, $A^3$ and $A^4$ is —N—;
$A^5$, $A^6$, $A^7$ and $A^8$ each independently represent —C($R_6$)— or —N—, provided that only one of $A^5$, $A^6$, $A^7$ and $A^8$ is —N—;
$R_1$ and $R_1'$ are independently selected from a hydrogen atom, a hydroxyl group, a $C_{1-6}$ alkyl group, a $C_{1-6}$ alkyloxy group, a $C_{1-6}$ alkylsulfonylamino group, and a $C_{1-6}$ alkylcarbonylamino group, or $R_1$ and $R_1'$ together form an oxo group or a $C_{1-3}$ alkyleneketal group;
$R_2$ represents a hydrogen atom;
$R_2'$ represents a hydrogen atom, or $R_2'$ and $R_2$ together form a $C_{1-3}$ alkylene group;
$R_3$ is selected from a hydrogen atom, a hydroxyl group, a halogen atom, a $C_{1-6}$ alkyloxy group, a $C_{1-6}$ alkyl group, a hydroxy-$C_{1-6}$ alkyl group, a halo-$C_{1-6}$ alkyl group, a $C_{1-6}$ alkylsulfonylamino group, a $C_{1-6}$ alkylsulfonyl $C_{1-6}$ alkylamino group, a $C_{1-6}$ alkyloxy carbonylamino $C_{1-6}$ alkyl group and a dimethylsulfamoylaminomethyl group;
$R_3'$ is selected from a hydrogen atom, a hydroxyl group, a halogen atom, a $C_{1-6}$ alkyloxy group, a $C_{1-6}$ alkyl group, a hydroxy-$C_{1-6}$ alkyl group, a halo-$C_{1-6}$ alkyl group, a $C_{1-6}$ alkylsulfonylamino group, a $C_{1-6}$ alkylsulfonyl $C_{1-6}$ alkylamino group, a $C_{1-6}$ alkyloxy carbonylamino $C_{1-6}$ alkyl group and a dimethylsulfamoylaminomethyl group;
$R_4$ is selected from a hydrogen atom, a halogen atom, a $C_{1-6}$ alkyl group, a cyano group, a formyl group and a halogeno-$C_{1-6}$ alkyl group; or when Z is —C($R_7$)—, then $R_4$ and $R_7$ together form a —CH$_2$—O—, —CH(CH$_3$)—O—, —C(CH$_3$)$_2$—O— or —N(CH$_3$)—CH$_2$— group;
$R_5$ is selected from a hydrogen atom, a hydroxyl group, a fluorine atom, a chlorine atom, a $C_{1-6}$ alkyl group, a $C_{1-6}$ alkylamino group, a $C_{1-6}$ alkylcarbonyl group, a $C_{1-6}$ alkylcarbonylamino group, a $C_{1-6}$ alkylcarbonyl-($C_{1-6}$) alkylamino group, and a cyano group;
$R_6$ is selected from a hydrogen atom, a halogen atom, a $C_{1-6}$ alkyl group, a halogeno-$C_{1-6}$ alkyl group, a $C_{1-6}$ alkyloxy-$C_{1-6}$ alkyl group, a $C_{1-6}$ alkylcarbonyl group, a cyano group, and a formyl group;
$R_7$ is selected from a hydrogen atom, a halogen atom and a $C_{1-6}$ alkyl group; or $R_7$ and $R_4$ together form a —CH$_2$—O—, —CH(CH$_3$)—O—, —C(CH$_3$)$_2$—O— or —N(CH$_3$)—CH$_2$— group;
Ra is selected from a hydrogen atom, a $C_{1-6}$ alkyl group, a $C_{1-6}$ alkyloxycarbonyl group, a carbamoyl group, a ($C_{1-6}$ alkyl)carbamoyl group, a di($C_{1-6}$ alkyl)carbamoyl group, a $C_{1-6}$ alkylsulfonyl group, a pyrazolyl group, a triazolyl group, and an oxazolyl group;
X represents —CH$_2$— or —CH(OH)—;

Y represents —CH$_2$— or —N(Ra)—;
Z represents —C(R$_7$)— or —N—;
n indicates an integer which is 0;
or a pharmaceutically acceptable salt thereof.

2. The compound of claim 1 wherein A$^4$ is —N—, A$^1$ is —C(R$_5$)—, A$^2$ is —C(R$_5$)— and A$^3$ is —C(R$_5$)—.

3. The compound of claim 1 wherein A$^7$ is —N—, A$^5$ is —C(R$_6$)—, A$^6$ is —C(R$_6$)—, and A$^8$ is —C(R$_6$)—.

4. The compound of claim 1 wherein R$_6$ is selected from a hydrogen atom, a fluorine atom, a chlorine atom, a methyl group, an ethyl group, an isopropyl group, a trifluoromethyl group, a methylcarbonyl group, a methoxymethyl group, a formyl group and a cyano group.

5. The compound of claim 1 wherein R$_1$ and R$_1$' are selected from a hydrogen atom, a hydroxyl group, a methyl group, a methoxy group, a methylsulfonylamino group and a methylcarbonylamino group.

6. The compound of claim 1 wherein R$_1$ and R$_1$' together form an oxo group or an ethylene-ketal group.

7. The compound of claim 1 wherein R$_2$ and R$_2$' are both hydrogen atoms.

8. The compound of claim 1 wherein R$_2$ and R$_2$' together form a —CH$_2$CH$_2$— group.

9. The compound of claim 1 wherein R$_3$ and R$_3$' are selected from a hydrogen atom, a hydroxyl group, a fluorine atom, a methoxy group, a methyl group, a hydroxymethyl group, a fluoromethyl group, a methanesulfonylaminomethyl group, a methanesulfonylmethylaminomethyl group, a methoxycarbonylaminomethyl group and a dimethylsulfamoylaminomethyl group.

10. The compound of claim 1 wherein R$_4$ is selected from a hydrogen atom, a fluorine atom, a chlorine atom, a methyl group, an ethyl group, a cyano group, a formyl group and a trifluoromethyl group.

11. The compound of claim 1 wherein R$_4$ and R$_7$ together form —CH$_2$—O—, —CH(CH$_3$)—O—, —C(CH$_3$)$_2$—O— or —N(CH$_3$)—CH$_2$—.

12. The compound of claim 1 wherein Z is —C(R$_7$)—, and R$_7$ is selected from a hydrogen atom, a fluorine atom and a methyl group.

13. The compound of claim 1 wherein X is —CH$_2$—.

14. A compound which is selected from the group consisting of:
(6R,8S)-6-(spiro[isobenzofuran-1-(3H), 4'-piperidin]-1'-ylmethyl)-5,6,7,8-tetrahydroquinolin-8-ol);
(6R,8S)-6-(3,3-dimethyl-spiro[isobenzofuran-1(3H), 4'-piperidin-1'-ylmethyl)-5,6,7,8-tetrahydro-quinolin-8-ol;
(6R,8S)-6-[4-(2-chlorophenyl)-4-fluoropiperidin-1-ylmethyl]-5,6,7,8-tetrahydroquinolin-8-ol;
(6R,8S)-6-[(3R,4R)-4-(2-chloro-4-fluorophenyl)-3-hydroxypiperidin-1-ylmethyl]-5,6,7,8-tetrahydroquinolin-8-ol;
(6R,8S)-6-[(5'-fluoro-3',3'-dimethyl-3'H-6'-azaspiro[8-azabicyclo[3.2.1]octane-3,1'-isobenzofuran]-8-yl)methyl]-5,6,7,8-tetrahydroquinolin-8-ol; and
(6R,8S)-6-[(1S*,2R*,3R*)-3-(2-chloro-4-fluorophenyl)-2-hydroxy-8-azabicyclo[3.2.1]octan-8-ylmethyl]-5,6,7,8-tetrahydroquinolin-8-ol;
or a pharmaceutically acceptable salt thereof.

15. A compound which is selected from the group consisting of:
(6R,8S)-6-[(3R,4R)-4-(2-chloro-4-fluorophenyl)-3-hydroxypiperidin-1-ylmethyl]-5,6,7,8-tetrahydroquinolin-8-ol;
(6R,8S)-6-[(5'-fluoro-3',3'-dimethyl-3'H-6'-azaspiro[8-azabicyclo[3.2.1]octane-3,1'-isobenzofuran]-8-yl)methyl]-5,6,7,8-tetrahydroquinolin-8-ol;
(6R,8S)-6-[(1S*,2R*,3R*)-3-(2-chloro-4-fluorophenyl)-2-hydroxy-8-azabicyclo[3.2.1]octan-8-ylmethyl]-5,6,7,8-tetrahydroquinolin-8-ol;
or a pharmaceutically acceptable salt thereof.

16. The compound of claim 15 which is:
(6R,8S)-6-[(3R,4R)-4-(2-chloro-4-fluorophenyl)-3-hydroxypiperidin-1-ylmethyl]-5,6,7,8-tetrahydroquinolin-8-ol;
or a pharmaceutically acceptable salt thereof.

17. A pharmaceutical composition which comprises an inert carrier and a compound of claim 1, or a pharmaceutically acceptable salt thereof.

18. A pharmaceutical composition which comprises an inert carrier and a compound of claim 14, or a pharmaceutically acceptable salt thereof.

19. A pharmaceutical composition which comprises an inert carrier and a compound of claim 15, or a pharmaceutically acceptable salt thereof.

20. A pharmaceutical composition which comprises an inert carrier and a compound of claim 16, or a pharmaceutically acceptable salt thereof.

* * * * *